(12) United States Patent
Combs et al.

(10) Patent No.: US 8,846,726 B2
(45) Date of Patent: *Sep. 30, 2014

(54) MODULATORS OF INDOLEAMINE 2,3-DIOXYGENASE AND METHODS OF USING THE SAME

(71) Applicant: Incyte Corporation, Wilmington, DE (US)

(72) Inventors: Andrew P. Combs, Kennett Square, PA (US); Eddy W. Yue, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/734,263

(22) Filed: Jan. 4, 2013

(65) Prior Publication Data

US 2013/0123246 A1   May 16, 2013

Related U.S. Application Data

(60) Continuation of application No. 13/220,406, filed on Aug. 29, 2011, now Pat. No. 8,372,870, which is a division of application No. 11/430,441, filed on May 9, 2006, now Pat. No. 8,034,953.

(60) Provisional application No. 60/679,507, filed on May 10, 2005.

(51) Int. Cl.
| | | |
|---|---|---|
| *A61K 31/41* | (2006.01) | |
| *A61K 45/06* | (2006.01) | |
| *A61K 31/541* | (2006.01) | |
| *A61K 31/433* | (2006.01) | |
| *C07D 285/10* | (2006.01) | |
| *C07D 413/12* | (2006.01) | |
| *A61K 31/5377* | (2006.01) | |
| *A61K 31/4245* | (2006.01) | |
| *C07D 413/14* | (2006.01) | |
| *C07D 271/08* | (2006.01) | |

(52) U.S. Cl.
CPC ............. *C07D 285/10* (2013.01); *A61K 45/06* (2013.01); *A61K 31/541* (2013.01); *A61K 31/433* (2013.01); *C07D 413/12* (2013.01); *A61K 31/5377* (2013.01); *A61K 31/4245* (2013.01); *C07D 413/14* (2013.01); *C07D 271/08* (2013.01)
USPC ........... 514/360; 514/359; 514/183; 548/124; 548/126; 548/100

(58) Field of Classification Search
None
See application file for complete search history.

(56) References Cited

U.S. PATENT DOCUMENTS

| | | | |
|---|---|---|---|
| 3,236,855 A | 2/1966 | Jones et al. | |
| 3,286,855 A | 11/1966 | Bill | |
| 3,553,228 A | 1/1971 | Freedman et al. | |
| 3,948,928 A | 4/1976 | Nishimura et al. | |
| 4,116,974 A | 9/1978 | Farge et al. | |
| 4,323,681 A | 4/1982 | Wolf et al. | |
| 4,699,916 A | 10/1987 | Sirrenberg et al. | |
| 5,364,864 A | 11/1994 | Bigg et al. | |
| 5,712,294 A | 1/1998 | Robert et al. | |
| 6,482,416 B2 | 11/2002 | Munn et al. | |
| 6,482,822 B1 | 11/2002 | Bigg et al. | |
| 6,780,858 B2 | 8/2004 | Li et al. | |
| 8,008,281 B2 | 8/2011 | Prendergast et al. | |
| 8,034,953 B2 | 10/2011 | Combs et al. | |
| 8,088,803 B2 | 1/2012 | Combs et al. | |
| 8,372,870 B2 | 2/2013 | Combs et al. | |
| 8,377,976 B2 | 2/2013 | Combs et al. | |
| 8,450,351 B2 | 5/2013 | Combs et al. | |
| 8,507,541 B2 | 8/2013 | Combs et al. | |
| 2002/0155104 A1 | 10/2002 | Munn et al. | |
| 2004/0234623 A1 | 11/2004 | Munn et al. | |
| 2006/0194802 A1 | 8/2006 | Abdellaoui et al. | |
| 2006/0258719 A1 | 11/2006 | Combs et al. | |
| 2007/0037752 A1 | 2/2007 | Ansorge et al. | |
| 2007/0037785 A1 | 2/2007 | Ansorge et al. | |
| 2007/0038298 A1 | 2/2007 | Sulner et al. | |
| 2007/0185165 A1 | 8/2007 | Combs et al. | |
| 2007/0203140 A1 | 8/2007 | Combs et al. | |
| 2007/0265257 A1 | 11/2007 | Tanaka et al. | |
| 2008/0119491 A1 | 5/2008 | Combs | |
| 2008/0125470 A1 | 5/2008 | Combs et al. | |
| 2008/0146624 A1 | 6/2008 | Combs et al. | |
| 2008/0182882 A1 | 7/2008 | Combs et al. | |
| 2008/0214546 A1 | 9/2008 | Combs et al. | |
| 2008/0214549 A1 | 9/2008 | Shaw et al. | |
| 2009/0163545 A1 | 6/2009 | Goldfarb | |

(Continued)

FOREIGN PATENT DOCUMENTS

| | | |
|---|---|---|
| BE | 659457 | 8/1965 |
| BE | 659467 | 8/1965 |

(Continued)

OTHER PUBLICATIONS

Ait-Mohand, Samia. and Dolbier, Jr. William R., "New and Convenient Method for Incorporation of pentafluorosulfanyl (SF5) Substituents Into Aliphatic Organic Compounds", Organic Letters, 4(17), 3013-3015, 2002.

(Continued)

*Primary Examiner* — Wu-Cheng Winston Shen
*Assistant Examiner* — Theodore R West
(74) *Attorney, Agent, or Firm* — Fish & Richardson P.C.

(57) ABSTRACT

The present invention is directed to modulators of indoleamine 2,3-dioxygenase (IDO), as well as compositions and pharmaceutical methods thereof.

38 Claims, No Drawings

(56) References Cited

U.S. PATENT DOCUMENTS

| | | |
|---|---|---|
| 2009/0247586 A1 | 10/2009 | Dunkel et al. |
| 2011/0165188 A1 | 7/2011 | Combs et al. |
| 2011/0172279 A1 | 7/2011 | Combs et al. |
| 2011/0311479 A1 | 12/2011 | Combs et al. |
| 2012/0058079 A1 | 3/2012 | Combs et al. |
| 2013/0177590 A1 | 7/2013 | Combs et al. |

FOREIGN PATENT DOCUMENTS

| | | |
|---|---|---|
| CA | 2500113 | 4/2004 |
| DE | 2040628 A1 | 2/1972 |
| EP | 0352832 | 1/1990 |
| EP | 0516520 | 12/1992 |
| EP | 0536424 | 4/1993 |
| EP | 1038874 | 9/2000 |
| EP | 1188747 | 3/2002 |
| JP | 40 020710 | 9/1965 |
| JP | 4020710 | 9/1965 |
| JP | 58 208275 | 12/1983 |
| JP | 60 193968 | 10/1985 |
| JP | 62059283 | 3/1987 |
| JP | 02 006453 | 1/1990 |
| JP | 4297449 | 10/1992 |
| JP | 06-065269 | 3/1994 |
| JP | 11171702 | 6/1999 |
| JP | 11-513679 | 11/1999 |
| JP | 2001158785 | 6/2001 |
| JP | 2001158786 | 6/2001 |
| JP | 2001-233861 | 8/2001 |
| RU | 2230742 | 6/2004 |
| SU | 886740 | 12/1981 |
| WO | WO97/14686 | 4/1997 |
| WO | WO97/30047 | 8/1997 |
| WO | WO97/42183 | 11/1997 |
| WO | WO99/29310 | 6/1999 |
| WO | WO99/62903 | 12/1999 |
| WO | WO00/52001 | 9/2000 |
| WO | WO01/51456 | 7/2001 |
| WO | WO0151456 | 7/2001 |
| WO | WO02/00196 | 1/2002 |
| WO | WO02/079200 | 10/2002 |
| WO | WO02/102799 | 12/2002 |
| WO | WO03/045901 | 6/2003 |
| WO | WO03045901 | 6/2003 |
| WO | WO 03/070236 | 8/2003 |
| WO | WO03/087347 | 10/2003 |
| WO | WO03/099805 | 12/2003 |
| WO | WO2004/029031 | 4/2004 |
| WO | WO 2004/093871 | 11/2004 |
| WO | WO2004/094409 | 11/2004 |
| WO | WO2005/019190 | 3/2005 |
| WO | WO2005/037257 | 4/2005 |
| WO | WO2005/037779 | 4/2005 |
| WO | WO2006/028284 | 3/2006 |
| WO | WO2006/067532 | 6/2006 |
| WO | WO2006/122150 | 11/2006 |
| WO | WO2006/133417 | 12/2006 |
| WO | WO2007068377 | 6/2007 |
| WO | WO2007/075598 | 7/2007 |
| WO | WO2008/036642 | 3/2008 |
| WO | WO2008/036643 | 3/2008 |
| WO | WO2008/036652 | 3/2008 |
| WO | WO2008/036653 | 3/2008 |
| WO | WO2008/058178 | 5/2008 |
| WO | WO2008/073825 | 6/2008 |

OTHER PUBLICATIONS

An English translation of Andrianov et al., *Ahurnal Organicheskoi Khimii*, 1993, 29(5), pp. 1062-1066.

Andrianov et al., "Ammonia- and amine-induced rearrangements of 5-(trifluoromethyl)-1,2,4-oxadiazoles", *Khimiya Geterotsiklicheskikh Soedinenii*, (1988), (6), 856-7, and abstract.

Andrianov et al., "Ammonia- and amine-induced rearrangements of 5-(trifluoromethyl)-1,2,4-oxadiazoles", *Khimiya Geterotsiklicheskikh Soedinenii*, (1988), (6), 856-7.

Andrianov et al., "Rearrangements of 1-oxa-2-azoles. 2. Structure and isomerization of pentamethyleneamidoximes of 4-aminofurazan-3-carboxylic acid", Khimiya Geterotsiklicheskikh Soedinenii, (1991), (1), 122-3, and abstract.

Andrianov et al., "Rearrangements of 1-oxa-2-azoles. 2. Structure and isomerization of pentamethyleneamidoximes of 4-aminofurazan-3-carboxylic acid", Khimiya Geterotsiklicheskikh Soedinenii, (1991), (1), 122-3.

Andrianov et al., "Acid halides of 4-aminofurazan-3-carbohydroximic acid", *Khimiya Geterotsiklicheskikh Soedinenii*, (1992), (5), 687-91, and abstract.

Andrianov et al., "Acid halides of 4-aminofurazan-3-carbohydroximic acid", Khimiya Geterotsiklicheskikh Soedinenii, (1992), (5), 687-91.

Andrianov et al., "Synthesis and properties of derivatives of 4-aminofuroxan-3-carboxylic acid", abstract, Chemistry of Heterocyclic Compounds (NewYork)(Translation of Khimiya Geterotsiklicheskikh Soedinenii), (1998), vol. Date 1997, 33(8), 973-976, and abstract.

Andrianov et al., "4-Aminofurazan-3-carbohydroximic acid halides", *Khimiya Geterotsiklicheskikh Soedinenii*, (1994), (3), 420-5, and abstract.

Andrianov et al., "4-Aminofurazan-3-carbohydroximic acid halides", Khimiya Geterotsiklicheskikh Soedinenii, (1994), (3), 420-5.

Andrianov et al. "New preparation of 5-amino derivatives of 1,2,4-oxadiazole", *Khimiya Geterotsiklicheskikh Soedinenii*,(1988), (12), 1701.

Andrianov, B.G. et al., "Acid halides of r-aminofurazan-3-carbohydroxamic acids", Latvian Institute of Organic Chemistry, 3:370-371 (1994).

Andrianov, V.G. et al., "4-aminofurazan-3-carboxamidoxime cyclization", Khimiya Geterotsiklicheskikh Soedinenii (4):534-8 (1994)(Abstract only).

Andrianov, V.G. et al., "4-aminofurazan-3-hydroximic halides", Institute of Organic Synthesis, 5:581-585 (1992).

Andrianov, V.G. et al., "Rearrangements of 5-trifluoromethyl-1,2,4-oxadiazoles by action of ammonia and amines", UDC 547.793.2/3. 04, 2406(88):707 (1988).

Andrianov, V.G. et al., "Ring formation reactions of 4-aminofurazan-3-carboxyamidoximes", Chemistry of Heterocyclic Compounds, 30(4):470-474 (1994).

Andrianov, V.G. et al., "Synthesis of furazans by rearrangement of 3-acyl-1-oxa-2-azole oximes", UDC 547.793.07(047) 2611(90):1199-1213 (1991).

Andrianov, V.G. et al., "Synthesis, structure, and rearrangement of 4-aminofurazan-3-carboxiamide oximes", UDC 547.793.2, 29(5):877-880 (1994).

Andrianov, V.G. et al., "Synthesis, structure, and rearrangement of 4-aminofurazan-3-carboxylic acid amidoximes", Zhurnal Organicheskoi Khimii 29(5):1062-6 (1993)(Abstract only) XP002526508; Database accession No. 1994:270259.

Andrianov, V.G. et al., "Synthesis, structure, and rearrangement of 4-aminofurazan-3-carboxylic acid amidoximes", Zhurnal Organicheskoi Khimii 29(5):1062-6 (1993).

Andrianov et al. "Degenerate Rearrangement of 3-amino-1,2,5-oxadiazole-4-carboxamidoxime", *Khimiya Geterotsiklicheskikh Soedinenii*, (1988), (12), 1701 and abstract.

Andrianov, et al., "Synthesis and properties of 4-amino-3-cyanofurazan", *Chemistry of Heterocyclic* Compounds, vol. 30, No. 5, pp. 608-611 (1994), translation of Khimiya Geterotsiklicheskikh Soedinenii, (5), 693-6 (1994) with abstract.

Areschka, et al., "Studies on the benzofuran series. LXI. 3-Benzofuranylacetamidoximes with antihypertenstive potential", European Journal of Medicinal Chemistry, (1977), 12(1), 87-91 (with English abstract).

Astigiano, et al., *Neoplasia*, 7(4):390-396 (2005).

Bagdasarov et al., "Extraction—photometric determination of copper and cobalt with oxime derivatives of benzimidazole", *Zavodskaya Laboratoriya* (1976), 42(2), 143-144 (Non-English Reference).

(56) References Cited

OTHER PUBLICATIONS

Beaudegenies et al., "Synthesis of furazan conjugated new heterocycles", Heterocycles, (2003) 60(11) 2417-2424 and abstract.
Berge, et al., "Pharmaceutical Salts", *J. of Pharmaceutical Science*, vol. 66 No. 1, pp. 1-19 (1977).
Bonda, et al., "Indoleamine 2,3-dioxygenase and 3-hydroxykynurenine modifications are found in the neuropathology of Alzheimer's disease", Redox Rep., 15(4):161-8 (2010).
Brandacher, et al., *Clin. Cancer Res.*, 12(4):1144-1151 (2006) (abstract).
Brown, et al., 1991, Adv. Exp. Med. Biol., 294: 425-35.
Burger et al., "Janus kinase inhibitor INCB20 has antiproliferative and apoptotic effects on human myeloma cells in vitro and in vivo," Mol. Cancer Ther 2009;8(1) Jan. 2009, 26-35.
Chauhan et al., "Antifilarial profile of substituted pyrazoles: a new class of antifilarial agents," Indian Journal of Chemistry, Section B: Organic Chemistry Including Medicinal Chemistry (1993), 32B(8), 858-61 (with abstract Database Hcaplus STN File CA, 120:244819; 1994:244819).
Cited ref_Wikipedia indoleamine 2,3-dioxygenase (3 pages), Jan. 16, 2009.
Cited ref_STN search_11641284 (93 pages), Jan. 16, 2009.
Clercq, Journal of Clinical Virology, vol. 30, 2004, pp. 115-133.
Corbett et al. In vivo methods for screening and preclinical testing. Cancer Drug Discovery and Development: Anticancer Drug Development Guide: Preclinical Screening, Clinical Trials, and Approval, 2nd Ed. Teicher, B.A. and Andrews, P.A., Gumana Press Inc., Totowa, NJ, 2004*.
Current Protocols in Immunology, vol. 4, Coligan, J.E., et al; Immunotherapy of Cancer, Human Press, 2006, Disis, M.L.*.
Daubener, et al., 1999, Adv. Exp. Med. Biol., 467: 517-24.
Database CAPLUS, on STN (Columbus, OH, USA), 1975:606233, No,83, 32463a, 32466a "Amidoxime Derivatives", abstract, Nishimura, Haruki et al., see RN 55942-51-3 CAPLUS, XP-002467961.
Database CAPLUS, on STN (Columbus, OH, USA), 1963: 73272, No,83, 12528c-e "Compaunds with Potential Antitubercular Activity. VI. Amidoximes, amide Hydrazones, and S-Oxides of Thioamides of some Heterocyclic acids", abstract, Sysheva, et al., see RN 90585-88-9 CAPLUS, XP-002467962.
Database CAPLUS, on STN (Columbus, OH, USA), 1992: 6493, No. 116, 6493 "Rearrangement of 1-oxa-2-azoles. 4. synthesis and rearrangement of Amidoximes of soxazole-and 4,5-dihydrosoxazole-3-carboxylic acid", abstract, Andrianov, V. et al., see RN 137890-17-6 CAPLUS, XP-002467964.
Database CAPLUS, on STN (Columbus, OH, USA), 1966: 35828, No. 64, 6633a-d "Compaunds with Potential Antitubercular Activity. X. Derivatives of Benzoxazole-2-carboxylic acid", abstract, Sysheva, et al., see RN 4698-75-3 CAPLUS, XP-002467245.
Database Caplus No. 1995:393128, Andrianov et al., "4-Aminofurazan-3-carboxamidoxime cyclization reactions," XP002526509.
Database Caplus No. 2004:589877, Sheremetev et al., "Synthesis of secondary and tertiary ammofurazans,," XP002526510.
Database Hcaplus, on STN, 2007:1104249, No. 148:33190, "New and Original pKa Prediction Method Using Grid Molecular Interaction Fields", abstract, Milletti et al., *Journal of Chemical Information and Modeling*, 2007, 47(6), 2172-2181.
Database Hcaplus, on STN, 2007:633470, No. 148:561814, "Synthesis and crystal structure of 3,6-bis(3'-aminofurazan-4-yl)-1,4-dioxa-2,5-diazacyclohexane-2,5-diene", abstract, Wang et al., *Huaxue Yanjiu Yu Yingyong*(2006), 18(12), 1398-1402.
Database Hcaplus, on STN, 2007:380035, No. 148:382415, "Crystal structure of 3-amino-4-acylaminoximinofurazan", abstract, Wang et al., *Hanneng Cailiao*, (2006), 14(6), 441-445.
Database Hcaplus, on STN, 2006:616681, No. 146:206250, "Synthesis of 3-amino-4-aminoximidofurazan and its crystal structure", abstract, Wang et al., *Hecheng Huaxue*, (2006), 14(3), 234-239.

Database Hcaplus, on STN, 2003:865834, No. 140:59538, "Synthesis of furazan conjugated new heterocycles", abstract, Beaudegnies et al., *Heterocycles*, (2003), 60(11), 2417-2424.
Database Hcaplus, on STN, 2003:641413, No. 139:383553, "Hydroxylammonium salts of Furazan family", abstract, Sheremetev et al., *International Annual Conference of ICT* (2003), 34th, 101/1-101/10.
Database Hcaplus, on STN, 2002:953422, No. 138:368816, "New Heterocycles with a 3-Aminofurazanyl Substituent", abstract, Shaposhnikov et al., *Russian Journal of Organic Chemistry (Translation of Zhurnal Organicheskoi Khimii)*, (2002), 38(9), 1351-1355.
Database Hcaplus, on STN, 2000:643842, No. 133:321845, "Effect of particular structural features of aminooximes on formation of final products in reactions with 5-aryl-2,3-dihydrofuran-2,3-diones", abstract, Nekrasov et al., *Russian Journal of Organic Chemistry (Translation of Zhurnal Organicheskoi Khimii)* (2000), 36(2), 263-268.
Database Hcaplus, on STN, 1998:498929, No. 129:163569, "Study on combustion of new energetic furazans", abstract, Sinditskii et al., *International Annual Conference of ICT (1998),29$^{th}$ (Energetic Materials)*, 170.1-170.11.
Database Hcaplus, on STN, 1995:376582, No. 123:198702, "4-Aminofurazan-3-carbohydroximic acid halides", abstract, Andrianov et al., *Khimiya Geterotsiklicheskikh Soedinenii*, (1994), (3), 420-5.
Database Hcaplus, on STN, 1994:244883, No. 120:244883, "Reaction of furoxannitrolic acids with nitrogen tetroxide", abstract, Rakitin et al., *Khimiya Geterotsiklicheskikh Soedinenii*, (1993), (9), 1283-7.
Database Hcaplus, on STN, 1994:164073, No. 120:164073, "Synthesis of nitrolic acids of furoxane series", abstract, Rakitin et al., *Khimiya Geterotsiklicheskikh Soedinenii*,(1993), (8), 117-19.
Database Hcaplus, on STN, 1932:6117, No. 26:6117, "Dioximes. LXXVIII", abstract, Longo, G., *Gazzetta Chimica Italiana*, (1931), 61, 575-83.
Database Hcaplus, on STN, 2002:880171, No. 138:204550, "Estimation and prediction on heats of formation for nitro furazan series compounds with new molecular subgraph", abstract, Liu et al., *Huaxue Wuli Xuebao*, (2002), 15(5), 351-356.
Database Hcaplus, on STN, 1995:464236, No. 122:217824, "Comparative characteristic of energy content calculating methods for the furazan series as an example of energetic materials", abstract, Pivina et al., *Propellants, Explosives, Pyrotechnics*, (1995), 20(1) 5-10.
Daubener, et al., 1999, Adv. Exp. Med. Biol., 467: 517-24.
Dranoff et al., "Vaccination with irradiated tumor cells engineered to secrete murine granulocyte-macrophage colony-stimulating factor stimulates potent, specific, and long-lasting anti-tumor immunity," Proc. Natl. Acad. Sci, USA. 90:3539-3543 (1993).
Friberg, M., Jennings, R., et al. Indoleamine 2,3-dioxygenase contributes to tumor cell evasion of T cell-mediated rejection. Int. J. Cancer: 101:151-155, 2002.
Giron, D.J., "Investigations of Polymorphism and Pseudo-Polymorphism in Pharmaceuticals by Combined Thermoanalytical Techniques", *J. Therm. Anal. Cal.* (2001), 64, pp. 37-60.
Giron, D.J., "Applications of Thermal Analysis and Coupled Techniques in Pharmaceutical Industry", *J. Therm. Anal. Cal.* (2002), 68, pp. 335-357.
Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. 1-20-38.
Greene, et al., Protective Groups in Organic Synthesis, 2d. Ed., Wiley & Sons, 1991*.
Grohmann, et al., 2003, Trends Immunol , 24: 242-8.
Higuchi et al., "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987*.
Honig et al., "From bench to clinic and back: perspective on the 1st IQPC Translational Research Conference", Journal of Translational Medicine, 2:44 (2004) pp. 1-8.
Hou, et al., *Cancer Res* 67(2):792-801 (2007).

(56) References Cited

OTHER PUBLICATIONS

Hwu P, et al., "Indoleamine 2,3-dioxygenase production by human dendritic cells results in the inhibition of T cell proliferation", J. Immunol 164(7):3596-9, (2000).

Ichikawa, T. et al., "A new synthesis of adenine and 4-aminoimidazole-5-carboxamide", Central Research Laboratories, Ajinomoto Co., Inc., pp. 253-255 (1965).

Inaba et al., "Role of the immunosuppressive enzyme indoleamine 2,3-dioxygenase in the progression of ovarian cancer", *Gyn. Oncol.*, 115, 185-92 (2009).

Ino, et al., *British Journal of Cancer*, 95:1555-1561 (2006).

Itaya et al., "Purines. XVIII. Kinetic studies of the Dimroth rearrangement of 1-alkoxy-9-methyladenines and 1-benzyloxyadenosine. Effect of 1-benzyloxy and 9-β-D-ribofuranosyl groups on the rates of the ring opening and the reclosure," *Chemical & Pharmaceutical Bulletin* (1975), 23(11), 2643-53 (with abstract Database Hcaplus STN File CA, Abstract 84:44592; 1976:44592).

Itaya et al., "Purines. LXXII. Oxidation of N6-alkyladenines with m-chloroperoxybenzoic acid leading to N6-alkyladenine 1-oxides," *Chemical &Pharmaceutical Bulletin* (1996), 44(5), 967-971, (with abstract Database Hcaplus STN File CA, 125:86583; 1996:325165; CAS RN 155720-89-1).

J. Exp. Med. 196(4):447-57, Aug. 2002.

J. Heterocycl. Chem. (1965), 2, 253.

Ji, et al., J. Immunol, 2005, 175:1456-63.

Journal of Pharmaceutical Science, 66, 2 (1977).

A.R. Katritzky et al., "Synthesis of mono and symmetrical di-N-hydroxy- and N-ammoguanidines", Journal of Organic Chemistry, 71(18):6753-8 (2006).

Koblish, et al., "Hydroxyamidine Inhibitors of Indoleamine-2,3-dioxygenase Potently Suppress Systemic Tryptophan Catabolism and the Growth of IDO-Expressing Tumors", *Molecular Cancer Therapeutics*, 9(2):489-498 (Published Online Feb. 2, 2010).

Koblish, et al., "Potent, Orally Active Hydroxylamidine Inhibitors of Indoleamine-2,3dioxygenase Suppress Growth of ID01-expressing Tumors through Systemic Inhibition of Tryptophan Catabolism", 24th Annual Meeting of the International Society for the Biological Therapy of Cancer (ISBTC) in National Harbor MD/Washington DC (Oct. 30, 2009) (poster and abstract).

Kohl, et al., "IDO and clinical conditions associated with depressive symptoms", Curr. Drug Metab., 8:283-7 (2007).

Liu, et al., "Estimation and prediction on heats of formation for nitro furazan series compounds with new molecular subgraph", *Huaxue Wuli Xuebao*, (2002), 15(5), 351-56, and abstract.

Liu, et al., "INCB024360, a Potent and Selective Inhibitor of Indoleamine 2,3- dioxygenase (IDO1) as a Novel Cancer Immunotherapeutic Agent", *Mol Cancer Ther*, 8(12 Suppl):Poster #C106 (2009).

Liu, et al., "Indoleamine 2,3-Dioxygenase, an Emerging Target for Anti-Cancer Therapy", *Current Cancer Drug Targets*, 9:938-952 (2009).

Lob, et al., "Inhibitors of indoleamine-2,3-dioxygenase for cancer therapy: can we see the wood for the trees?", Nature Reviews Cancer, 9:445-52 (2009).

Logan, et al., 2002, Immunology, 105: 478-87.

Longo, G., "Dioximes. LXXVIII", *Gazzetta Chimica Italiana*, (1931), 61, 575-83, and abstract.

Luo et al. Cell, 2009, 136, pp. 823-837.

Mailankot, et al., "Cell Cycle Arrest by Kynurenine in Lens Epithelial Cells", IOVS, 49:5466-5475 at 5474 (2008).

Medawar, 1953, Symp. Soc. Exp. Biol. 7: 320-38.

Meyer, Kevin G., "Improved synthesis of 3-aminofurazan-4-carboxylic acid", Organic Preparations and Procedures INt. 36(4):361-363 (2004).

Milletti et al., "New and Original pKa Prediction Method Using Grid Molecular Interaction Fields", Journal of Chemical Information and Modeling, 2007, 47(6), 2172-2181, and abstract.

Mishnev, A.F. et al., "Crystal and molecular structure of isomers of the oxime of 3-aminofurazanoyl piperidine", Translated from Zhurnal Strukturnoi Khimii, 32(3):45-48 (1991).

Muller et al., 2005, Nature Med., 11:312-9.

Munn, et al., 1998, Science 281: 1191-3.

Munn, et al., 2002, Science 297: 1867-70.

Munn, et al., 2004, J. Clin. Invest., 114(2): 280-90.

Munn, et al., *Journal of Clinical Investigation*, 117(5):1147-1154 (2007).

Nekrasov et al., "Effect of particular structural features of aminooximes on formation of final products in reactions with 5-aryl-2,3-dihydrofuran-2,3-diones", Russian Journal of Organic Chemistry, (2000), 36(2), 263-268, (Translation of Zhurnal Organicheskoi Khimii,vol. 36, No. 2 (2000) pp. 285-90) and abstract.

Okamoto, et al., Clin Cancer Res 11(16):6030-6039, at 6037-6038 (2005).

Pellegrin, et al., "Enhanced enzymatic degradation of tryptophan by indoleamine 2,3-dioxygenase contributes to the tryptophan-deficient state seen after major trauma", Shock, 23:209-215 (2005).

Peterson, A.C. et al., Evaluation of Functionalized Tryptophan Derivatives and related Compounds as Competitive Inhibitors of Indoleamine 2,3-Dioxygenase Med. Chem. Res. 3, 531-544, 1994.

"Physicians' Desk Reference" (PDR, e.g., 1996 edition, Medical Economics Company, Montvale, NJ) Zh. Org. Chim. (1993), 29, 1062-1066.

Pivina et al., "Comparative characteristic of energy content calculating methods for the furazan series as an example of energetic materials", Propellants, Explosives, Pyrotechnics, (1995), 20(1) 5-10, and abstract.

Poluektova LY, Munn DH, Persidsky Y, and Gendelman HE (2002). Generation of cytotoxic T cells against virus-infected human brain macrophages in a murine model of HIV-1 encephalitis. J. Immunol. 168(8):3941-9.

Portula et al., 2005, Blood, 106:2382-90.

Quan, et al., Expert Opin. Biol. Ther., 8:1705 at 1714 (2008).

Rakitin et al., "Reaction of furoxannitrolic acids with nitrogen tetroxide", Khimiya Geterotsiklicheskikh Soedinenii, (1993), (9), 1283-7, and abstract.

Rakitin et al, "Synthesis of Furaxonenitrolic Acids", N. D. Zelinskii Institute of Organic Chemistry, Russian Academy of Sciences, 117913 Moscow pp. 952-954 (1994), Translated from., "Synthesis of nitrolic acids of furoxane series" Khimiya Geterotsiklicheskikh Soedinenii,(1993), (8), 117-119 and abstract.

Ravin, Louis J., "Preformulation", *Remington's Pharmaceutical Sciences*, 17th ed., Mack Publishing Company, Easton, PA., Chapter 76, pp. 1409-1423 (1985).

Riffaud, et al., "Sur les propriétiés analgésiqués at antiinflammatoires des benzofuryl-2 amidoximes", *European Journal of Medicinal Chemistry*, Editions Scientifique Elsevier, Paris, Fr., vol. 1796, pp. 577-580, (1982).

Riffaud, et al., European Journal of Medicinal Chemistry, Editions Scientifique Elsevier, Paris, Fr., vol. 1796, pp. 577-580, (1982).

Remington's Pharmaceutical Sciences, 17th ed., Mack Publishing Company, Easton, Pa., 1985, p. 1418.

Roche, Edward B., Bioreversible Carriers in Drug Design, ed., American Pharmaceutical Association and Pergamon Press, 1987*.

B. Rodriguez-Spong et al., "General principles of pharmaceutical solid polymorphism: a supramolecular perspective", Advanced Drug Delivery Review, (2004), 56, pp. 241-274.

Romanova et al., "Synthesis and reactivity of azidomes: III 1-Azido (4-amino-1, 2, 5-oxadiazol-3-yl) aldoxime in the Cycloaddtion Reaction," Russian J. of Org. Chem., 39(4), 574-578 2003.

Rozhov et al., "Synthesis of 1,2,4-oxadiazole-, pyrrole- and 1,2,3-triazole-substituted (1,2,3-triazol-l-yl)furazans", Mendeleev Communications, 2008, 18(3), 161-163.

Rozhov et al., "Synthesis of 1,2,4-oxadiazole-, pyrrole- and 1,2,3-triazole-substituted (1,2,3-triazol-l-yl)furazans", *Mendeleev Communications*, 2008, 18(3), 161-163 and abstract.

Sambrook, J, Russel, D. Molecular Cloning: A laboratory Manual (3rd edition). Cold Spring Harbor Laboratory Press. Cold Spring Harbor, NY, USA. 2001*.

(56) References Cited

OTHER PUBLICATIONS

Schafer et al., "Failure is an option: learning from unsuccessful proof of concept trials", Drug Discovery Today, vol. 13, Nos. 21/22, pp. 913-16 (2008).
Scherle, P., "Characterization of Novel and Potent Inhibitors of the Immunoregulatory Enzyme Indoleamine 2,3-Dioxygenase (IDO) for Use as Cancer Therapy" presented on Mar. 5, 2009 at the Translational Research Cancer Center Consortium annual meeting in Philadelphia, PA.
"Search Run Jul. 28, 2009 / HCAPLUS", 95 pgs.
"Search Run Jul. 28, 2009/Registry File Compounds", 107 pgs.
Search Run Jul. 13, 2010/Scifinder, 10 pages.
Search Run STN International "11641284" dated Jan. 16, 2009 (93 pages).
Shaposhnikov et al., "New Heterocycles with a 3-Aminofurazanyl Substituent", Russian Journal of Organic Chemistry (Translation of Zhurnal Organicheskoi Khimii), (2002), 38(9), 1351-1355, and abstract.
Sheremetev et al., "Hydroxylammonium salts of Furazan family", International Annual Conference of ICT (2003), 34th, 101/1-101/10, and abstract.
Sheremetev, A. B., Izvestiya Akademii Nauk, Seriya Khimicheskaya, (3), 569-586 (2004) (English Translation).
Shih et al., Medicinal Research Reviews, vol. 24, 2004, pp. 449-474.
Sinditskii et al., "Study on combustion of new energetic furazans", International Annual Conference of ICT (1998),29th (Energetic Materials), 170.1-170.11, and abstract.
Soliman et al., "Indoleamine 2,3-Dioxygenase: Is It an Immune Suppressor?", *Cancer J.* 16,354-59 (2010).
Sono, M., Taniguchi, T., Watanabe, Y., and Hayaishi, O. (1980) J. Biol. Chem. 255, 1339-1345.
Souillac, et al., Characterization of Delivery Systems, Differential Scanning Calorimetry, pp. 217-218 in Encyclopedia of Controlled Drug Delivery, (1999), John Wiley & Sons, pp. 212-227.
Synth. Commun (1988), 18, 1427.
STN File CA, Abstract 145:457146; Wang et al, "Experimental study on synthesis of 3-ammo-4-chloroximinofurazan" Hanneng Cailiao (2005), 13 (Suppl.), 1-3.
STN File CA, Abstract 145:191465; Wang et al., "500 Gram-grade synthesis of 3-amino-4-aminoximinofurazan," Hanneng Cailiao (2006), 14(1), 27-28.
STN File CA, Abstract 123:198701; Andrianov et al., "Synthesis and properties of 4-amino-3-cyanofurazan," Khimiya Geterotsiklicheskikh Soedinenii (1994), (5), 693-6.
STN File CA, Abstract 130:209340; Belik et al., "Theoretical investigation of rearrangements of 1-oxa-2-azole-3-carboxamidoximes," Russian Journal of Organic Chemistry (Translation of Zhurnal Organicheskoi Khimii) (1998), 34(4), 543-548.
STN File CA, Abstract 122:238877; Belik et al., "Descriptor v'cp-aided study of the rearrangement of 1-oxa-2-azoles,"Zhurnal Organicheskoi Khimii (1994), 30(5), 757-9.
STN File CA, Abstract 87:111278; Fujii , "Antitumor activities of some fifty compounds related to adenine derivatives," Yakugaku Zasshi (1977), 97(6), 689-91.
STN File CA, Abstract 75:76739; Fujii et al., "Purines. III. Rearrangement of 1-alkoxy-9-alkyladenines to 6-alkoxyamino-9-alkylpurines through isolatable N'-alkoxy-l-alkyl-5-formamidoimidazole-4-carboxamidines ," Tetrahedron (1971), 27(12), 2415-23.
STN File CA, Abstract 127:65632; Itaya et al., "Purines. LXXV. Dimroth rearrangement, hydrolytic deamination, and pyrimidine-ring breakdown of 7-alkylated 1-alkoxyadenines: N(1)-C(2) versus N(1)-C(6) bond fission," Chemical & Pharmaceutical Bulletin (1997), 45(5), 832-841.
STN File CA, Abstract 125:86583; Itaya et al., "Purines. LXXII. Oxidation of N6-alkyladenines with m-chloroperoxybenzoic acid leading to N6-alkyladenine 1-oxides," Chemical & Pharmaceutical Bulletin (1996), 44(5), 967-971.

STN File CA, Abstract 121:35143; Fujii et al., "Oxidation of N6-benzyladenine with m-chloroperoxybenzoic acid: formation of the N(1)-oxide," Heterocycles (1994), 37(1), 219-22.
STN File CA, Abstract 114:247645; Fujii et al., "Purines. XLVIII. Syntheses and proton nuclear magnetic resonance study of 2-deuterioadenines substituted or unsubstituted at the 9-position and of their N-oxygenated derivatives," Chemical & Pharmaceutical Bulletin (1991), 39(2), 301-8.
STN File CA, Abstract 84:44592; Fujii et al., "Purines. XVIII. Kinetic studies of the Dimroth rearrangement of 1-alkoxy-9-methyladenines and 1-benzyloxyadenosine. Effect of 1-benzyloxy and 9-β-D-ribofuranosyl groups on the rates of the ring opening and the reclosure," Chemical & Pharmaceutical Bulletin (1975), 23(11), 2643-5.
STN File CA, Abstract 82:43349; Fujii et al., "Purines. XV. Conversion of N,9-dimethyladenine into the 1,9-dimethyl isomer. Reverse operation of the dimroth rearrangement," Chemical & Pharmaceutical Bulletin (1974), 22(10), 2211-16.
STN File CA, Abstract 75:110279; Fujii et al., "Purines. V. Dimroth rearrangement of 1-alkoxyadenines. Synthesis of N-alkoxyadenines," Chemical & Pharmaceutical Bulletin (1971), 19(8), 1731-4.
STN File CA, Abstract 120:244819; Chauhan et al., "Antifilarial profile of substituted pyrazoles: a new class of antifilarial agents," Indian Journal of Chemistry, Section B: Organic Chemistry Including Medicinal Chemistry (1993), 32B(8), 858-61.
STN File CA, Abstract 113:231330; El-Mobayed et al., "Synthesis of heterocyclic compounds containing nitrogen and sulfur from 3-amino-4-cyanopyrazole," Journal of the Chemical Society of Pakistan (1989), 11(4), 287-90.
STN File CA, Abstract 113:97502; Deeb et al., "Heterocyclic synthesis from 3-amino-4cyanopyrazole," Collection of Czechoslovak Chemical Communications (1990), 55(3), 728-33.
STN File CA, Abstract 84:99208; Spasova et al., "Inhibition of the growth of *L. casei* by some pyrazole analogues of 5(4)-aminoimidazole-4(5)-carboxamide," Doklady Bolgarskoi Akademii Nauk (1975), 28(11), 1517-20.
STN File CA, Abstract 84:54765; Spasova et al., "Certain derivatives of pyrazole as potential antimetabolites of 4(5)-amino-imidazole-5(4)-carboxamide," Proc. Chemother. (Antibacterial, Antiviral, Antineoplast.), Proc. Int. Congr. Chemother., 8th (1974), Meeting Date 1973, vol. 3, 841-4. Editor(s): Daikos, George K. Hell. Soc. Chemother.: Athens, Greece.
STN File CA, Abstract 79:74187; Zidarova et al., "Certain derivatives of 3-aminopyrazole4-carboxylic acid as potential antimetabolites of 4(5)-aminoimidazole-5(4)-carboxamide in microorganisms," Doklady Bolgarskoi Akademii Nauk (1973), 26(3), 419-22.
STN File CA, Abstract 97:182276; Kocevar et al., "Neighboring group participation in formation of condensed azines. Formation of pyrazolo[3,4-b]pyrazines, isoxazolo[4,5-b]pyrazines and isothiazolo[5,4-b]pyridine. Heterocycles. CCX," Monatshefte fuer Chemie (1982), 113(6-7), 731-44.
STN File CA, Abstract 96:162655; Kocevar et al., "New synthetic approach for pyrazolo[3,4-b] pyrazines and isoxazolo[4,5-b] pyrazines," Heterocycles (1982), 19(2), 339-42.
STN File CA, Abstract 94:121470; Kocevar et al., "Some new synthetic approaches for the preparation of pteridine 3-oxides and pteridines," Heterocycles (1981), 15(1), 293-6.
STN File CA, Abstract 98:191493; Robev et al., " Pharmacological study of newly synthesized 2-phenyl-4-anilinopyrimidine-5-amidoxime," Doklady Bolgarskoi Akademii Nauk (1982), 35(10), 1451-4.
STN File CA, Abstract 142:197902; Sako, "Product class 19: pyridopyrimidines," Science of Synthesis (2004), 16, 1155-1267.
STN File CA, Abstract 127:331458; Sherif et al., "Syntheses with heterocyclic β-enamino nitriles. An expeditious synthetic approach to polyfunctionally substituted 5-phenyl-sulfonylthiophenes and their fused derivatives," Monatshefte fuer Chemie (1997), 128(6/7), 687-696.
Takikawa et al., "Mechanism of Interferon-γ Action," J. Biol. Chem. 263(4):2041-8 (1988).

(56) References Cited

OTHER PUBLICATIONS

Tan, et al., "Manipulation of indoleamine 2,3 dioxygenase; a novel therapeutic target for treatment of diseases", Expert Opin. Ther. Targets, 13:987-1012 (2009).

Taylor, et al., 1991, FASEB J., 5: 2516-22).

Terness, P et al., "Inhibition of Allogenieic T cell Proliferation by Indoleamine 3,3-Dioxygenase-expressing Dendritic Cells: Mediation of Suppression by Tryptophan Metabolites", J.Exp. med., 196,(4),447-457, 2002.

Tselinskii et al., "Synthesis and reactivity of carbohydroximoyl azides: II. 4-substituted 1,2,5-oxadiazole-3-carbohydroximoylazides and 1-hydroxy-5-(4-R-1,2,5-oxadiazol-3-yl)tetrazoles", Russian Journal of Organic Chemistry (Translation of Zhurnal Organicheskoi Khimii) (2001), 37(11), 1638-1642, and abstract.

Tselinskii et al., "Synthesis and reactivity of carbohydroximoyl azides: II. 4-substituted 1-2-5-oxadiazole-3-carbohydroximoylazides and 1-hydroxy-5-(4-R-1,2,5-oxadiazol-3-yl)tetrazoles", Russian Journal of Organic Chemistry (Translation of Zhurnal Organicheskoi Khimii) (2001), 37(11), 1638-1642.

Uyttenhove et al., 2003, Nature Med., 9: 1269-74.

Uyttenhove, C., Pilotte, L., et al. Evidence for a tumoral immune resistance mechanism based on tryptophan degradation by indoleamine 2,3-dioxygenase. Nat. Med. 9:1269-1274, 2003.

Von Heinrich Wieland et al, "Zur Konstitution der polymeren Knallsauren. Pericyanilsaure, Epicyanilsaure and Metacyanilsaure", Eingelaufen am 25 pp. 54-79 (1929).

Von Heinrich Wieland et al., "Zur Konstitution der polymeren Knallsauren. X", Aus dem Chem. Laboratorium der Bayr. Akademie der Wissenschaften zu Munchen, Eingelaufen am 23, pp. 43-53 (1929).

Wang et al., "Furazan-functionalized tetrazolate-based salts: a new family of insensitive energetic materials", Chemistry—A European Journal, 2009, 15(11), 2625-2634, and abstract.

Wang et al., "Furazan-functionalized tetrazolate-based salts: a new family of insensitive energetic materials", Chemistry—A European Journal, 2009, 15(11), 2625-2634.

Wang et al.,, "Crystal structure of 3-amino-4-acylaminoximinofurazan", Chinese Journal of Energetic Materials, translation of *Hanneng Cailiao*, 14(6), 441-445 (2006) with abstract.

Wang et al.,, "Synthesis and crystal structure of 3,6-bis(3'-aminofurazan-4-yl)-1,4-dioxa-2,5-diazacyclohexane-2,5-diene", *Huaxue Yanjiu Yu Yingyong* (2006), 18(12), 1398-1402 (with abstract).

Wang et al., "Synthesis of 3-amino-4-aminoximidofurazan and its crystal structure", *Hecheng Huaxue*, (2006), 14(3), 234-239 (with abstract).

WebMD entry for Parkinson's Disease Prevention, obtained from http://www.webmd.com/parkinsons-disease/guide/parkinsonsdisease-prevention on Jul. 19th, 2012 (2 pages).

Wichers and Maes, 2004, J. Psychiatry Neurosci., 29: 11-17.

Wikipedia, "indoleamine 2,3-dioxygenase"; downloaded on Jan. 16, 2009 http://en.wikipedia.org/wiki/Indoleamine_2,3-dioxygenase (3 pages).

Wiley-VCH Verlag GmbH & Co. KGaA, Weinheim, "Organic Synthesis: General Remarks", pp. 1-16 (2005).

Wirleitner, et al., 2003, Curr. Med. Chem., 10: 1581-91.

Yarovenko et al., "A new method for the synthesis of nitriles enriched with 15N isotope", Russian Chemical Bulletin, vol. 43 (3) pp. 402-4 (1994) English translation of Izvestiya Akademii Nauk, Seriya Khimicheskaya, (1994), (3), 444-6 and abstract.

Yarovenko et al., "New synthesis of nitriles enriched with 15N isotope", *Izvestiya Akademii Nauk, Seriya Khimicheskaya*, (1994) (3) pp. 444-6, and abstract.

Yarovenko et al., "New syntheses of 3-substituted 5-guanidino-1,2,4-oxadiazoles", *Izvestiya Akademii Nauk, Seriya Khimicheskaya*, (1994), (1), 118-21, and abstract.

Yarovenko et al., "New preparation of 5-amino derivatives of 1,2,4-oxadiazole", Izvestiya Akademii Nauk SSSR, Seriya Khimicheskaya, (1991), (9), 2166-7, and abstract.

Yarovenko et al., "New preparation of 5-amino derivatives of 1,2,4-oxadiazole", Izvestiya Akademii Nauk SSSR, Seriya Khimicheskaya, (1991), (9), 2166-7.

Yarovenko et al., *Tetrahedron*, 1990, 46(11), pp. 3941-3952.

Youngdale, Gilbert A. et al., "Synthesis and antifertility activity of 5-(phenoxymethyl)-2-oxazolidinethiones", Journal of Medicinal Chemistry, 9(1), 155-7, 1966.

Yue et al., "Discovery of Potent Competitive Inhibitors of Indoleamine 2,3-Dioxygenase with in Vivo Pharmacodynamic Activity and Efficacy in a Mouse Melanoma Model," J. Med. Chem. XXXX, received Apr. 23, 2009 (4 pages).

Zhou, et al., "Synthesis and properties of [3,3':4',3"-ter-1,2,5-oxadiazole]-4,4"-diamine, 2'-oxide", Huozhayao Xuebao, 30(1), 54-56 (2007) and abstract.

Eurasian Patent Office, Application No. 200702455, Office Action, Oct. 9, 2009 (English translation) (6 pages).

Examination Report, Australian Patent Office, Application No. SG 200717302-4, mailed Sep. 23, 2009 by Officer Wright, (9 pages).

Examination Report—EP Patent Application No. 06759438.2 dated Jul. 29, 2010 (4 pages).

Extended European Search Report from corresponding EP Application No. 06759438.2, dated Jun. 5, 2009.

Final Examination Report, Singapore Patent Application No. 2007/17302-4 dated Sep. 23, 2009 (11 pages).

Georgian Patent Office, Application No. AP2006010418, Office Action, Jul. 14, 2009 (2 pages).

Intellectual Property Office of New Zealand, Application No. 562919, Examination Report, Sep. 17, 2009 (4 pages).

International Search Report for PCT/US06/17983, dated Aug. 2, 2006.

International Search Report and Written Opinion for PCT/US2007/078745 dated Jun. 16, 2008.

International Search Report and Written Opinion for PCT/US2007/078759 dated Jun. 16, 2008.

International Search Report and Written Opinion for PCT/US2007/078758 dated May 9, 2008.

International Search Report and Written Opinion for PCT/US2007/003364 dated Sep. 12, 2007.

International Search Report and Written Opinion for PCT/US2006/048290 dated Sep. 17, 2007.

International Search Report and Written Opinion PCT/US2009/049794 dated Apr. 26, 2010 (27 pages).

International Preliminary Report on Patentability for PCT/US06/17983 dated Nov. 13, 2007.

International Preliminary Report on Patentability for PCT/US2006/048290 dated Jun. 24, 2008.

International Preliminary Report on Patentability for PCT/US2007/078758 dated Mar. 24, 2009 (8 pages).

International Preliminary Report on Patentability for PCT/US2007/003364 dated Aug. 12, 2008 (9 pages).

International Preliminary Report on Patentability for PCT/US2007/078745 dated Mar. 24, 2009 (13 pages).

International Preliminary Report on Patentability for PCT/US2007/078759 dated Mar. 24, 2009 (15 pages).

International Preliminary Report on Patentability PCT/US2009/049794 issued Jan. 11, 2011 (12 pages).

Malaysian Patent Office, Application No. PI20062122, Office Action, Oct. 18, 2010 (2 pages).

Notification on the Result of Substantive Examination, National Office of Intellectual Property, No. 60636/SHTT-SC2, Vietnamese Application No. 1-2007-02634, dated Oct. 7, 2009 (3 pages).

Office Action (final) for U.S. Appl. No. 11/641,284 dated Oct. 21, 2009.

Office Action (nonfinal) for U.S. Appl. No. 12/498,782 mailed Jan. 14, 2011 (14 pages).

Office Action (nonfinal) for U.S. Appl. No. 11/641,284 mailed Jan. 29, 2009 (13 pages).

Office Action (nonfinal) for U.S. Appl. No. 11/641,284 mailed May 7, 2010 (9 pages).

Office Action (final) for U.S. Appl. No. 11/641,284 mailed Dec. 15, 2010 (8 pages).

Office Action (nonfinal) for U.S. Appl. No. 11/856,967 mailed Jan. 19, 2010 (5 pages).

(56) References Cited

OTHER PUBLICATIONS

Office Action (final) for U.S. Appl. No. 11/856,967 mailed Sep. 24, 2010 (11 pages).
Office Action (nonfinal) for U.S. Appl. No. 11/856,982 mailed Jan. 29, 2010 (10 pages).
Office Action (final) for U.S. Appl. No. 11/856,982 mailed Sep. 17, 2010 (6 pages).
Office Action dated Apr. 22, 2007 for Chilean Application No. 1096-2006 (2 pages).
Office Action (non-final) mailed Aug. 3, 2009, U.S. Appl. No. 11/430,441 (15 pages).
Office Action (final) mailed Jun. 7, 2010, U.S. Appl. No. 11/430,441 (20 pages).
Office Action—JP Patent Appl. No. 2008-547407 mailed Aug. 21, 2012 (7 pages).
The Eurasian Search Report for Application No. 200702455 dated Apr. 28, 2008.
Search Report and Written Opinion from Singapore Application No. 200717302-4, dated Feb. 6, 2009.
State Intellectual Property Office—PR China, Application No. 200680024326-1, Office Action, Jan. 19, 2011 (10 pages).
State Intellectual Property Office—PR China, Application No. 200680024326-1, Office Action, Oct. 23, 2009 (6 pages).
Office Action dated Nov. 8, 2011 for Japanese Patent Appln. No. 2008-511287 with English translation (5 pgs.).
Keith Guillory, "Generation of Polymorphs, Hydrates, Solvates, and Amorphous Solids", in Polymorphism in Pharmaceutical Solids, 183-226 (Harry G. Britain, ed., 1999).
Griesser, "The Importance of Solvates" in Polymorphism in the Pharmaceutical Industry, 211-233 (Rolf Hilfiker, ed., 2006).
Storey, et al., "Automation of Solid Form Screening Procedures in the Pharmaceutical Industry—How to Avoid the Bottlenecks", Crystallography Reviews, 10(1):45-46 (2004).
Morissette, et al., "High-Throughput Crystallization: Polymorphs, Salts, Co-Crystals and Solvates", Adv. Drug Delivery Rev., 56:275-300 (2004).
Vippagunta, et al., "Crystalline Forms", Adv. Drug Delivery Rev., 48:3-26 (2001).
Office Action (final) U.S. Appl. No. 12/498,782 mailed May 31, 2011 (35 pages).
Search Report, Taiwan Application No. 117382 dated Mar. 7, 2012 (English translation 1 page—Taiwan Search Report 4 pages).
Office Action (non-final), Mexico Application No. MX/1/2007/013977 as communicated to undersigned representative on Nov. 18, 2011 (2 pages).
'ClinicalTrials.gov' [online] "A Phase 2 Study of the IDO Inhibitor INCB024360 Versus Tamoxifen for Subjects with Biochemical-recurrent-only EOC, PPC or PTC Following Complete Remission with First-line Chemotherapy," [2013], [retrieved on Jul. 25, 2013] URL:<http://clinicaltrials.gov/ct2/show/NCT01685255?-term=incyte&rank=4> 4 pages.
'ClinicalTrials.gov' [online] "A Phase 1/2 Randomized, Blinded, Placebo Controlled Study of Ipilimumab in Combination with INCB024360 or Placebo in Subjects with Unresectable or Metastatic Melanoma," [2012] [retrieved on Jul. 25, 2013] URL: http://clinicaltrials.gov/et2/show/NCT01604889?term=incyte&rank=8> 3 pages.
Expert Scientific Group on Phase One Clinical Trials Final Report, Nov. 30, 2006, pp. C1, C35-C38.
Feder-Mengus, et al., "High expression of indoleamine 2,3-dioxygenase gene in prostate cancer", European J. Cancer, 44 (2008) pp. 2266-2275.
Gasparri, et al., "Critical role of indoleamine 2,3-dioxygenase in tumor resistance to repeated treatments with targeted IFNγ", Mol. Cancer Ther., 7(12) pp. 3859-3866 (2008).
Gura, "Cancer Models: Systems for Identifying New Drugs are Often Faulty," Science, vol. 278, No. 5340, pp. 1041-1042 (1997).
Hoshi et al., "Indoleamine 2,3-dioxygenase is highly expressed in human adult T-cell leukemia/lymphoma and chemotherapy changes tryptophan catabolism in serum and reduced activity", Leukemia Research, 33 pp. 29-45 (2009).
Kamb, "What wrong with our cancer models?" Nature Reviews Drug Discovery 4, pp. 161-165 (2005).
Karanikas et al., "Indoleamine 2,3-Dioxygenase (IDO) Expression in Lung Cancer", *Cancer Biology & Therapy*, vol. 6, Issue 8 pp. 1258-1262, (2007).
Kola and Landis, "Can the pharmaceutical industry reduce attrition rates?" Nature Reviews Drug Discovery 3, pp. 711-715 (2004).
Leaf, Clifton, "Why are we losing the war on cancer (and how to win it)," Health Administrator vol. XVII, No. 1:172-183 (2005).
Liu et al., "Selective inhibition of IDO1 effectively regulates mediators of antitumor immunity," Blood, 2010, 115:3520-3530.
Mellman et al., "Cancer immunotherapy comes of age," Nature, 2011, 480:480-489.
Neidle, Stephen, "Cancer Drug Design and Discovery," (Elsevier/Academic Press, 2008) pp. 427-431.
Newton et al., "Pharmacodynamic assessment of INCB024360, an inhibitor of indoleamine 2,3-dioxygenase 1 (IDO1) in advanced cancer patients," *ASCO Annual Meeting*, 2012, 16 pages.
Nonaka et al., "Indoleamine 2,3-dioxygenase promotes peritoneal dissemination of ovarian cancer through inhibition of natural killercell function and angiogenesis promotion," *Int. J Oncology*, 2011, 38:113-120.
Riesenberg et al., "Expression of Indoleamine 2,3-Dioxygenase inTumor Endothelial Cells Correlateswith Long-term Survival of Patients with Renal Cell Carcinoma", Clin. Cancer Res., vol. 13 Issue 23 pp. 2993-3002 (2007).
Roberts Jr. et al., "Trends in the Risks and Benefits to Patient with Cancer Participating in Phase 1 Clinical Trials," JAMA 292(17):2130-2140 (2004).
Soliman et al., "A phase I study of 1-methyl-D-tryptophan in patients with advanced malignancies," J Clin Oncol., 2012, suppl; abstr 2501.
Speeckaert et al., "Indoleamine 2,3-dioxygenase, a new prognostic marker in sentinel lymph nodes of melanoma patients", European Journal of Cancer, (2012), 48, 2004-2011.
Tang, et al., Zhongguo Shi Yan Xue Ye Xue Za Zhi. 14(3):539-42 (2006) (Abstract).
Taneja et al., "MMTV mouse models and the diagnostic values of MMTV-like sequences in human breast cancer," *Expert Rev Mol Diagn.*, 2009, 9(5):423-440.
Trinh and Hwu, "Ipilimumab in the treatment of melanoma," Expert. Opin, Biol. Ther., 2012, 12(6):773-782.
Witkiewicz et al., "Expression of Indoleamine 2,3-Dioxygenase in Metastatic Pancreatic Ductal Adenocarcinoma Recruits Regulatory T Cells to Avoid Immune Detection", *J. Am. Coll. Surg.*, vol. 206, No. 5, pp. 849-856 (May 2008).
Witkiewicz et al., "IDO2 Genotyping and Expression in Pancreatic Cancer", *J. Am. Coll. Surg.*, vol. 208, No. 5 pp. 781-789 (May 2008).
Wong et al., "Programmed death-1 blockage enhances expansion and functional capacity of human melanoma antigen-specific CTLs," International Immunology, 2007, 19:1223-1234.
Office Action (nonfinal) for U.S. Appl. No. 13/294,711 mailed Jan. 30, 2013 (110 pages).
Office Action (nonfinal) for U.S. Appl. No. 13/294,711 mailed Jul. 25, 2012, (26 pages).
Office Action—JP Patent Appl. No. 2009-529341 mailed Oct. 16, 2012 (3 pages).
Office Action—JP Patent Appl. No. 2009-529343 mailed Oct. 16, 2012 (4 pages).
Extended European Search Report in EP Application No. 12178315.3, dated Jan. 18, 2013, 8 pages.
Costa Rican Office Action in CR Application No. 9485, Feb. 11, 2013, 14 pages (with English translation).
Robinson et al., "The Role of IFN-γ and TNF-α-Responsive Regulatory Elements in the Synergistic Induction of Indoleamine Dioxygenase," J Interferon Cytokin Res., 2005, 25(1):20-30.
Office Action in Chinese Application No. 201210562826.8, mailed Mar. 18, 2014, 12 pages.

MODULATORS OF INDOLEAMINE 2,3-DIOXYGENASE AND METHODS OF USING THE SAME

CROSS REFERENCE TO RELATED APPLICATIONS

This application is a continuation of U.S. Ser. No. 13/220,406 filed on Aug. 29, 2011, which is a divisional of U.S. Ser. No. 11/430,441, filed May 9, 2006, which claims the benefit of U.S. Provisional Application No. 60/679,507, filed May 10, 2005, each of which is incorporated herein by reference in its entirety.

FIELD OF THE INVENTION

The present invention is directed to modulators of indoleamine 2,3-dioxygenase (IDO), as well as compositions and pharmaceutical methods thereof.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, a depletion of Trp resulting from IDO activity is a prominent gamma interferon (IFN-γ) inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al., 1999, Adv. Exp. Med. Biol., 467: 517-24; Taylor, et al., 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with inter-leukin-2 (IL2) was believed to result from IDO released by the tumor cells in response to IFNG secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Recently, an immunoregulatory role of Trp depletion has received much attention. Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106:2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8). In states of persistant immune activation, availability of free serum Trp is diminished and, as a consequence of reduced serotonin production, serotonergic functions may also be affected (Wirleitner, et al., 2003, Curr. Med. Chem., 10: 1581-91).

Interestingly, administration of interferon-α has been observed to induce neuropsychiatric side effects, such as depressive symptoms and changes in cognitive function. Direct influence on serotonergic neurotransmission may contribute to these side effects. In addition, because IDO activation leads to reduced levels of tryptophan, the precursor of serotonin (5-HT), IDO may play a role in these neuropsychiatric side effects by reducing central 5-HT synthesis. Furthermore, kynurenine metabolites such as 3-hydroxy-kynurenine (3-OH-KYN) and quinolinic acid (QUIN) have toxic effects on brain function. 3-OH-KYN is able to produce oxidative stress by increasing the production of reactive oxygen species (ROS), and QUIN may produce overstimulation of hippocampal N-methyl-D-aspartate (NMDA) receptors, which leads to apoptosis and hippocampal atrophy. Both ROS overproduction and hippocampal atrophy caused by NMDA overstimulation have been associated with depression (Wichers and Maes, 2004, J. Psychiatry Neurosci., 29: 11-17). Thus, IDO activity may play a role in depression.

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3 benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2, 3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

The present invention provides, inter alia, compounds of Formula I:

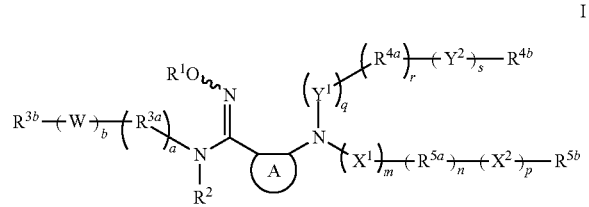

or pharmaceutically acceptable salt forms or prodrugs thereof.

The present invention further provides compositions comprising a compound of Formula I and a pharmaceutically acceptable carrier.

The present invention further provides methods of modulating enzyme activity of IDO comprising contacting a compound of Formula I with the IDO.

The present invention further provides methods of treating IDO-associated diseases, including, for example, cancer, viral infection, depression, a neurodegenerative disorder, trauma, age-related cataracts, organ transplant rejection, or an autoimmune disease, comprising administering to a patient a therapeutically effective amount of a compound of Formula I.

The present invention further provides methods of altering extracellular tryptophan levels in a mammal comprising administering to the mammal an effective amount of a compound of Formula I.

The present invention further provides methods of inhibiting immunosuppression, such as IDO-mediated immunosupresion, in a patient comprising administering to the patient an effective amount of a compound of Formula I.

DETAILED DESCRIPTION

The present invention provides, inter alia, compounds of Formula I:

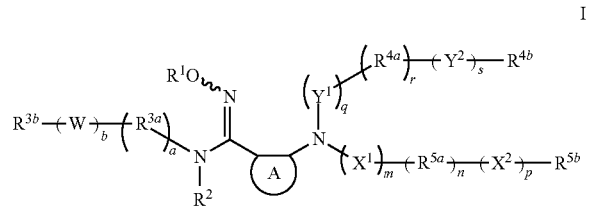

or pharmaceutically acceptable salt forms or prodrugs thereof, wherein:

Ring A is carbocyclyl or heterocyclyl optionally substituted by 1, 2, 3, 4 or 5 $R^6$;

W, $X^1$, $X^2$, $Y^1$, and $Y^2$ are independently selected from $(CR^aR^b)_t$, $(CR^aR^b)_u O(CR^aR^b)_v$, $(CR^aR^b)_u C(O)(CR^aR^b)_v$, $(CR^aR^b)_u C(O)NR^c(CR^aR^b)_v$, $(CR^aR^b)_u NR^cC(O)(CR^aR^b)_v$, $(CR^aR^b)_u C(O)O(CR^aR^b)_v$, $(CR^aR^b)_u OC(O)(CR^aR^b)_v$, $(CR^aR^b)_u OC(O)NR^c(CR^aR^b)_v$, $(CR^aR^b)_u C(S)(CR^aR^b)_u$, $(CR^aR^b)_u C(S)NR^c(CR^aR^b)_v$, $(CR^aR^b)_u NR^cC(S)(CR^aR^b)_v$, $(CR^aR^b)_u S(O)(CR^aR^b)_v$, $(CR^aR^b)_u S(O)NR^c(CR^aR^b)_v$, $(CR^aR^b)_u NR^cS(O)(CR^aR^b)_v$, $(CR^aR^b)_u S(O)_2(CR^aR^b)_v$, $(CR^aR^b)_u S(O)_2 NR^c(CR^aR^b)_v$, $(CR^aR^b)_u NR^c(CR^aR^b)_v$, and $(CR^aR^b)_u C(=NR^d)NR^c(CR^aR^b)_v$;

$R^1$ is H, $C(O)R^7$, $C(O)NR^{8a}R^{8b}$, $C(O)OR^8$, $C_{1-8}$ alkyl, $C_{2-8}$ alkenyl, $C_{2-8}$ alkynyl, aryl, cycloalkyl, heteroaryl, heterocycloalkyl, arylalkyl, cycloalkylalkyl, heteroarylalkyl, or heterocycloalkylalkyl;

$R^2$ is H, $C_{1-6}$ alkyl, or $C_{3-7}$ cycloalkyl;

$R^{3a}$, $R^{4a}$, and $R^{5a}$ are independently selected from $C_{1-8}$ alkyl, $C_{2-8}$ alkenyl, $C_{2-8}$ alkynyl, aryl, cycloalkyl, heteroaryl, and heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{3b}$, $R^{4b}$, and $R^{5b}$ are independently selected from H, $C_{1-8}$ alkyl, $C_{2-8}$ alkenyl, $C_{2-8}$ alkynyl, aryl, cycloalkyl, heteroaryl, and heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

or $R^2$ and —$(R^{3a})_a$—$(W)_b$—$R^{3b}$ together with the N atom to which they are attached form a 4- to 20-membered heterocycloalkyl group optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^3$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, or $S(O)_2NR^{g1}R^{h1}$;

or —$(Y^1)_q$—$(R^{4a})_r$—$(Y^2)_s$—$R^{4b}$ and —$(X^1)_m$—$(R^{5a})_n$—$(X^2)_p$—$R^{5b}$ together with the N atom to which they are attached form a 4- to 20-membered heterocycloalkyl group optionally substituted by 1, 2, 3, 4 or 5 substituents selected from halo, $C_{1-6}$ alkyl, $C_{2-6}$ alkenyl, $C_{2-6}$ alkynyl, $C_{1-4}$ haloalkyl, $Cy^4$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^6$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e2}$, $SR^{e2}$, $C(O)R^{f2}$, $C(O)NR^{g2}R^{h2}$, $C(O)OR^{e2}$, $OC(O)R^{f2}$, $OC(O)NR^{g2}R^{h2}$, $NR^{g2}R^{h2}$, $NR^{g2}C(O)R^{f2}$, $NR^{g2}C(O)OR^{e2}$, $C(=NR^i)NR^{g1}R^{h1}$, $NR^{g1}C(=NR^i)NR^{g1}R^{h1}$, $P(R^{f2})_2$, $P(OR^{e1})_2$, $P(O)R^{e2}R^{f2}$, $P(O)OR^{e2}OR^{f2}$, $S(O)R^{f2}$, $S(O)NR^{g2}R^{h2}$, $S(O)_2R^{f2}$, or $S(O)_2NR^{g2}R^{h2}$;

$R^7$ and $R^8$ are independently selected from H, $C_{1-8}$ alkyl, aryl, heteroaryl, cycloalkyl, heterocycloalkyl, arylalkyl, heteroarylalkyl, cycloalkylalkyl, and heterocycloalkylalkyl, each optionally substituted by one or more substituents independently selected from halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, and $C_{2-6}$ alkynyl;

$R^{8a}$ and $R^{8b}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

$Cy^1$, $Cy^2$, $Cy^3$, and $Cy^4$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{e3}$, $SR^{e3}$, $C(O)R^{f3}$, $C(O)NR^{g3}R^{h3}$, $C(O)OR^{e3}$, $OC(O)R^{f3}$, $OC(O)NR^{g3}R^{h3}$, $NR^{g3}R^{h3}$, $NR^{g3}C(O)R^{h3}$, $NR^{g3}C(O)OR^{e3}$, $C(=NR^i)NR^{g1}R^{h1}$, $NR^{g1}C(=NR^i)NR^{g1}R^{h1}$, $P(R^{f3})_2$, $P(OR^{e3})_2$, $P(O)R^{e3}R^{f3}$, $P(O)OR^{e3}OR^{f3}$, $S(O)R^{f3}$, $S(O)NR^{g3}R^{h3}$, $S(O)_2R^{f3}$, and $S(O)_2NR^{g3}R^{h3}$;

$R^a$ and $R^b$ are independently selected from H, halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e4}$, $SR^{e4}$, $C(O)R^{f4}$, $C(O)NR^{g4}R^{h4}$, $C(O)OR^{e4}$, $OC(O)R^{f4}$, $OC(O)NR^{g4}R^{h4}$, $NR^{g4}R^{h4}$, $NR^{g4}C(O)R^{h4}$, $NR^{g4}C(O)OR^{e4}$, $C(=NR^i)NR^{g1}R^{h1}$, $NR^{g1}C(=NR^i)NR^{g1}R^{h1}$, $P(R^{f4})_2$, $P(OR^{e4})_2$, $P(O)R^{e4}R^{f4}$, $P(O)OR^{e4}OR^{f4}$, $S(O)R^{f4}$, $S(O)NR^{g4}R^{h4}$, $S(O)_2R^{f4}$, and $S(O)_2NR^{g4}R^{h4}$;

$R^c$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^d$ is H, $OR^{d1}$, CN or $NO_2$;

$R^{d1}$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{e1}$, $R^{e2}$, $R^{e3}$, and $R^{e4}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl and heterocycloalkylalkyl;

$R^{f1}$, $R^{f2}$, $R^{f3}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl and heterocycloalkyl;

$R^{g1}$, $R^{g2}$, $R^{g3}$, and $R^{g4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

$R^{h1}$, $R^{h2}$, $R^{h3}$, and $R^{h4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

or $R^{g1}$ and $R^{h1}$ together with the N atom to which they are attached form a 4-, 5-, 6- or 7-membered heterocycloalkyl group;

or $R^{g2}$ and $R^{h2}$ together with the N atom to which they are attached form a 4-, 5-, 6- or 7-membered heterocycloalkyl group;

or $R^{g3}$ and $R^{h3}$ together with the N atom to which they are attached form a 4-, 5-, 6- or 7-membered heterocycloalkyl group;

or $R^{g4}$ and $R^{h4}$ together with the N atom to which they are attached form a 4-, 5-, 6- or 7-membered heterocycloalkyl group;

$R^i$ is H, CN, or $NO_2$;

a is 0 or 1;
b is 0 or 1;
m is 0 or 1;
n is 0 or 1;
p is 0 or 1;
q is 0 or 1;
r is 0 or 1;
s is 0 or 1;

t is 1, 2, 3, 4, 5 or 6;
u is 0, 1, 2, 3, 4, 5 or 6; and
v is 0, 1, 2, 3, 4, 5 or 6.

In some embodiments, when Ring A is

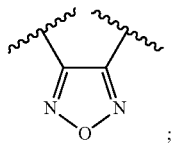 [SMILES: *c1nonc1*]

$R^2$ is H;
—$(Y^1)_q$—$(R^{4a})_r$—$(Y^2)_s$—$R^{4b}$ is H; and
—$(X^1)_m$—$(R^{5a})_n$—$(X^2)_p$—$R^{5b}$ is H;
then —$(R^{3a})_a$—(W)—$R^{3b}$ is other than:

i) phenyl, 4-iodophenyl, 4-chlorophenyl, 4-bromophenyl, 4-methylphenyl, 3-methylphenyl, 2-methylphenyl, 2,4-dimethylphenyl, 2,6-dimethylphenyl, 2,5-dimethylphenyl, 3,4-dimethylphenyl, 2-methoxyphenyl, or 2-dimethylamino-5-nitrophenyl;

ii) —$CH_2CH_2NR^xR^y$, wherein each $R^x$ and $R^y$ is, independently, H, ethyl, —C(O)-oxadiazole optionally substituted with amino, or phenyl optionally having at least one substituent which is nitro; or iii) $C_{1-3}$ alkyl, —C(O)—($C_{1-4}$ haloalkyl), naphthyl, or benzyl.

In some embodiments, when Ring A is phenyl having at least two substituents which are methyl;
—$(Y^1)_q$—$(R^{4a})_r$—$(Y^2)_s$—$R^{4b}$ is H; and
—$(X^1)_m$—$(R^{5a})_n$—$(X^2)_p$—$R^{5b}$ is H;
then —$(R^{3a})_a$—(W)—$R^{3b}$ is other than unsubstituted phenyl.

In some embodiments, when Ring A is phenyl having at least one substitutent which is nitro;
—$(Y^1)_q$—$(R^{4a})_r$—$(Y^2)_s$—$R^{4b}$ is H; and
—$(X^1)_m$—$(R^{5a})_n$—$(X^2)_p$—$R^{5b}$ is H;
then —$(R^{3a})_a$—(W)—$R^{3b}$ is other than pyrazolyl substituted by $C_{1-4}$ alkyl.

In some embodiments, when Ring A is

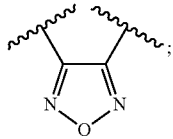 [SMILES: *c1nonc1*]

$R^2$ is H;
—$(Y^1)_q$—$(R^{4a})_r$—$(Y^2)_s$—$R^{4b}$ is H; and
—$(X^1)_m$—$(R^{5a})_n$—$(X^2)_p$—$R^{5b}$ is H;
then —$(R^{3a})_a$—(W)—$R^{3b}$ is other than:

i) phenyl optionally substituted by 1 or 2 substituents selected from halo, $C_{1-4}$ alkyl, and $C_{1-4}$ alkoxy;

ii) $CH_2CH_2NR^xR^y$, wherein each $R^x$ and $R^y$ is, independently, H, $C_{1-4}$ alkyl, —C(O)— heteroaryl optionally substituted with amino, or phenyl optionally substituted with 1 or 2 nitro or 1 or 2 halo; or iii) $C_{1-4}$ alkyl, —C(O)—($C_{1-4}$ haloalkyl), naphthyl, or benzyl.

In some embodiments, when r is 0, then the sum of q and s is 0 or 1.

In some embodiments, when n is 0, then the sum of m and p is 0 or 1.

In some embodiments, Ring A is heterocyclyl optionally substituted by 1, 2, 3, 4 or 5 $R^6$.

In some embodiments, Ring A is 5- or 6-membered heterocyclyl optionally substituted by 1, 2, 3, 4 or 5 $R^6$.

In some embodiments, Ring A is 5-membered heterocyclyl optionally substituted by 1, 2, 3, 4 or 5 $R^6$.

In some embodiments, Ring A is 5-membered heterocyclyl containing at least one ring-forming N atom and Ring A is optionally substituted by 1, 2, 3, 4 or 5 $R^6$.

In some embodiments, Ring A is 5-membered heterocyclyl containing at least one ring-forming O atom and Ring A is optionally substituted by 1, 2, 3, 4 or 5 $R^6$.

In some embodiments, Ring A is 5-membered heterocyclyl containing at least one ring-forming O atom and containing at least one ring-forming N atom, and Ring A is optionally substituted by 1, 2, 3, 4 or 5 $R^6$.

In some embodiments, Ring A is

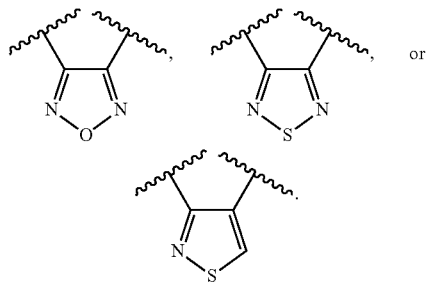

In some embodiments, Ring A is

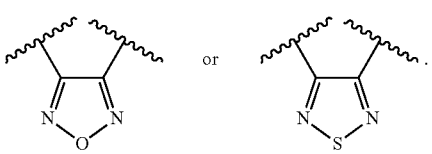 [SMILES: *c1nonc1* ; *c1nsnc1*]

In some embodiments, Ring A is

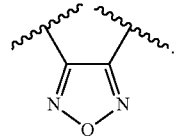 [SMILES: *c1nonc1*]

In some embodiments, $R^1$ is H, $C(O)R^7$, $C(O)OR^8$, $C_{1-8}$ alkyl, $C_{2-8}$ alkenyl, $C_{2-8}$ alkynyl, aryl, cycloalkyl, heteroaryl, heterocycloalkyl, arylalkyl, cycloalkylalkyl, heteroarylalkyl, or heterocycloalkylalkyl.

In some embodiments, $R^1$ is H, $C(O)R^7$, $C(O)NR^{8a}R^{8b}$, or $C(O)OR^8$.

In some embodiments, $R^1$ is H, $C(O)R^7$, or $C(O)OR^8$.

In some embodiments, $R^1$ is H.

In some embodiments, $R^2$ is H.

In some embodiments, $R^{3a}$ is aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)$ $NR^{g1}R^{h1}$, $NR^{g1}C(=NR^i)NR^{g1}R^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{3a}$ is aryl or heteroaryl each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{3a}$ is phenyl optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{3b}$ is aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{3b}$ is aryl or heteroaryl each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{3b}$ is phenyl optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, W is $(CR^aR^b)_t$, $(CR^aR^b)_uO(CR^aR^b)_v$, $(CR^aR^b)_uC(O)(CR^aR^b)_v$, $(CR^aR^b)_uC(O)NR^c(CR^aR^b)_v$, or $(CR^aR^b)_uC(O)O(CR^aR^b)_v$.

In some embodiments, W is $(CR^aR^b)_t$ or $(CR^aR^b)_uO(CR^aR^b)_v$.

In some embodiments, $Y^1$ is $(CR^aR^b)_t$, $(CR^aR^b)_uC(O)(CR^aR^b)_v$, $(CR^aR^b)_uC(O)NR^c(CR^aR^b)_v$, or $(CR^aR^b)_uC(O)O(CR^aR^b)_v$.

In some embodiments, $Y^1$ is $(CR^aR^b)_t$ or $(CR^aR^b)_uC(O)(CR^aR^b)_v$.

In some embodiments, $X^1$ is $(CR^aR^b)_t$, $(CR^aR^b)_uC(O)(CR^aR^b)_v$, $(CR^aR^b)_uC(O)NR^c(CR^aR^b)_v$, or $(CR^aR^b)_uC(O)O(CR^aR^b)_v$.

In some embodiments, $X^1$ is $(CR^aR^b)_t$ or $(CR^aR^b)_uC(O)(CR^aR^b)_v$.

In some embodiments, $R^{4a}$ is $C_{1-8}$ alkyl, $C_{2-8}$ alkenyl, or $C_{2-8}$ alkynyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}R^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{4a}$ is aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{5a}$ is $C_{1-8}$ alkyl, $C_{2-8}$ alkenyl, or $C_{2-8}$ alkynyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{5a}$ is aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{4b}$ is H, $C_{1-8}$ alkyl, $C_{2-8}$ alkenyl, or $C_{2-8}$ alkynyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)NR^{g1}R^{h1}$, $C(=NR^i)$ $NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{4b}$ is aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{4b}$ is H.

In some embodiments, $R^{5b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{5b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}$, $NR^{g1}C(O)NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{5b}$ is H.

In some embodiments, $R^{4b}$ is H and $R^{5b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}NR^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $R^{4b}$ is H and $R^{5b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{hi}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

In some embodiments, $-(Y^1)_q-(R^{4a})_r-(Y^2)_s-R^{4b}$ is H and $-(X^1)_m-(R^{5a})_n-(X^2)_p-R^{5b}$ is H.

In some embodiments, a and b are both 0.
In some embodiments, r and s are both 0.
In some embodiments, q, r, and s are all 0.
In some embodiments, n and p are both 0.
In some embodiments, a is 0.
In some embodiments, a is 1.
In some embodiments, b is 0.
In some embodiments, b is 1.

In some embodiments, q is 0.
In some embodiments, q is 1.
In some embodiments, r is 0.
In some embodiments, r is 1.
In some embodiments, s is 0.
In some embodiments, s is 1.
In some embodiments, m is 0.
In some embodiments, m is 1.
In some embodiments, n is 0.
In some embodiments, n is 1.
In some embodiments, p is 0.
In some embodiments, p is 1.
In some embodiments, t is 1.
In some embodiments, t is 2.
In some embodiments, t is 3.
In some embodiments, t is 4.
In some embodiments, u is 0.
In some embodiments, u is 1.
In some embodiments, u is 2.
In some embodiments, u is 3.
In some embodiments, v is 0.
In some embodiments, v is 1.
In some embodiments, v is 2.
In some embodiments, v is 3.

In some embodiments, the compounds of the invention have Formula II:

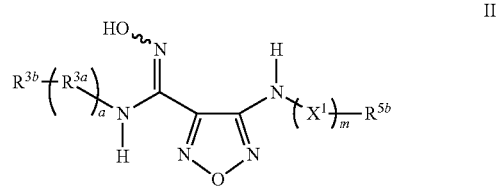

wherein:

$X^1$ is $(CR^aR^b)_t$ or $(CR^aR^b)_uC(O)(CR^aR^b)_v$;

$R^{3a}$ is $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_{2R}^{f1}$, and $S(O)_2NR^{g1}R^{h1}$;

$R^{3b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{5b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

Cy$^1$ and Cy$^2$ are independently selected from aryl, heteroaryl, cycloalkyl, or heterocycloalkyl, each optionally substituted by 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, CN, NO$_2$, OR$^{e3}$, SR$^{e3}$, C(O)R$^{e3}$, C(O)NR$^{g3}$R$^{h3}$, C(O)OR$^{e3}$, OC(O)R$^{e3}$, OC(O)NR$^{g3}$R$^{h3}$, NR$^{g3}$R$^{h3}$, NR$^{g3}$C(O)R$^{h3}$, NR$^{g3}$C(O)OR$^{e3}$, P(R$^{f3}$)$_2$, P(OR$^{e3}$)$_2$, P(O)R$^{e3}$R$^{f3}$, P(O)OR$^{e3}$OR$^{f3}$, S(O)R$^{f3}$, S(O)NR$^{g3}$R$^{h3}$, S(O)$_2$R$^{f3}$, and S(O)$_2$NR$^{g3}$R$^{h3}$;

R$^a$ and R$^b$ are independently selected from H, halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{e4}$, SR$^{e4}$, C(O)R$^{e4}$, C(O)NR$^{g4}$R$^{h4}$, C(O)OR$^{e4}$, OC(O)R$^{f4}$, OC(O)NR$^{g4}$R$^{h4}$, NR$^{g4}$R$^{h4}$, NR$^{g4}$C(O)R$^{h4}$, NR$^{g4}$C(O)OR$^{e4}$, P(R$^{e4}$)$_2$, P(OR$^{e4}$)$_2$, P(O)R$^{e4}$R$^{e4}$, P(O)OR$^{e4}$OR$^{e4}$, S(O)R$^{e4}$, S(O)NR$^{g4}$R$^{h4}$, S(O)$_2$R$^{f4}$, and S(O)$_2$NR$^{g4}$R$^{h4}$;

R$^{e1}$, R$^{e3}$, and R$^{e4}$ are independently selected from H, C$_{1-6}$ alkyl, C$_{1-6}$ haloalkyl, C$_{2-6}$ alkenyl, (C$_{1-6}$ alkoxy)-C$_{1-6}$ alkyl, C$_{2-6}$ alkynyl, aryl, cycloalkyl, heteroaryl, heterocycloalkyl, arylalkyl, cycloalkylalkyl, heteroarylalkyl and heterocycloalkylalkyl;

R$^{f1}$, R$^{f3}$, and R$^{f4}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl and heterocycloalkyl;

R$^{g1}$, R$^{g3}$, and R$^{g4}$ are independently selected from H, C$_{1-6}$ alkyl, C$_{1-6}$ haloalkyl, C$_{2-6}$ alkenyl, C$_{2-6}$ alkynyl, aryl, cycloalkyl, arylalkyl, and cycloalkylalkyl;

R$^{h1}$, R$^{h3}$, and R$^{h4}$ are independently selected from H, C$_{1-6}$ alkyl, C$_{1-6}$ haloalkyl, C$_{2-6}$ alkenyl, C$_{2-6}$ alkynyl, aryl, cycloalkyl, arylalkyl, and cycloalkylalkyl;

or R$^{g1}$ and R$^{h1}$ together with the N atom to which they are attached form a 4-, 5-, 6- or 7-membered heterocycloalkyl group;

or R$^{g3}$ and R$^{h3}$ together with the N atom to which they are attached form a 4-, 5-, 6- or 7-membered heterocycloalkyl group;

or R$^{g4}$ and R$^{h4}$ together with the N atom to which they are attached form a 4-, 5-, 6- or 7-membered heterocycloalkyl group;

a is 0 or 1;
m is 0 or 1;
t is 1, 2, 3, 4, 5 or 6;
u is 0, 1, 2, 3, 4, 5 or 6; and
v is 0, 1, 2, 3, 4, 5 or 6.

In some embodiments of Formula II, when —(X$^1$)$_m$—R$^{5h}$ is H; then —(R$^{3a}$)$_a$—R$^{3b}$ is other than:
i) phenyl, 4-iodophenyl, 4-chlorophenyl, 4-bromophenyl, 4-methylphenyl, 3-methylphenyl, 2-methylphenyl, 2,4-dimethylphenyl, 2,6-dimethylphenyl, 2,5-dimethylphenyl, 3,4-dimethylphenyl, 2-methoxyphenyl, or 2-dimethylamino-5-nitrophenyl;
ii) —CH$_2$CH$_2$NR$^x$R$^y$, wherein each R$^x$ and R$^y$ is, independently, H, ethyl, —C(O)— oxadiazole optionally substituted with amino, or phenyl optionally having at least one substituent which is nitro; or
iii) C$_{1-3}$ alkyl, —C(O)—(C$_{1-4}$ haloalkyl), naphthyl, or benzyl.

In some embodiments, R$^{3a}$ is C$_{1-8}$ alkyl.

In some embodiments, R$^{3b}$ is aryl or heteroaryl, each optionally substituted by 1, 2, 3, 4 or 5 substituents independently selected from halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$C(O)NR$^{g1}$NR$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, and S(O)$_2$NR$^{g1}$R$^{h1}$.

In some embodiments, R$^{5b}$ is H, aryl, or heteroaryl, each optionally substituted by 1, 2, 3, 4 or 5 substituents independently selected from halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$C(O)NR$^{g1}$NR$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, and S(O)$_2$NR$^{g1}$R$^{h1}$.

In some embodiments, the present invention provides, inter alia, compounds of Formula I:

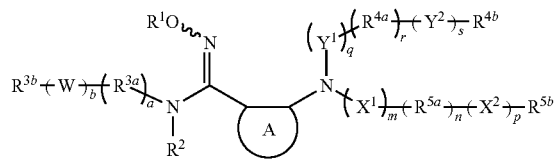

I or pharmaceutically acceptable salt forms or prodrugs thereof, wherein:

Ring A is carbocyclyl or heterocyclyl optionally substituted by 1, 2, 3, 4 or 5 R$^6$;

W, X$^1$, X$^2$, Y$^1$, and Y$^2$ are independently (CR$^a$R$^b$)$_t$, (CR$^a$R$^b$)$_u$O(CR$^a$R$^b$)$_v$, (CR$^a$R$^b$)$_u$C(O)(CR$^a$R$^b$)$_v$, (CR$^a$R$^b$)$_u$C(O)N-R$^c$(CR$^a$R$^b$)$_v$, (CR$^a$R$^b$)$_u$C(O)O(CR$^a$R$^b$)$_v$, (CR$^a$R$^b$)$_u$C(S)(CR$^a$R$^b$)$_u$, (CR$^a$R$^b$)$_u$C(S)NR$^c$(CR$^a$R$^b$)$_v$, (CR$^a$R$^b$)$_u$S(O)(CR$^a$R$^b$)$_v$, (CR$^a$R$^b$)$_u$S(O)NR$^c$(CR$^a$R$^b$)$_v$, (CR$^a$R$^b$)$_u$S(O)$_2$(CR$^a$R$^b$)$_v$, (CR$^a$R$^b$)$_u$S(O)$_2$NR$^c$(CR$^a$R$^b$)$_v$, (CR$^a$R$^b$)$_u$NR$^c$(CR$^a$R$^b$)$_v$, or (CR$^a$R$^b$)$_u$C(=NR$^d$)NR$^c$(CR$^a$R$^b$)$_v$;

R$^1$ is H, C(O)R$^7$, C(O)OR$^8$, C$_{1-8}$ alkyl, C$_{2-8}$ alkenyl, C$_{2-8}$ alkynyl, aryl, cycloalkyl, heteroaryl, heterocycloalkyl, arylalkyl, cycloalkylalkyl, heteroarylalkyl, or heterocycloalkylalkyl;

R$^2$ is H, C$_{1-6}$ alkyl, or C$_{3-7}$ cycloalkyl;

R$^{3a}$, R$^{4a}$, and R$^{5a}$ are independently C$_{1-8}$ alkyl, C$_{2-8}$ alkenyl, C$_{2-8}$ alkynyl, aryl, cycloalkyl, heteroaryl, or heterocycloalkyl, each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^1$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$;

R$^{3b}$, R$^{4b}$, and R$^{5b}$ are independently H, C$_{1-8}$ alkyl, C$_{2-8}$ alkenyl, C$_{2-8}$ alkynyl, aryl, cycloalkyl, heteroaryl, or heterocycloalkyl, each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$;

or R$^2$ and —(R$^{3a}$)$_a$—(W)$_b$—R$^{3b}$ together with the N atom to which they are attached form a 4- to 20-membered heterocycloalkyl group optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^3$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$;

or —(Y$^1$)$_q$—(R$^{4a}$)$_r$—(Y$^2$)$_s$—R$^{4b}$ and —(X$^1$)$_m$—(R$^{5a}$)$_n$—(X$^2$)$_p$—R$^{5b}$ together with the N atom to which they are attached form a 4- to 20-membered heterocycloalkyl group optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^4$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$;

R$^6$ is halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{e2}$, SR$^{e2}$, C(O)R$^{f2}$, C(O)NR$^{g2}$R$^{h2}$, C(O)OR$^{e2}$, OC(O)R$^{f2}$, OC(O)NR$^{g2}$R$^{h2}$, NR$^{g2}$R$^{h2}$, NR$^{g2}$C(O)R$^{f2}$, NR$^{g2}$C(O)OR$^{e2}$, P(R$^{f2}$)$_2$, P(OR$^{e2}$)$_2$, P(O)R$^{e2}$R$^{f2}$, P(O)OR$^{e2}$OR$^{f2}$, S(O)R$^{f2}$, S(O)NR$^{g2}$R$^{h2}$, S(O)$_2$R$^{f2}$, or S(O)$_2$NR$^{g2}$R$^{h2}$;

R$^7$ and R$^8$ are independently H, C$_{1-8}$ alkyl, aryl, heteroaryl, cycloalkyl, heterocycloalkyl, arylalkyl, heteroarylalkyl, cycloalkylalkyl, or heterocycloalkylalkyl, each optionally substituted by one or more halo, CN, NO$_2$, OH, C$_{1-4}$ alkoxy, C$_{1-4}$ haloalkoxy, amino, C$_{1-4}$ alkylamino or C$_{2-8}$ dialkylamino, C$_{1-6}$ alkyl, C$_{2-6}$ alkenyl, or C$_{2-6}$ alkynyl;

Cy$^1$, Cy$^2$, Cy$^3$, and Cy$^4$ are independently aryl, heteroaryl, cycloalkyl, or heterocycloalkyl, each optionally substituted by 1, 2, 3, 4 or 5 halo, C$_{1-4}$ alkyl, C$_{2-4}$ alkenyl, C$_{2-4}$ alkynyl, C$_{1-4}$ haloalkyl, CN, NO$_2$, OR$^{e3}$, SR$^{e3}$, C(O)R$^{f3}$, C(O)NR$^{g3}$R$^{h3}$, C(O)OR$^{e3}$, OC(O)R$^{f3}$, OC(O)NR$^{g3}$R$^{h3}$, NR$^{g3}$R$^{h3}$, NR$^{g3}$C(O)R$^{h3}$, NR$^{g3}$C(O)OR$^{e3}$, P(R$^{f3}$)$_2$, P(OR$^{e3}$)$_2$, P(O)R$^{e3}$R$^{f3}$, P(O)OR$^{e3}$OR$^{f3}$, S(O)R$^{f3}$, S(O)NR$^{g3}$R$^{h3}$, S(O)$_2$R$^{f3}$, or S(O)$_2$NR$^{g3}$R$^{h3}$;

R$^a$ and R$^b$ are independently H, halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{e4}$, SR$^{e4}$, C(O)R$^{f4}$, C(O)NR$^{g4}$R$^{h4}$, C(O)OR$^{e4}$, OC(O)R$^{f4}$, OC(O)NR$^{g4}$R$^{h4}$, NR$^{g4}$R$^{h4}$, NR$^{g4}$C(O)R$^{h4}$, NR$^{g4}$C(O)OR$^{e4}$, P(R$^{f4}$)$_2$, P(OR$^{e4}$)$_2$, P(O)R$^{e4}$R$^{f4}$, P(O)OR$^{e4}$OR$^{f4}$, S(O)R$^{f4}$, S(O)NR$^{g4}$R$^{h4}$, S(O)$_2$R$^{f4}$, or S(O)$_2$NR$^{g4}$R$^{h4}$;

R$^c$ is H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

R$^d$ is H, OR$^{d1}$, CN or NO$_2$;

R$^{d1}$ is H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

R$^{e1}$, R$^{e2}$, R$^{e3}$, and R$^{e4}$ are independently H, C$_{1-6}$ alkyl, C$_{1-6}$ haloalkyl, C$_{2-6}$ alkenyl, (C$_{1-6}$ alkoxy)-C$_{1-6}$ alkyl, C$_{2-6}$ alkynyl, aryl, cycloalkyl, heteroaryl, heterocycloalkyl, arylalkyl, cycloalkylalkyl, heteroarylalkyl or heterocycloalkylalkyl;

R$^{f1}$, R$^{f2}$, R$^{f3}$, and R$^{f4}$ are independently H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^{g1}$, R$^{g2}$, R$^{g3}$, and R$^{g4}$ are independently H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

R$^{h1}$, R$^{h2}$, R$^{h3}$, and R$^{h4}$ are independently H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^{g1}$ and R$^{h1}$ together with the N atom to which they are attached form a 4-, 5-, 6- or 7-membered heterocycloalkyl group;

or R$^{g2}$ and R$^{h2}$ together with the N atom to which they are attached form a 4-, 5-, 6- or 7-membered heterocycloalkyl group;

or R$^{g3}$ and R$^{h3}$ together with the N atom to which they are attached form a 4-, 5-, 6- or 7-membered heterocycloalkyl group;

or R$^{g4}$ and R$^{h4}$ together with the N atom to which they are attached form a 4-, 5-, 6- or 7-membered heterocycloalkyl group;

a is 0 or 1;

b is 0 or 1;

m is 0 or 1;

n is 0 or 1;

p is 0 or 1;

q is 0 or 1;

r is 0 or 1;

s is 0 or 1;

t is 1, 2, 3, 4, 5 or 6;

u is 0, 1, 2, 3, 4, 5 or 6; and v is 0, 1, 2, 3, 4, 5 or 6.

In some embodiments, R$^{3b}$ is aryl, cycloalkyl, heteroaryl, or heterocycloalkyl, each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$.

In some embodiments, R$^{3b}$ is aryl or heteroaryl each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$.

In some embodiments, R$^{3b}$ is phenyl optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$.

In some embodiments, R$^{5b}$ is H, C$_{1-8}$ alkyl, C$_{2-8}$ alkenyl, C$_{2-8}$ alkynyl, aryl, cycloalkyl, heteroaryl, or heterocycloalkyl, each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$.

In some embodiments, R$^{4b}$ is H and R$^{5b}$ is H, C$_{1-8}$ alkyl, C$_{2-8}$ alkenyl, C$_{2-8}$ alkynyl, aryl, cycloalkyl, heteroaryl, or heterocycloalkyl, each optionally substituted by 1, 2, 3, 4 or 5 halo, C$_{1-6}$ alkyl, C$_{2-6}$ alkenyl, C$_{2-6}$ alkynyl, C$_{1-4}$ haloalkyl, Cy$^2$, CN, NO$_2$, OR$^{e1}$, SR$^{e1}$, C(O)R$^{f1}$, C(O)NR$^{g1}$R$^{h1}$, C(O)OR$^{e1}$, OC(O)R$^{f1}$, OC(O)NR$^{g1}$R$^{h1}$, NR$^{g1}$R$^{h1}$C(O)NR$^{g1}$R$^{h1}$, NR$^{g1}$R$^{h1}$, NR$^{g1}$C(O)R$^{f1}$, NR$^{g1}$C(O)OR$^{e1}$, P(R$^{f1}$)$_2$, P(OR$^{e1}$)$_2$, P(O)R$^{e1}$R$^{f1}$, P(O)OR$^{e1}$OR$^{f1}$, S(O)R$^{f1}$, S(O)NR$^{g1}$R$^{h1}$, S(O)$_2$R$^{f1}$, or S(O)$_2$NR$^{g1}$R$^{h1}$.

In some embodiments, the compounds of the invention have Formula I:

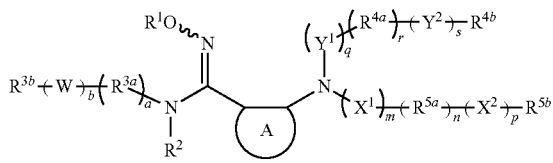

wherein:

Ring A is a 5-membered carbocyclyl or heterocyclyl ring optionally substituted by 1, 2, 3, 4 or 5 $R^6$;

$W$, $X^1$, $X^2$, $Y^1$, and $Y^2$ are independently $(CR^aR^b)_t$, $(CR^aR^b)_uO(CR^aR^b)_v$, $(CR^aR^b)_uC(O)(CR^aR^b)_v$, $(CR^aR^b)_uC(O)NR^c(CR^aR^b)_v$, $(CR^aR^b)_uC(O)O(CR^aR^b)_v$, $(CR^aR^b)_uC(S)(CR^aR^b)_u$, $(CR^aR^b)_uC(S)NR^c(CR^aR^b)_v$, $(CR^aR^b)_uS(O)(CR^aR^b)_v$, $(CR^aR^b)_uS(O)NR^c(CR^aR^b)_v$, $(CR^aR^b)_uS(O)_2(CR^aR^b)_v$, $(CR^aR^b)_uS(O)_2NR^c(CR^aR^b)_v$, $(CR^aR^b)_uNR^c(CR^aR^b)_v$, or $(CR^aR^b)_uC(=NR^d)NR^c(CR^aR^b)_v$;

$R^1$ is H, $C(O)R^7$, $C(O)OR^8$, $C_{1-8}$ alkyl, $C_{2-8}$ alkenyl, $C_{2-8}$ alkynyl, aryl, cycloalkyl, heteroaryl, heterocycloalkyl, arylalkyl, cycloalkylalkyl, heteroarylalkyl, or heterocycloalkylalkyl;

$R^2$ is H, $C_{1-6}$ alkyl, or $C_{3-7}$ cycloalkyl;

$R^{3a}$, $R^{4a}$, and $R^{5a}$ are independently $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, or $S(O)_2NR^{g1}R^{h1}$;

$R^{3b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, or $S(O)_2NR^{g1}R^{h1}$;

$R^{4b}$ is H;

$R^{5b}$ is $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, or $S(O)_2NR^{g1}R^{h1}$;

or $R^2$ and $-(R^{3a})_a-(W)_b-R^{3b}$ together with the N atom to which they are attached form a 4- to 20-membered heterocycloalkyl group optionally substituted by 1, 2, 3, 4 or 5 halo, $C_{1-6}$ alkyl, $C_{2-6}$ alkenyl, $C_{2-6}$ alkynyl, $C_{1-4}$ haloalkyl, $Cy^3$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}C(O)NR^{g1}R^{h1}$, $NR^{g1}R^{h1}$, $NR^{g1}C(O)R^{f1}$, $NR^{g1}C(O)OR^{e1}$, $S(O)R^{f1}$, $S(O)NR^{g1}R^{h1}$, $S(O)_2R^{f1}$, or $S(O)_2NR^{g1}R^{h1}$;

or $-(Y^1)_q-(R^{4a})_r-(Y^2)_s-R^{4b}$ and $-(X^1)_m-(R^{5a})_n-(X^2)_p-R^{5b}$ together with the N atom to which they are attached form a 4- to 20-membered heterocycloalkyl group optionally substituted by 1, 2, 3, 4 or 5 halo, $C_{1-6}$ alkyl, $C_{2-6}$ alkenyl, $C_{2-6}$ alkynyl, $C_{1-4}$ haloalkyl, $Cy^4$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}R^{h1}C(O)NR^{g1}R^{h1}$, $NR^{g1}R^{h1}$, $NR^{g1}C(O)R^{f1}$, $NR^{g1}C(O)OR^{e1}$, $S(O)R^{f1}$, $S(O)NR^{g1}R^{h1}$, $S(O)_2R^{f1}$, or $S(O)_2NR^{g1}R^{h1}$;

$R^6$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e2}$, $SR^{e2}$, $C(O)R^{f2}$, $C(O)NR^{g2}R^{h2}$, $C(O)OR^{e2}$, $OC(O)R^{f2}$, $OC(O)NR^{g2}R^{h2}$, $NR^{g2}R^{h2}$, $NR^{g2}C(O)R^{f2}$, $NR^{g2}C(O)OR^{e2}$, $P(R^{f2})_2$, $P(OR^{e2})_2$, $P(O)R^{e2}R^{f2}$, $P(O)OR^{e2}OR^{f2}$, $S(O)R^{f2}$, $S(O)NR^{g2}R^{h2}$, $S(O)_2R^{f2}$, or $S(O)_2NR^{g2}R^{h2}$;

$R^7$ and $R^8$ are independently H, $C_{1-8}$ alkyl, aryl, heteroaryl, cycloalkyl, heterocycloalkyl, arylalkyl, heteroarylalkyl, cycloalkylalkyl, or heterocycloalkylalkyl, each optionally substituted by one or more halo, CN, $NO_2$, OH, $C_{1-4}$ alkoxy, $C_{1-4}$ haloalkoxy, amino, $C_{1-4}$ alkylamino or $C_{2-8}$ dialkylamino, $C_{1-6}$ alkyl, $C_{2-6}$ alkenyl, or $C_{2-6}$ alkynyl;

$Cy^1$, $Cy^2$, $Cy^3$, and $Cy^4$ are independently aryl, heteroaryl, cycloalkyl, or heterocycloalkyl, each optionally substituted by halo, $C_{1-4}$ alkyl, $C_{2-4}$ alkenyl, $C_{2-4}$ alkynyl, $C_{1-4}$ haloalkyl, CN, $NO_2$, $OR^{e3}$, $SR^{e3}$, $C(O)R^{f3}$, $C(O)NR^{g3}R^{h3}$, $C(O)OR^{e3}$, $OC(O)R^{f3}$, $OC(O)NR^{g3}R^{h3}$, $NR^{g3}R^{h3}$, $NR^{g3}C(O)R^{h3}$, $NR^{g3}C(O)OR^{e3}$, $S(O)R^{f3}$, $S(O)NR^{g3}R^{h3}$, $S(O)_2R^{f3}$, or $S(O)_2NR^{g3}R^{h3}$;

$R^a$ and $R^b$ are independently H, halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e4}$, $SR^{e4}$, $C(O)R^{f4}$, $C(O)NR^{g4}R^{h4}$, $C(O)OR^{e4}$, $OC(O)R^{f4}$, $OC(O)NR^{g4}R^{h4}$, $NR^{g4}R^{h4}$, $NR^{g4}C(O)R^{h4}$, $NR^{g4}C(O)OR^{e4}$, $P(R^{f4})_2$, $P(OR^{e4})_2$, $P(O)R^{e4}R^{f4}$, $P(O)OR^{e4}OR^{f4}$, $S(O)R^{f4}$, $S(O)NR^{g4}R^{h4}$, $S(O)_2R^{f4}$, or $S(O)_2NR^{g4}R^{h4}$;

$R^c$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^d$ is H, $OR^{d1}$, CN or $NO_2$;

$R^{d1}$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{e1}$, $R^{e2}$, $R^{e3}$, and $R^{e4}$ are independently H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl or heterocycloalkylalkyl;

$R^{f1}$, $R^{f2}$, $R^{f3}$, and $R^{f4}$ are independently H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^{g1}$, $R^{g2}$, $R^{g3}$, and $R^{g4}$ are independently H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{h1}$, $R^{h2}$, $R^{h3}$, and $R^{h4}$ are independently H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^{g1}$ and $R^{h1}$ together with the N atom to which they are attached form a 4-, 5-, 6- or 7-membered heterocycloalkyl group;

or $R^{g2}$ and $R^{h2}$ together with the N atom to which they are attached form a 4-, 5-, 6- or 7-membered heterocycloalkyl group;

or $R^{g3}$ and $R^{h3}$ together with the N atom to which they are attached form a 4-, 5-, 6- or 7-membered heterocycloalkyl group;

or $R^{g4}$ and $R^{h4}$ together with the N atom to which they are attached form a 4-, 5-, 6- or 7-membered heterocycloalkyl group;

a is 0 or 1;
b is 0 or 1;
m is 0 or 1;
n is 0 or 1;
p is 0 or 1;
q is 0;
r is 0;
s is 0;

t is 1, 2, 3, 4, 5 or 6;
u is 0, 1, 2, 3, 4, 5 or 6; and
v is 0, 1, 2, 3, 4, 5 or 6.

In some embodiments, the compounds of the invention have Formula I:

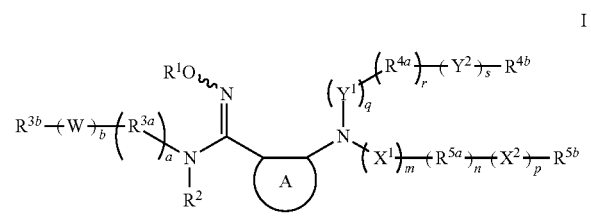

I wherein:

Ring A is a 5-membered carbocyclyl or heterocyclyl ring optionally substituted by 1, 2, 3, 4 or 5 $R^6$;

W, $X^1$, $X^2$, $Y^1$, and $Y^2$ are independently selected from $(CR^aR^b)_t$, $(CR^aR^b)_uO(CR^aR^b)_v$, $(CR^aR^b)_uC(O)(CR^aR^b)_v$, $(CR^aR^b)_uC(O)NR^c(CR^aR^b)_v$, $(CR^aR^b)_uC(O)O(CR^aR^b)_v$, $(CR^aR^b)_uC(S)(CR^aR^b)_v$, $(CR^aR^b)_uC(S)NR^c(CR^aR^b)_v$, $(CR^aR^b)_uS(O)(CR^aR^b)_v$, $(CR^aR^b)_uS(O)NR^c(CR^aR^b)_v$, $(CR^aR^b)_uS(O)_2(CR^aR^b)_v$, $(CR^aR^b)_uS(O)_2NR^c(CR^aR^b)_v$, $(CR^aR^b)_uNR^c(CR^aR^b)_v$, and $(CR^aR^b)_uC(=NR^d)NR^c(CR^aR^b)_v$;

$R^1$ is H, $C(O)R^7$, $C(O)NR^{8a}R^{8b}$, $C(O)OR^8$, $C_{1-8}$ alkyl, $C_{2-8}$ alkenyl, $C_{2-8}$ alkynyl, aryl, cycloalkyl, heteroaryl, heterocycloalkyl, arylalkyl, cycloalkylalkyl, heteroarylalkyl, or heterocycloalkylalkyl;

$R^2$ is H, $C_{1-6}$ alkyl, or $C_{3-7}$ cycloalkyl;

$R^{3a}$, $R^{4a}$, and $R^{5a}$ are independently selected from $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{3b}$ is H, $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{4b}$ is H;

$R^{5b}$ is $C_{1-8}$ alkyl, $C_{2-8}$ alkenyl, $C_{2-8}$ alkynyl, aryl, cycloalkyl, heteroaryl, or heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $C_{1-4}$ hydroxyalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $C(=NR^i)NR^{g1}R^{h1}$, $NR^{g1}C(=NR^i)NR^{g1}R^{h1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

or $R^2$ and $—(R^{3a})_a—(W)_b—R^{3b}$ together with the N atom to which they are attached form a 4- to 20-membered heterocycloalkyl group optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^3$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $S(O)R^{f1}$, $S(O)NR^{g1}R^{h1}$, $S(O)_2R^{f1}$, and $S(O)_2NR^{g1}R^{h1}$;

or $—(Y^1)_q—(R^{4a})_r—(Y^2)_s—R^{4b}$ and $—(X^1)_m—(R^{5a})_n—(X^2)_p—R^{5b}$ together with the N atom to which they are attached form a 4- to 20-membered heterocycloalkyl group optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^4$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $S(O)R^{f1}$, $S(O)NR^{g1}R^{h1}$, $S(O)_2R^{f1}$, and $S(O)_2NR^{g1}R^{h1}$;

$R^6$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e2}$, $SR^{e2}$, $C(O)R^{f2}$, $C(O)NR^{g2}R^{h2}$, $C(O)OR^{e2}$, $OC(O)R^{f2}$, $OC(O)NR^{g2}R^{h2}$, $NR^{g2}R^{h2}$, $NR^{g2}C(O)R^{f2}$, $NR^{g2}C(O)OR^{e2}$, $C(=NR^i)NR^{g1}R^{h1}$, $NR^{g1}C(=NR^i)NR^{g1}R^{h1}$, $P(R^{f2})_2$, $P(OR^{e2})_2$, $P(O)R^{e2}R^{f2}$, $P(O)OR^{e2}OR^{f2}$, $S(O)R^{f2}$, $S(O)NR^{g2}R^{h2}$, $S(O)_2R^{f2}$, or $S(O)_2NR^{g2}R^{h2}$;

$R^7$ and $R^8$ are independently selected from H, $C_{1-8}$ alkyl, aryl, heteroaryl, cycloalkyl, heterocycloalkyl, arylalkyl, heteroarylalkyl, cycloalkylalkyl, and heterocycloalkylalkyl, each optionally substituted by one or more substituents independently selected from halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, and $C_{2-6}$ alkynyl;

$R^{8a}$ and $R^{8b}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

$Cy^1$, $Cy^2$, $Cy^1$, and $Cy^4$ are independently selected from aryl, heteroaryl, cycloalkyl, or heterocycloalkyl, each optionally substituted by 1, 2, 3, 4, or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{e3}$, $SR^{e3}$, $C(O)R^{f3}$, $C(O)NR^{g3}R^{h3}$, $C(O)OR^{e3}$, $OC(O)R^{f3}$, $OC(O)NR^{g3}R^{h3}$, $NR^{g3}R^{h3}$, $NR^{g3}C(O)R^{h3}$, $NR^{g3}C(O)OR^{e3}$, $S(O)R^{f3}$, $S(O)NR^{g3}R^{h3}$, $S(O)_2R^{f3}$, and $S(O)_2NR^{g3}R^{h3}$;

$R^a$ and $R^b$ are independently selected from H, halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e4}$, $SR^{e4}$, $C(O)R^{f4}$, $C(O)NR^{g4}R^{h4}$, $C(O)OR^{e4}$, $OC(O)R^{f4}$, $OC(O)NR^{g4}R^{h4}$, $NR^{g4}R^{h4}$, $NR^{g4}C(O)R^{h4}$, $NR^{g4}C(O)OR^{e4}$, $C(=NR^i)NR^{g1}R^{h1}$, $NR^{g1}C(=NR^i)NR^{g1}R^{h1}$, $P(R^{f4})_2$, $P(OR^{e4})_2$, $P(O)R^{e4}R^{f4}$, $P(O)OR^{e4}OR^{f4}$, $S(O)R^{f4}$, $S(O)NR^{g4}R^{h4}$, $S(O)_2R^{f4}$, and $S(O)_2NR^{g4}R^{h4}$;

$R^c$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^d$ is H, $OR^{d1}$, CN or $NO_2$;

$R^{d1}$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{e1}$, $R^{e2}$, $R^{e3}$, and $R^{e4}$ are independently selected from H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl or heterocycloalkylalkyl;

$R^{f1}$, $R^{f2}$, $R^{f3}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^{g1}$, $R^{g2}$, $R^{g3}$, and $R^{g4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{h1}$, $R^{h2}$, $R^{h3}$, and $R^{h4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^{g1}$ and $R^{h1}$ together with the N atom to which they are attached form a 4-, 5-, 6- or 7-membered heterocycloalkyl group;

or $R^{g2}$ and $R^{h2}$ together with the N atom to which they are attached form a 4-, 5-, 6- or 7-membered heterocycloalkyl group;

or $R^{g3}$ and $R^{h3}$ together with the N atom to which they are attached form a 4-, 5-, 6- or 7-membered heterocycloalkyl group;

or $R^{g4}$ and $R^{h4}$ together with the N atom to which they are attached form a 4-, 5-, 6- or 7-membered heterocycloalkyl group;

$R^i$ is H, CN, or $NO_2$;
a is 0 or 1;
b is 0 or 1;
m is 0 or 1;
n is 0 or 1;
p is 0 or 1;
q is 0;
r is 0;
s is 0;
t is 1, 2, 3, 4, 5 or 6;
u is 0, 1, 2, 3, 4, 5 or 6; and
v is 0, 1, 2, 3, 4, 5 or 6.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings or spirocycles). Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. One or more ring-forming carbon atoms of a cycloalkyl group can be oxidized, for example, having an oxo or sulfide substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "heterocyclyl" or "heterocycle" refers to a saturated or unsaturated cyclic group wherein one or more of the ring-forming atoms is a heteroatom such as O, S, or N. Heterocyclyl groups include mono- or polycyclic ring systems. Heterocyclyl groups can be aromatic (e.g., "heteroaryl") or non-aromatic (e.g., "heterocycloalkyl"). Heterocyclyl groups can be characterized as having 3-14, 3-12, 3-10, 3-7, or 3-6 ring-forming atoms. In some embodiments, heterocyclyl groups can contain, in addition to at least one heteroatom, from about 1 to about 13, about 2 to about 10, or about 2 to about 7 carbon atoms and can be attached/linked through either a carbon atom or a heteroatom. In further embodiments, the heteroatom can be oxidized (e.g., have an oxo or sulfido substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, decahydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "haloalkyl" refers to an alkyl group substituted by at least one halogen atom. Example haloalkyl groups include fluoromethyl, difluoromethyl, trifluoromethyl, and the like.

As used herein, "alkoxy" refers to an —O-alkyl group. Example alkoxy groups include methoxy, ethoxy, propoxy (e.g., n-propoxy and isopropoxy), t-butoxy, and the like.

As used herein, "alkoxyalkyl" refers to an alky group substituted by an alkoxy group.

As used here, "haloalkoxy" refers to an O-haloalkyl group. An example haloalkoxy group is $OCF_3$.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

It is understood that when a substituent is depicted structurally as a linking moiety, it is necessarily minimally divalent. For example, when the variable $R^{3a}$ of the structure depicted in Formula I is alkyl, the alkyl moiety is understood to be an alkyl linking moiety such as —$CH_2$—, —$CH_2CH_2$—, $CH_3CH<$, etc.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

Compounds of Formula I can be synthesized by those skilled in the art. An example is shown in Scheme 1 (Q is $N\{(X^1)_m(R^{5a})_n(X^2)_pR^{5b}\}\{Y^1)_q(R^{4a})_r(Y^2)_sR^{4b}\}$ and NR'R" is $N(R^2)\{(R^{3a})_a(W)_bR^{3b}\}$). Nitriles (1) can be converted into amide oximes (2). Chlorination of the amide oximes can give chloro oximes (3) which can be reacted with a variety of amines to give substituted amide oximes (4).

Scheme 1

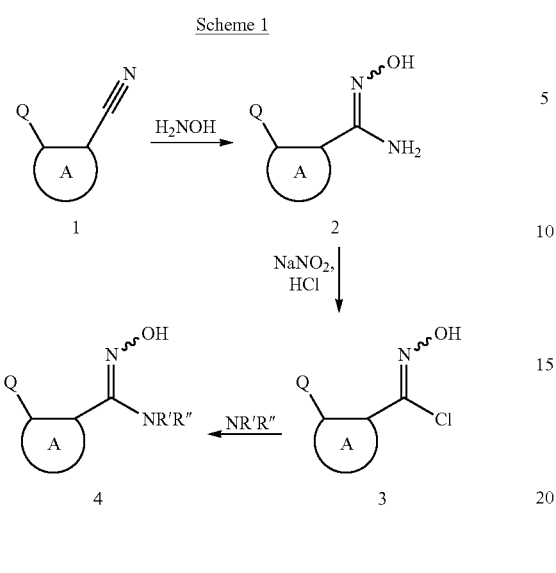

An example synthesis of oxadiazole cores is shown in Scheme 2. 4-Amino-N'-hydroxy-1,2,5-oxadiazole-3-carboximidamide (5) [*J. Heterocycl. Chem.* (1965), 2, 253] can be converted to the chloro oxime 6 [*Synth. Commun.* (1988), 18, 1427]. The addition of a variety of amines to 6 can give substituted amide oximes (7).

Scheme 2

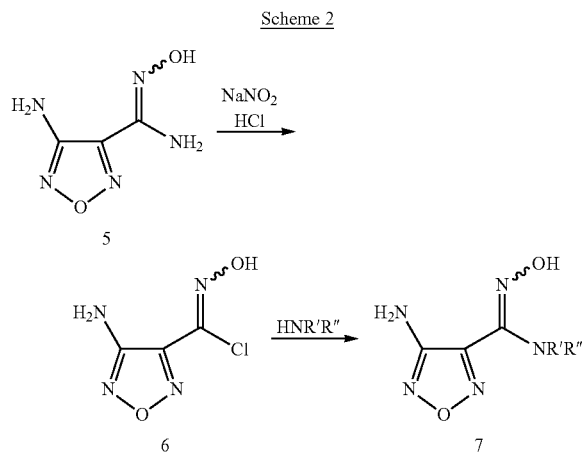

Additional compounds of Formula I can be synthesized as shown in Scheme 3. Protection of amide oxime 7 can give 8 which can be reacted with a variety of alkyl halides, acid halides, sulfonyl halides, isocyanates, and halo formates, etc. (X is a leaving group such as halo), to give their respective alkyl amines, amides, sulfonamides, ureas, and carbamates (9).

Scheme 3

Amide oximes can also be prepared as shown in Scheme 4. Coupling of an acid such as 10 with an amine can give amide 11. Amide 11 can be converted to the thioamide 12 which can be methylated to give the methyl thioimidate 13. Reaction of 13 with hydroxylamine can give the amide oxime 14. Alternatively, amide oxime 14 can be formed from the chloroimidate 15 which can be synthesized from amide 11 using phosphorus pentachloride.

Scheme 4

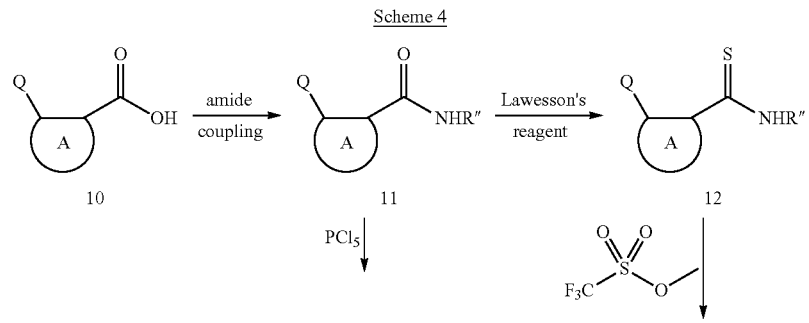

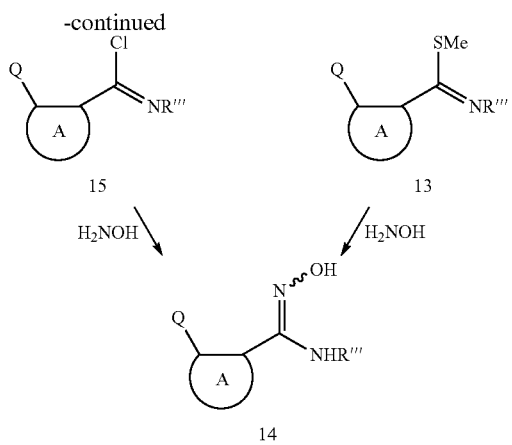

Additional amide oximes can be synthesized as described in Scheme 5 (X is a leaving group). Rearrangement of amide oxime 7 can give 16 which can be converted to 17 with sodium nitrite in HCl. Reaction of 17 with amines can give compounds such as 18.

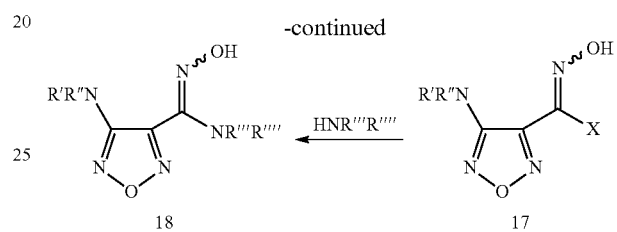

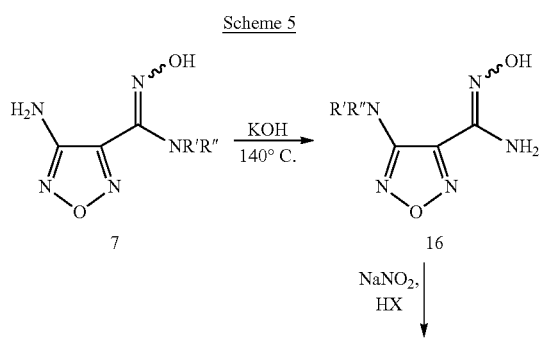

Additional compounds can be synthesized as shown in Scheme 6. Amide coupling of 8 can give 19 which can be treated with phosphorus pentachloride and subsequently reduced with a hydride such as sodium cyanoborohydride or borane to give 20. Deprotection of 20 with sodium hydroxide can give amide oxime 21. Amide 19 can also be deprotected to give 22. Compound 8 can also be converted to 23 which can be coupled with appropriate alcohols in a Mitsunobu coupling to give 24 after deprotection. Alternatively, compound 23 can be alkylated to give 25 which can be deprotected to give 26.

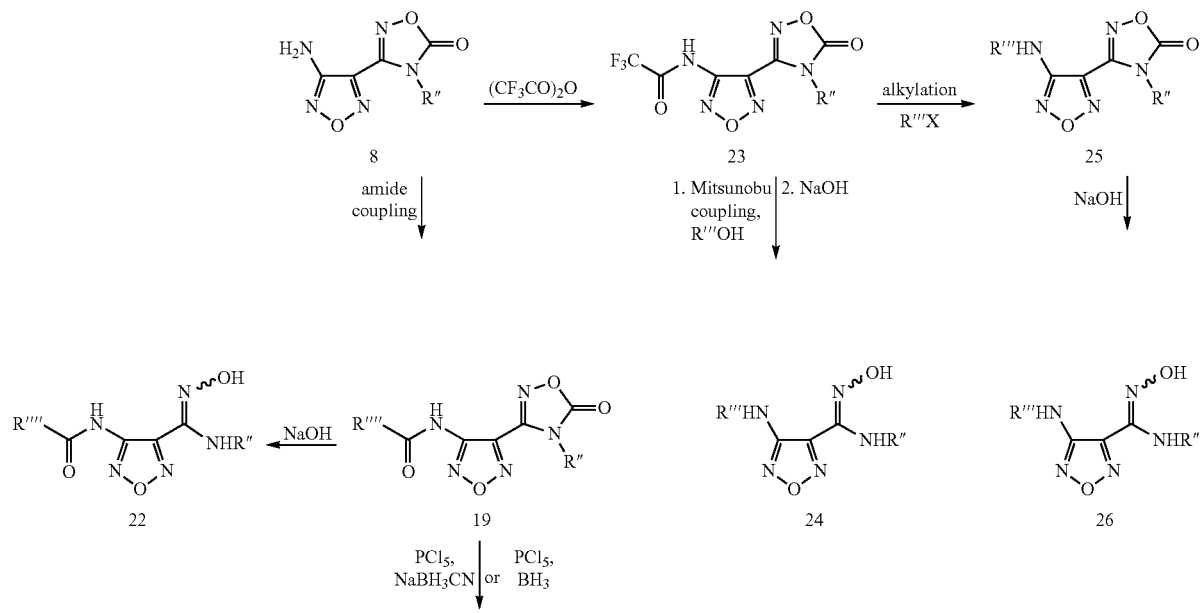

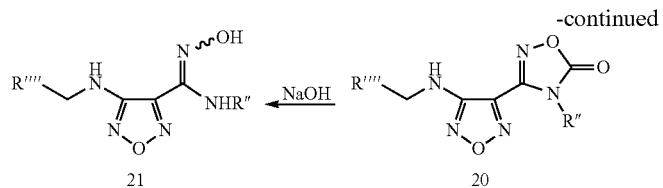

Methods of Use

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil[bis (POM)-PMEA]; lobucavir (BMS-180194); BCH-10652;

emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimidi nedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™) ifosfamide, melphalan, chlorambucil, pipobroman, triethylenemelamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which is a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents;

and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin lable, heavy metal or radio-labeled compounds of the invention that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, the present invention includes IDO enzyme assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro IDO enzyme labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the IDO enzyme. Accordingly, the ability of a test compound to compete with the radio-labeled compound for binding to the IDO enzyme directly correlates to its binding affinity.

Kits

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The example compounds below were found to be inhibitors of IDO according to one or more of the assays described herein.

EXAMPLES

As detected by $^1$H NMR, preparations of the example compounds below contained both E and Z isomers. While not wishing to be bound by theory, the major isomer was believed to be the Z isomer based on, for example, the data reported in Zh. Org. Chim. (1993), 29, 1062-1066.

Example 1

4-Amino-N-(3-fluorophenyl)-N'-hydroxy-1,2,5-oxa-diazole-3-carboximidamide

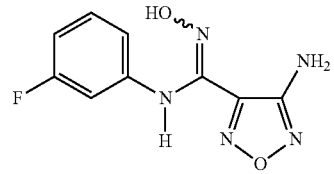 [SMILES: Nc1nonc1C(=NO)Nc1cccc(F)c1]

Step 1.
4-Amino-N-hydroxy-1,2,5-oxadiazole-3-carboximidoyl chloride

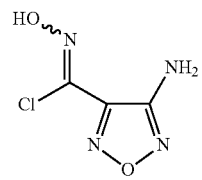

A solution of 3 M of hydrogen chloride in water (190 mL) was treated with 4-amino-N'-hydroxy-1,2,5-oxadiazole-3-carboximidamide [*J. Heterocycl. Chem.* (1965), 2, 253] (7.3 g, 0.051 mol) at 0° C. The reaction mixture was treated with enough 12 M hydrogen chloride (~19 mL) to dissolve the solid and then treated with a solution of sodium nitrite (4.4 g, 0.063 mol) in water (24 mL) dropwise while maintaining an internal temperature at 0-5° C. with an ice/brine bath. The reaction mixture was stirred at 0° C. for 1.5 h and filtered to yield a beige solid. Purification of the crude mixture by preparative HPLC gave the desired product (1.7 g, 21%) as an off-white solid.

Step 2: 4-Amino-N-(3-fluorophenyl)-N'-hydroxy-1,2,5-oxadiazole-3-carboximidamide A solution of 3-fluoroaniline (36 μL, 0.37 mmol) in ethanol (0.5 mL) was treated with a solution of 4-amino-N-hydroxy-1,2,5-oxadiazole-3-carboximidoyl chloride (50 mg, 0.31 mmol) in ethanol (1.5 mL) followed by triethylamine (51 μL, 0.37 mmol) dropwise. The reaction mixture was stirred at 25° C. for 1 h and purified by preparative LCMS to give the desired product (21 mg, 29%). LCMS for $C_9H_9FN_5O_2$ (M+H)$^+$: m/z=238.0.

Example 2

4-Amino-N'-hydroxy-N-phenyl-1,2,5-oxadiazole-3-carboximidamide

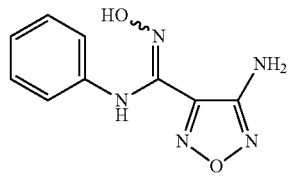 [SMILES: Nc1nonc1C(=NO)Nc1ccccc1]

This compound was prepared according to the procedure of Example 1 using aniline as the starting material. LCMS for $C_9H_{10}N_5O_2$ (M+H)$^+$: m/z=220.0.

Example 3

4-Amino-N-(2-chlorophenyl)-N'-hydroxy-1,2,5-oxa-diazole-3-carboximidamide

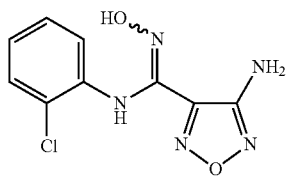 [SMILES: Nc1nonc1C(=NO)Nc1ccccc1Cl]

This compound was prepared according to the procedure of Example 1 using 2-chloroaniline as the starting material. LCMS for $C_9H_9ClN_5O_2$ (M+H)$^+$: m/z=254.0.

Example 4

4-Amino-N-(3-chlorophenyl)-N'-hydroxy-1,2,5-oxa-diazole-3-carboximidamide

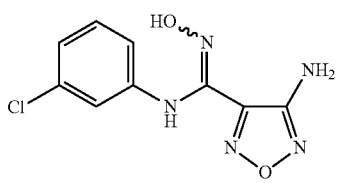 [SMILES: Nc1nonc1C(=NO)Nc1cccc(Cl)c1]

This compound was prepared according to the procedure of Example 1 using 3-chloroaniline as the starting material. LCMS for $C_9H_9ClN_5O_2$ (M+H)$^+$: m/z=254.1.

Example 5

4-Amino-N-(4-chlorophenyl)-N'-hydroxy-1,2,5-oxa-diazole-3-carboximidamide

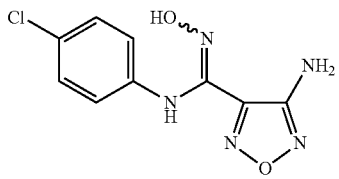 [SMILES: Nc1nonc1C(=NO)Nc1ccc(Cl)cc1]

This compound was prepared according to the procedure of Example 1 using 4-chloroaniline as the starting material. LCMS for $C_9H_9ClN_5O_2$ (M+H)$^+$: m/z=254.1.

Example 6

4-Amino-N-(4-bromophenyl)-N'-hydroxy-1,2,5-oxadiazole-3-carboximidamide

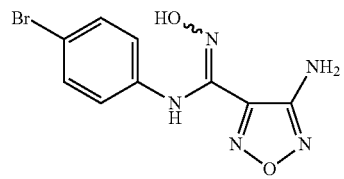

This compound was prepared according to the procedure of Example 1 using 4-bromoaniline as the starting material. LCMS for $C_9H_9BrN_5O_2$ (M+H)$^+$: m/z=297.9.

Example 7

4-Amino-N'-hydroxy-N-(2-methylphenyl)-1,2,5-oxadiazole-3-carboximidamide

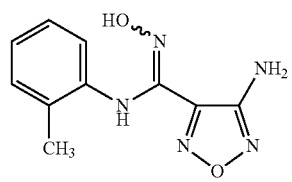 [SMILES: Cc1ccccc1NC(=NO)c1nonc1N]

This compound was prepared according to the procedure of Example 1 using 2-methylaniline as the starting material. LCMS for $C_{10}H_{12}N_5O_2$ (M+H)$^+$: m/z=234.1.

Example 8

4-Amino-N'-hydroxy-N-(3-methylphenyl)-1,2,5-oxadiazole-3-carboximidamide

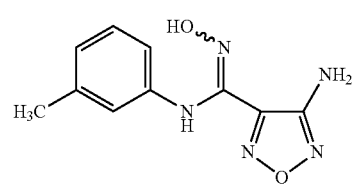 [SMILES: Cc1cccc(NC(=NO)c2nonc2N)c1]

This compound was prepared according to the procedure of Example 1 using 3-methylaniline as the starting material. LCMS for $C_{10}H_{12}N_5O_2$ (M+H)$^+$: m/z=234.0.

Example 9

4-Amino-N'-hydroxy-N-(4-methylphenyl)-1,2,5-oxadiazole-3-carboximidamide

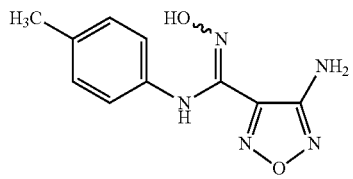 [SMILES: Cc1ccc(NC(=NO)c2nonc2N)cc1]

This compound was prepared according to the procedure of Example 1 using 4-methylaniline as the starting material. LCMS for $C_{10}H_{12}N_5O_2$ (M+H)$^+$: m/z=234.0.

Example 10

4-Amino-N'-hydroxy-N-[3-(trifluoromethyl)phenyl]-1,2,5-oxadiazole-3-carboximidamide

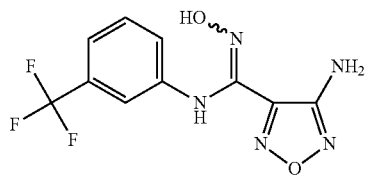 [SMILES: Nc1nonc1C(=NO)Nc1cccc(C(F)(F)F)c1]

This compound was prepared according to the procedure of Example 1 using 3-(trifluoromethyl)aniline as the starting material. LCMS for $C_{10}H_9F_3N_5O_2$ (M+H)$^+$: m/z=288.0.

Example 11

4-Amino-N'-hydroxy-N-(2-methoxyphenyl)-1,2,5-oxadiazole-3-carboximidamide

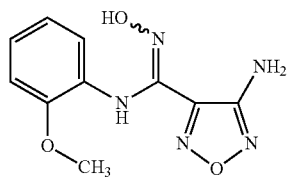 [SMILES: COc1ccccc1NC(=NO)c1nonc1N]

This compound was prepared according to the procedure of Example 1 using 2-methoxyaniline as the starting material. LCMS for $C_{10}H_{12}N_5O_3$ (M+H)$^+$: m/z=250.0.

Example 12

4-Amino-N'-hydroxy-N-(3-methoxyphenyl)-1,2,5-oxadiazole-3-carboximidamide

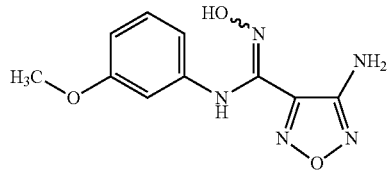 [SMILES: COc1cccc(NC(=NO)c2nonc2N)c1]

This compound was prepared according to the procedure of Example 1 using 3-methoxyaniline as the starting material. LCMS for $C_{10}H_{12}N_5O_3$ (M+H)$^+$: =250.0.

Example 13

4-Amino-N'-hydroxy-N-(4-methoxyphenyl)-1,2,5-oxa diazole-3-carboximidamide

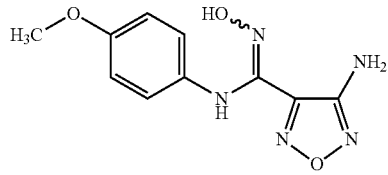 [SMILES: COc1ccc(NC(=NO)c2nonc2N)cc1]

This compound was prepared according to the procedure of Example 1 using 4-methoxyaniline as the starting material. LCMS for $C_{10}H_{12}N_5O_3$ (M+H)$^+$: =250.0.

Example 14

4-Amino-N-[3-(benzyloxy)phenyl]-N'-hydroxy-1,2,5-oxadiazole-3-carboximidamide

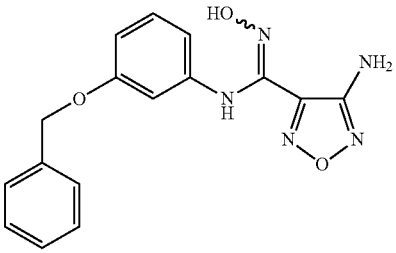 [SMILES: Nc1nonc1C(=NO)Nc1cccc(OCc2ccccc2)c1]

This compound was prepared according to the procedure of Example 1 using 3-(benzyloxy)aniline as the starting material. LCMS for $C_{16}H_{16}N_5O_3$ (M+H)$^+$: m/z=326.2.

Example 15

N-(3-Acetylphenyl)-4-amino-N'-hydroxy-1,2,5-oxa-diazole-3-carboximidamide

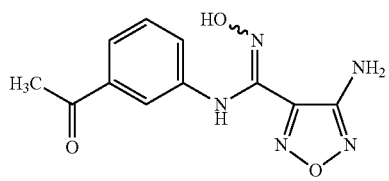 [SMILES: CC(=O)c1cccc(NC(=NO)c2nonc2N)c1]

This compound was prepared according to the procedure of Example 1 using 3-aminoacetophenone as the starting material. LCMS for $C_{11}H_{12}N_5O_3$ (M+H)$^+$: m/z=262.2.

Example 16

4-Amino-N-(3-cyanophenyl)-N'-hydroxy-1,2,5-oxa-diazole-3-carboximidamide

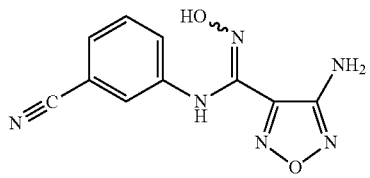 [SMILES: N#Cc1cccc(NC(=NO)c2nonc2N)c1]

This compound was prepared according to the procedure of Example 1 using 3-aminobenzonitrile as the starting material. LCMS for $C_{10}H_9N_6O_2$ (M+H)$^+$: m/z=245.0.

Example 17

4-Amino-N-(3,4-difluorophenyl)-N'-hydroxy-1,2,5-oxadiazole-3-carboximidamide

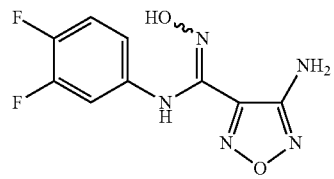 [SMILES: Nc1nonc1C(=NO)Nc1ccc(F)c(F)c1]

This compound was prepared according to the procedure of Example 1 using 3,4-difluoroaniline as the starting material. LCMS for $C_9H_8F_2N_5O_2$ (M+H)$^+$: m/z=256.1.

Example 18

4-Amino-N-(4-bromo-3-fluorophenyl)-N'-hydroxy-1,2,5-oxadiazole-3-carboximidamide

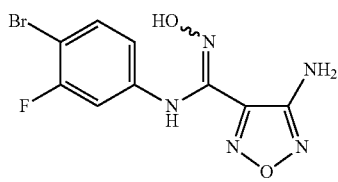 [SMILES: Nc1nonc1C(=NO)Nc1ccc(Br)c(F)c1]

This compound was prepared according to the procedure of Example 1 using 4-bromo-3-fluoroaniline as the starting material. LCMS for $C_9H_8BrFN_5O_2$ (M+H)$^+$: m/z=316.0, 318.0.

Example 19

4-Amino-N-(3-chloro-4-fluorophenyl)-N'-hydroxy-1,2,5-oxadiazole-3-carboximidamide

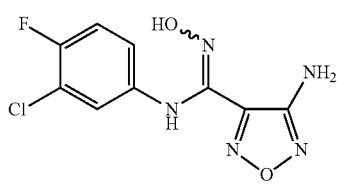 [SMILES: Nc1nonc1C(=NO)Nc1ccc(F)c(Cl)c1]

This compound was prepared according to the procedure of Example 1 using 3-chloro-4-fluoroaniline as the starting material. LCMS for $C_9H_8ClFN_5O_2$ (M+H)$^+$: m/z=272.0.

Example 20

4-Amino-N-(3-chloro-4-methylphenyl)-N'-hydroxy-1,2,5-oxadiazole-3-carboximidamide

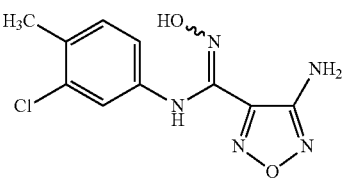 [SMILES: Cc1ccc(NC(=NO)c2nonc2N)cc1Cl]

This compound was prepared according to the procedure of Example 1 using 3-chloro-4-methylaniline as the starting material. LCMS for $C_{10}H_{11}ClN_5O_2$ (M+H)$^+$: m/z=268.1.

Example 21

4-Amino-N-(3,4-dimethylphenyl)-N'-hydroxy-1,2,5-oxadiazole-3-carboximidamide

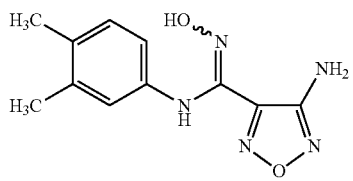 [SMILES: Cc1ccc(NC(=NO)c2nonc2N)cc1C]

This compound was prepared according to the procedure of Example 1 using 3,4-dimethylaniline as the starting material. LCMS for $C_{11}H_{14}N_5O_2$ (M+H)$^+$: m/z=248.0.

Example 22

4-Amino-N-[4-(benzyloxy)-3-chlorophenyl]-N'-hydroxy-1,2,5-oxadiazole-3-carboximidamide

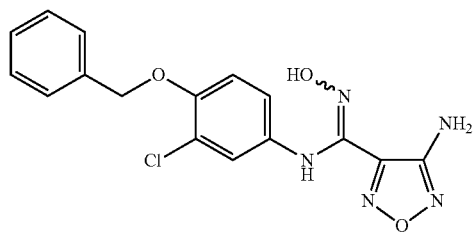 [SMILES: Nc1nonc1C(=NO)Nc1ccc(OCc2ccccc2)c(Cl)c1]

This compound was prepared according to the procedure of Example 1 using 4-(benzyloxy)-3-chloroaniline as the starting material. LCMS for $C_{16}H_{15}ClN_5O_3$ (M+H)$^+$: m/z=360.0.

Example 23

4-Amino-N-[4-fluoro-3-(trifluoromethyl)phenyl]-N'-hydroxy-1,2,5-oxadiazole-3-carboximidamide

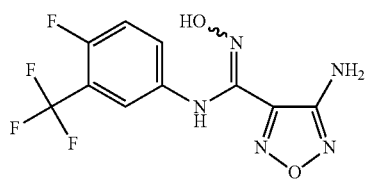 [SMILES: Nc1nonc1C(=NO)Nc1ccc(F)c(C(F)(F)F)c1]

This compound was prepared according to the procedure of Example 1 using 4-fluoro-3-(trifluoromethyl)aniline as the starting material. LCMS for $C_{10}H_8F_4N_5O_2$ (M+H)$^+$: m/z=306.1.

Example 24

4-Amino-N-benzyl-N'-hydroxy-1,2,5-oxadiazole-3-carboximidamide

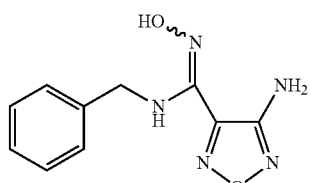

This compound was prepared according to the procedure of Example 1 using benzylamine as the starting material. LCMS for $C_{10}H_{12}N_5O_2$ (M+H)$^+$: m/z=234.2.

Example 25

4-Amino-N-(2-fluorobenzyl)-N'-hydroxy-1,2,5-oxadiazole-3-carboximidamide

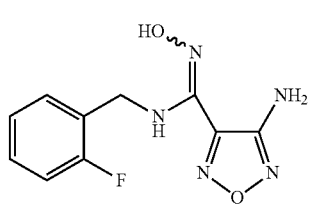 [SMILES: Nc1nonc1C(=NO)NCc1ccccc1F]

This compound was prepared according to the procedure of Example 1 using 2-fluorobenzylamine as the starting material. LCMS for $C_{10}H_{11}FN_5O_2$ (M+H)$^+$: m/z=252.0.

Example 26

4-Amino-N-(2-chlorobenzyl)-N'-hydroxy-1,2,5-oxadiazole-3-carboximidamide

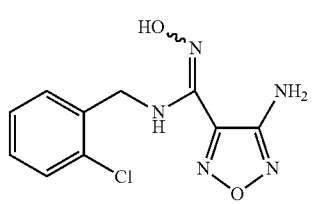 [SMILES: Nc1nonc1C(=NO)NCc1ccccc1Cl]

This compound was prepared according to the procedure of Example 1 using 2-chlorobenzylamine as the starting material. LCMS for $C_{10}H_{11}ClN_5O_2$ (M+H)$^+$: m/z=268.1.

Example 27

4-Amino-N-(3-chlorobenzyl)-N'-hydroxy-1,2,5-oxa-diazole-3-carboximidamide

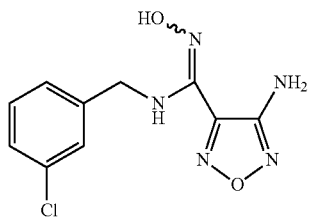 [SMILES: Nc1nonc1C(=NO)NCc1cccc(Cl)c1]

This compound was prepared according to the procedure of Example 1 using 3-chlorobenzylamine as the starting material. LCMS for $C_{10}H_{11}ClN_5O_2$ (M+H)$^+$: m/z=268.0.

Example 28

4-Amino-N-(4-chlorobenzyl)-N'-hydroxy-1,2,5-oxa-diazole-3-carboximidamide

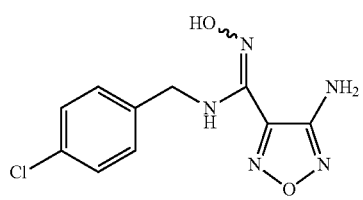 [SMILES: Nc1nonc1C(=NO)NCc1ccc(Cl)cc1]

This compound was prepared according to the procedure of Example 1 using 4-chlorobenzylamine as the starting material. LCMS for $C_{10}H_{11}ClN_5O_2$ (M+H)$^+$: m/z=268.1.

Example 29

4-Amino-N'-hydroxy-N-[3-(trifluoromethyl)benzyl]-1,2,5-oxadiazole-3-carboximidamide

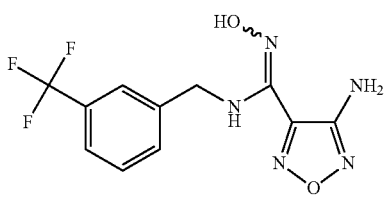 [SMILES: Nc1nonc1C(=NO)NCc1cccc(C(F)(F)F)c1]

This compound was prepared according to the procedure of Example 1 using 3-(trifluoromethyl)benzylamine as the starting material. LCMS for $C_{11}H_{11}F_3N_5O_2$ (M+H)$^+$: m/z=302.2.

Example 30

4-Amino-N'-hydroxy-N-(2-methoxybenzyl)-1,2,5-oxa diazole-3-carboximidamide

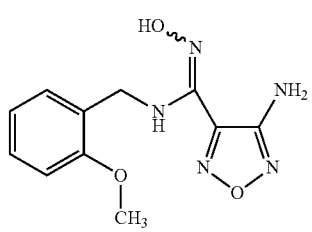 [SMILES: COc1ccccc1CNC(=NO)c1nonc1N]

This compound was prepared according to the procedure of Example 1 using 2-(methoxy)benzylamine as the starting material. LCMS for $C_{11}H_{14}N_5O_3$ (M+H)$^+$: m/z=264.0.

Example 31

4-Amino-N'-hydroxy-N-(pyridin-2-ylmethyl)-1,2,5-oxadiazole-3-carboximidamide

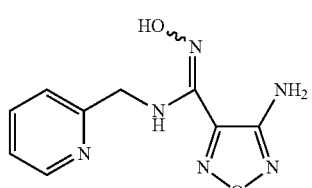

This compound was prepared according to the procedure of Example 1 using 2-(aminomethyl)pyridine as the starting material. LCMS for $C_9H_{11}N_6O_2$ (M+H)$^+$: m/z=235.0.

Example 32

4-Amino-N'-hydroxy-N-(2-phenylethyl)-1,2,5-oxa-diazole-3-carboximidamide

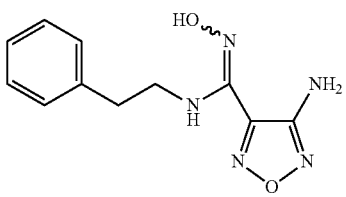 [SMILES: Nc1nonc1C(=NO)NCCc1ccccc1]

This compound was prepared according to the procedure of Example 1 using phenethylamine as the starting material. LCMS for $C_{11}H_{14}N_5O_2$ (M+H)$^+$: m/z=248.0.

Example 33

4-Amino-N'-hydroxy-N-1H-indol-5-yl-1,2,5-oxadiazole-3-carboximidamide

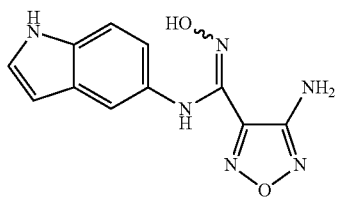 [SMILES: Nc1nonc1C(=NO)Nc1ccc2[nH]ccc2c1]

This compound was prepared according to the procedure of Example 1 using 5-aminoindole as the starting material. LCMS for $C_{11}H_{11}N_6O_2$ (M+H)$^+$: m/z=259.2.

Example 34

4-Amino-N-butyl-N'-hydroxy-1,2,5-oxadiazole-3-carboximidamide

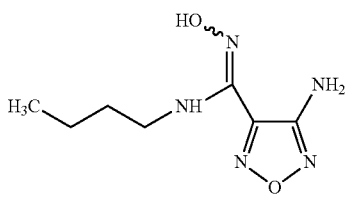

This compound was prepared according to the procedure of Example 1 using butylamine as the starting material. LCMS for $C_7H_{14}N_5O_2$ (M+H)$^+$: m/z=200.2.

Example 35

N-{4-[[(3-Chlorophenyl)amino](hydroxyimino)methyl]-1,2,5-oxadiazol-3-yl}-2-phenylacetamide

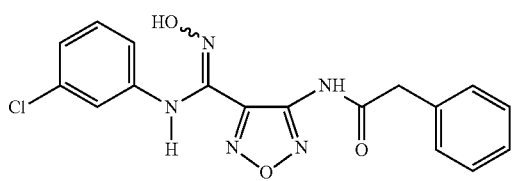 [SMILES: O=C(Cc1ccccc1)Nc1nonc1C(=NO)Nc1cccc(Cl)c1]

Step 1: 3-(4-Amino-1,2,5-oxadiazol-3-yl)-4-(3-chlorophenyl)-1,2,4-oxadiazol-5(4H)-one

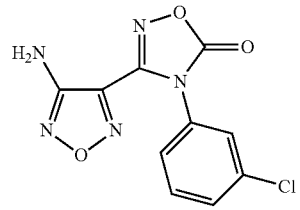 [SMILES: Nc1nonc1-c1noc(=O)n1-c1cccc(Cl)c1]

A solution of 4-amino-N-(3-chlorophenyl)-N'-hydroxy-1,2,5-oxadiazole-3-carboximidamide (540 mg, 2.1 mmol) and N,N-carbonyldiimidazole (380 mg, 2.3 mmol) in tetrahydrofuran (10 mL) was heated at 80° C. for 1 h. The reaction mixture was diluted with ethyl acetate (150 mL) and washed with 0.1 N HCl (3×75 mL) and brine (75 mL). The organic layer was dried with sodium sulfate, filtered, and concentrated to give the desired product (560 mg, 94%) as a white solid which was used without further purification. LCMS for $C_{10}H_7ClN_5O_3$ (M+H)$^+$: m/z=279.9.

Step 2: N-{4-[[(3-Chlorophenyl)amino](hydroxyimino)methyl]-1,2,5-oxadiazol-3-yl}-2-phenylacetamide A solution of 3-(4-amino-1,2,5-oxadiazol-3-yl)-4-(3-chlorophenyl)-1,2,4-oxadiazol-5(4H)-one (30.0 mg, 0.107 mmol) and 4-dimethylaminopyridine (2.6 mg, 0.021 mmol) in pyridine (0.50 mL) was treated with benzeneacetyl chloride (42.6 μL, 0.322 mmol) and stirred for 4 h. The reaction mixture was concentrated and rediluted with ethanol (1.0 mL) and 2 M of sodium hydroxide in water (0.30 mL) stirred for 45 min. Purification of the crude reaction mixture by preparative HPLC gave the desired product (18 mg, 45%). LCMS for $C_{17}H_{15}ClN_5O_3$ (M+H)$^+$: m/z=371.9.

Example 36

N-{4-[[(3-Chlorophenyl)amino](hydroxyimino)methyl]-1,2,5-oxadiazol-3-yl}benzamide

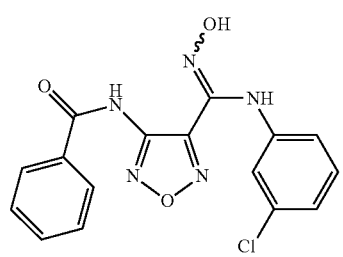 [SMILES: O=C(Nc1nonc1C(=NO)Nc1cccc(Cl)c1)c1ccccc1]

This compound was prepared according to the procedure of Example 35 using benzoyl chloride as the starting material. LCMS for $C_{16}H_{13}ClN_5O_3$ (M+H)$^+$: m/z=358.1.

Example 37

N-{4-[(Benzylamino)(hydroxyimino)methyl]-1,2,5-oxadiazol-3-yl}benzamide

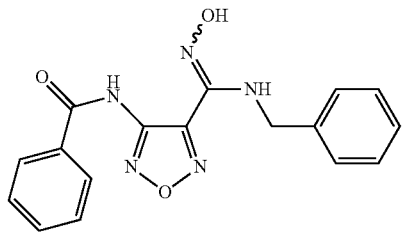 [SMILES: O=C(Nc1nonc1C(=NO)NCc1ccccc1)c1ccccc1]

This compound was prepared according to the procedure of Example 35 using 3-(4-amino-1,2,5-oxadiazol-3-yl)-4-benzyl-1,2,4-oxadiazol-5(4H)-one and benzoyl chloride as the starting materials. LCMS for $C_{17}H_{16}N_5O_3$ (M+H)$^+$: m/z=338.2.

Example 38

N-benzyl-4-(benzylamino)-N'-hydroxy-1,2,5-oxadiazole-3-carboximidamide

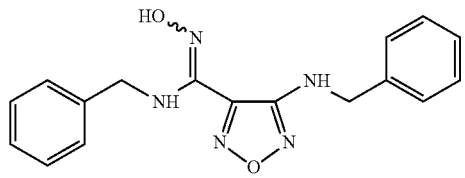 [SMILES: ON=C(NCc1ccccc1)c1nonc1NCc1ccccc1]

Step 1. 4-Benzyl-3-[4-(benzylamino)-1,2,5-oxadiazol-3-yl]-1,2,4-oxadiazol-5(4H)-one

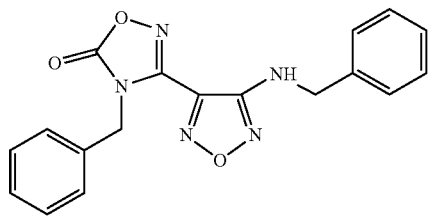 [SMILES: O=c1onc(-c2nonc2NCc2ccccc2)n1Cc1ccccc1]

A solution of 3-(4-amino-1,2,5-oxadiazol-3-yl)-4-benzyl-1,2,4-oxadiazol-5(4H)-one (60.0 mg, 0.231 mmol) and benzyl bromide (28 μL, 0.23 mmol) was heated at 150° C. for 5 h. Additional benzyl bromide (28 μL) was added to the incomplete reaction and heating was continued for another 16 h. Purification of the crude reaction mixture by preparative HPLC gave the desired product (12 mg, 15%). LCMS for $C_{18}H_{16}N_5O_3$ (M+H)$^+$: m/z=349.9.

Step 2. N-benzyl-4-(benzylamino)-N'-hydroxy-1,2,5-oxadiazole-3-carboximidamide

A solution of 4-benzyl-3-[4-(benzylamino)-1,2,5-oxadiazol-3-yl]-1,2,4-oxadiazol-5(4H)-one (12 mg, 34 μmol) in ethanol (1 mL) was treated with 2 M sodium hydroxide in water (300 μL) and stirred at 25° C. for 30 min. The reaction mixture was quenched with acetic acid and purified by preparative HPLC to give the desired product (10 mg, 90%) as a white solid. LCMS for $C_{17}H_{18}N_5O_2$ (M+H)$^+$: m/z=324.2.

Example 39

4-[(Anilinocarbonyl)amino]-N-(3-chlorophenyl)-N'-hydroxy-1,2,5-oxadiazole-3-carboximidamide

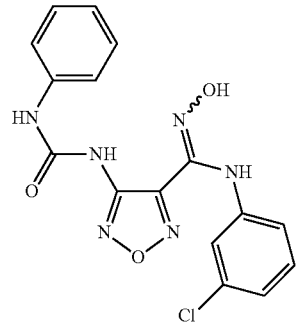 [SMILES: O=C(Nc1ccccc1)Nc1nonc1C(=NO)Nc1cccc(Cl)c1]

Example 40

4-[Bis(anilinocarbonyl)amino]-N-(3-chlorophenyl)-N'-hydroxy-1,2,5-oxadiazole-3-carboximidamide

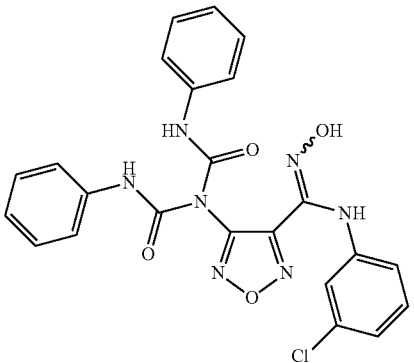 [SMILES: O=C(Nc1ccccc1)N(C(=O)Nc1ccccc1)c1nonc1C(=NO)Nc1cccc(Cl)c1]

Step 1. N-{4-[4-(3-Chlorophenyl)-5-oxo-4,5-dihydro-1,2,4-oxadiazol-3-yl]-1,2,5-oxadiazol-3-yl}-N'-phenylurea and N-{4-[4-(3-chlorophenyl)-5-oxo-4,5-dihydro-1,2,4-oxadiazol-3-yl]-1,2,5-oxadiazol-3-yl}-N,N'-diphenyldicarbonimidic diamide

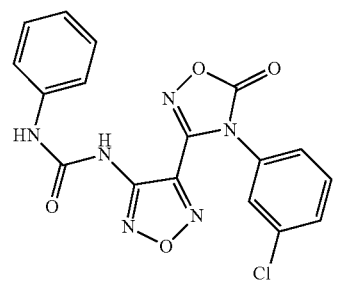

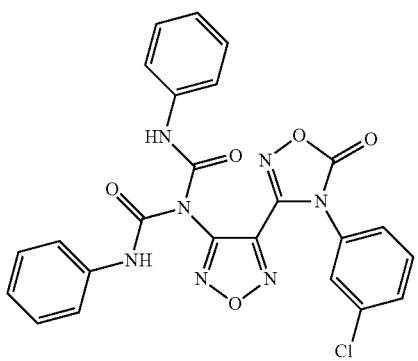

A solution of 3-(4-amino-1,2,5-oxadiazol-3-yl)-4-(3-chlorophenyl)-1,2,4-oxadiazol-5(4H)-one (30 mg, 0.1 mmol) in pyridine (0.5 mL, 6.2 mmol) was treated with phenyl isocyanate (12 μL, 0.1 mmol) and stirred for 2 h. The reaction mixture was treated with 4-dimethylaminopyridine (3 mg, 24 wimp and additional phenyl isocyanate (10 μL, 92 μmol) and stirred for another 2 h. Purification of the crude reaction mixture by preparative HPLC gave the desired products N-{4-[4-(3-chlorophenyl)-5-oxo-4,5-dihydro-1,2,4-oxadiazol-3-yl]-1,2,5-oxadiazol-3-yl}-N'-phenylurea (5 mg, 12%) and N-{4-[4-(3-chlorophenyl)-5-oxo-4,5-dihydro-1,2,4-oxadiazol-3-yl]-1,2,5-oxadiazol-3-yl}-N,N'-diphenyldicarbonimidic diamide (7 mg, 12%). LCMS for $C_{17}H_{12}ClN_6O_4$ (M+H)$^+$: m/z=398.9 and LCMS for $C_{24}H_{16}ClN_7O_5Na$ (M+H)$^+$: m/z=540.0.

Step 2. 4-[(Anilinocarbonyl)amino]-N-(3-chlorophenyl)-N'-hydroxy-1,2,5-oxadiazole-3-carboximidamide and 4-[Bis(anilinocarbonyl)amino]-N-(3-chlorophenyl)-N'-hydroxy-1,2,5-oxadiazole-3-carboximidamide A solution of N-{4-[4-(3-chlorophenyl)-5-oxo-4,5-dihydro-1,2,4-oxadiazol-3-yl]-1,2,5-oxadiazol-3-yl}-N'-phenylurea (17 mg, 43 μmol) in ethanol (1.5 mL) was treated with 2.0 M sodium hydroxide in water (0.3 mL) and stirred for 30 min. Purification of the crude reaction mixture by preparative HPLC gave the desired product 4-[(anilinocarbonyl)amino]-N-(3-chlorophenyl)-N'-hydroxy-1,2,5-oxadiazole-3-carboximidamide (6 mg, 38%). LCMS for $C_{16}H_{14}ClN_6O_3$ (M+H)$^+$: m/z=373.0.

4-[Bis(anilino carbonyl)amino]-N-(3-chlorophenyl)-N'-hydroxy-1,2,5-oxadiazole-3-carboximidamide was prepared in a similar fashion from N-{4-[4-(3-chlorophenyl)-5-oxo-4,5-dihydro-1,2,4-oxadiazol-3-yl]-1,2,5-oxadiazol-3-yl}-N,N'-diphenyldicarbonimidic diamide. LCMS for $C_{23}H_{19}ClN_7O_4$ (M+H)$^+$: m/z=492.0.

Example 41 tert-Butyl {4-[({4-[(E,Z)-[(3-chlorophenyl)amino](hydroxyimino)methyl]-1,2,5-oxadiazol-3-yl}amino)carbonyl]benzyl}carbamate

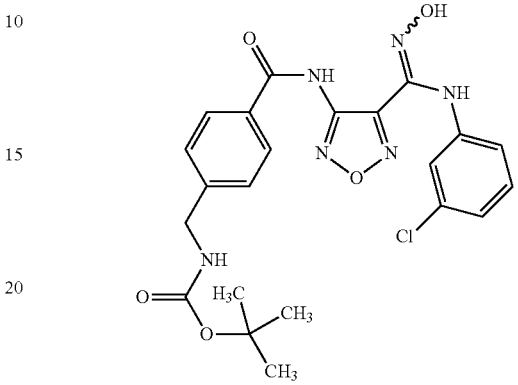

Step 1. tert-Butyl {4-[({4-[4-(3-chlorophenyl)-5-oxo-4,5-dihydro-1,2,4-oxadiazol-3-yl]-1,2,5-oxadiazol-3-yl}amino)carbonyl]benzyl}carbamate

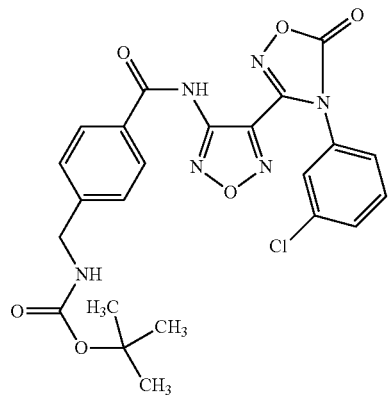 [SMILES: CC(C)(C)OC(=O)NCc1ccc(C(=O)Nc2nonc2-c2noc(=O)n2-c2cccc(Cl)c2)cc1]

A solution of 3-(4-amino-1,2,5-oxadiazol-3-yl)-4-(3-chlorophenyl)-1,2,4-oxadiazol-5(4H)-one (50 mg, 0.18 mmol) and 4-{[(tert-butoxycarbonyl)amino]methyl}benzoic acid (49 mg, 0.2 mmol) in dichloromethane (3.5 mL) was treated with 4-dimethylaminopyridine (13 mg, 0.1 mmol) and N,N-diisopropylethylamine (93 μL, 0.54 mmol). After the reaction mixture turned clear, it was treated with bromotris(pyrrolydino)phosphonium hexafluorophosphate (50 mg, 0.11 mmol) and additional N,N-diisopropylethylamine (93 μL, 0.54 mmol). The reaction mixture was stirred for 16 h, treated with additional bromotris(pyrrolydino)phosphonium hexafluorophosphate (50 mg, 0.11 mmol), and stirred for another 6 h. The reaction mixture was diluted with ethyl acetate (60 mL) and washed with 0.1 M HCl (2×25 mL) and brine (25 mL), dried with sodium sulfate, filtered, and concentrated. Purification of the crude reaction mixture by preparative LCMS gave the desired product (22 mg, 24%).

LCMS for $C_{19}H_{14}ClN_6O_6$ ([M-tBu+H]+H)$^+$: m/z=457.1.

Step 2. tert-Butyl {-[({4-[(E,Z)-[(3-chlorophenyl)
amino](hydroxyimino)methyl]-1,2,5-oxadiazol-3-
yl}amino)carbonyl]benzyl}carbamate This compound was prepared according to the procedure of Example 38, Step 2, using tert-butyl {4-[({4-[4-(3-chlorophenyl)-5-oxo-4,5-dihydro-1,2,4-oxadiazol-3-yl]-1,2,5-oxadiazol-3-yl}amino)carbonyl]benzyl}carbamate as the starting material. LCMS for $C_{22}H_{24}ClN_6O_5$ (M+H)$^+$: m/z=487.0.

Example 42

4-(Aminomethyl)-N-{4-[(E,Z)-[(3-chlorophenyl)
amino](hydroxyimino)methyl]-1,2,5-oxadiazol-3-
yl}benzamide trifluoroacetate

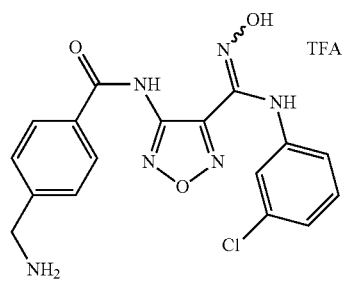 [SMILES: NCc1ccc(C(=O)Nc2nonc2C(=NO)Nc2cccc(Cl)c2)cc1]

Step 1. 4-(Aminomethyl)-N-{4-[4-(3-chlorophenyl)-
5-oxo-4,5-dihydro-1,2,4-oxadiazol-3-yl]-1,2,5-oxa-
diazol-3-yl}benzamide trifluoroacetate

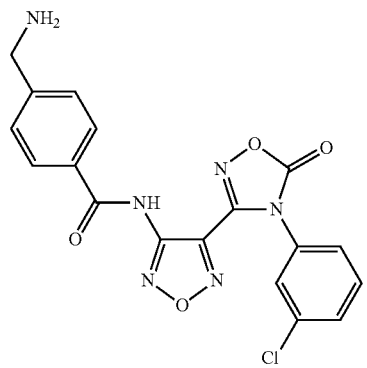 [SMILES: NCc1ccc(C(=O)Nc2nonc2-c2noc(=O)n2-c2cccc(Cl)c2)cc1]

A solution of 3-(4-amino-1,2,5-oxadiazol-3-yl)-4-(3-chlorophenyl)-1,2,4-oxadiazol-5(4H)-one (0.5 g, 1.8 mmol) and 4-{[(tert-butoxycarbonyl)amino]methyl}benzoic acid (0.67 g, 2.7 mmol) in dichloromethane (35 mL) was treated with 4-dimethylaminopyridine (0.13 g, 1.1 mmol) and N,N-diisopropylethylamine (0.93 mL, 5.4 mmol) followed by bromotris(pyrrolydino)phosphonium hexafluorophosphate (1.3 g, 2.7 mmol) and additional N,N-diisopropylethylamine (0.93 mL, 5.4 mmol). The reaction mixture was stirred for 16 h, diluted with ethyl acetate (~200 mL) and washed with 0.1 M HCl (2×100 mL) and brine (25 mL), dried with sodium sulfate, filtered, and concentrated. Purification of the crude reaction mixture on silica gel gave the intermediate tert-butyl {4-[({4-[4-(3-chlorophenyl)-5-oxo-4,5-dihydro-1,2,4-oxadiazol-3-yl]-1,2,5-oxadiazol-3-yl}amino)carbonyl]benzyl}carbamate. This material was diluted with dichloromethane (30 mL), treated with 4.0 M HCl in 1,4-dioxane (4.5 mL), and stirred for 1 h. The reaction mixture was concentrated and purified by preparative LCMS to give the desired product (542 mg, 58%). LCMS for $C_{18}H_{14}ClN_6O_4$ (M+H)$^+$: m/z=413.0.

Step 2. 4-(Aminomethyl)-N-{4-[(E,Z)-[(3-chlorophenyl)amino](hydroxyimino)methyl]-1,2,5-oxadiazol-3-yl}benzamide trifluoroacetate This compound was prepared according to the procedure of Example 38, Step 2, using 4-(aminomethyl)-N-{4-[4-(3-chlorophenyl)-5-oxo-4,5-dihydro-1,2,4-oxadiazol-3-yl]-1,2,5-oxadiazol-3-yl}benzamide trifluoroacetate as the starting material. LCMS for $C_{17}H_{16}ClN_6O_3$ (M+H)$^+$: m/z=387.0.

Example 43

4-{[(Benzylamino)carbonyl]amino}-N-(3-bromo-4-
fluorophenyl)-N'-hydroxy-1,2,5-oxadiazole-3-car-
boximidamide

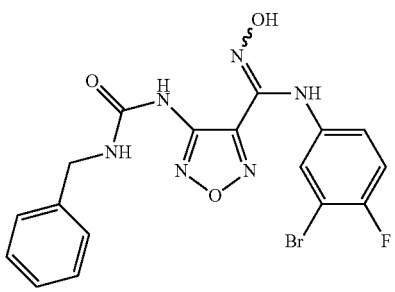 [SMILES: O=C(NCc1ccccc1)Nc1nonc1C(=NO)Nc1ccc(F)c(Br)c1]

A solution of 3-(4-amino-1,2,5-oxadiazol-3-yl)-4-(3-bromo-4-fluorophenyl)-1,2,4-oxadiazol-5(4H)-one (30 mg, 88 μmol) and 4-dimethylaminopyridine (5 mg, 40 μmol) in pyridine (0.5 mL) was treated with benzyl isocyanate (29 mg, 0.2 mmol) and heated in the microwave at 150° C. for 20 min. The reaction mixture was concentrated and purified by preparative LCMS to give the intermediate N-benzyl-N'-{4-[4-(3-bromo-4-fluorophenyl)-5-oxo-4,5-dihydro-1,2,4-oxadiazol-3-yl]-1,2,5-oxadiazol-3-yl}urea. This material was diluted with ethanol (1.5 mL), treated with 2.0 M sodium hydroxide in water (0.3 mL), and stirred for 30 min. Purification of the crude reaction mixture by preparative HPLC gave the desired product (11 mg, 28%). LCMS for $C_{17}H_{15}BrFN_6O_3$ (M+H)$^+$: m/z=448.9, 451.0.

Example 44

4-Amino-N-(3-bromo-4-fluorophenyl)-N'-hydroxy-
1,2,5-thiadiazole-3-carboximidamide

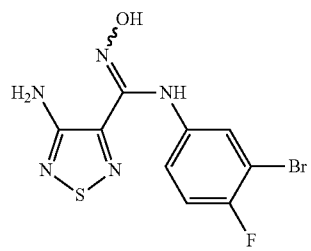 [SMILES: Nc1nsnc1C(=NO)Nc1ccc(F)c(Br)c1]

Step 1. 4-Amino-N-(3-bromo-4-fluorophenyl)-1,2,5-thiadiazole-3-carboxamide

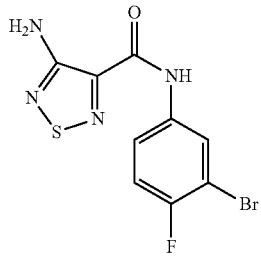 [SMILES: Nc1nsnc1C(=O)Nc1ccc(F)c(Br)c1]

A solution of 4-amino-1,2,5-thiadiazole-3-carboxylic acid (250 mg, 1.7 mmol) and 3-bromo-4-fluoroaniline (393 mg, 2.1 mmol) in N,N-dimethylformamide (5 mL) was treated with O-(benzotriazol-1-yl)-N,N,N',N'-tetramethyluronium hexafluorophosphate (784 mg, 2.1 mmol) followed by N,N-diisopropylethylamine (0.36 mL, 2.1 mmol) and stirred for 16 h. The reaction mixture was diluted with brine (50 mL) and 0.1 N HCl (100 mL) and extracted with ethyl acetate (2×150 mL). The combined organic extracts were washed with brine (50 mL), dried with sodium sulfate, filtered, and concentrated. Purification of the crude reaction mixture on silica gel gave the desired product (414 mg, 76%). LCMS for $C_9H_7BrFN_4OS$ (M+H)$^+$: m/z=316.9, 318.8.

Step 2. 4-Amino-N-(3-bromo-4-fluorophenyl)-1,2,5-thiadiazole-3-carbothioamide

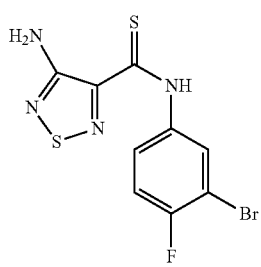 [SMILES: Nc1nsnc1C(=S)Nc1ccc(F)c(Br)c1]

A solution of 4-amino-N-(3-bromo-4-fluorophenyl)-1,2,5-thiadiazole-3-carboxamide (225 mg, 0.7 mmol) and 2,4-bis(4-methoxyphenyl)-2,4-dithioxo-1,3,2,4-dithiadiphosphetane (570 mg, 1.4 mmol) in toluene (6.8 mL) was stirred at 95° C. for 16 h. The reaction mixture was diluted with ethyl acetate (50 mL) and the insoluble salts were filtered. The filtrate was concentrated to a crude residue which was purified on silica gel to give the desired product (130 mg, 55%). LCMS for $C_9H_7BrFN_4S_2$ (M+H)$^+$: m/z=332.8, 334.9.

Step 3. Methyl 4-amino-N-(3-bromo-4-fluorophenyl)-1,2,5-thiadiazole-3-carbimidothioate

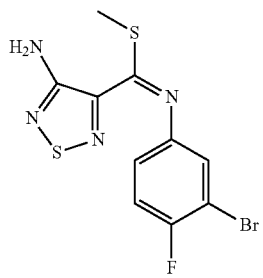

A solution of 4-amino-N-(3-bromo-4-fluorophenyl)-1,2,5-thiadiazole-3-carbothioamide (130 mg, 0.4 mmol) in dichloromethane (5.2 mL) was treated with methyl trifluoromethanesulfonate (64 μL, 0.6 mmol) followed by N,N-diisopropylethylamine (102 μL, 0.6 mmol) and stirred for 1 h. The reaction mixture was diluted with dichloromethane (100 mL), washed with water (50 mL) and brine (50 mL), dried with sodium sulfate, filtered, and concentrated to give the desired product (133 mg, 98%). LCMS for $C_{10}H_9BrFN_4S_2$ (M+H)$^+$: m/z=346.8, 348.8.

Step 4. 4-Amino-N-(3-bromo-4-fluorophenyl)-N'-hydroxy-1,2,5-thiadiazole-3-carboximidamide A solution of methyl 4-amino-N-(3-bromo-4-fluorophenyl)-1,2,5-thiadiazole-3-carbimidothioate (78 mg, 0.22 mmol) in ethanol (2.3 mL) was treated with hydroxylamine hydrochloride (62 mg, 0.9 mmol) followed by N,N-diisopropylethylamine (180 μL, 1.0 mmol) and stirred at 90° C. for 16 h. The reaction mixture was purified by preparative HPLC to give the desired product (58 mg, 78%). LCMS for $C_9H_8BrFN_5OS$ (M+H)$^+$: m/z=331.9, 333.9.

Example 45

4-Amino-N-(6-chloropyridin-2-yl)-N'-hydroxy-1,2,5-oxadiazole-3-carboximidamide trifluoroacetate

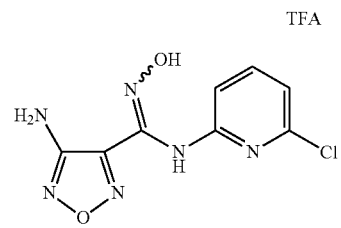 [SMILES: Nc1nonc1C(=NO)Nc1cccc(Cl)n1]

Step 1. 4-Amino-N-(6-chloropyridin-2-yl)-1,2,5-oxadiazole-3-carboxamide

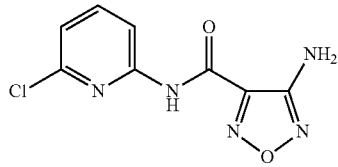 [SMILES: Nc1nonc1C(=O)Nc1cccc(Cl)n1]

A solution of 4-amino-1,2,5-oxadiazole-3-carboxylic acid (0.4 g, 3.1 mmol) and 6-chloropyridin-2-amine (0.56 g, 4.3 mmol) in N,N-dimethylformamide (6.2 mL) was treated with N,N,N',N'-tetramethyl-O-(7-azabenzotriazol-1-yl)uronium hexafluorophosphate (1.4 g, 3.7 mmol) followed by N,N-diisopropylethylamine (0.76 mL, 4.3 mmol) at 0° C. The reaction mixture was stirred at 25° C. for 2 h, poured into saturated NaHCO$_3$ (50 mL) and extracted with ethyl acetate (100 mL). The organic layer was separated and washed with brine (25 mL), dried with sodium sulfate, filtered, and concentrated to a crude solid. The crude solid was washed with ethyl acetate and filtered. The filtrate was concentrated and purified on silica gel to give the desired product with some impurities. The impurities were removed by washing the solid with chloroform to yield the desired product (65 mg, 9%). LCMS for $C_8H_7ClN_5O_2$ (M+H)$^+$: m/z=240.1.

Step 2. 4-Amino-N-(6-chloropyridin-2-yl)-1,2,5-oxadiazole-3-carboximidoyl chloride

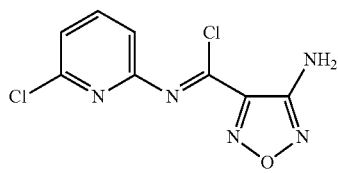 [SMILES: Nc1nonc1/C(Cl)=N/c1cccc(Cl)n1]

A solution of 4-amino-N-(6-chloropyridin-2-yl)-1,2,5-oxadiazole-3-carboxamide (62 mg, 0.26 mmol) in benzene (5 mL) was treated with phosphorus pentachloride (0.12 g, 0.57 mmol) and stirred at reflux for 3 h. The reaction mixture was concentrated and rediluted with benzene and concentrated (3×) to give the desired product which was used immediately in the next step.

Step 3. 4-Amino-N-(6-chloropyridin-2-yl)-N'-hydroxy-1,2,5-oxadiazole-3-carboximidamide trifluoroacetate A solution of 4-amino-N-(6-chloropyridin-2-yl)-1,2,5-oxadiazole-3-carboximidoyl chloride (67 mg, 0.26 mmol) in tetrahydrofuran (3 mL) was treated with 20 M hydroxylamine in water (0.26 mL, 5 mmol) and stirred at 60° C. for 4 h. The reaction mixture was treated with additional 20 M hydroxylamine in water (0.13 mL, 2.5 mmol) and heated at 70° C. for 1.5 h. The reaction mixture was concentrated to a crude residue which was purified by preparative LCMS to give the desired product (12 mg, 12%). LCMS for $C_8H_8ClN_6O_2$ (M+H)$^+$: m/z=255.0.

Example 46

4-Amino-N-(3-bromo-4-fluorophenyl)-N'-hydroxy-isothiazole-3-carboximidamide trifluoroacetate

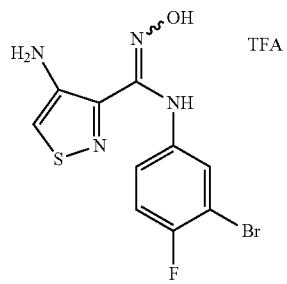 [SMILES: Nc1csnc1C(=NO)Nc1ccc(F)c(Br)c1]

Step 1. 4-Amino-N-(3-bromo-4-fluorophenyl)isothiazole-3-carboxamide

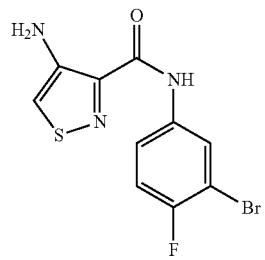

This compound was prepared according to the procedure of Example 44, Step 1, using 4-aminoisothiazole-3-carboxylic acid hydrochloride and 3-bromo-4-fluoroaniline as the starting materials. LCMS for $C_{10}H_8BrFN_3OS$ (M+H)$^+$: m/z=315.9, 317.9.

Step 2. 4-Amino-N-(3-bromo-4-fluorophenyl)isothiazole-3-carboximidoyl chloride

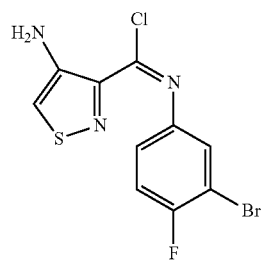

This compound was prepared according to the procedure of Example 45, Step 2, using 4-amino-N-(3-bromo-4-fluorophenyl)isothiazole-3-carboxamide as the starting material and was used immediately in the next step.

Step 3. 4-Amino-N-(3-bromo-4-fluorophenyl)-N'-hydroxyisothiazole-3-carboximidamide trifluoroacetate This compound was prepared according to the procedure of Example 45, Step 3, using 4-amino-N-(3-bromo-4-fluorophenyl)isothiazole-3-carboximidoyl chloride as the starting material. LCMS for $C_{10}H_9BrFN_4OS$ (M+H)$^+$: m/z=330.9, 332.9.

Example 47

4-Amino-N-(2,5-dichlorophenyl)-N'-hydroxy-1,2,5-oxadiazole-3-carboximidamide

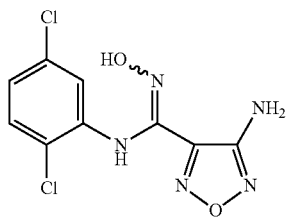 [SMILES: Nc1nonc1C(=NO)Nc1cc(Cl)ccc1Cl]

Step 1. 4-Amino-N-(2,5-dichlorophenyl)-1,2,5-oxadiazole-3-carboxamide

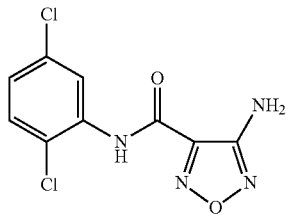 [SMILES: Nc1nonc1C(=O)Nc1cc(Cl)ccc1Cl]

This compound was prepared according to the procedure of Example 45, Step 1, using 4-amino-1,2,5-oxadiazole-3-carboxylic acid and 2,5-dichloroaniline as the starting materials. LCMS for $C_9H_7Cl_2N_4O_2$ (M+H)$^+$: m/z=273.0.

Step 2. 4-Amino-N-(2,5-dichlorophenyl)-1,2,5-oxadiazole-3-carbothioamide

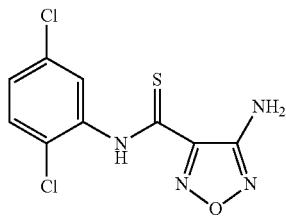 [SMILES: Nc1nonc1C(=S)Nc1cc(Cl)ccc1Cl]

This compound was prepared according to the procedure of Example 44, Step 2, using 4-amino-N-(2,5-dichlorophenyl)-1,2,5-oxadiazole-3-carboxamide as the starting material. LCMS for $C_9H_7Cl_2N_4OS$ (M+H)$^+$: m/z=289.0.

Step 3. Methyl 4-amino-N-(2,5-dichlorophenyl)-1,2,5-oxadiazole-3-carbimidothioate

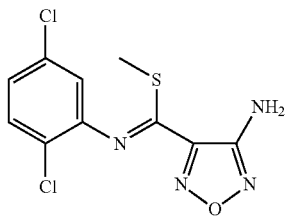 [SMILES: CS/C(=N\c1cc(Cl)ccc1Cl)c1nonc1N]

This compound was prepared according to the procedure of Example 44, Step 3, using 4-amino-N-(2,5-dichlorophenyl)-1,2,5-oxadiazole-3-carbothioamide as the starting material and was used immediately in the next step.

Step 4. 4-Amino-N-(2,5-dichlorophenyl)-N'-hydroxy-1,2,5-oxadiazole-3-carboximidamide This compound was prepared according to the procedure of Example 44, Step 4, using methyl 4-amino-N-(2,5-dichlorophenyl)-1,2,5-oxadiazole-3-carbimidothioate as the starting material. LCMS for $C_9H_8Cl_2N_5O_2$ (M+H)$^+$: m/z=288.0.

Example 48

N-{4-[(E,Z)-[(3-Bromo-4-fluorophenyl)amino](hydroxyimino)methyl]-1,2,5-oxadiazol-3-yl}morpholine-4-carboxamide

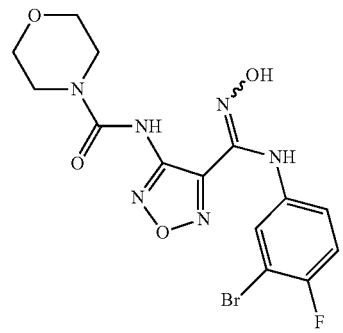 [SMILES: O=C(Nc1nonc1C(=NO)Nc1ccc(F)c(Br)c1)N1CCOCC1]

Step 1. Phenyl {4-[4-(3-bromo-4-fluorophenyl)-5-oxo-4,5-dihydro-1,2,4-oxadiazol-3-yl]-1,2,5-oxadiazol-3-yl}carbamate

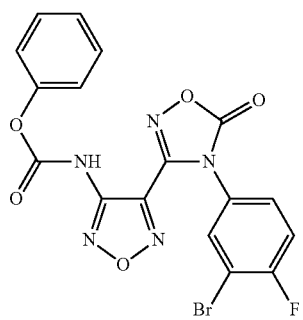 [SMILES: O=C(Nc1nonc1-c1noc(=O)n1-c1ccc(F)c(Br)c1)Oc1ccccc1]

This compound was prepared according to the procedure of Example 35 using 3-(4-amino-1,2,5-oxadiazol-3-yl)-4-(3-bromo-4-fluorophenyl)-1,2,4-oxadiazol-5(4H)-one and phenyl chloroformate as the starting materials. LCMS for $C_{17}H_{10}BrFN_5O_5$ (M+H)$^+$: m/z=461.9, 463.7.

Step 2. N-{4-[(E,Z)-[(3-Bromo-4-fluorophenyl)amino](hydroxyimino)methyl]-1,2,5-oxadiazol-3-yl}morpholine-4-carboxamide A solution of phenyl {4-[4-(3-bromo-4-fluorophenyl)-5-oxo-4,5-dihydro-1,2,4-oxadiazol-3-yl]-1,2,5-oxadiazol-3-yl}carbamate (25 mg, 54 µmol) in dichloromethane (1 mL) was treated with morpholine (14 µL, 0.16 mmol) and stirred for 2 h. The reaction mixture was concentrated to a crude residue which was diluted with ethanol (1 mL), treated with 2.0 M sodium hydroxide in water (0.15 mL, 3 mmol), and stirred for 45 min. The reaction mixture was purified by preparative HPLC to give the desired product (6 mg, 26%). LCMS for $C_{14}H_{15}BrFN_6O_4$ (M+H)$^+$: m/z=428.9, 430.9.

Example 49

N-(3-Bromo-4-fluorophenyl)-N'-hydroxy-4-(methylamino)-1,2,5-oxadiazole-3-carboximidamide

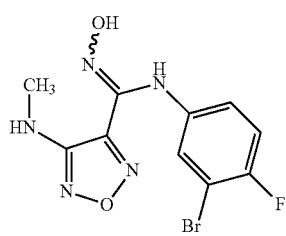 [SMILES: CNc1nonc1C(=NO)Nc1ccc(F)c(Br)c1]

Step 1. N-{4-[4-(3-Bromo-4-fluorophenyl)-5-oxo-4,5-dihydro-1,2,4-oxadiazol-3-yl]-1,2,5-oxadiazol-3-yl}-2,2,2-trifluoroacetamide

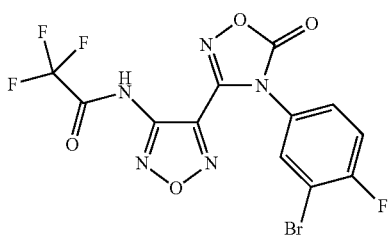 [SMILES: O=C(Nc1nonc1-c1noc(=O)n1-c1ccc(F)c(Br)c1)C(F)(F)F]

A solution of 3-(4-amino-1,2,5-oxadiazol-3-yl)-4-(3-bromo-4-fluorophenyl)-1,2,4-oxadiazol-5(4H)-one (0.4 g, 1.2 mmol) in pyridine (6.5 mL) was treated with 4-dimethylaminopyridine (71 mg, 0.6 mmol) and trifluoroacetic anhydride (0.41 mL, 2.9 mmol) and stirred for 20 min. The reaction mixture was concentrated to a crude residue which was purified by silica gel to give the desired product (0.46 g, 89%). LCMS for $C_{12}H_5BrF_4N_5O_4$ (M+H)$^+$: m/z=438.0, 439.9.

Step 2. 4-(3-Bromo-4-fluorophenyl)-3-[4-(methylamino)-1,2,5-oxadiazol-3-yl]-1,2,4-oxadiazol-5(4H)-one

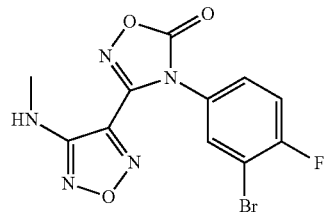 [SMILES: CNc1nonc1-c1noc(=O)n1-c1ccc(F)c(Br)c1]

A solution of N-{4-[4-(3-bromo-4-fluorophenyl)-5-oxo-4,5-dihydro-1,2,4-oxadiazol-3-yl]-1,2,5-oxadiazol-3-yl}-2,2,2-trifluoroacetamide (0.59 mg, 1.3 mmol) in N,N-dimethylformamide (3 mL) was treated with potassium carbonate (0.28 g, 2.0 mmol) followed by methyl iodide (125 µL, 2 mmol) and stirred for 2 h. The reaction mixture was treated with additional methyl iodide (200 µL, 3.2 mmol) and stirred for 16 h. The reaction mixture was diluted with water (100 mL) and brine (25 mL) and extracted with ethyl acetate (2×100 mL). The combined organic extracts were washed with water (3×100 mL) and brine (100 mL), dried with sodium sulfate, filtered, and concentrated to a crude residue which was purified by silica gel to give the desired product (0.39 g, 81%).

LCMS for $C_{11}H_8BrFN_5O_3$ (M+H)$^+$: m/z=355.9, 358.0.

Step 3. N-(3-Bromo-4-fluorophenyl)-N'-hydroxy-4-(methylamino)-1,2,5-oxadiazole-3-carboximidamide This compound was prepared according to the procedure of Example 38, Step 2, using 4-(3-bromo-4-fluorophenyl)-3-[4-(methylamino)-1,2,5-oxadiazol-3-yl]-1,2,4-oxadiazol-5(4H)-one as the starting material. LCMS for $C_{10}H_{10}BrFN_5O_2$ (M+H)$^+$: m/z=329.9, 332.0.

Example 50

N-{4-[(E,Z)-[(3-Bromo-4-fluorophenyl)amino](hydroxyimino)methyl]-1,2,5-oxadiazol-3-yl}piperidine-4-carboxamide trifluoroacetate

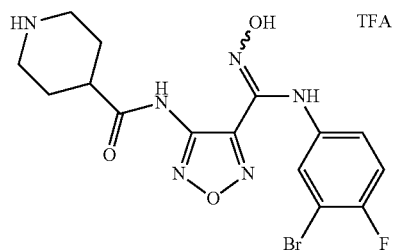 [SMILES: O=C(Nc1nonc1C(=NO)Nc1ccc(F)c(Br)c1)C1CCNCC1]

Step 1. N-{4-[4-(3-Bromo-4-fluorophenyl)-5-oxo-4,5-dihydro-1,2,4-oxadiazol-3-yl]-1,2,5-oxadiazol-3-yl}-1-(trifluoroacetyl)piperidine-4-carboxamide

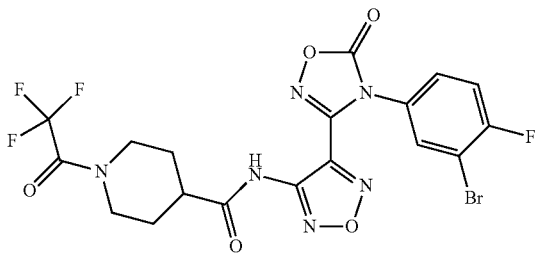 [SMILES: O=C(Nc1nonc1-c1noc(=O)n1-c1ccc(F)c(Br)c1)C1CCN(C(=O)C(F)(F)F)CC1]

This compound was prepared according to the procedure of Example 35 using 3-(4-amino-1,2,5-oxadiazol-3-yl)-4-(3-bromo-4-fluorophenyl)-1,2,4-oxadiazol-5(4H)-one and 1-(trifluoroacetyl)piperidine-4-carbonyl chloride as the starting materials. LCMS for $C_{18}H_{14}BrF_4N_6O_5$ (M+H)$^+$: m/z=549.0, 550.9.

Step 2. N-{4-[(E,Z)-[(3-Bromo-4-fluorophenyl)amino](hydroxyimino)methyl]-1,2,5-oxadiazol-3-yl}piperidine-4-carboxamide trifluoroacetate This compound was prepared according to the procedure of Example 38, Step 2, using N-{4-[4-(3-bromo-4-fluorophenyl)-5-oxo-4,5-dihydro-1,2,4-oxadiazol-3-yl]-1,2,5-oxadiazol-3-yl}-1-(trifluoroacetyl)piperidine-4-carboxamide as the starting material. LCMS for $C_{15}H_{17}BrFN_6O_3$ (M+H)$^+$: m/z=427.0, 429.9.

Example 51 tert-Butyl 4-{4-[({4-[(E,Z)-[(3-bromo-4-fluorophenyl)amino](hydroxyimino)methyl]-1,2,5-oxadiazol-3-yl}amino)carbonyl]benzyl}piperazine-1-carboxylate trifluoroacetate

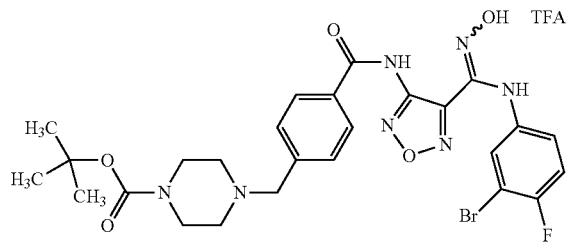 [SMILES: CC(C)(C)OC(=O)N1CCN(Cc2ccc(C(=O)Nc3nonc3C(=NO)Nc3ccc(F)c(Br)c3)cc2)CC1 ; "TFA"]

A solution of 3-(4-amino-1,2,5-oxadiazol-3-yl)-4-(3-bromo-4-fluorophenyl)-1,2,4-oxadiazol-5(4H)-one (30 mg, 88 µmol), 4-{[4-(tert-butoxycarbonyl)piperazin-1-yl]methyl}benzoic acid (84 mg, 0.26 mmol), and 4-dimethylaminopyridine (6.4 mg, 53 µmol) in pyridine (0.75 mL) was treated with phosphoryl chloride (25 µL, 0.27 mmol) dropwise at −15° C. The reaction mixture was heated in a microwave at 100° C. for 5 min. The reaction mixture was concentrated to residue which was rediluted with methanol (1 mL), treated with 2.0 M sodium hydroxide in water (0.3 mL, 0.6 mmol), and stirred for 30 min. The reaction mixture was quenched with acetic acid (50 µL, 0.9 mmol), filtered, and purified by preparative LCMS to give the desired product (29 mg, 45%). LCMS for $C_{26}H_{30}BrFN_7O_5$ (M+H)$^+$: m/z=618.0, 620.0.

Example 52

N-{4-[(E,Z)-[(3-Bromo-4-fluorophenyl)amino](hydroxyimino)methyl]-1,2,5-oxadiazol-3-yl}-4-(piperazin-1-ylmethyl)benzamide bis(trifluoroacetate)

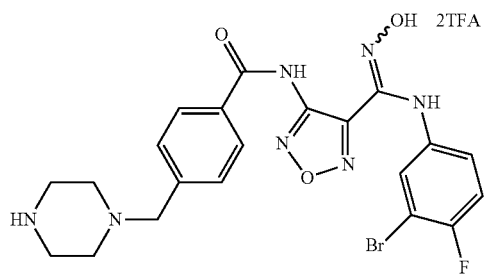 [SMILES: O=C(Nc1nonc1C(=NO)Nc1ccc(F)c(Br)c1)c1ccc(CN2CCNCC2)cc1 ; "2TFA"]

A solution of tert-butyl 4-{4-[({4-[(E,Z)-[(3-bromo-4-fluorophenyl)amino]-(hydroxyimino)-methyl]-1,2,5-oxadiazol-3-yl}amino)carbonyl]-benzyl}piperazine-1-carboxylate trifluoroacetate (25 mg, 34 µmol) in dichloromethane (2 mL) was treated with 4.0 M HCl in 1,4-dioxane (1 mL), and stirred for 1 h. The reaction mixture was concentrated and purified by preparative HPLC to give the desired product (15 mg, 59%). LCMS for $C_{21}H_{22}BrFN_7O_3$ (M+H)$^+$: m/z=518.0, 520.0.

Example 53

1-Benzoyl-N-{4-[(E,Z)-[(3-bromo-4-fluorophenyl)amino](hydroxyimino)methyl]-1,2,5-oxadiazol-3-yl}piperidine-4-carboxamide

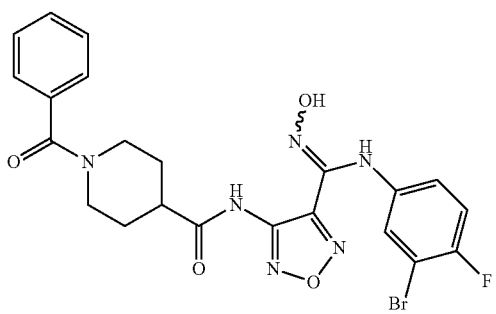 [SMILES: O=C(Nc1nonc1C(=NO)Nc1ccc(F)c(Br)c1)C1CCN(C(=O)c2ccccc2)CC1]

This compound was prepared according to the procedure of Example 35, Step 2, using N-{4-[4-(3-bromo-4-fluorophenyl)-5-oxo-4,5-dihydro-1,2,4-oxadiazol-3-yl]-1,2,5-oxadiazol-3-yl}piperidine-4-carboxamide trifluoroacetate and benzoyl chloride as the starting materials. LCMS for $C_{22}H_{21}BrFN_6O_4$ (M+H)$^+$: m/z=531.0, 5310.

Example 54

N(4)-{4-[(E,Z)-[(3-Bromo-4-fluorophenyl)amino](hydroxyimino)methyl]-1,2,5-oxadiazol-3-yl}-N(1)-phenylpiperidine-1,4-dicarboxamide

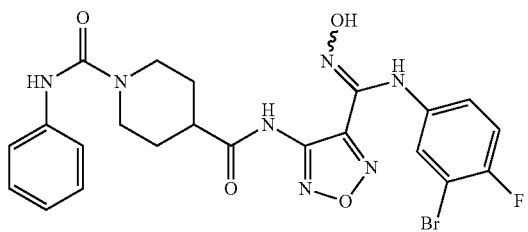 [SMILES: O=C(Nc1nonc1C(=NO)Nc1ccc(F)c(Br)c1)C1CCN(C(=O)Nc2ccccc2)CC1]

A solution of N-{4-[4-(3-bromo-4-fluorophenyl)-5-oxo-4,5-dihydro-1,2,4-oxadiazol-3-yl]-1,2,5-oxadiazol-3-yl}piperidine-4-carboxamide trifluoroacetate (20 mg, 35 µmol) and 4-dimethylaminopyridine (2 mg, 20 µmol) in acetonitrile (0.13 mL) was treated with phenyl isocyante and stirred for 16 h. The reaction mixture was concentrated, rediluted with ethanol (0.4 mL), treated with 2.0 M sodium hydroxide in water (0.12 mL, 0.24 mmol), and stirred for 30 min. The reaction mixture was quenched with acetic acid (20 µL, 0.35 mmol), filtered, and purified by preparative HPLC to give the desired product (6 mg, 31%). LCMS for $C_{22}H_{22}BrFN_7O_4$ (M+H)$^+$: m/z=546.0, 548.0.

Example 55

N-{4-[(E,Z)-[(3-Bromo-4-fluorophenyl)amino](hydroxyimino)methyl]-1,2,5-oxadiazol-3-yl}-1-ethylpiperidine-4-carboxamide trifluoroacetate

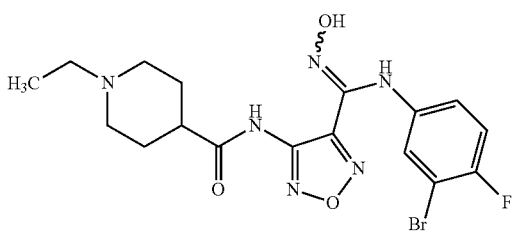 [SMILES: CCN1CCC(C(=O)Nc2nonc2C(=NO)Nc2ccc(F)c(Br)c2)CC1]

A solution of N-{4-[4-(3-bromo-4-fluorophenyl)-5-oxo-4,5-dihydro-1,2,4-oxadiazol-3-yl]-1,2,5-oxadiazol-3-yl}piperidine-4-carboxamide trifluoroacetate (20 mg, 35 µmol) in acetonitrile (1 mL) was treated with N,N-diisopropylethylamine (12 µL, 71 µmol) followed by iodoethane (4 µL, 53 µmol) and stirred for 16 h. The reaction mixture was concentrated, rediluted with ethanol (1 mL), treated with 2.0 M sodium hydroxide in water (0.2 mL, 0.4 mmol), and stirred for 30 min. The reaction mixture was quenched with acetic acid (50 µL, 0.88 mmol), filtered, and purified by preparative HPLC to give the desired product (5 mg, 25%). LCMS for $C_{17}H_{21}BrFN_6O_3$ (M+H)$^+$: m/z=455.0, 457.0.

Example 56

4-[(Benzoylamino)methyl]-N-{4-[(E,Z)-[(3-bromo-4-fluorophenyl)amino](hydroxyimino)methyl]-1,2,5-oxadiazol-3-yl}benzamide

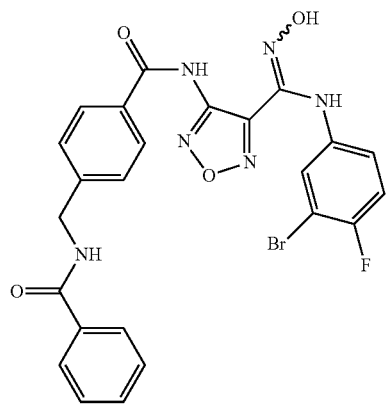 [SMILES: O=C(NCc1ccc(C(=O)Nc2nonc2C(=NO)Nc2ccc(F)c(Br)c2)cc1)c1ccccc1]

A solution of 4-(aminomethyl)-N-{4-[(E,Z)-[(3-bromo-4-fluorophenyl)amino]-(hydroxyimino)methyl]-1,2,5-oxadiazol-3-yl}benzamide trifluoroacetate (30 mg, 51 µmol) and benzoic acid (9.3 mg, 76 µmol) in dichloromethane (0.4 mL) and N,N-dimethylformamide (0.1 mL) was treated with N,N-diisopropylethylamine (22 µL, 0.1 mmol) and 0.6 M of 1-hydroxy-7-azabenzotriazole in N,N-dimethylformamide (20 µL, 10 µmol) followed by N-(3-dimethylaminopropyl)-N'-ethylcarbodiimide hydrochloride (14.5 mg, 76 µmol) and stirred for 16 h. The reaction mixture was concentrated, rediluted with ethanol (1 mL), treated with 2.0 M sodium hydroxide in water (0.3 mL, 0.6 mmol), and stirred for 30 min. The reaction mixture was quenched with acetic acid (50 µL, 0.88 mmol), filtered, and purified by preparative HPLC to give the desired product (4 mg, 14%). LCMS for $C_{24}H_{19}BrFN_6O_4$ (M+H)$^+$: m/z=553.0, 555.0.

Example 57

N-{4-[(E,Z)-[(3-Bromo-4-fluorophenyl)amino](hydroxyimino)methyl]-1,2,5-oxadiazol-3-yl}-2-(2-cyanophenoxy)acetamide

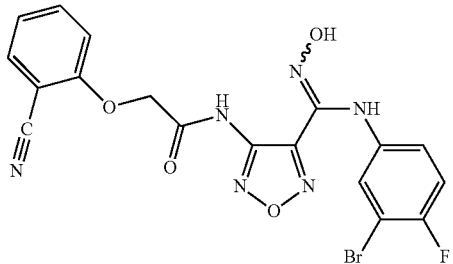 [SMILES: N#Cc1ccccc1OCC(=O)Nc1nonc1C(=NO)Nc1ccc(F)c(Br)c1]

A solution of (2-cyanophenoxy)acetic acid (62 mg, 0.35 mmol) in dichloromethane (3 mL) was treated with oxalyl chloride (60 µL, 0.7 mmol) followed by N,N-dimethylformamide (10 µL) at 0° C. The reaction mixture was stirred at 25° C. for 2 h and concentrated to a crude residue which was diluted with pyridine and treated with 3-(4-amino-1,2,5-oxadiazol-3-yl)-4-(3-bromo-4-fluorophenyl)-1,2,4-oxadiazol-5 (4H)-one (40 mg, 0.12 mmol) and 4-dimethylaminopyridine (7 mg, 58 µmol). The reaction mixture was heated in the microwave at 150° C. for 20 min. The reaction mixture was concentrated, rediluted with ethanol (1.45 mL), treated with 2.0 M sodium hydroxide in water (0.3 mL, 0.6 mmol), and stirred for 30 min. The reaction mixture was quenched with acetic acid (50 µL, 0.88 mmol), filtered, and purified by preparative LCMS to give the desired product (4 mg, 7%). LCMS for $C_{18}H_{13}BrFN_6O_4$ (M+H)$^+$: m/z=474.9, 477.0.

Example 58

N-{4-[(E,Z)-[(3-Bromo-4-fluorophenyl)amino](hydroxyimino)methyl]-1,2,5-oxadiazol-3-yl}-4-phenylpiperidine-4-carboxamide trifluoroacetate

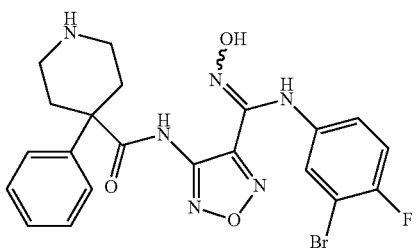 [SMILES: O=C(Nc1nonc1C(=NO)Nc1ccc(F)c(Br)c1)C1(c2ccccc2)CCNCC1]

Step 1. N-{4-[4-(3-Bromo-4-fluorophenyl)-5-oxo-4,5-dihydro-1,2,4-oxadiazol-3-yl]-1,2,5-oxadiazol-3-yl}-4-phenylpiperidine-4-carboxamide trifluoroacetate

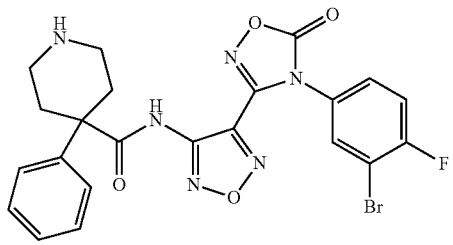 [SMILES: O=C(Nc1nonc1-c1noc(=O)n1-c1ccc(F)c(Br)c1)C1(c2ccccc2)CCNCC1]

A solution of 3-(4-amino-1,2,5-oxadiazol-3-yl)-4-(3-bromo-4-fluorophenyl)-1,2,4-oxadiazol-5(4H)-one (0.15 g, 0.44 mmol), 1-(tert-butoxycarbonyl)-4-phenylpiperidine-4-carboxylic acid (0.4 g, 1.3 mmol), and 4-dimethylaminopyridine (32 mg, 0.26 mmol) in acetonitrile (2 mL) was treated with phosphoryl chloride (0.13 mL, 1.4 mmol) and heated in the microwave at 100° C. for 10 min. The reaction mixture was concentrated and the residue was diluted with ethyl acetate (25 mL) and washed with water (25 mL) and brine (25 mL), dried with sodium sulfate, filtered, and concentrated to a crude residue which was purified by silica gel to give the coupled product, tert-butyl 4-[({4-[4-(3-bromo-4-fluorophenyl)-5-oxo-4,5-dihydro-1,2,4-oxadiazol-3-yl]-1,2,5-oxadiazol-3-yl}amino)carbonyl]-4-phenylpiperidine-1-carboxylate. This material was diluted with dichloromethane (5 mL) and treated with 4.0 M HCl in 1,4-dioxane (3 mL) and stirred for 45 min. The reaction mixture was concentrated and the crude residue was purified by preparative LCMS to give the desired product (10 mg, 4%). LCMS for $C_{22}H_{19}BrFN_6O_4$ (M+H)$^+$: m/z=529.0, 531.0.

Step 2. N-{4-[(E,Z)-[(3-Bromo-4-fluorophenyl)amino](hydroxyimino)methyl]-1,2,5-oxadiazol-3-yl}-4-phenylpiperidine-4-carboxamide trifluoroacetate This compound was prepared according to the procedure of Example 38, Step 2, using N-{4-[4-(3-bromo-4-fluorophenyl)-5-oxo-4,5-dihydro-1,2,4-oxadiazol-3-yl]-1,2,5-oxadiazol-3-yl}-4-phenylpiperidine-4-carboxamide trifluoroacetate as the starting material. LCMS for $C_{21}H_{21}BrFN_6O_3$ (M+H)$^+$: m/z=503.0, 504.9.

Example 59

N-(3-Bromo-4-fluorophenyl)-4-({4-[(1,1-dioxidothiomorpholin-4-yl)methyl]benzyl}amino)-N'-hydroxy-1,2,5-oxadiazole-3-carboximidamide trifluoroacetate

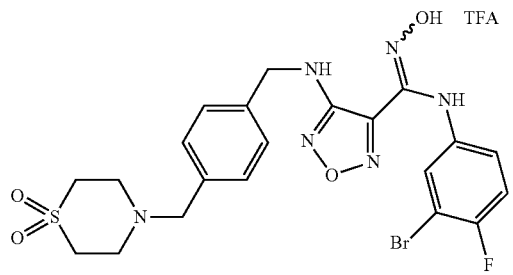 [SMILES: O=S1(=O)CCN(Cc2ccc(CNc3nonc3C(=NO)Nc3ccc(F)c(Br)c3)cc2)CC1 ; "TFA"]

Step 1. N-{4-[4-(3-Bromo-4-fluorophenyl)-5-oxo-4,5-dihydro-1,2,4-oxadiazol-3-yl]-1,2,5-oxadiazol-3-yl}-4-[(1,1-dioxidothiomorpholin-4-yl)methyl]benzamide trifluoroacetate

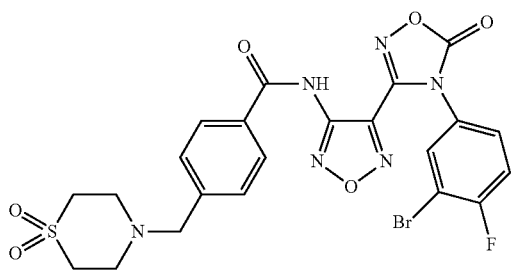 [SMILES: O=C(Nc1nonc1-c1noc(=O)n1-c1ccc(F)c(Br)c1)c1ccc(CN2CCS(=O)(=O)CC2)cc1]

A solution of 3-(4-amino-1,2,5-oxadiazol-3-yl)-4-(3-bromo-4-fluorophenyl)-1,2,4-oxadiazol-5(4H)-one (0.50 g, 1.5 mmol), 4-[(1,1-dioxidothiomorpholin-4-yl)methyl]benzoic acid (1.0 g, 3.7 mmol), and 4-dimethylaminopyridine (110 mg, 0.88 mmol) in acetonitrile (8.3 mL) and pyridine (1.2 mL) was treated with phosphoryl chloride (0.42 mL, 4.5 mmol) dropwise at 0° C. The reaction mixture was heated in the microwave at 120° C. for 20 min., diluted with ethyl acetate (150 mL) and washed with water (50 mL), saturated sodium bicarbonate (50 mL), and brine (50 mL), dried with sodium sulfate, filtered, and concentrated. Purification of the crude reaction mixture by preparative LCMS gave the desired product (0.36 g, 35%). LCMS for $C_{22}H_{19}BrFN_6O_6S$ (M+H)$^+$: m/z=593.0, 595.0.

Step 2. N-(3-Bromo-4-fluorophenyl)-4-({4-[(1,1-dioxidothiomorpholin-4-yl)methyl]benzyl}amino)-N'-hydroxy-1,2,5-oxadiazole-3-carboximidamide trifluoroacetate A solution of N-{4-[4-(3-bromo-4-fluorophenyl)-5-oxo-4,5-dihydro-1,2,4-oxadiazol-3-yl]-1,2,5-oxadiazol-3-yl}-4-[(1,1-dioxidothiomorpholin-4-yl)methyl]-benzamide trifluoroacetate (20 mg, 28 µmol) in tetrahydrofuran (0.83 mL) was treated with 2.0 M of borane-dimethyl sulfide complex in toluene (42 µL, 85 µmol) was heated in the microwave at 130° C. for 5 min. The reaction mixture was treated with additional 2.0 M of borane-dimethyl sulfide complex in toluene (40 µL, 80 µmol) and heated in the microwave at 130° C. for 10 min. The reaction mixture was quenched with acetic acid, concentrated and purified by preparative LCMS to give the desired product (1 mg, 5%). LCMS for $C_{21}H_{23}BrFN_6O_4S$ (M+H)$^+$: m/z=553.0, 554.9.

Example 60

N-(3-Bromo-4-fluorophenyl)-N'-hydroxy-4-{[4-(morpholin-4-ylmethyl)benzyl]amino}-1,2,5-oxadiazole-3-carboximidamide trifluoroacetate

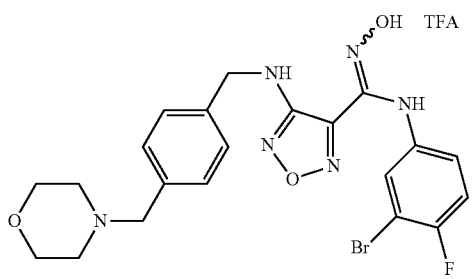 [SMILES: ON=C(Nc1ccc(F)c(Br)c1)c1nonc1NCc1ccc(CN2CCOCC2)cc1 ; "TFA"]

Step 1. N-{4-[4-(3-Bromo-4-fluorophenyl)-5-oxo-4,5-dihydro-1,2,4-oxadiazol-3-yl]-1,2,5-oxadiazol-3-yl}-4-(morpholin-4-ylmethyl)benzamide trifluoroacetate

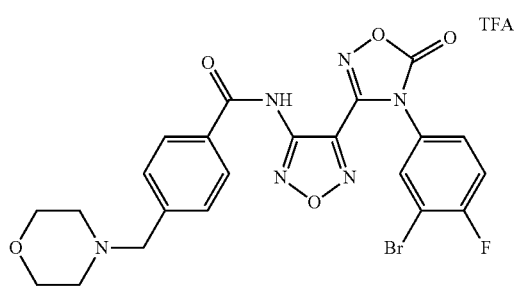 [SMILES: O=C(Nc1nonc1-c1noc(=O)n1-c1ccc(F)c(Br)c1)c1ccc(CN2CCOCC2)cc1]

This compound was prepared according to the procedure of Example 59, Step 1, using 4-(morpholin-4-ylmethyl)benzoic acid as the starting material. LCMS for $C_{22}H_{19}BrFN_6O_5$ (M+H)$^+$: m/z=544.9, 547.0.

Step 2. N-(3-Bromo-4-fluorophenyl)-N'-hydroxy-4-{[4-(morpholin-4-ylmethyl)benzyl]amino}-1,2,5-oxadiazole-3-carboximidamide trifluoroacetate A solution of N-{4-[4-(3-bromo-4-fluorophenyl)-5-oxo-4,5-dihydro-1,2,4-oxadiazol-3-yl]-1,2,5-oxadiazol-3-yl}-4-(morpholin-4-ylmethyl)benzamide trifluoroacetate (60 mg, 91 µmol) in benzene (1.8 mL) was treated with phosphorus pentachloride (76 mg, 0.36 mmol) and stirred at reflux for 2.5 h. The reaction mixture was concentrated to a residue which was diluted with ethanol (1.4 mL), treated with sodium cyanoborohydride (17 mg, 0.27 mmol), and stirred for 2 h. The reaction mixture was quenched with acetic acid (50 µL) and purified by preparative LCMS to give the intermediate, 4-(3-bromo-4-fluorophenyl)-3-(4-{[4-(morpholin-4-ylmethyl)benzyl]amino}-1,2,5-oxadiazol-3-yl)-1,2,4-oxadiazol-5(4H)-one. This material was diluted with ethanol (1 mL), treated with 2.0 M sodium hydroxide in water (0.2 mL, 4 mmol), and stirred for 45 min. The reaction mixture was purified by preparative LCMS to give the desired product (15 mg, 27%). LCMS for $C_{21}H_{23}BrFN_6O_3$ (M+H)$^+$: m/z=505.0, 507.0.

Example 61

N-(3-Cyano-4-fluorophenyl)-4-({4-[(1,1-dioxidothiomorpholin-4-yl)methyl]benzyl}amino)-N'-hydroxy-1,2,5-oxadiazole-3-carboximidamide trifluoroacetate

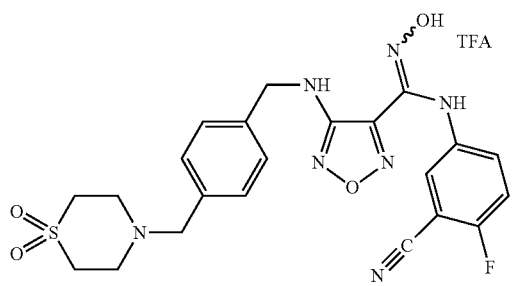 [SMILES: N#Cc1cc(NC(=NO)c2nonc2NCc2ccc(CN3CCS(=O)(=O)CC3)cc2)ccc1F ; "TFA"]

Step 1. 4-(3-Bromo-4-fluorophenyl)-3-[4-({4-[(1,1-dioxidothiomorpholin-4-yl)methyl]benzyl}amino)-1,2,5-oxadiazol-3-yl]-1,2,4-oxadiazol-5(4H)-one trifluoroacetate

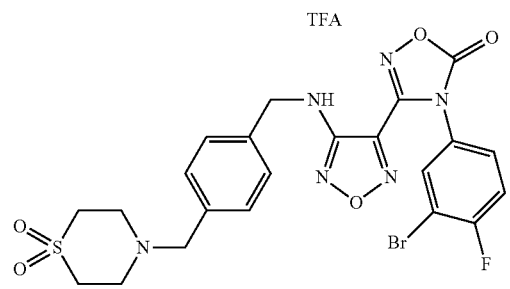 [SMILES: O=c1onc(-c2nonc2NCc2ccc(CN3CCS(=O)(=O)CC3)cc2)n1-c1ccc(F)c(Br)c1]

A solution of N-{4-[4-(3-bromo-4-fluorophenyl)-5-oxo-4,5-dihydro-1,2,4-oxadiazol-3-yl]-1,2,5-oxadiazol-3-yl}-4-[(1,1-dioxidothiomorpholin-4-yl)methyl]benzamide trifluoroacetate (20 mg, 28 µmol) in pyridine (0.5 mL) was treated with phosphorus pentachloride (18 mg, 85 µmol) and stirred at 0° C. for 4.5 h. The reaction mixture was concentrated, diluted with ethanol (1 mL), treated with sodium cyanoborohydride (5 mg, 85 mop, and stirred for 2 h. The reaction mixture was purified by preparative LCMS to give the desired product (9 mg, 47%). LCMS for C$_{22}$H$_{21}$BrFN$_6$O$_5$S (M+H)$^+$: m/z=579.0, 581.0.

Step 2. N-(3-Cyano-4-fluorophenyl)-4-({4-[(1,1-dioxidothiomorpholin-4-yl)methyl]benzyl}amino)-N'-hydroxy-1,2,5-oxadiazole-3-carboximidamide trifluoroacetate A solution of 4-(3-bromo-4-fluorophenyl)-3-[4-({4-[(1,1-dioxidothiomorpholin-4-yl)methyl]benzyl}amino)-1,2,5-oxadiazol-3-yl]-1,2,4-oxadiazol-5(4H)-one trifluoroacetate (10 mg, 14 μmol), zinc cyanide (5 mg, 43 mmol), and tetrakis(triphenylphosphine)palladium(0) (8 mg, 7 μmol) in N,N-dimethylformamide (0.25 mL) was heated in the microwave at 150° C. for 5 min. The reaction mixture was diluted with 3:1 acetonitrile/water (2 mL), filtered, and purified by preparative LCMS to give the intermediate 5-[3-[4-({4-[(1,1-dioxidothiomorpholin-4-yl)methyl]benzyl}amino)-1,2,5-oxadiazol-3-yl]-5-oxo-1,2,4-oxadiazol-4(5H)-yl]-2-fluorobenzonitrile trifluoroacetate. This material was diluted with ethanol (1 mL), treated with 2.0 M sodium hydroxide in water (0.1 mL), and stirred for 45 min. The reaction mixture was quenched with acetic acid (50 μL, 0.9 mmol), filtered, and purified by preparative LCMS to give the desired product (1 mg, 11%). LCMS for C$_{22}$H$_{23}$FN$_7$O$_4$S (M+H)$^+$: m/z=500.0.

Example 62

N-(3-Bromo-4-fluorophenyl)-N'-hydroxy-4-[(pyridin-3-ylmethyl)amino]-1,2,5-oxadiazole-3-carboximidamide trifluoroacetate

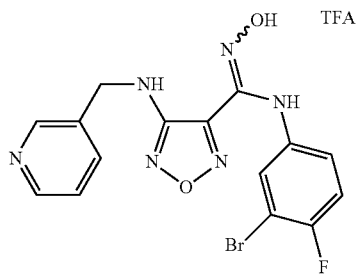 [SMILES: ON=C(Nc1ccc(F)c(Br)c1)c1nonc1NCc1cccnc1]

Step 1. 4-(3-Bromo-4-fluorophenyl)-3-{4-[(pyridin-3-ylmethyl)amino]-1,2,5-oxadiazol-3-yl}-1,2,4-oxadiazol-5(4H)-one trifluoroacetate

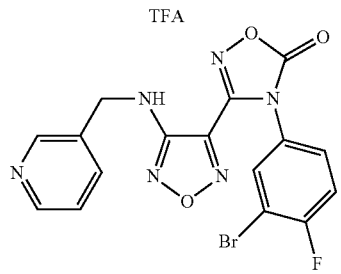 [SMILES: O=c1onc(-c2nonc2NCc2cccnc2)n1-c1ccc(F)c(Br)c1]

A solution of N-{4-[4-(3-bromo-4-fluorophenyl)-5-oxo-4,5-dihydro-1,2,4-oxadiazol-3-yl]-1,2,5-oxadiazol-3-yl}-2,2,2-trifluoroacetamide (50 mg, 0.11 mmol), nicotinyl alcohol (14 μL, 0.15 mmol), and triphenylphosphine (42 mg, 0.16 mmol) in tetrahydrofuran (0.35 mL) at 0° C. was treated with diisopropyl azodicarboxylate (34 μL, 0.17 mmol). The reaction mixture was stirred at 25° C. for 16 h and purified by preparative LCMS to give the desired product (4 mg, 6%). LCMS for C$_6$H$_{11}$BrFN$_6$O$_3$ (M+H)$^+$: m/z=432.9, 434.9.

Step 2. N-(3-Bromo-4-fluorophenyl)-N'-hydroxy-4-[(pyridin-3-ylmethyl)amino]-1,2,5-oxadiazole-3-carboximidamide trifluoroacetate This compound was prepared according to the procedure of Example 38, Step 2, using 4-(3-bromo-4-fluorophenyl)-3-{4-[(pyridin-3-ylmethyl)amino]-1,2,5-oxadiazol-3-yl}-1,2,4-oxadiazol-5(4H)-one trifluoroacetate as the starting material. LCMS for C$_{15}$H$_{13}$BrFN$_6$O$_2$ (M+H)$^+$: m/z=406.9, 408.9.

Example 63

N-(3-Cyano-4-fluorophenyl)-N'-hydroxy-4-[(pyridin-4-ylmethyl)amino]-1,2,5-oxadiazole-3-carboximidamide trifluoroacetate

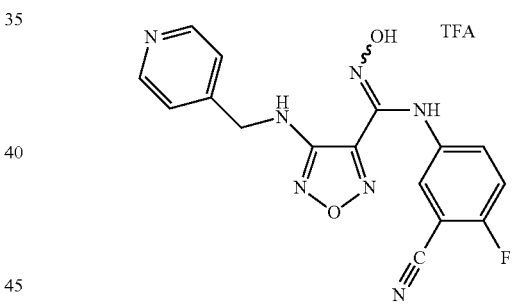

A solution of N-{4-[4-(3-cyano-4-fluorophenyl)-5-oxo-4,5-dihydro-1,2,4-oxadiazol-3-yl]-1,2,5-oxadiazol-3-yl}isonicotinamide trifluoroacetate (37 mg, 72 μmol) in pyridine (1.5 mL) at 0° C. was treated with phosphorus pentachloride (45 mg, 0.22 mmol) and stirred for 3 h. The reaction mixture was concentrated, diluted with ethanol (2.5 mL), treated with sodium cyanoborohydride (14 mg, 0.22 mmol), and stirred for 16 h. The reaction mixture was purified by preparative LCMS to give the intermediate 2-fluoro-5-[5-oxo-3-{4-[(pyridin-4-ylmethyl)amino]-1,2,5-oxadiazol-3-yl]-1,2,4-oxadiazol-4(5H)-yl}benzonitrile trifluoroacetate. This material was diluted with ethanol (1 mL), treated with 2.0 M sodium hydroxide in water (0.2 mL), and stirred for 45 min. Purification of the crude reaction mixture by preparative HPLC gave the desired product (8 mg, 24%). LCMS for C$_{16}$H$_{13}$FN$_7$O$_2$ (M+H)$^+$: m/z=354.0.

Example 64

4-[(3-Cyanobenzyl)amino]-N-(3-cyano-4-fluorophenyl)-N'-hydroxy-1,2,5-oxadiazole-3-carboximidamide

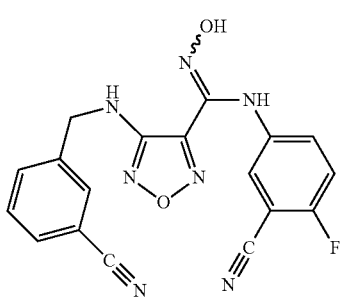 [SMILES: N#Cc1cccc(CNc2nonc2C(=NO)Nc2ccc(F)c(C#N)c2)c1]

A solution of 3-cyano-N-{4-[4-(3-cyano-4-fluorophenyl)-5-oxo-4,5-dihydro-1,2,4-oxadiazol-3-yl]-1,2,5-oxadiazol-3-yl}benzamide (30 mg, 72 μmol) in benzene (2 mL) at 0° C. was treated with phosphorus pentachloride (45 mg, 0.22 mmol) and stirred at 90° C. for 2 h. The reaction mixture was concentrated, diluted with ethanol (2.5 mL), treated with sodium cyanoborohydride (14 mg, 0.22 mmol), and stirred for 16 h. The reaction mixture was purified by preparative LCMS to give the intermediate 5-[3-{4-[(3-cyanobenzyl)amino]-1,2,5-oxadiazol-3-yl}-5-oxo-1,2,4-oxadiazol-4(5H)-yl]-2-fluorobenzonitrile. This material was diluted with ethanol (1 mL), treated with 2.0 M sodium hydroxide in water (0.2 mL), and stirred for 45 min. Purification of the crude reaction mixture by preparative HPLC gave the desired product (3 mg, 11%). LCMS for $C_{18}H_{13}FN_7O_2$ (M+H)$^+$: m/z=378.0.

Example 65

N-(3-Bromo-4-fluorophenyl)-N'-hydroxy-4-[(1H-tetrazol-5-ylmethyl)amino]-1,2,5-oxadiazole-3-carboximidamide

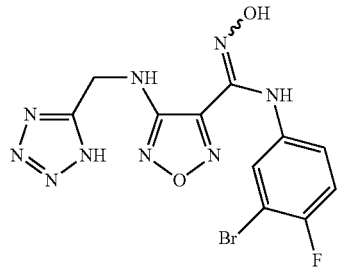 [SMILES: ON=C(Nc1ccc(F)c(Br)c1)c1nonc1NCc1nnn[nH]1]

Step 1. N-{4-[4-(3-Bromo-4-fluorophenyl)-5-oxo-4,5-dihydro-1,2,4-oxadiazol-3-yl]-1,2,5-oxadiazol-3-yl}-1H-tetrazole-5-carboxamide

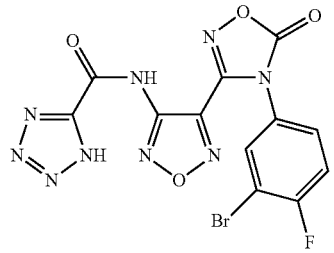 [SMILES: O=C(Nc1nonc1-c1noc(=O)n1-c1ccc(F)c(Br)c1)c1nnn[nH]1]

A solution of 3-(4-amino-1,2,5-oxadiazol-3-yl)-4-(3-bromo-4-fluorophenyl)-1,2,4-oxadiazol-5(4H)-one (50 mg, 0.15 mmol) and 4-dimethylaminopyridine (11 mg, 88 μmol) in acetonitrile (0.8 mL) and pyridine (0.12 mL) was treated with phosphoryl chloride (42 μL, 0.45 mmol) and stirred for 1 h. The reaction mixture was concentrated, dissolved in 3:1 acetonitrile/water, and purified by preparative LCMS to give the desired product (14 mg, 22%). LCMS for $C_{12}H_6BrFN_9O_4$ (M+H)$^+$: m/z=437.8, 439.9.

Step 2. N-(3-Bromo-4-fluorophenyl)-N'-hydroxy-4-[(1H-tetrazol-5-ylmethyl)amino]-1,2,5-oxadiazole-3-carboximidamide A solution of N-{4-[4-(3-bromo-4-fluorophenyl)-5-oxo-4,5-dihydro-1,2,4-oxadiazol-3-yl]-1,2,5-oxadiazol-3-yl}-1H-tetrazole-5-carboxamide (12 mg, 27 μmol) in pyridine (0.3 mL) was treated with phosphorus pentachloride (13 mg, 60 μmol) at 25° C. The reaction mixture was stirred at 0° C. for 2 h, concentrated, rediluted with toluene and concentrated to a residue. This material was diluted with ethanol (1 mL), treated with sodium cyanoborohydride (5 mg, 82 μmol), and stirred for 2 h. The reaction mixture was concentrated, diluted with ethanol (1 mL), treated with 2.0 M sodium hydroxide in water (0.2 mL), and stirred for 45 min. Purification of the crude reaction mixture by preparative LCMS gave the desired product (2 mg, 19%). LCMS for $C_{11}H_{10}BrFN_9O_2$ (M+H)$^+$: m/z=398.0, 400.0.

Example 66

N'-(Acetyloxy)-4-amino-N-(3-chloro-4-fluorophenyl)-1,2,5-oxadiazole-3-carboximidamide

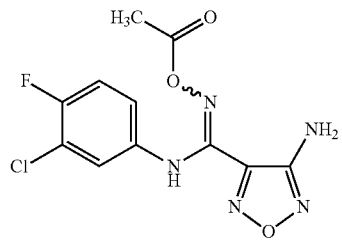 [SMILES: CC(=O)ON=C(Nc1ccc(F)c(Cl)c1)c1nonc1N]

A solution of 4-amino-N-(3-chloro-4-fluorophenyl)-N'-hydroxy-1,2,5-oxadiazole-3-carboximidamide (0.1 g, 0.37 mmol) in acetic anhydride was stirred for 2 h. The reaction mixture was concentrated and purified by preparative LCMS to give the desired product (625 mg, 54%). LCMS for $C_{11}H_{10}ClFN_5O_3$ (M+H)$^+$: m/z=314.1.

Example 67

4-Amino-N-(3-chloro-4-fluorophenyl)-N'-(propionyloxy)-1,2,5-oxadiazole-3-carboximidamide

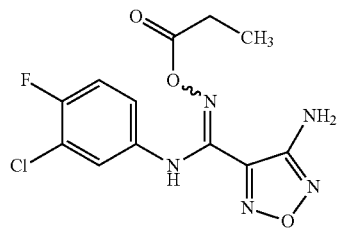 [SMILES: CCC(=O)ON=C(Nc1ccc(F)c(Cl)c1)c1nonc1N]

A solution of 4-amino-N-(3-chloro-4-fluorophenyl)-N'-hydroxy-1,2,5-oxadiazole-3-carboximidamide (0.1 g, 0.37 mmol) and N,N-diisopropylethylamine (0.16 mL, 0.92 mmol) in dichloromethane (4 mL) was treated with propanoyl chloride (38 μL, 0.44 mmol) and stirred for 1 h. The reaction mixture was concentrated and purified by preparative LCMS to give the desired product (57 mg, 47%). LCMS for $C_{12}H_{12}ClFN_5O_3$ (M+H)$^+$: m/z=328.0.

Example 68

4-Amino-N'-{[(benzylamino)carbonyl]oxy}-N-(3-chloro-4-fluorophenyl)-1,2,5-oxadiazole-3-carboximidamide

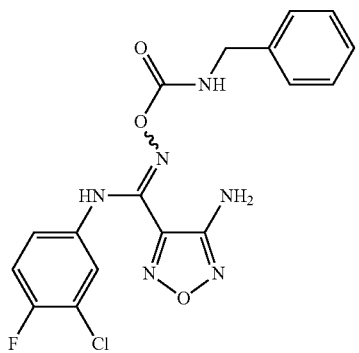 [SMILES: Nc1nonc1C(=NOC(=O)NCc1ccccc1)Nc1ccc(F)c(Cl)c1]

A solution of 4-amino-N-(3-chloro-4-fluorophenyl)-N'-hydroxy-1,2,5-oxadiazole-3-carboximidamide (50 mg, 0.18 mmol) and N,N-diisopropylethylamine (64 μL, 0.37 mmol) in dichloromethane (2 mL) was treated with benzyl isocyanate (29 mg, 0.22 mmol) and stirred for 3 h. The reaction mixture was concentrated and purified by preparative LCMS to give the desired product (18 mg, 24%). LCMS for $C_{17}H_{15}ClFN_6O_3$ (M+H)$^+$: m/z=405.0.

Example 69

N-(3-Bromo-4-fluorophenyl)-N'-hydroxy-4-morpholin-4-yl-1,2,5-oxadiazole-3-carboximidamide

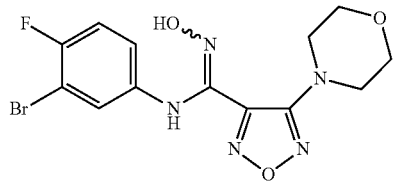 [SMILES: ON=C(Nc1ccc(F)c(Br)c1)c1nonc1N1CCOCC1]

Step 1. 4-[(E,Z)-(Hydroxyimino)(morpholin-4-yl)methyl]-1,2,5-oxadiazol-3-amine

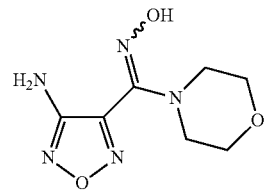 [SMILES: Nc1nonc1C(=NO)N1CCOCC1]

This compound was prepared according to the procedure of Example 1 using morpholine as the starting material. LCMS for $C_7H_{12}N_5O_3$ (M+H)$^+$: m/z=214.0.

Step 2. N'-Hydroxy-4-morpholin-4-yl-1,2,5-oxadiazole-3-carboximidamide

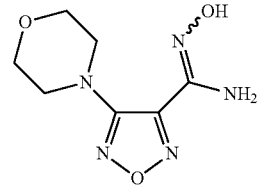 [SMILES: NC(=NO)c1nonc1N1CCOCC1]

A solution of 4-[(E,Z)-(hydroxyimino)(morpholin-4-yl)methyl]-1,2,5-oxadiazol-3-amine (0.1 g, 0.47 mmol) in 1,2-ethanediol (1.6 mL) was treated with potassium hydroxide (94 mg, 1.7 mmol) and stirred at 130° C. for 7 h. The reaction mixture was treated with additional potassium hydroxide (53 mg, 0.94 mmol) and stirred at 140° C. for 5.5 h. The reaction mixture was cooled to 0° C., neutralized with 6.0 M HCl, and purified by preparative LCMS to give the desired product desired product (70 mg, 70%). LCMS for $C_7H_{12}N_5O_3$ (M+H)$^+$: m/z=214.1.

Step 3. N-Hydroxy-4-morpholin-4-yl-1,2,5-oxadiazole-3-carboximidoyl chloride

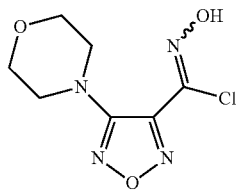 [SMILES: ON=C(Cl)c1nonc1N1CCOCC1]

A solution of N'-hydroxy-4-morpholin-4-yl-1,2,5-oxadiazole-3-carboximidamide (66 mg, 0.3 mmol) in 6.0 M HCl (0.62 mL) at 5-10° C. was treated with a solution of sodium nitrite (32 mg, 0.47 mmol) in water (0.5 mL) dropwise and stirred for 2 h at 0° C. The suspension was filtered and the solid washed with ice water to give desired product (22 mg, 30%). The filtrate was extracted with ethyl acetate (30 mL) which was washed with brine (10 mL), filtered and concentrated to give additional product (23 mg, 32%) that contained minor impurities. The combined material was used immediately in the next step.

Step 4. N-(3-Bromo-4-fluorophenyl)-N'-hydroxy-4-morpholin-4-yl-1,2,5-oxadiazole-3-carboximidamide A solution of N-Hydroxy-4-morpholin-4-yl-1,2,5-oxadiazole-3-carboximidoyl chloride (40 mg, 0.17 mmol) and 3-bromo-4-fluoroaniline (49 mg, 0.26 mmol) in ethanol (1 mL) was treated with a solution of N,N-diisopropylethylamine (45 µL, 0.26 mmol) in acetonitrile (1 mL) and stirred for 62 h. The reaction mixture was purified by preparative HPLC to give the desired product (32 mg, 48%). LCMS for $C_{13}H_{14}ClFN_5O_3$ $(M+H)^+$: m/z=386.0, 388.0.

Example 70

4-Amino-N'-hydroxy-N-[3-(3-hydroxyprop-1-yn-1-yl)phenyl]-1,2,5-oxadiazole-3-carboximidamide

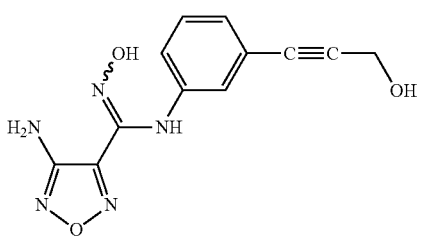 [SMILES: Nc1nonc1C(=NO)Nc1cccc(C#CCO)c1]

A solution of 4-amino-N'-hydroxy-N-(3-iodophenyl)-1,2,5-oxadiazole-3-carboximidamide (19 mg, 55 µmol), 2-propyn-1-ol (3.6 µL, 62 µmol), bis(triphenylphosphine)palladium(II) chloride (1 mg, 2 µmol), and copper (I) iodide (0.4 mg, 2 µmol) in N,N-dimethylformamide (0.5 mL) was treated with N,N-diethylamine (74 µl, 0.72 mmol) and heated in the microwave at 120° C. for 15 min. The reaction mixture was diluted with 1:1 acetonitrile/water (1.5 mL), filtered, and purified by preparative LCMS to give the desired product (4 mg, 28%). LCMS for $C_{12}H_{12}N_5O_3$ $(M+H)^+$: m/z=274.0.

Further example compounds of the invention are provided below in Table 1.

TABLE 1

| Ex. No. | Structure | Name | Prep. Method | MS (M + 1) |
|---|---|---|---|---|
| 71 | (cyclopentanecarboxamide-oxadiazole-chlorophenyl structure) | N-{4-[(E,Z)-[(3-Chlorophenyl)amino](hydroxyimino)methyl]-1,2,5-oxadiazol-3-yl}cyclopentanecarboxamide | Ex. 35 | 350.0 |
| 72 | (nicotinamide-oxadiazole-chlorophenyl structure, TFA) | N-{4-[(E,Z)-[(3-Chlorophenyl)amino](hydroxyimino)methyl]-1,2,5-oxadiazol-3-yl}nicotinamide trifluoroacetate | Ex. 35 | 359.0 |

TABLE 1-continued

| Ex. No. | Structure | Name | Prep. Method | MS (M + 1) |
|---|---|---|---|---|
| 73 | 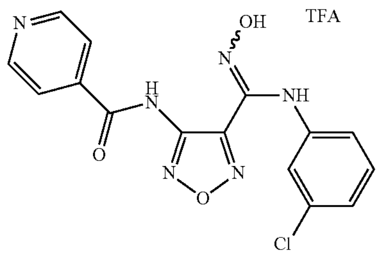 [SMILES: O=C(Nc1nonc1C(=NO)Nc1cccc(Cl)c1)c1ccncc1] | N-{4-[(E,Z)-[(3-Chlorophenyl)amino](hydroxy-imino)methyl]-1,2,5-oxadiazol-3-yl}isonicotinamide trifluoroacetate | Ex. 35 | 359.0 |
| 74 | 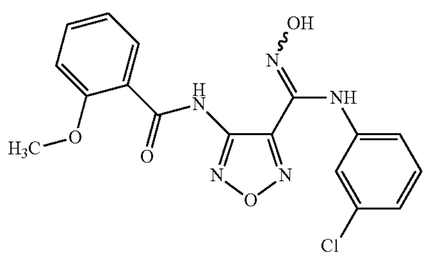 [SMILES: COc1ccccc1C(=O)Nc1nonc1C(=NO)Nc1cccc(Cl)c1] | N-{4-[(E,Z)-[(3-Chlorophenyl)amino](hydroxy-imino)methyl]-1,2,5-oxadiazol-3-yl}-2-methoxybenzamide | Ex. 35 | 388.1 |
| 75 | 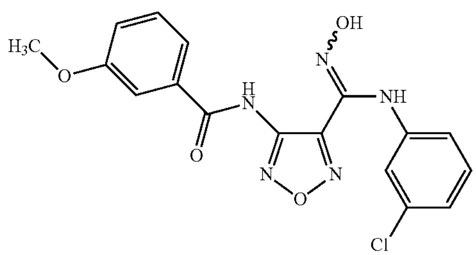 [SMILES: COc1cccc(C(=O)Nc2nonc2C(=NO)Nc2cccc(Cl)c2)c1] | N-{4-[(E,Z)-[(3-Chlorophenyl)amino](hydroxy-imino)methyl]-1,2,5-oxadiazol-3-yl}-3-methoxybenzamide | Ex. 35 | 387.9 |
| 76 | 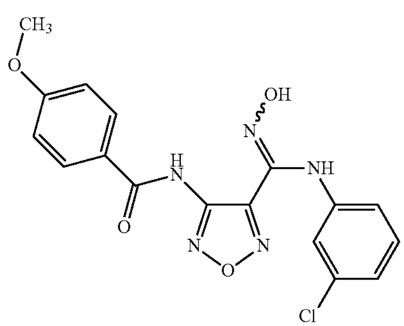 [SMILES: COc1ccc(C(=O)Nc2nonc2C(=NO)Nc2cccc(Cl)c2)cc1] | N-{4-[(E,Z)-[(3-Chlorophenyl)amino](hydroxy-imino)methyl]-1,2,5-oxadiazol-3-yl}-4-methoxybenzamide | Ex. 35 | 388.0 |
| 77 | 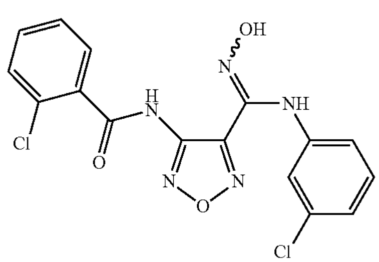 [SMILES: O=C(Nc1nonc1C(=NO)Nc1cccc(Cl)c1)c1ccccc1Cl] | 2-Chloro-N-{4-[(E,Z)-[(3-chlorophenyl)amino](hydroxy-imino)methyl]-1,2,5-oxadiazol-3-yl}benzamide | Ex. 35 | 391.9 |

TABLE 1-continued

| Ex. No. | Structure | Name | Prep. Method | MS (M + 1) |
|---|---|---|---|---|
| 78 | 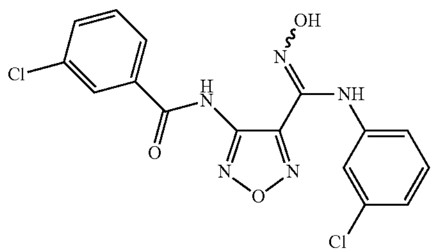 [SMILES: O=C(Nc1nonc1C(=NO)Nc1cccc(Cl)c1)c1cccc(Cl)c1] | 3-Chloro-N-{4-[(E,Z)-[(3-chlorophenyl)amino](hydroxyimino)methyl]-1,2,5-oxadiazol-3-yl}benzamide | Ex. 35 | 391.9 |
| 79 | 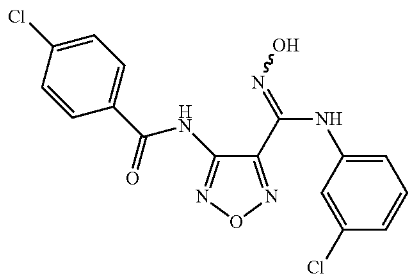 [SMILES: O=C(Nc1nonc1C(=NO)Nc1cccc(Cl)c1)c1ccc(Cl)cc1] | 4-Chloro-N-{4-[(E,Z)-[(3-chlorophenyl)amino](hydroxyimino)methyl]-1,2,5-oxadiazol-3-yl}benzamide | Ex. 35 | 391.9 |
| 80 | 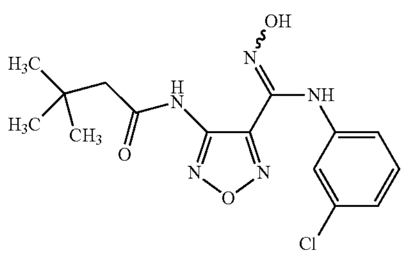 [SMILES: CC(C)(C)CC(=O)Nc1nonc1C(=NO)Nc1cccc(Cl)c1] | N-{4-[(E,Z)-[(3-Chlorophenyl)amino](hydroxyimino)methyl]-1,2,5-oxadiazol-3-yl}-3,3-dimethylbutanamide | Ex. 35 | 352.0 |
| 81 | 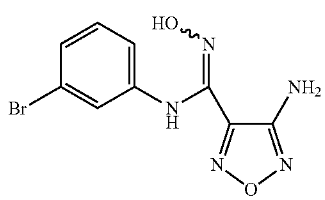 [SMILES: Nc1nonc1C(=NO)Nc1cccc(Br)c1] | 4-Amino-N-(3-bromophenyl)-N'-hydroxy-1,2,5-oxadiazole-3-carboximidamide | Ex. 1 | 298.0, 300.0 |
| 82 | 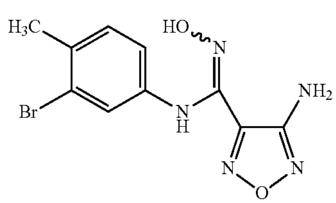 [SMILES: Cc1ccc(NC(=NO)c2nonc2N)cc1Br] | 4-Amino-N-(3-bromo-4-methylphenyl)-N'-hydroxy-1,2,5-oxadiazole-3-carboximidamide | Ex. 1 | 312.1, 314.1 |
| 83 | 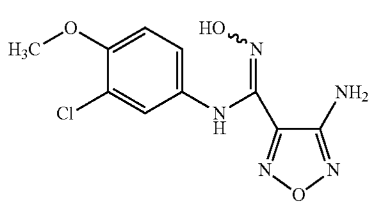 [SMILES: COc1ccc(NC(=NO)c2nonc2N)cc1Cl] | 4-Amino-N-(3-chloro-4-methoxyphenyl)-N'-hydroxy-1,2,5-oxadiazole-3-carboximidamide | Ex. 1 | 284.1 |

TABLE 1-continued

| Ex. No. | Structure | Name | Prep. Method | MS (M + 1) |
|---|---|---|---|---|
| 84 | 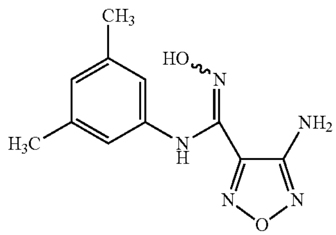 [SMILES: Cc1cc(C)cc(NC(=NO)c2nonc2N)c1] | 4-Amino-N-(3,5-dimethylphenyl)-N'-hydroxy-1,2,5-oxadiazole-3-carboximidamide | Ex. 1 | 248.2 |
| 85 | 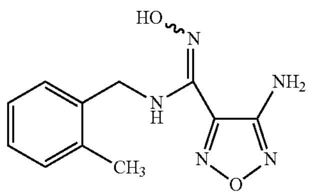 [SMILES: Cc1ccccc1CNC(=NO)c1nonc1N] | 4-Amino-N'-hydroxy-N-(2-methylbenzyl)-1,2,5-oxadiazole-3-carboximidamide | Ex. 1 | 248.2 |
| 86 | 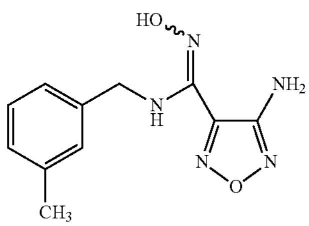 [SMILES: Cc1cccc(CNC(=NO)c2nonc2N)c1] | 4-Amino-N'-hydroxy-N-(3-methylbenzyl)-1,2,5-oxadiazole-3-carboximidamide | Ex. 1 | 248.2 |
| 87 | 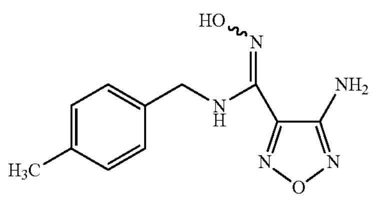 [SMILES: Cc1ccc(CNC(=NO)c2nonc2N)cc1] | 4-Amino-N'-hydroxy-N-(4-methylbenzyl)-1,2,5-oxadiazole-3-carboximidamide | Ex. 1 | 248.2 |
| 88 | 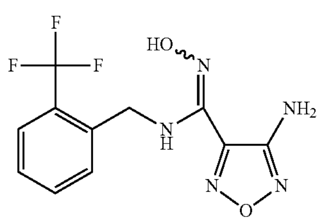 [SMILES: Nc1nonc1C(=NO)NCc1ccccc1C(F)(F)F] | 4-Amino-N'-hydroxy-N-[2-(trifluoromethyl)benzyl]-1,2,5-oxadiazole-3-carboximidamide | Ex. 1 | 302.1 |
| 89 | 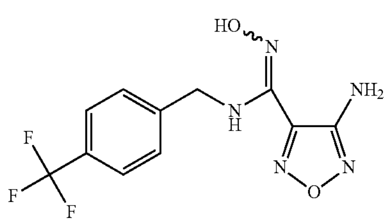 [SMILES: Nc1nonc1C(=NO)NCc1ccc(C(F)(F)F)cc1] | 4-Amino-N'-hydroxy-N-[4-(trifluoromethyl)benzyl]-1,2,5-oxadiazole-3-carboximidamide | Ex. 1 | 302.1 |
| 90 | 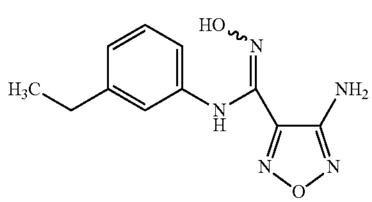 | 4-Amino-N-(3-ethylphenyl)-N'-hydroxy-1,2,5-oxadiazole-3-carboximidamide | Ex. 1 | 248.1 |

TABLE 1-continued

| Ex. No. | Structure | Name | Prep. Method | MS (M + 1) |
|---|---|---|---|---|
| 91 | 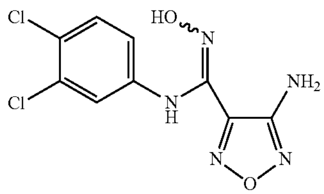 [SMILES: Nc1nonc1C(=NO)Nc1ccc(Cl)c(Cl)c1] | 4-Amino-N-(3,4-dichlorophenyl)-N'-hydroxy-1,2,5-oxadiazole-3-carboximidamide | Ex. 1 | 288.1 |
| 92 | 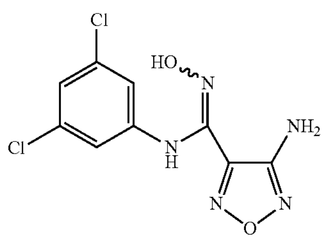 [SMILES: Nc1nonc1C(=NO)Nc1cc(Cl)cc(Cl)c1] | 4-Amino-N-(3,5-dichlorophenyl)-N'-hydroxy-1,2,5-oxadiazole-3-carboximidamide | Ex. 1 | 288.1 |
| 93 | 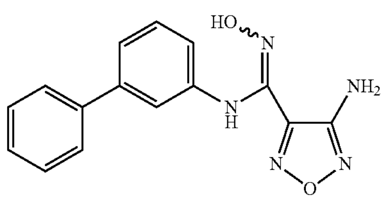 [SMILES: Nc1nonc1C(=NO)Nc1cccc(-c2ccccc2)c1] | 4-Amino-N-biphenyl-3-yl-N'-hydroxy-1,2,5-oxadiazole-3-carboximidamide | Ex. 1 | 296.1 |
| 94 | 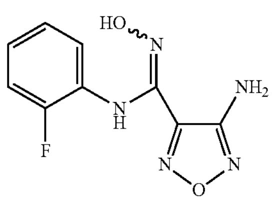 [SMILES: Nc1nonc1C(=NO)Nc1ccccc1F] | 4-Amino-N-(2-fluorophenyl)-N'-hydroxy-1,2,5-oxadiazole-3-carboximidamide | Ex. 1 | 238.1 |
| 95 | 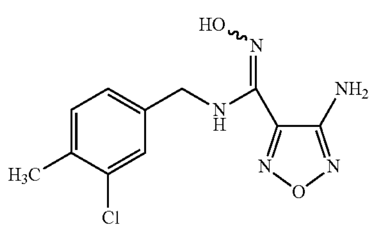 [SMILES: Cc1ccc(CNC(=NO)c2nonc2N)cc1Cl] | 4-Amino-N-(3-chloro-4-methylbenzyl)-N'-hydroxy-1,2,5-oxadiazole-3-carboximidamide | Ex. 1 | 282.1 |
| 96 | 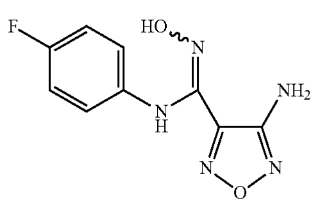 [SMILES: Nc1nonc1C(=NO)Nc1ccc(F)cc1] | 4-Amino-N-(4-fluorophenyl)-N'-hydroxy-1,2,5-oxadiazole-3-carboximidamide | Ex. 1 | 238.1 |
| 97 | 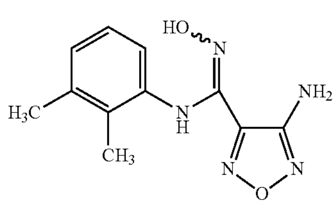 [SMILES: Cc1cccc(NC(=NO)c2nonc2N)c1C] | 4-Amino-N-(2,3-dimethylphenyl)-N'-hydroxy-1,2,5-oxadiazole-3-carboximidamide | Ex. 1 | 248.2 |

TABLE 1-continued

| Ex. No. | Structure | Name | Prep. Method | MS (M + 1) |
|---|---|---|---|---|
| 98 | 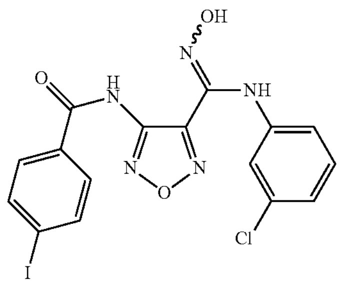 [SMILES: O=C(Nc1nonc1C(=NO)Nc1cccc(Cl)c1)c1ccc(I)cc1] | N-{4-[(E,Z)-[(3-Chlorophenyl)amino](hydroxyimino)methyl]-1,2,5-oxadiazol-3-yl}-4-iodobenzamide | Ex. 35 | 483.8 |
| 99 | 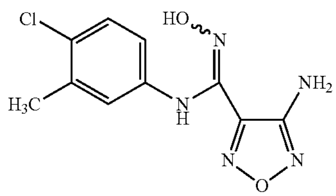 [SMILES: Cc1cc(NC(=NO)c2nonc2N)ccc1Cl] | 4-Amino-N-(4-chloro-3-methylphenyl)-N'-hydroxy-1,2,5-oxadiazole-3-carboximidamide | Ex. 1 | 268.2 |
| 100 | 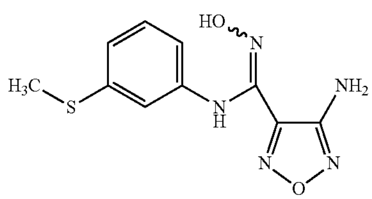 | 4-Amino-N'-hydroxy-N-[3-(methylthio)phenyl]-1,2,5-oxadiazole-3-carboximidamide | Ex. 1 | 266.0 |
| 101 | 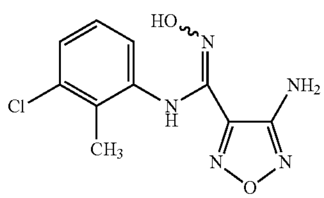 [SMILES: Cc1c(Cl)cccc1NC(=NO)c1nonc1N] | 4-Amino-N-(3-chloro-2-methylphenyl)-N'-hydroxy-1,2,5-oxadiazole-3-carboximidamide | Ex. 1 | 268.1 |
| 102 | 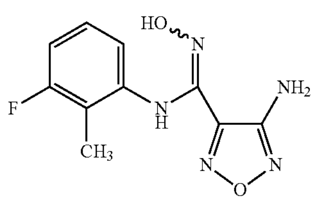 [SMILES: Cc1c(F)cccc1NC(=NO)c1nonc1N] | 4-Amino-N-(3-fluoro-2-methylphenyl)-N'-hydroxy-1,2,5-oxadiazole-3-carboximidamide | Ex. 1 | 252.1 |
| 103 | 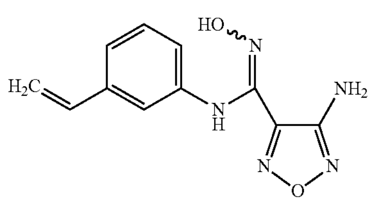 [SMILES: C=Cc1cccc(NC(=NO)c2nonc2N)c1] | 4-Amino-N'-hydroxy-N-(3-vinylphenyl)-1,2,5-oxadiazole-3-carboximidamide | Ex. 1 | 246.1 |
| 104 | 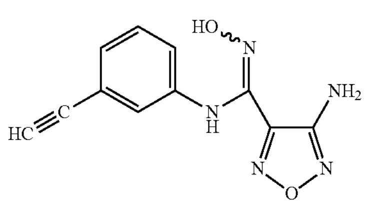 [SMILES: C#Cc1cccc(NC(=NO)c2nonc2N)c1] | 4-Amino-N-(3-ethynylphenyl)-N'-hydroxy-1,2,5-oxadiazole-3-carboximidamide | Ex. 1 | 244.0 |

TABLE 1-continued

| Ex. No. | Structure | Name | Prep. Method | MS (M + 1) |
|---|---|---|---|---|
| 105 | 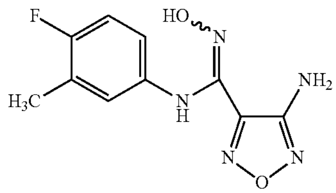 [SMILES: Cc1cc(NC(=NO)c2nonc2N)ccc1F] | 4-Amino-N-(4-fluoro-3-methylphenyl)-N'-hydroxy-1,2,5-oxadiazole-3-carboximidamide | Ex. 1 | 252.0 |
| 106 | 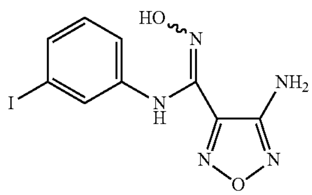 [SMILES: Nc1nonc1C(=NO)Nc1cccc(I)c1] | 4-Amino-N'-hydroxy-N-(3-iodophenyl)-1,2,5-oxadiazole-3-carboximidamide | Ex. 1 | 345.9 |
| 107 | 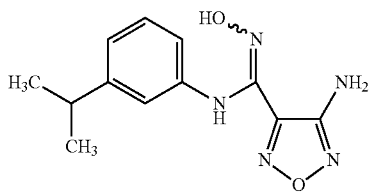 [SMILES: CC(C)c1cccc(NC(=NO)c2nonc2N)c1] | 4-Amino-N'-hydroxy-N-(3-isopropylphenyl)-1,2,5-oxadiazole-3-carboximidamide | Ex. 1 | 262.2 |
| 108 | 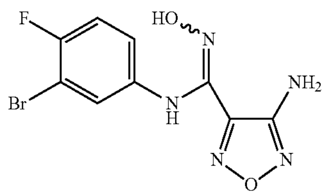 [SMILES: Nc1nonc1C(=NO)Nc1ccc(F)c(Br)c1] | 4-Amino-N-(3-bromo-4-fluorophenyl)-N'-hydroxy-1,2,5-oxadiazole-3-carboximidamide | Ex. 1 | 316.1 |
| 109 | 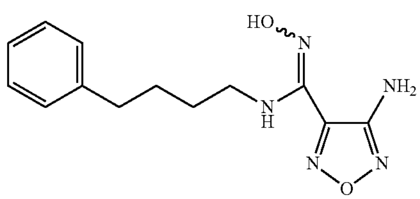 [SMILES: Nc1nonc1C(=NO)NCCCCc1ccccc1] | 4-Amino-N'-hydroxy-N-(4-phenylbutyl)-1,2,5-oxadiazole-3-carboximidamide | Ex. 1 | 276.2 |
| 110 | 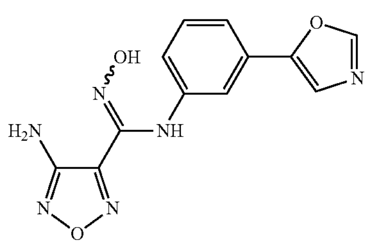 [SMILES: Nc1nonc1C(=NO)Nc1cccc(-c2cnco2)c1] | 4-Amino-N'-hydroxy-N-[3-(1,3-oxazol-5-yl)phenyl]-1,2,5-oxadiazole-3-carboximidamide | Ex. 1 | 287.0 |
| 111 | 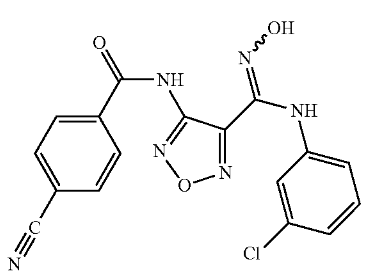 [SMILES: N#Cc1ccc(C(=O)Nc2nonc2C(=NO)Nc2cccc(Cl)c2)cc1] | N-{4-[(E,Z)-[(3-Chlorophenyl)amino](hydroxyimino)methyl]-1,2,5-oxadiazol-3-yl}-4-cyanobenzamide | Ex. 35 | 382.9 |

TABLE 1-continued

| Ex. No. | Structure | Name | Prep. Method | MS (M + 1) |
|---|---|---|---|---|
| 112 | 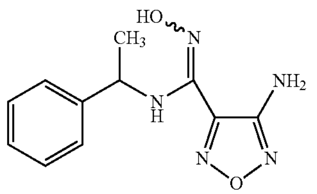 [SMILES: CC(NC(=NO)c1nonc1N)c1ccccc1] | 4-Amino-N'-hydroxy-N-[1-phenylethyl]-1,2,5-oxadiazole-3-carboximidamide | Ex. 1 | 248.2 |
| 113 | 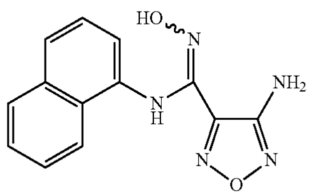 [SMILES: Nc1nonc1C(=NO)Nc1cccc2ccccc12] | 4-Amino-N'-hydroxy-N-1-naphthyl-1,2,5-oxadiazole-3-carboximidamide | Ex. 1 | 270.2 |
| 114 | 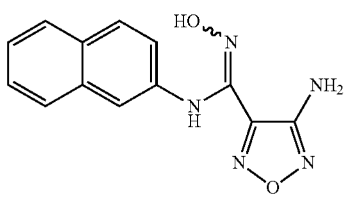 [SMILES: Nc1nonc1C(=NO)Nc1ccc2ccccc2c1] | 4-Amino-N'-hydroxy-N-2-naphthyl-1,2,5-oxadiazole-3-carboximidamide | Ex. 1 | 270.2 |
| 115 | 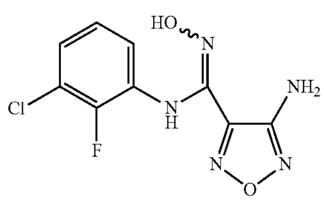 [SMILES: Nc1nonc1C(=NO)Nc1cccc(Cl)c1F] | 4-Amino-N-(3-chloro-2-fluorophenyl)-N'-hydroxy-1,2,5-oxadiazole-3-carboximidamide | Ex. 1 | 272.1 |
| 116 | 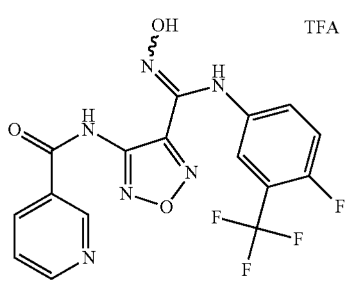 [SMILES: O=C(Nc1nonc1C(=NO)Nc1ccc(F)c(C(F)(F)F)c1)c1cccnc1] | N-{4-[(E,Z)-{[4-Fluoro-3-(trifluoromethyl)phenyl]amino}(hydroxyimino)methyl]-1,2,5-oxadiazol-3-yl}nicotinamide trifluoroacetate | Ex. 35 | 411.1 |
| 117 | 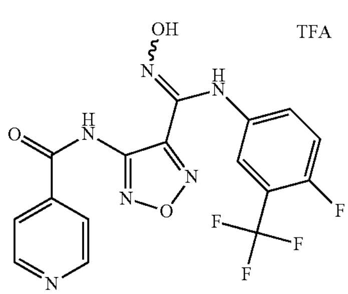 [SMILES: O=C(Nc1nonc1C(=NO)Nc1ccc(F)c(C(F)(F)F)c1)c1ccncc1] | N-{4-[(E,Z)-{[4Fluoro-3-(trifluoromethyl)phenyl]amino}(hydroxyimino)methyl]-1,2,5-oxadiazol-3-yl}isonicotinamide trifluoroacetate | Ex. 35 | 411.1 |

TABLE 1-continued

| Ex. No. | Structure | Name | Prep. Method | MS (M + 1) |
|---|---|---|---|---|
| 118 | 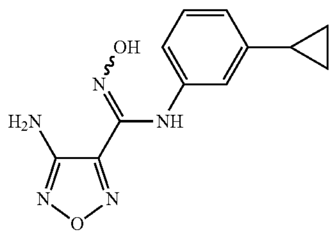 [SMILES: Nc1nonc1C(=NO)Nc1cccc(C2CC2)c1] | 4-Amino-N-(3-cyclopropylphenyl)-N'-hydroxy-1,2,5-oxadiazole-3-carboximidamide | Ex. 1 | 260.2 |
| 119 | 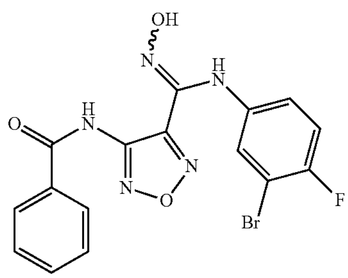 [SMILES: O=C(Nc1nonc1C(=NO)Nc1ccc(F)c(Br)c1)c1ccccc1] | N-{4-[(E,Z)-[(3-Bromo-4-fluorophenyl)amino](hydroxyimino)methyl]-1,2,5-oxadiazol-3-yl}benzamide | Ex. 35 | 420.0, 421.9 |
| 120 | 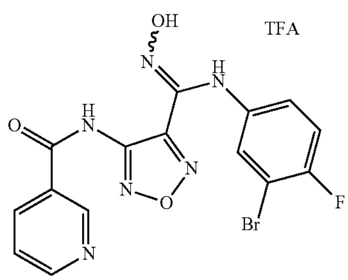 [SMILES: O=C(Nc1nonc1C(=NO)Nc1ccc(F)c(Br)c1)c1cccnc1] | N-{4-[(E,Z)-[(3-Bromo-4-fluorophenyl)amino](hydroxyimino)methyl]-1,2,5-oxadiazol-3-yl}nicotinamide trifluoroacetate | Ex. 35 | 420.9, 422.9 |
| 121 | 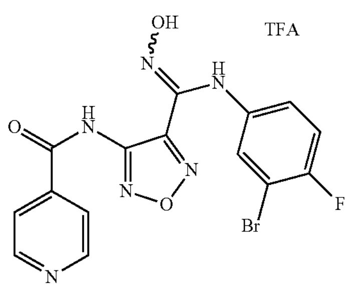 [SMILES: O=C(Nc1nonc1C(=NO)Nc1ccc(F)c(Br)c1)c1ccncc1] | N-{4-[(E,Z)-[(3-Bromo-4-fluorophenyl)amino](hydroxyimino)methyl]-1,2,5-oxadiazol-3-yl}isonicotinamide trifluoroacetate | Ex. 35 | 421.0, 422.9 |
| 122 | 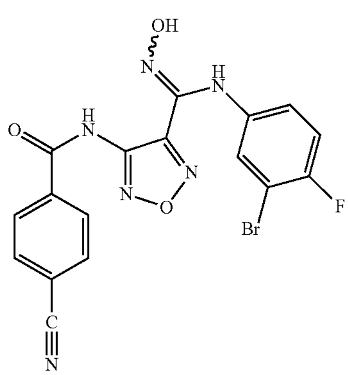 [SMILES: N#Cc1ccc(C(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-4-cyanobenzamide | Ex. 35 | 444.9, 446.9 |

TABLE 1-continued

| Ex. No. | Structure | Name | Prep. Method | MS (M + 1) |
|---|---|---|---|---|
| 123 | 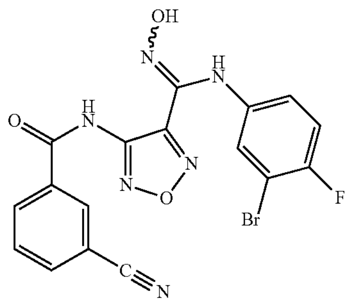 [SMILES: N#Cc1cccc(C(=O)Nc2nonc2C(=NO)Nc2ccc(F)c(Br)c2)c1] | N-{4-[(E,Z)-[(3-Bromo-4-fluorophenyl)amino](hydroxyimino)methyl]-1,2,5-oxadiazol-3-yl}-3-cyanobenzamide | Ex. 35 | 445.0, 447.0 |
| 124 | 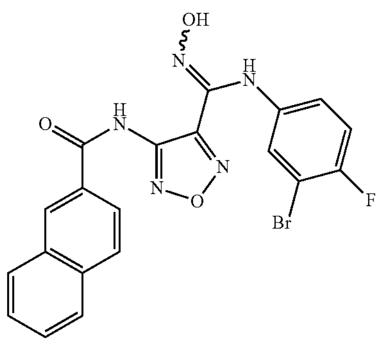 [SMILES: O=C(Nc1nonc1C(=NO)Nc1ccc(F)c(Br)c1)c1ccc2ccccc2c1] | N-{4-[(E,Z)-[(3-Bromo-4-fluorophenyl)amino](hydroxyimino)methyl]-1,2,5-oxadiazol-3-yl}-2-naphthamide | Ex. 35 | 470.0, 472.0 |
| 125 | 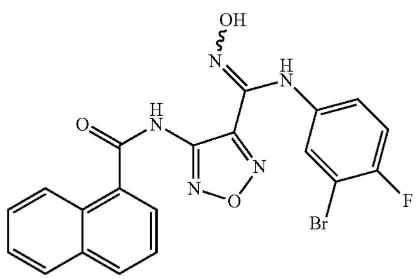 [SMILES: O=C(Nc1nonc1C(=NO)Nc1ccc(F)c(Br)c1)c1cccc2ccccc12] | N-{4-[(E,Z)-[(3-Bromo-4-fluorophenyl)amino](hydroxyimino)methyl]-1,2,5-oxadiazol-3-yl}-1-naphthamide | Ex. 35 | 470.0, 472.0 |
| 126 | 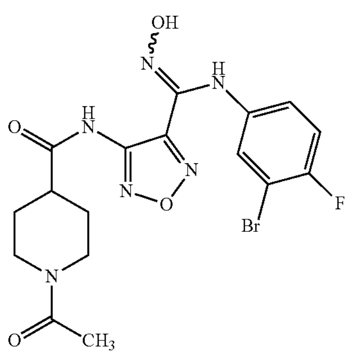 [SMILES: CC(=O)N1CCC(C(=O)Nc2nonc2C(=NO)Nc2ccc(F)c(Br)c2)CC1] | 1-Acetyl-N-{4-[(E,Z)-[(3-bromo-4-fluorophenyl)amino](hydroxyimino)methyl]-1,2,5-oxadiazol-3-yl}piperidine-4-carboxamide | Ex. 35 | 469.0, 471.0 |
| 127 | 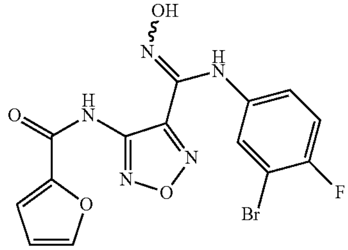 | N-{4-[(E,Z)-[(3-Bromo-4-fluorophenyl)amino](hydroxyimino)methyl]-1,2,5-oxadiazol-3-yl}-2-furamide | Ex. 35 | 409.9, 411.9 |

TABLE 1-continued

| Ex. No. | Structure | Name | Prep. Method | MS (M + 1) |
|---|---|---|---|---|
| 128 | 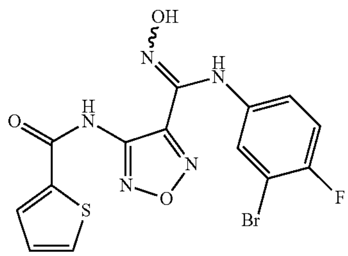 [SMILES: O=C(Nc1nonc1C(=NO)Nc1ccc(F)c(Br)c1)c1cccs1] | N-{4-[(E,Z)-[(3-Bromo-4-fluorophenyl)amino](hydroxy-imino)methyl]-1,2,5-oxadiazol-3-yl}thiophene-2-carboxamide | Ex. 35 | 425.9, 427.9 |
| 129 | 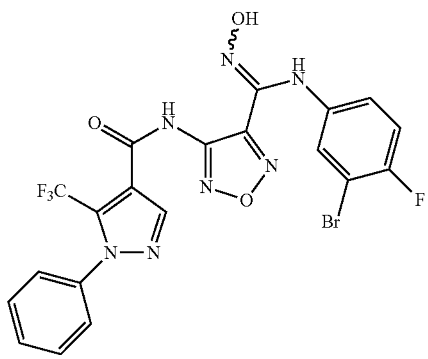 [SMILES: O=C(Nc1nonc1C(=NO)Nc1ccc(F)c(Br)c1)c1cnn(-c2ccccc2)c1C(F)(F)F] | N-{4-[(E,Z)-[(3-Bromo-4-fluorophenyl)amino](hydroxy-imino)methyl]-1,2,5-oxadiazol-3-yl}-1-phenyl-5-(trifluoromethyl)-1H-pyrazole-4-carboxamide | Ex. 35 | 553.9, 556.0 |
| 130 | 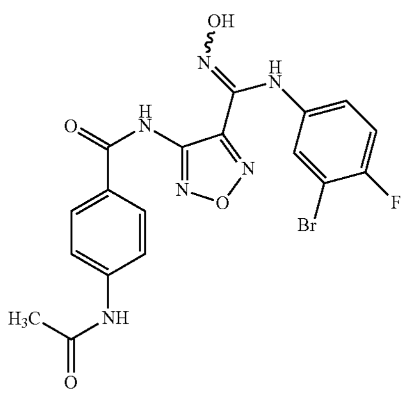 [SMILES: CC(=O)Nc1ccc(C(=O)Nc2nonc2C(=NO)Nc2ccc(F)c(Br)c2)cc1] | 4-(Acetylamino)-N-{4-[(E,Z)-[(3-bromo-4-fluorophenyl)amino](hydroxy-imino)methyl]-1,2,5-oxadiazol-3-yl}benzamide | Ex. 35 | 476.9, 479.0 |
| 131 | 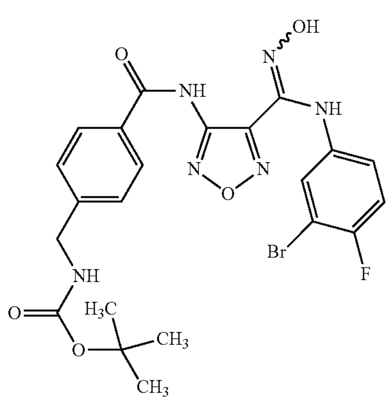 [SMILES: CC(C)(C)OC(=O)NCc1ccc(C(=O)Nc2nonc2C(=NO)Nc2ccc(F)c(Br)c2)cc1] | tert-Butyl {4-[({4-[(E,Z)-[(3-bromo-4-fluorophenyl)amino](hydroxy-imino)methyl]-1,2,5-oxadiazol-3-yl}amino)carbonyl]benzyl}carbamate | Ex. 41 | 548.9, 551.0 |

TABLE 1-continued

| Ex. No. | Structure | Name | Prep. Method | MS (M + 1) |
|---|---|---|---|---|
| 132 | 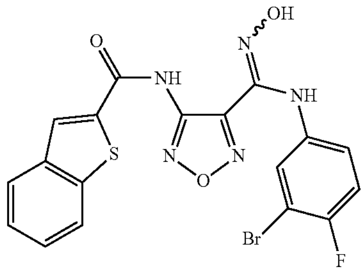 [SMILES: O=C(Nc1nonc1C(=NO)Nc1ccc(F)c(Br)c1)c1cc2ccccc2s1] | N-{4-[(E,Z)-[(3-Bromo-4-fluorophenyl)amino](hydroxyimino)methyl]-1,2,5-oxadiazol-3-yl}-1-benzothiophene-2-carboxamide | Ex. 41 | 475.9, 477.9 |
| 133 | 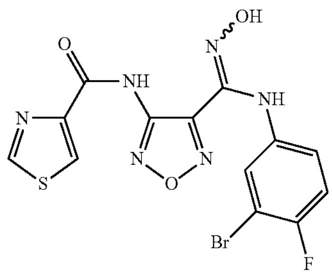 [SMILES: O=C(Nc1nonc1C(=NO)Nc1ccc(F)c(Br)c1)c1cscn1] | N-{4-[(E,Z)-[(3-Bromo-4-fluorophenyl)amino](hydroxyimino)methyl]-1,2,5-oxadiazol-3-yl}-1,3-thiazole-4-carboxamide | Ex. 41 | 426.9, 428.9 |
| 134 | 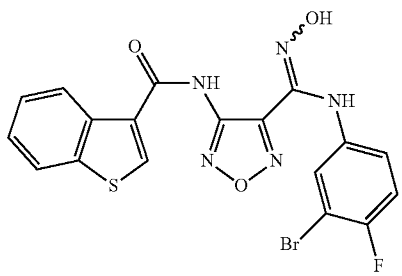 [SMILES: O=C(Nc1nonc1C(=NO)Nc1ccc(F)c(Br)c1)c1csc2ccccc12] | N-{4-[(E,Z)-[(3-Bromo-4-fluorophenyl)amino](hydroxyimino)methyl]-1,2,5-oxadiazol-3-yl}-1-benzothiophene-3-carboxamide | Ex. 41 | 475.9, 477.9 |
| 135 | 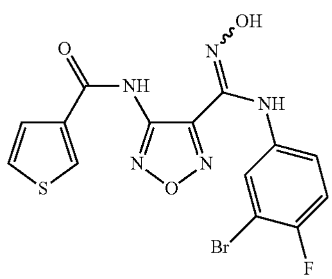 | N-{4-[(E,Z)-[(3-Bromo-4-fluorophenyl)amino](hydroxyimino)methyl]-1,2,5-oxadiazol-3-yl}thiophene-3-carboxamide | Ex. 41 | 425.8, 427.9 |
| 136 | 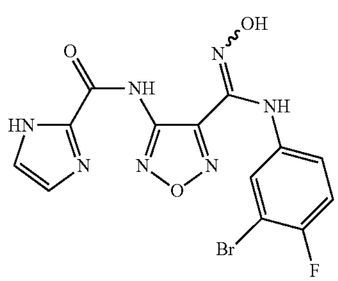 [SMILES: O=C(Nc1nonc1C(=NO)Nc1ccc(F)c(Br)c1)c1ncc[nH]1] | N-{4-[(E,Z)-[(3-Bromo-4-fluorophenyl)amino](hydroxyimino)methyl]-1,2,5-oxadiazol-3-yl}-1H-imidazole-2-carboxamide | Ex. 41 | 409.9, 411.9 |

TABLE 1-continued

| Ex. No. | Structure | Name | Prep. Method | MS (M + 1) |
|---|---|---|---|---|
| 137 | 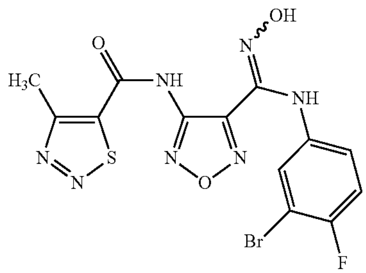 [SMILES: Cc1nnsc1C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-4-methyl-1,2,3-thiadiazole-5-carboxamide | Ex. 41 | 441.9, 443.9 |
| 138 | 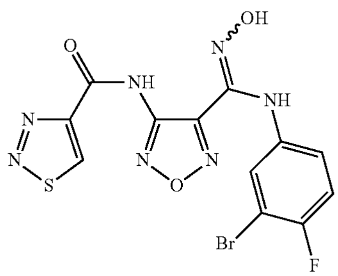 [SMILES: O=C(Nc1nonc1C(=NO)Nc1ccc(F)c(Br)c1)c1csnn1] | N-{4-[(E,Z)-[(3-Bromo-4-fluorophenyl)amino](hydroxyimino)methyl]-1,2,5-oxadiazol-3-yl}-1,2,3-thiadiazole-4-carboxamide | Ex. 41 | 427.9, 429.9 |
| 139 | 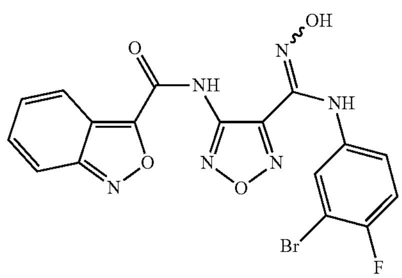 [SMILES: O=C(Nc1nonc1C(=NO)Nc1ccc(F)c(Br)c1)c1onc2ccccc12] | N-{4-[(E,Z)-[(3-Bromo-4-fluorophenyl)amino](hydroxyimino)methyl]-1,2,5-oxadiazol-3-yl}-2,1-benzisoxazole-3-carboxamide | Ex. 41 | 460.9, 462.9 |
| 140 | 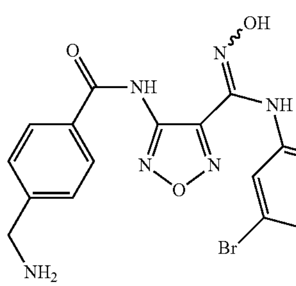 | 4-(Aminomethyl)-N-{4-[(E,Z)-[(3-bromo-4-fluorophenyl)amino](hydroxyimino)methyl]-1,2,5-oxadiazol-3-yl}benzamide trifluoroacetate | Ex. 41 | 448.9, 450.9 |
| 141 | 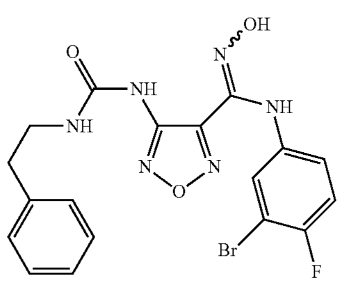 [SMILES: O=C(NCCc1ccccc1)Nc1nonc1C(=NO)Nc1ccc(F)c(Br)c1] | N-(3-Bromo-4-fluorophenyl)-N'-hydroxy-4-({[(2-phenylethyl)amino]carbonyl}amino)-1,2,5-oxadiazole-3-carboximidamide | Ex. 43 | 463.0, 465.0 |

TABLE 1-continued

| Ex. No. | Structure | Name | Prep. Method | MS (M + 1) |
|---|---|---|---|---|
| 142 | 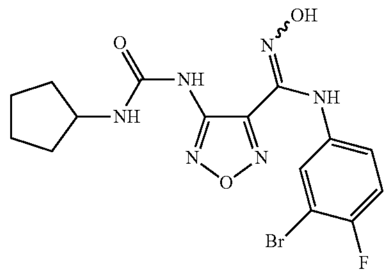 [SMILES: O=C(Nc1nonc1C(=NO)Nc1ccc(F)c(Br)c1)NC1CCCC1] | N-(3-Bromo-4-fluorophenyl)-4-{[(cyclopentylamino)carbonyl]amino}-N'-hydroxy-1,2,5-oxadiazole-3-carboximidamide | Ex. 43 | 426.9, 428.9 |
| 143 | 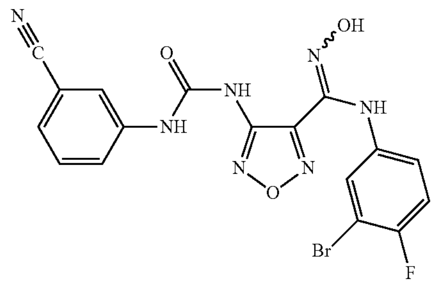 [SMILES: N#Cc1cccc(NC(=O)Nc2nonc2C(=NO)Nc2ccc(F)c(Br)c2)c1] | N-(3-Bromo-4-fluorophenyl)-4-({[(3-cyanophenyl)amino]carbonyl}amino)-N'-hydroxy-1,2,5-oxadiazole-3-carboximidamide | Ex. 43 | 459.9, 461.9 |
| 144 | 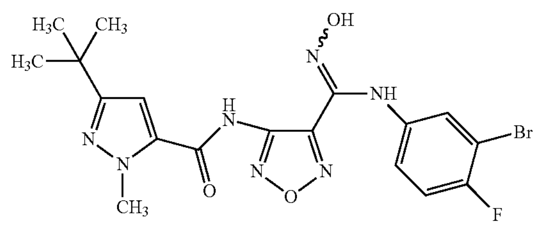 [SMILES: Cn1nc(C(C)(C)C)cc1C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-tert-butyl-1-methyl-1H-pyrazole-5-carboxamide | Ex. 35 | 480.0, 482.0 |
| 145 | 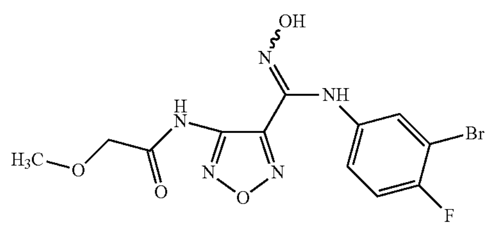 [SMILES: COCC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-methoxyacetamide | Ex. 35 | 387.9, 389.9 |
| 146 | 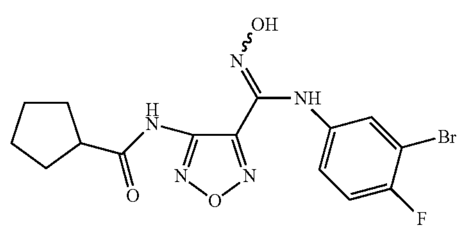 [SMILES: O=C(Nc1nonc1C(=NO)Nc1ccc(F)c(Br)c1)C1CCCC1] | N-{4-[(E,Z)-[(3-Bromo-4-fluorophenyl)amino](hydroxyimino)methyl]-1,2,5-oxadiazol-3-yl}cyclopentanecarboxamide | Ex. 35 | 412.0, 413.9 |
| 147 | 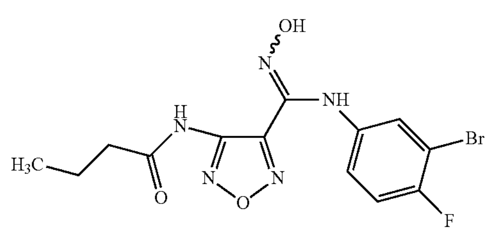 [SMILES: CCCC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}butanamide | Ex. 35 | 385.9, 388.0 |

TABLE 1-continued

| Ex. No. | Structure | Name | Prep. Method | MS (M + 1) |
|---|---|---|---|---|
| 148 | 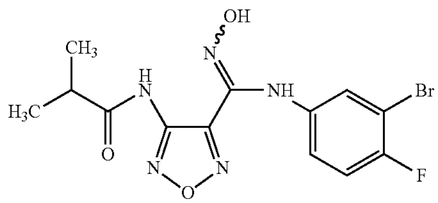 [SMILES: CC(C)C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-methylpropanamide | Ex. 35 | 386.0, 387.9 |
| 149 | 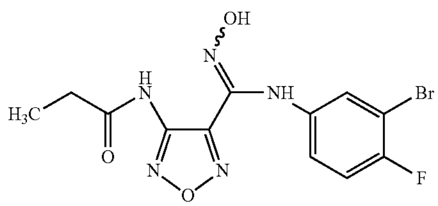 [SMILES: CCC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}propanamide | Ex. 35 | 371.9, 373.9 |
| 150 | 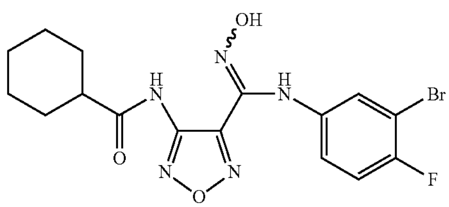 [SMILES: O=C(Nc1nonc1C(=NO)Nc1ccc(F)c(Br)c1)C1CCCCC1] | N-{4-[(E,Z)-[(3-Bromo-4-fluorophenyl)amino](hydroxyimino)methyl]-1,2,5-oxadiazol-3-yl}cyclohexanecarboxamide | Ex. 35 | 426.0, 427.9 |
| 151 | 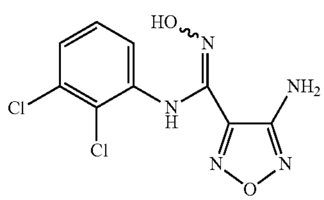 [SMILES: Nc1nonc1C(=NO)Nc1cccc(Cl)c1Cl] | 4-Amino-N-(2,3-dichlorophenyl)-N'-hydroxy-1,2,5-oxadiazole-3-carboximidamide | Ex. 47 | 288.0 |
| 152 | 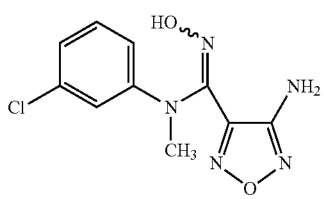 [SMILES: CN(C(=NO)c1nonc1N)c1cccc(Cl)c1] | 4-Amino-N-(3-chlorophenyl)-N'-hydroxy-N-methyl-1,2,5-oxadiazole-3-carboximidamide | Ex. 1 | 268.1 |
| 153 | 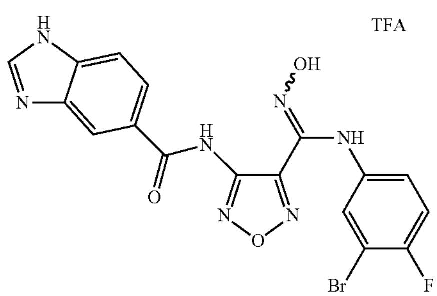 [SMILES: O=C(Nc1nonc1C(=NO)Nc1ccc(F)c(Br)c1)c1ccc2[nH]cnc2c1] | N-{4-[(E,Z)-[(3-Bromo-4-fluorophenyl)amino](hydroxyimino)methyl]-1,2,5-oxadiazol-3-yl}-1H-benzimidazole-5-carboxamide trifluoroacetate | Ex. 35 | 460.0, 462.0 |
| 154 | 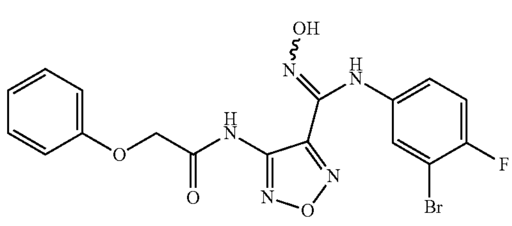 [SMILES: O=C(COc1ccccc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-phenoxyacetamide | Ex. 35 | 449.9, 451.8 |

TABLE 1-continued

| Ex. No. | Structure | Name | Prep. Method | MS (M + 1) |
|---|---|---|---|---|
| 155 | 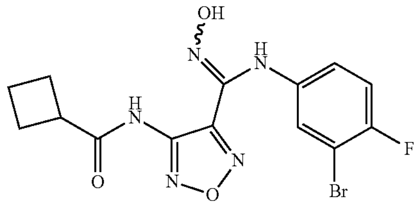 [SMILES: O=C(Nc1nonc1C(=NO)Nc1ccc(F)c(Br)c1)C1CCC1] | N-{4-[(E,Z)-[(3-Bromo-4-fluorophenyl)amino](hydroxyimino)methyl]-1,2,5-oxadiazol-3-yl}cyclobutanecarboxamide | Ex. 35 | 398.0, 400.0 |
| 156 | 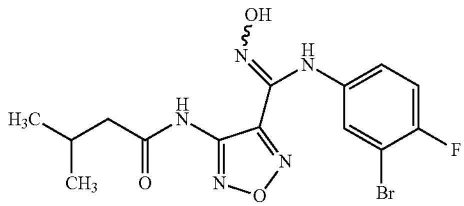 [SMILES: CC(C)CC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-methylbutanamide | Ex. 35 | 400.0, 402.0 |
| 157 | 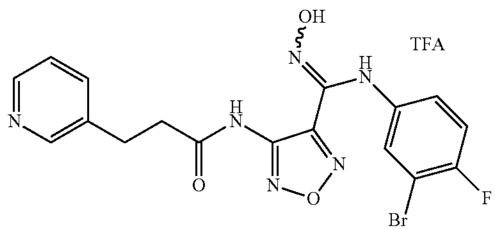 [SMILES: O=C(CCc1cccnc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-pyridin-3-ylpropanamide trifluoroacetate | Ex. 35 | 449.0, 450.9 |
| 158 | 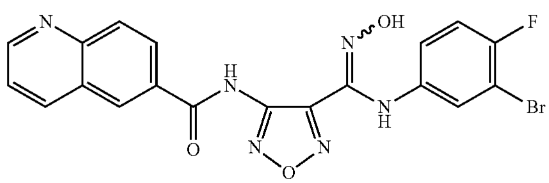 [SMILES: O=C(Nc1nonc1C(=NO)Nc1ccc(F)c(Br)c1)c1ccc2ncccc2c1] | N-{4-[(E,Z)-[(3-Bromo-4-fluorophenyl)amino](hydroxyimino)methyl]-1,2,5-oxadiazol-3-yl}quinoline-6-carboxamide | Ex. 35 | 470.9, 472.9 |
| 159 | 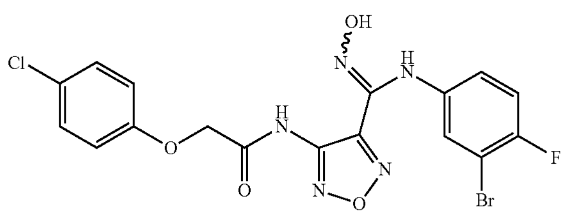 [SMILES: O=C(COc1ccc(Cl)cc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(4-chlorophenoxy)acetamide | Ex. 35 | 483.9, 485.9 |
| 160 | 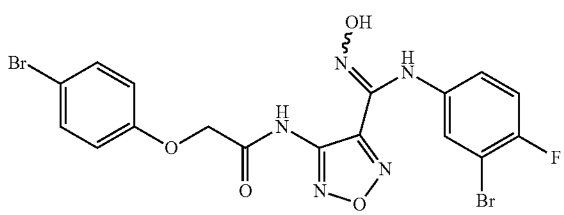 | N-{4-[(E,Z)-[(3-Bromo-4-fluorophenyl)amino](hydroxyimino)methyl]-1,2,5-oxadiazol-3-yl}-2-(4-bromophenoxy)acetamide | Ex. 35 | 527.8, 529.9, 531.8 |
| 161 | 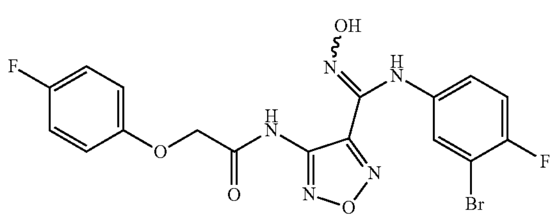 [SMILES: O=C(COc1ccc(F)cc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(4-fluorophenoxy)acetamide | Ex. 35 | 468.0, 470.0 |

TABLE 1-continued

| Ex. No. | Structure | Name | Prep. Method | MS (M + 1) |
|---|---|---|---|---|
| 162 | 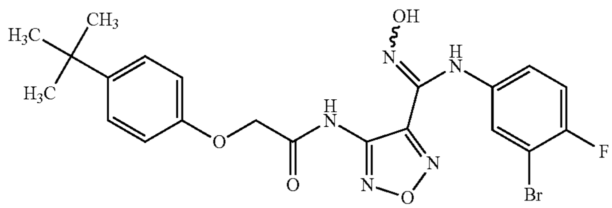 [SMILES: CC(C)(C)c1ccc(OCC(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-2-(4-tert-butylphenoxy)acetamide | Ex. 35 | 506.0, 508.0 |
| 163 | 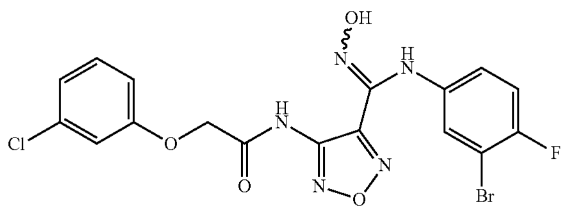 [SMILES: O=C(COc1cccc(Cl)c1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(3-chlorophenoxy)acetamide | Ex. 35 | 483.9, 485.9 |
| 164 | 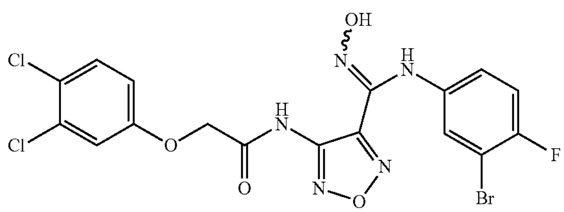 [SMILES: O=C(COc1ccc(Cl)c(Cl)c1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(3,4-dichlorophenoxy)acetamide | Ex. 35 | 518.0, 519.9, 522.0 |
| 165 | 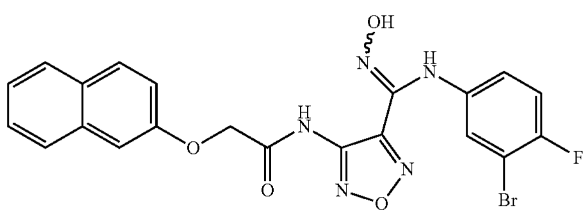 [SMILES: O=C(COc1ccc2ccccc2c1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(2-naphthyloxy)acetamide | Ex. 35 | 500.1, 502.0 |
| 166 | 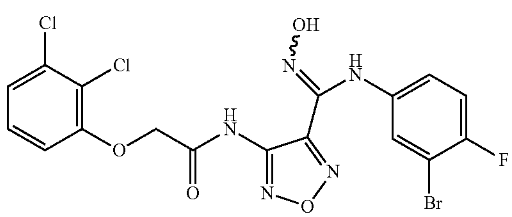 [SMILES: O=C(COc1cccc(Cl)c1Cl)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(2,3-dichlorophenoxy)acetamide | Ex. 35 | 517.8, 519.8, 521.8 |
| 167 | 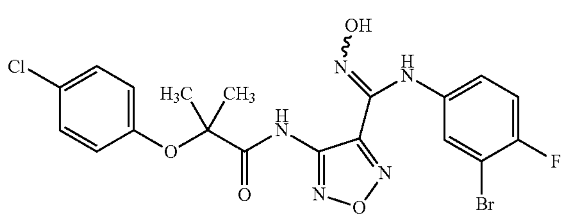 [SMILES: CC(C)(Oc1ccc(Cl)cc1)C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(4-chlorophenoxy)-2-methylpropanamide | Ex. 35 | 511.9, 513.9 |
| 168 | 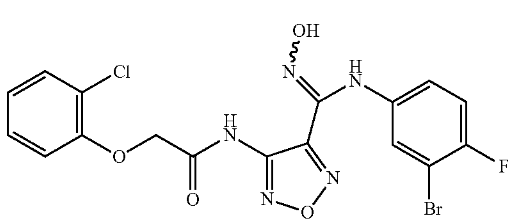 [SMILES: O=C(COc1ccccc1Cl)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(2-chlorophenoxy)acetamide | Ex. 35 | 483.8, 485.9 |

TABLE 1-continued

| Ex. No. | Structure | Name | Prep. Method | MS (M + 1) |
|---|---|---|---|---|
| 169 | 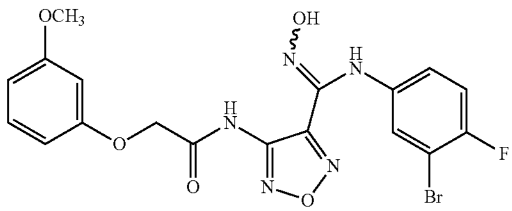 [SMILES: COc1cccc(OCC(=O)Nc2nonc2C(=NO)Nc2ccc(F)c(Br)c2)c1] | N-{4-[(E,Z)-[(3-Bromo-4-fluorophenyl)amino](hydroxyimino)methyl]-1,2,5-oxadiazol-3-yl}-2-(3-methoxyphenoxy)acetamide | Ex. 35 | 480.0, 481.9 |
| 170 | 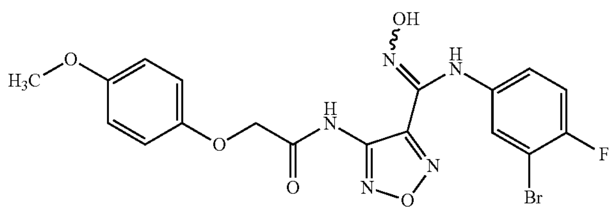 [SMILES: COc1ccc(OCC(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-2-(4-methoxyphenoxy)acetamide | Ex. 35 | 479.9, 481.9 |
| 171 | 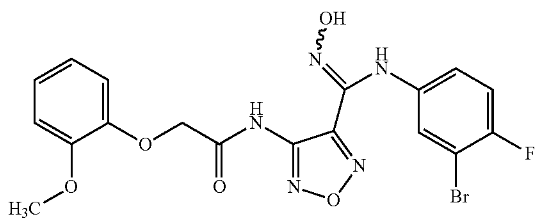 [SMILES: COc1ccccc1OCC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-(2-methoxyphenoxy)acetamide | Ex. 35 | 480.0, 482.0 |
| 172 | 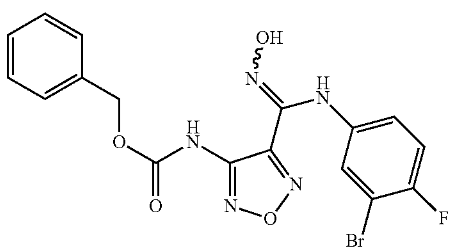 [SMILES: O=C(Nc1nonc1C(=NO)Nc1ccc(F)c(Br)c1)OCc1ccccc1] | Benzyl {4-[(E,Z)-[(3-bromo-4-fluorophenyl)amino](hydroxyimino)methyl]-1,2,5-oxadiazol-3-yl}carbamate | Ex. 35 | 449.9, 451.9 |
| 173 | 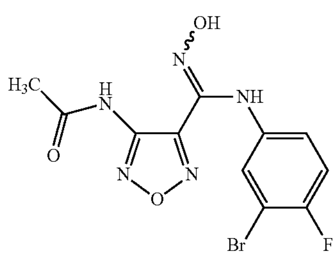 [SMILES: CC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}acetamide | Ex. 35 | 357.9, 359.9 |
| 174 | 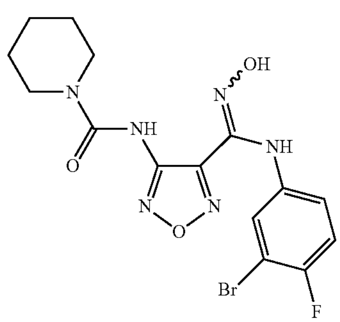 [SMILES: O=C(Nc1nonc1C(=NO)Nc1ccc(F)c(Br)c1)N1CCCCC1] | N-{4-[(E,Z)-[(3-Bromo-4-fluorophenyl)amino](hydroxyimino)methyl]-1,2,5-oxadiazol-3-yl}piperidine-1-carboxamide | Ex. 48 | 427.0, 429.0 |

TABLE 1-continued

| Ex. No. | Structure | Name | Prep. Method | MS (M + 1) |
|---|---|---|---|---|
| 175 | 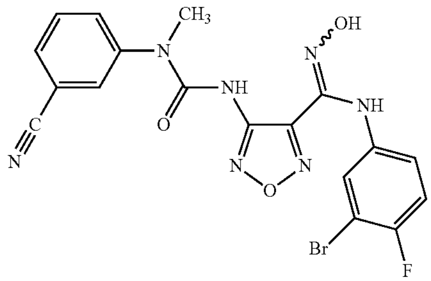 [SMILES: CN(C(=O)Nc1nonc1C(=NO)Nc1ccc(F)c(Br)c1)c1cccc(C#N)c1] | N-(3-Bromo-4-fluorophenyl)-4-({[(3-cyanophenyl)(methyl)amino]carbonyl}amino)-N'-hydroxy-1,2,5-oxadiazole-3-carboximidamide | Ex. 48 | 473.9, 476.0 |
| 176 | 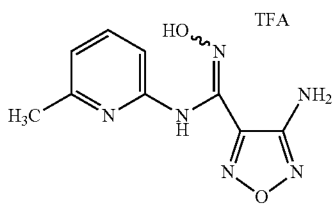 [SMILES: Cc1cccc(NC(=NO)c2nonc2N)n1] | 4-Amino-N'-hydroxy-N-(6-methylpyridin-2-yl)-1,2,5-oxadiazole-3-carboximidamide trifluoroacetate | Ex. 45 | 235.1 |
| 177 | 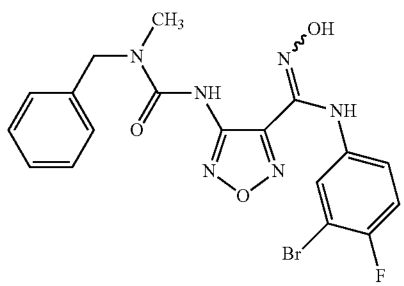 [SMILES: CN(Cc1ccccc1)C(=O)Nc1nonc1C(=NO)Nc1ccc(F)c(Br)c1] | 4-({[Benzyl(methyl)amino]carbonyl}amino)-N-(3-bromo-4-fluorophenyl)-N'-hydroxy-1,2,5-oxadiazole-3-carboximidamide | Ex. 48 | 463.0, 464.9 |
| 178 | 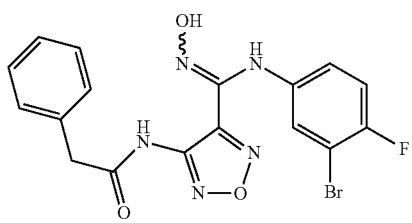 [SMILES: O=C(Cc1ccccc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-phenylacetamide | Ex. 35 | 434.0, 436.0 |
| 179 | 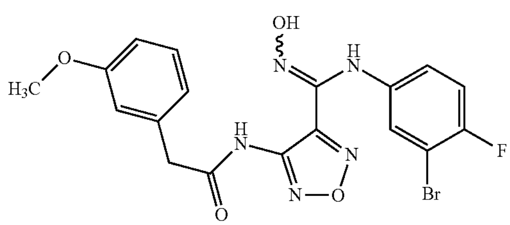 [SMILES: COc1cccc(CC(=O)Nc2nonc2C(=NO)Nc2ccc(F)c(Br)c2)c1] | N-{4-[(E,Z)-[(3-Bromo-4-fluorophenyl)amino](hydroxyimino)methyl]-1,2,5-oxadiazol-3-yl}-2-(3-methoxyphenyl)acetamide | Ex. 35 | 464.0, 466.0 |
| 180 | 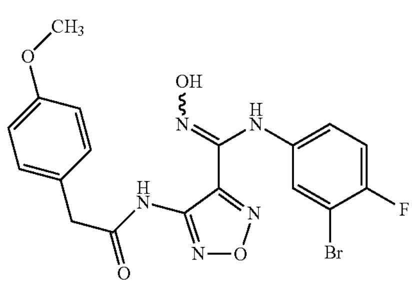 [SMILES: COc1ccc(CC(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-2-(4-methoxyphenyl)acetamide | Ex. 35 | 464.0, 466.0 |

TABLE 1-continued

| Ex. No. | Structure | Name | Prep. Method | MS (M + 1) |
|---|---|---|---|---|
| 181 | 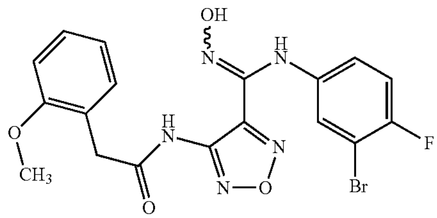 [SMILES: COc1ccccc1CC(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-2-(2-methoxyphenyl)acetamide | Ex. 35 | 464.0, 466.0 |
| 182 | 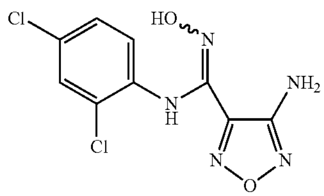 [SMILES: Nc1nonc1C(=NO)Nc1ccc(Cl)cc1Cl] | 4-Amino-N-(2,4-dichlorophenyl)-N'-hydroxy-1,2,5-oxadiazole-3-carboximidamide | Ex. 45 | 288.0 |
| 183 | 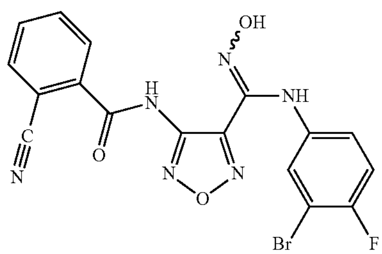 [SMILES: N#Cc1ccccc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-2-cyanobenzamide | Ex. 35 | 444.9, 446.9 |
| 184 | 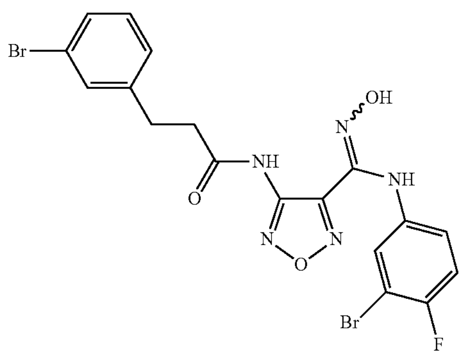 [SMILES: O=C(CCc1cccc(Br)c1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(3-bromophenyl)propanamide | Ex. 35 | 525.9, 527.8, 529.8 |
| 185 | 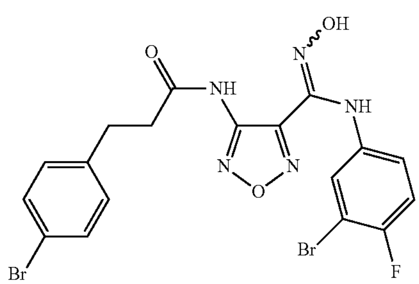 [SMILES: O=C(CCc1ccc(Cl)cc1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(4-bromophenyl)propanamide | Ex. 35 | 525.8, 527.8, 529.8 |
| 186 | 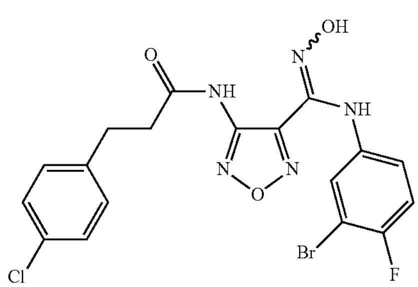 | N-{4-[(E,Z)-[(3-Bromo-4-fluorophenyl)amino](hydroxy-imino)methyl]-1,2,5-oxadiazol-3-yl}-3-(4-chlorophenyl)propanamide | Ex. 35 | 481.9, 483.9 |

TABLE 1-continued

| Ex. No. | Structure | Name | Prep. Method | MS (M + 1) |
|---|---|---|---|---|
| 187 | 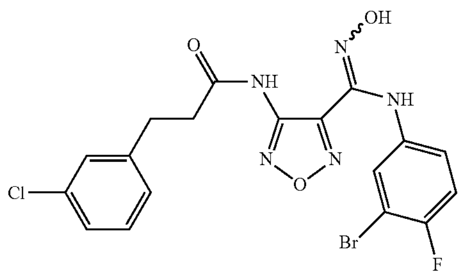 [SMILES: O=C(CCc1cccc(Cl)c1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(3-chlorophenyl)propanamide | Ex. 35 | 481.9, 483.9 |
| 188 | 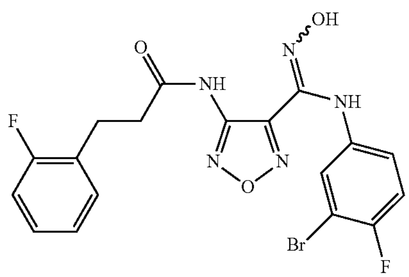 [SMILES: O=C(CCc1ccccc1F)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(2-fluorophenyl)propanamide | Ex. 35 | 466.0, 467.9 |
| 189 | 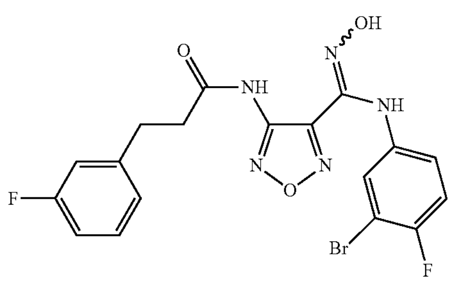 [SMILES: O=C(CCc1cccc(F)c1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(3-fluorophenyl)propanamide | Ex. 35 | 465.9, 467.9 |
| 190 | 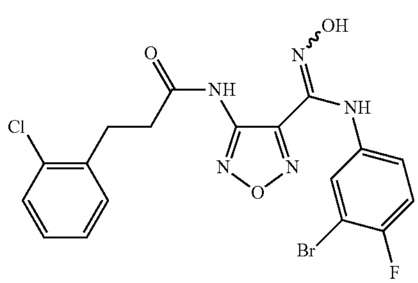 [SMILES: O=C(CCc1ccccc1Cl)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3-(2-chlorophenyl)propanamide | Ex. 35 | 481.9, 483.9 |
| 191 | 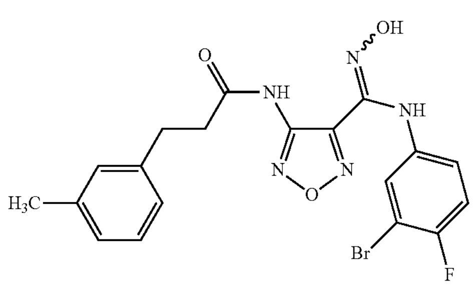 [SMILES: Cc1cccc(CCC(=O)Nc2nonc2C(=NO)Nc2ccc(F)c(Br)c2)c1] | N-{4-[(E,Z)-[(3-Bromo-4-fluorophenyl)amino](hydroxy-imino)methyl]-1,2,5-oxadiazol-3-yl}-3-(3-methylphenyl)propanamide | Ex. 35 | 462.0, 464.0 |

TABLE 1-continued

| Ex. No. | Structure | Name | Prep. Method | MS (M + 1) |
|---|---|---|---|---|
| 192 | 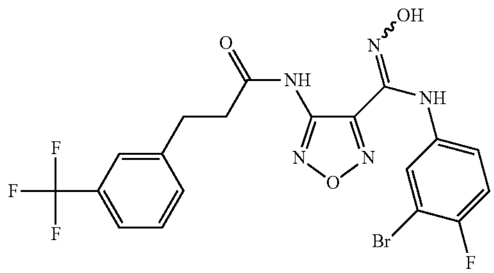 [SMILES: O=C(CCc1cccc(C(F)(F)F)c1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-(3-(trifluoromethyl)phenyl)propanamide | Ex. 35 | 515.9, 517.9 |
| 193 | 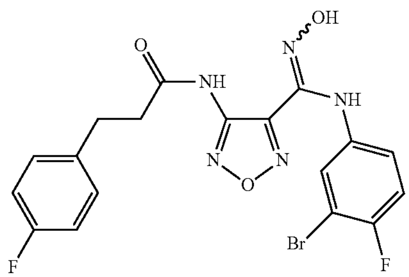 [SMILES: O=C(CCc1ccc(F)cc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-(4-fluorophenyl)propanamide | Ex. 35 | 465.9, 468.0 |
| 194 | 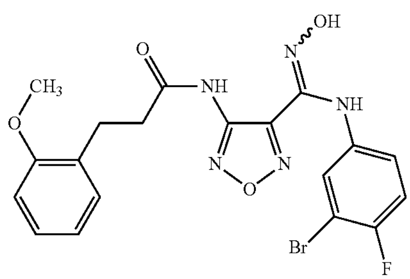 [SMILES: COc1ccccc1CCC(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-(2-methoxyphenyl)propanamide | Ex. 35 | 477.9, 479.9 |
| 195 | 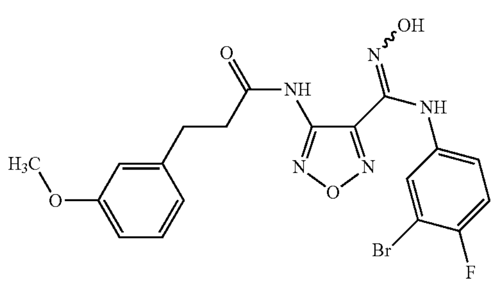 [SMILES: COc1cccc(CCC(=O)Nc2nonc2C(=NO)Nc2ccc(F)c(Br)c2)c1] | N-{4-[(E,Z)-[(3-Bromo-4-fluorophenyl)amino](hydroxyimino)methyl]-1,2,5-oxadiazol-3-yl}-3-(3-methoxyphenyl)propanamide | Ex. 35 | 477.9, 480.0 |
| 196 | 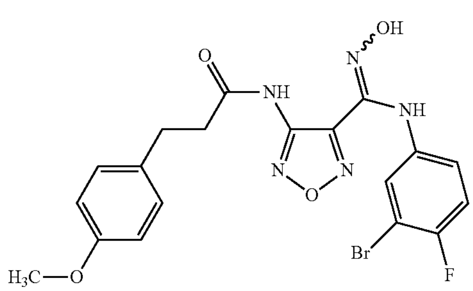 [SMILES: COc1ccc(CCC(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-3-(4-methoxyphenyl)propanamide | Ex. 35 | 477.9, 479.9 |

TABLE 1-continued

| Ex. No. | Structure | Name | Prep. Method | MS (M + 1) |
|---|---|---|---|---|
| 197 | 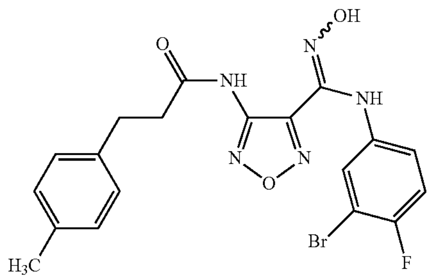 [SMILES: Cc1ccc(CCC(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-3-(4-methylphenyl)propanamide | Ex. 35 | 462.0, 463.9 |
| 198 | 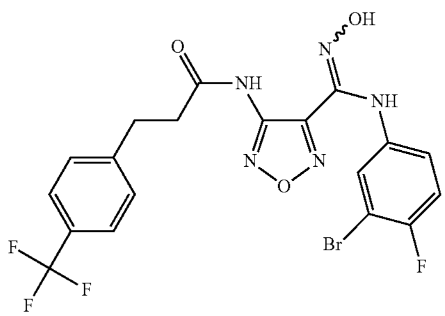 [SMILES: O=C(CCc1ccc(C(F)(F)F)cc1)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-3-[4-(trifluoromethyl)phenyl]propanamide | Ex. 35 | 515.9, 517.9 |
| 199 | 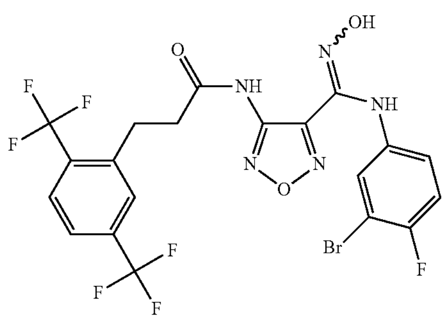 [SMILES: O=C(CCc1cc(C(F)(F)F)ccc1C(F)(F)F)Nc1nonc1C(=NO)Nc1ccc(F)c(Br)c1] | 3-[2,5-Bis(trifluoromethyl)phenyl]-N-{4-[(E,Z)-[(3-bromo-4-fluorophenyl)amino](hydroxyimino)methyl]-1,2,5-oxadiazol-3-yl}propanamide | Ex. 35 | 583.9, 585.9 |
| 200 | 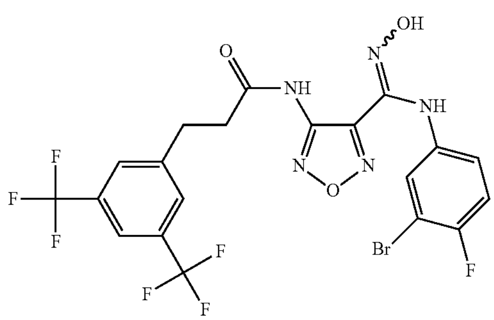 [SMILES: O=C(CCc1cc(C(F)(F)F)cc(C(F)(F)F)c1)Nc1nonc1C(=NO)Nc1ccc(F)c(Br)c1] | 3-[3,5-Bis(trifluoromethyl)phenyl]-N-{4-[(EZ)-[(3-bromo-4-fluoropheny)amino](hydroxyimino)methyl]-1,2,5-oxadiazol-3-yl}propanamide | Ex. 35 | 583.9, 585.9 |
| 201 | 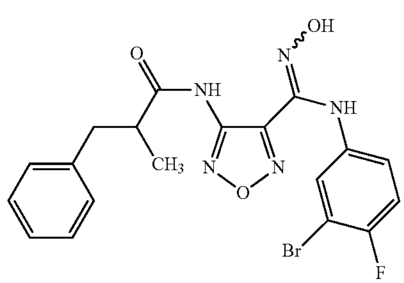 [SMILES: CC(Cc1ccccc1)C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-methyl-3-phenylpropanamide | Ex. 35 | 462.0, 464.0 |

TABLE 1-continued

| Ex. No. | Structure | Name | Prep. Method | MS (M + 1) |
|---|---|---|---|---|
| 202 | 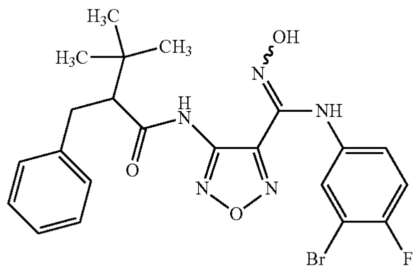 [SMILES: CC(C)(C)C(Cc1ccccc1)C(=O)Nc1nonc1C(=NO)Nc1ccc(F)c(Br)c1] | 2-Benzyl-N-{4-[(E,Z)-[(3-bromo-4-fluorophenyl)amino](hydroxyimino)methyl]-1,2,5-oxadiazol-3-yl}-3,3-dimethylbutanamide | Ex. 35 | 504.0, 506.0 |
| 203 | 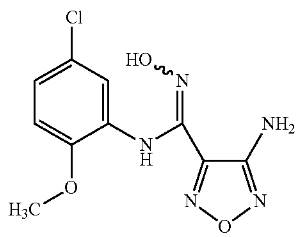 [SMILES: COc1ccc(Cl)cc1NC(=NO)c1nonc1N] | 4-Amino-N-(5-chloro-2-methoxyphenyl)-N'-hydroxy-1,2,5-oxadiazole-3-carboximidamide | Ex. 1 | 284.1 |
| 204 | 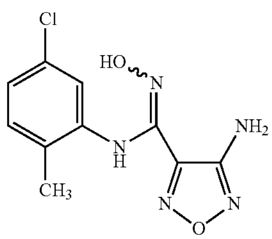 [SMILES: Cc1ccc(Cl)cc1NC(=NO)c1nonc1N] | 4-Amino-N-(5-chloro-2-methylphenyl)-N'-hydroxy-1,2,5-oxadiazole-3-carboximidamide | Ex. 1 | 268.1 |
| 205 | 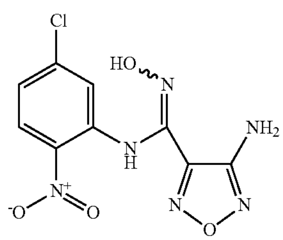 | 4-Amino-N-(5-chloro-2-nitrophenyl)-N'-hydroxy-1,2,5-oxadiazole-3-carboximidamide | Ex. 47 | 299.0 |
| 206 | 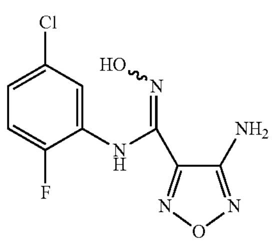 [SMILES: Nc1nonc1C(=NO)Nc1cc(Cl)ccc1F] | 4-Amino-N-(5-chloro-2-fluorophenyl)-N'-hydroxy-1,2,5-oxadiazole-3-carboximidamide | Ex. 47 | 272.1 |
| 207 | 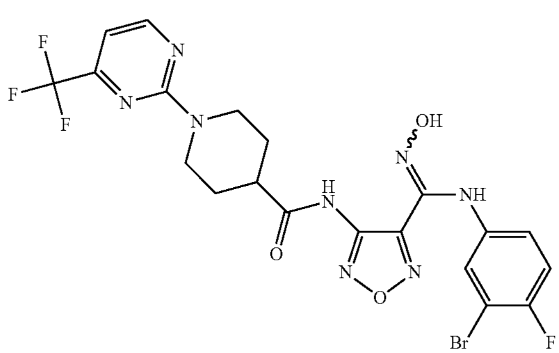 [SMILES: O=C(Nc1nonc1C(=NO)Nc1ccc(F)c(Br)c1)C1CCN(c2nccc(C(F)(F)F)n2)CC1] | N-{4-[(E,Z)-[(3-Bromo-4-fluorophenyl)amino](hydroxyimino)methyl]-1,2,5-oxadiazol-3-yl}-1-[4-(trifluoromethyl)pyrimidin-2-yl]piperidine-4-carboxamide | Ex. 35 | 573.0, 575.0 |

TABLE 1-continued

| Ex. No. | Structure | Name | Prep. Method | MS (M + 1) |
|---|---|---|---|---|
| 208 | 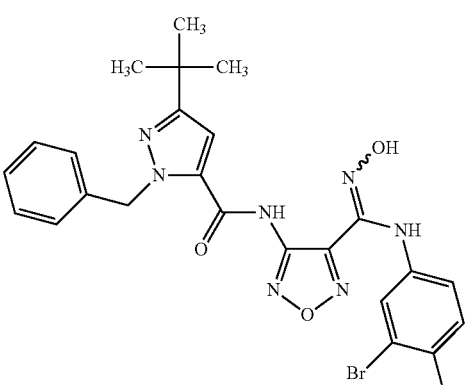 | 1-Benzyl-N-{4-[(E,Z)-[(3-bromo-4-fluorophenyl)amino](hydroxyimino)methyl]-1,2,5-oxadiazol-3-yl}-3-tert-butyl-1H-pyrazole-5-carboxamide | Ex. 35 | 556.0, 558.0 |
| 209 | 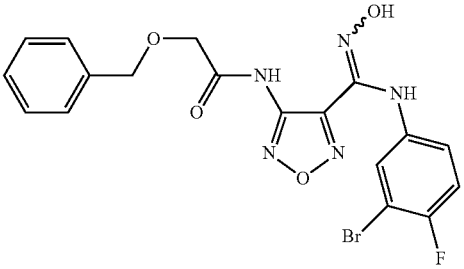 [SMILES: O=C(COCc1ccccc1)Nc1nonc1C(=NO)Nc1ccc(F)c(Br)c1] | 2-(Benzyloxy)-N-{4-[(E,Z)-[(3-bromo-4-fluorophenyl)amino](hydroxyimino)methyl]-1,2,5-oxadiazol-3-yl}acetamide | Ex. 35 | 463.9, 466.0 |
| 210 | 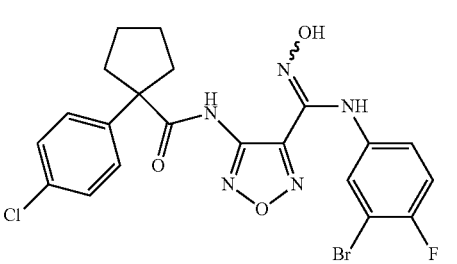 [SMILES: O=C(Nc1nonc1C(=NO)Nc1ccc(F)c(Br)c1)C1(c2ccc(Cl)cc2)CCCC1] | N-{4-[(E,Z)-[(3-Bromo-4-fluorophenyl)amino](hydroxyimino)methyl]-1,2,5-oxadiazol-3-yl}-1-(4-chlorophenyl)cyclopentanecarboxamide | Ex. 35 | 521.9, 523.9 |
| 211 | 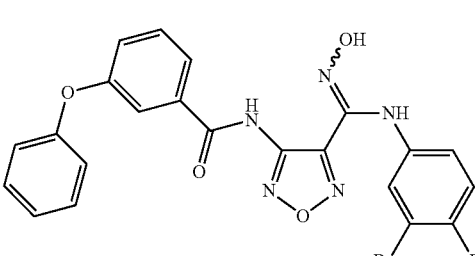 | N-{4-[(E,Z)-[(3-Bromo-4-fluorophenyl)amino](hydroxyimino)methyl]-1,2,5-oxadiazol-3-yl}-3-phenoxybenzamide | Ex. 35 | 511.9, 513.9 |
| 212 | 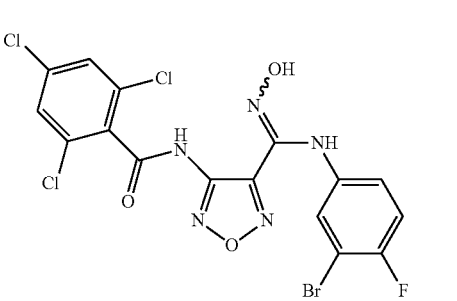 [SMILES: O=C(Nc1nonc1C(=NO)Nc1ccc(F)c(Br)c1)c1c(Cl)cc(Cl)cc1Cl] | N-{4-[(E,Z)-[(3-Bromo-4-fluorophenyl)amino](hydroxyimino)methyl]-1,2,5-oxadiazol-3-yl}-2,4,6-trichlorobenzamide | Ex. 35 | 521.8, 523.8, 525.8 |

| Ex. No. | Structure | Name | Prep. Method | MS (M + 1) |
|---|---|---|---|---|
| 213 | 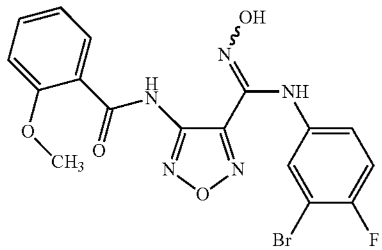 [SMILES: COc1ccccc1C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2-methoxybenzamide | Ex. 35 | 449.9, 451.9 |
| 214 | 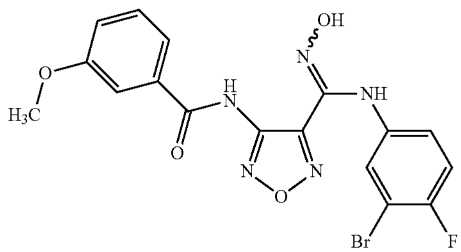 [SMILES: COc1cccc(C(=O)Nc2nonc2C(=NO)Nc2ccc(F)c(Br)c2)c1] | N-{4-[(E,Z)-[(3-Bromo-4-fluorophenyl)amino](hydroxyimino)methyl]-1,2,5-oxadiazol-3-yl}-3-methoxybenzamide | Ex. 35 | 449.9, 451.9 |
| 215 | 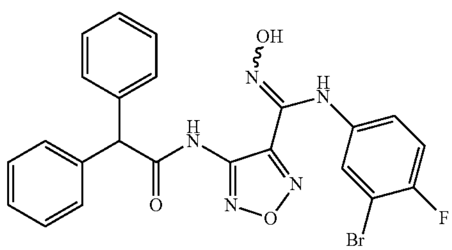 [SMILES: O=C(Nc1nonc1C(=NO)Nc1ccc(F)c(Br)c1)C(c1ccccc1)c1ccccc1] | N-{4-[(E,Z)-[(3-Bromo-4-fluorophenyl)amino](hydroxyimino)methyl]-1,2,5-oxadiazol-3-yl}-2,2-diphenylacetamide | Ex. 35 | 510.0, 512.0 |
| 216 | 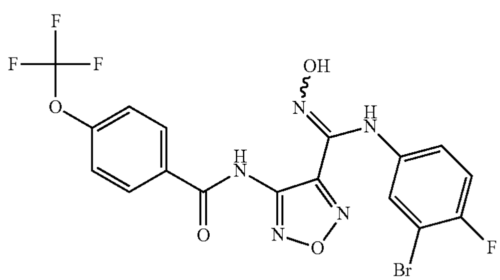 [SMILES: O=C(Nc1nonc1C(=NO)Nc1ccc(F)c(Br)c1)c1ccc(OC(F)(F)F)cc1] | N-{4-[(E,Z)-[(3-Bromo-4-fluorophenyl)amino](hydroxyimino)methyl]-1,2,5-oxadiazol-3-yl}-4-(trifluoromethoxy)benzamide | Ex. 35 | 503.9, 505.9 |
| 217 | 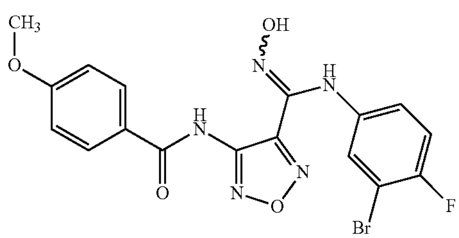 [SMILES: COc1ccc(C(=O)Nc2nonc2C(=NO)Nc2ccc(F)c(Br)c2)cc1] | N-{4-[(E,Z)-[(3-Bromo-4-fluorophenyl)amino](hydroxyimino)methyl]-1,2,5-oxadiazol-3-yl}-4-methoxybenzamide | Ex. 35 | 449.9, 451.8 |
| 218 | 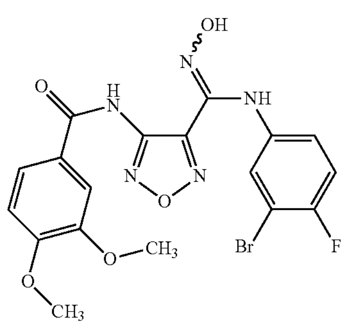 [SMILES: COc1ccc(C(=O)Nc2nonc2C(=NO)Nc2ccc(F)c(Br)c2)cc1OC] | N-{4-[(E,Z)-[(3-Bromo-4-fluorophenyl)amino](hydroxyimino)methyl]-1,2,5-oxadiazol-3-yl}-3,4-dimethoxybenzamide | Ex. 35 | 479.9, 481.9 |

TABLE 1-continued

| Ex. No. | Structure | Name | Prep. Method | MS (M + 1) |
|---|---|---|---|---|
| 219 | 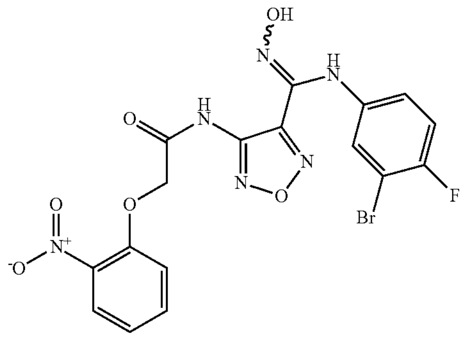 | N-{4-[(E,Z)-[(3-Bromo-4-fluorophenyl)amino](hydroxy-imino)methyl]-1,2,5-oxadiazol-3-yl}-2-(2-nitrophenoxy)acetamide | Ex. 35 | 494.9, 496.9 |
| 220 | 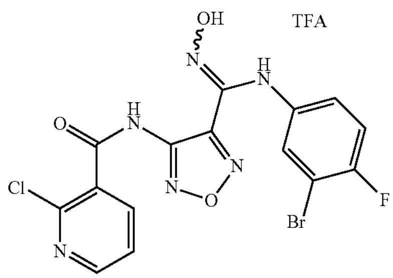 [SMILES: O=C(Nc1nonc1C(=NO)Nc1ccc(F)c(Br)c1)c1cccnc1Cl] | N-{4-[(E,Z)-[(3-Bromo-4-fluorophenyl)amino](hydroxy-imino)methyl]-1,2,5-oxadiazol-3-yl}-2-chloronicotinamide trifluoroacetate | Ex. 35 | 454.9, 456.9 |
| 221 | 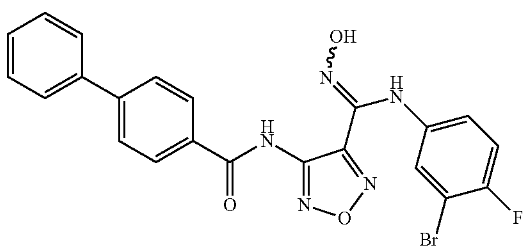 [SMILES: O=C(Nc1nonc1C(=NO)Nc1ccc(F)c(Br)c1)c1ccc(-c2ccccc2)cc1] | N-{4-[(E,Z)-[(3-Bromo-4-fluorophenyl)amino](hydroxy-imino)methyl]-1,2,5-oxadiazol-3-yl}biphenyl-4-carboxamide | Ex. 35 | 496.0, 497.9 |
| 222 | 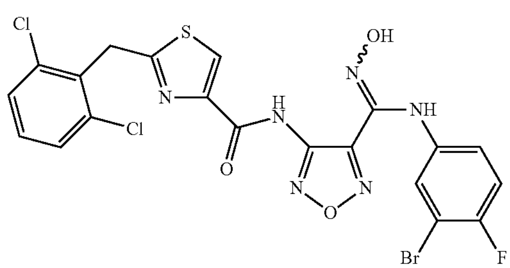 [SMILES: O=C(Nc1nonc1C(=NO)Nc1ccc(F)c(Br)c1)c1csc(Cc2c(Cl)cccc2Cl)n1] | N-{4-[(E,Z)-[(3-Bromo-4-fluorophenyl)amino](hydroxy-imino)methyl]-1,2,5-oxadiazol-3-yl}-2-(2,6-dichlorobenzyl)-1,3-thiazole-4-carboxamide | Ex. 35 | 584.8, 586.8, 588.8 |
| 223 | 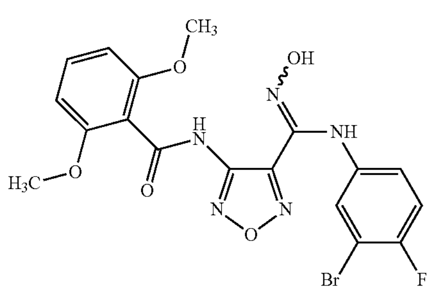 [SMILES: COc1cccc(OC)c1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-2,6-dimethoxybenzamide | Ex. 35 | 479.9, 482.0 |

TABLE 1-continued

| Ex. No. | Structure | Name | Prep. Method | MS (M + 1) |
|---|---|---|---|---|
| 224 | 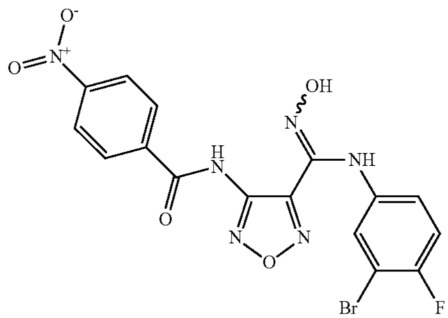 [SMILES: O=C(Nc1nonc1C(=NO)Nc1ccc(F)c(Br)c1)c1ccc([N+](=O)[O-])cc1] | N-{4-[(E,Z)-[(3-Bromo-4-fluorophenyl)amino](hydroxy-imino)methyl]-1,2,5-oxadiazol-3-yl}-4-nitrobenzamide | Ex. 35 | 464.9, 466.9 |
| 225 | 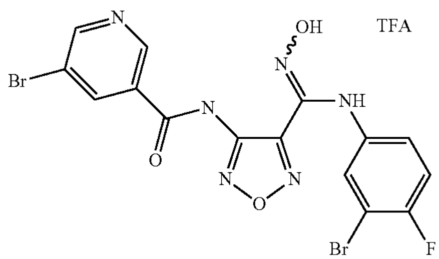 [SMILES: O=C(Nc1nonc1C(=NO)Nc1ccc(F)c(Br)c1)c1cncc(Br)c1] | 5-Bromo-N-{4-[(E,Z)-[(3-bromo-4-fluorophenyl)amino](hydroxy-imino)methyl]-1,2,5-oxadiazol-3-yl}nicotinamide trifluoroacetate | Ex. 35 | 498.8, 500.8, 502.8 |
| 226 | 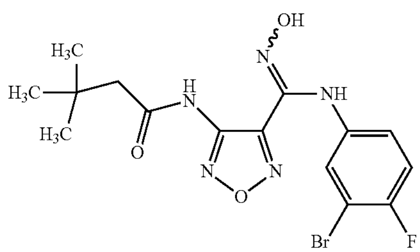 [SMILES: CC(C)(C)CC(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-3,3-dimethylbutanamide | Ex. 35 | 413.9, 415.9 |
| 227 | 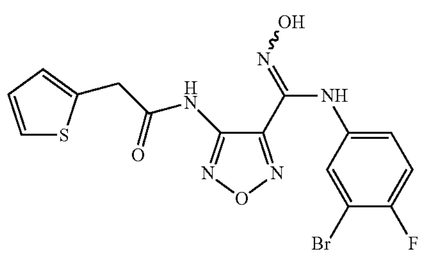 [SMILES: O=C(Cc1cccs1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-2-(2-thienyl)acetamide | Ex. 35 | 439.9, 441.9 |
| 228 | 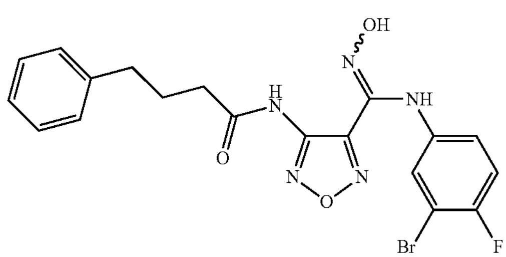 [SMILES: O=C(CCCc1ccccc1)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-4-phenylbutanamide | Ex. 35 | 462.0, 464.0 |
| 229 | 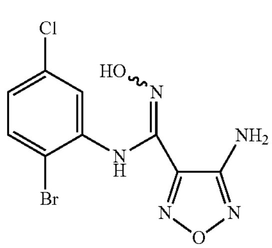 [SMILES: Nc1nonc1C(=NO)Nc1cc(Cl)ccc1Br] | 4-Amino-N-(2-bromo-5-chlorophenyl)-N'-hydroxy-1,2,5-oxadiazole-3-carboximidamide | Ex. 47 | 332.0, 334.0 |

TABLE 1-continued

| Ex. No. | Structure | Name | Prep. Method | MS (M + 1) |
|---|---|---|---|---|
| 230 | 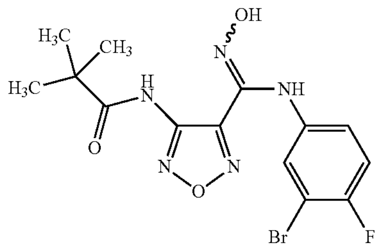 [SMILES: CC(C)(C)C(=O)Nc1nonc1C(=NO)Nc1ccc(F)c(Br)c1] | N-{4-[(E,Z)-[(3-Bromo-4-fluorophenyl)amino](hydroxyimino)methyl]-1,2,5-oxadiazol-3-yl}-2,2-dimethylpropanamide | Ex. 35 | 400.0, 401.9 |
| 231 | 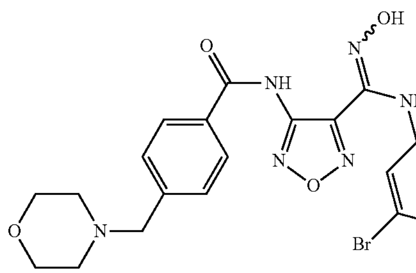 | N-{4-[(E,Z)-[(3-Bromo-4-fluorophenyl)amino](hydroxyimino)methyl]-1,2,5-oxadiazol-3-yl}-4-(morpholin-4-ylmethyl)benzamide trifluoroacetate | Ex. 35 | 519.0, 521.0 |
| 232 | 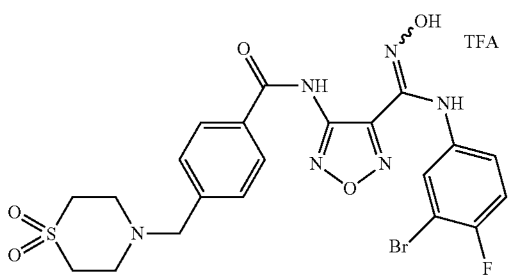 [SMILES: O=C(Nc1nonc1C(=NO)Nc1ccc(F)c(Br)c1)c1ccc(CN2CCS(=O)(=O)CC2)cc1] | N-{4-[(E,Z)-[(3-Bromo-4-fluorophenyl)amino](hydroxyimino)methyl]-1,2,5-oxadiazol-3-yl}-4-[(1,1-dioxidothiomorpholin-4-yl)methyl]benzamide trifluoroacetate | Ex. 35 | 567.0, 569.0 |
| 233 | 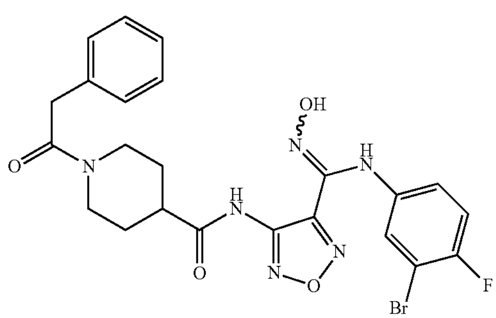 [SMILES: O=C(Nc1nonc1C(=NO)Nc1ccc(F)c(Br)c1)C1CCN(C(=O)Cc2ccccc2)CC1] | N-{4-[(E,Z)-[(3-Bromo-4-fluorophenyl)amino](hydroxyimino)methyl]-1,2,5-oxadiazol-3-yl}-1-(phenylacetyl)piperidine-4-carboxamide | Ex. 53 | 545.0, 547.6 |
| 234 | 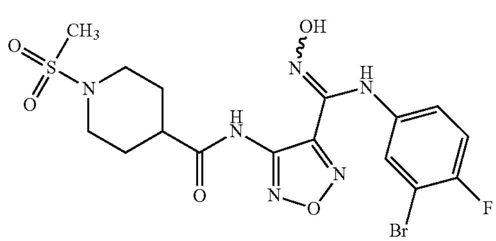 [SMILES: CS(=O)(=O)N1CCC(C(=O)Nc2nonc2C(=NO)Nc2ccc(F)c(Br)c2)CC1] | N-{4-[(E,Z)-[(3-Bromo-4-fluorophenyl)amino](hydroxyimino)methyl]-1,2,5-oxadiazol-3-yl}-1-(methylsulfonyl)piperidine-4-carboxamide | Ex. 53 | 505.0, 507.0 |
| 235 | 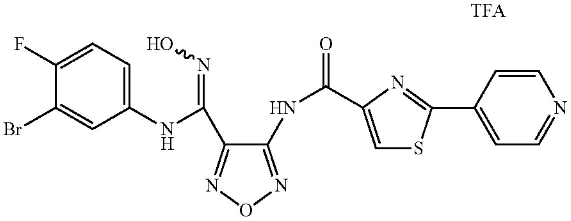 [SMILES: O=C(Nc1nonc1C(=NO)Nc1ccc(F)c(Br)c1)c1csc(-c2ccncc2)n1] | N-{4-[(E,Z)-[(3-Bromo-4-fluorophenyl)amino](hydroxyimino)methyl]-1,2,5-oxadiazol-3-yl}-2-pyridin-4-yl-1,3-thiazole-4-carboxamide trifluoroacetate | Ex. 35 | 504.0, 506.0 |

TABLE 1-continued

| Ex. No. | Structure | Name | Prep. Method | MS (M + 1) |
|---|---|---|---|---|
| 236 | 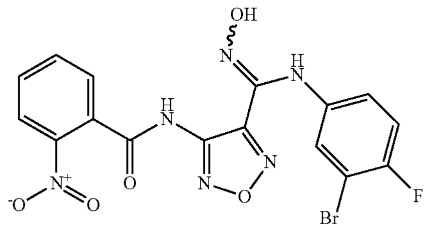 | N-{4-[(E,Z)-[(3-Bromo-4-fluorophenyl)amino](hydroxyimino)methyl]-1,2,5-oxadiazol-3-yl}-2-nitrobenzamide | Ex. 35 | 464.9, 466.9 |
| 237 | 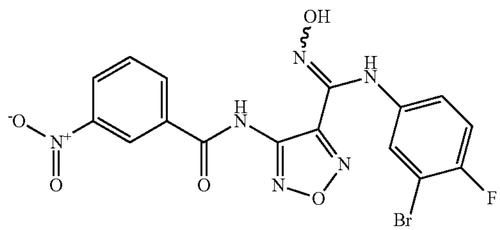 | N-{4-[(E,Z)-[(3-Bromo-4-fluorophenyl)amino](hydroxyimino)methyl]-1,2,5-oxadiazol-3-yl}-3-nitrobenzamide | Ex. 35 | 464.9, 466.9 |
| 238 | 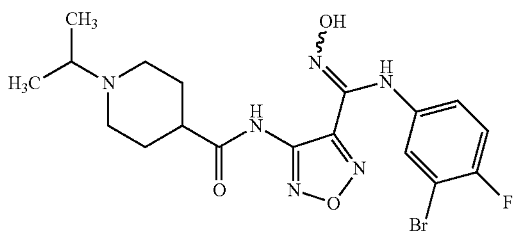 [SMILES: CC(C)N1CCC(C(=O)Nc2nonc2C(=NO)Nc2ccc(F)c(Br)c2)CC1] | N-{4-[(E,Z)-[(3-Bromo-4-fluorophenyl)amino](hydroxyimino)methyl]-1,2,5-oxadiazol-3-yl}-1-isopropylpiperidine-4-carboxamide trifluoroacetate | Ex. 55 | 469.0, 471.0 |
| 239 | 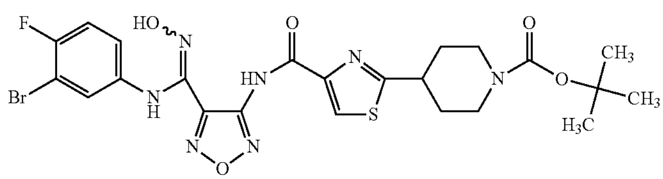 [SMILES: CC(C)(C)OC(=O)N1CCC(c2nc(C(=O)Nc3nonc3C(=NO)Nc3ccc(F)c(Br)c3)cs2)CC1] | tert-Butyl 4-{4-[({4-[(E,Z)-[(3-bromo-4-fluorophenyl)amino](hydroxyimino)methyl]-1,2,5-oxadiazol-3-yl}amino)carbonyl]-1,3-thiazol-2-yl}piperidine-1-carboxylate | Ex. 51 | 510.0, 512.0* |
| 240 | 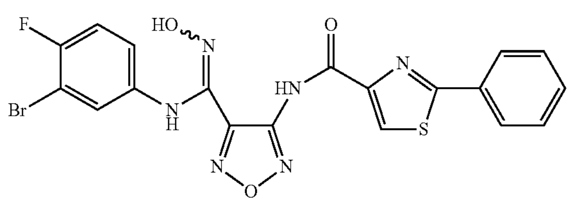 [SMILES: O=C(Nc1nonc1C(=NO)Nc1ccc(F)c(Br)c1)c1csc(-c2ccccc2)n1] | N-{4-[(E,Z)-[(3-Bromo-4-fluorophenyl)amino](hydroxyimino)methyl]-1,2,5-oxadiazol-3-yl}-2-phenyl-1,3-thiazole-4-carboxamide | Ex. 35 | 502.9, 504.9 |
| 241 | 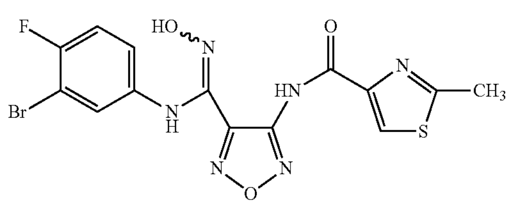 [SMILES: Cc1nc(C(=O)Nc2nonc2C(=NO)Nc2ccc(F)c(Br)c2)cs1] | N-{4-[(E,Z)-[(3-Bromo-4-fluorophenyl)amino](hydroxyimino)methyl]-1,2,5-oxadiazol-3-yl}-2-methyl-1,3-thiazole-4-carboxamide | Ex. 35 | 441.0, 443.0 |
| 242 | 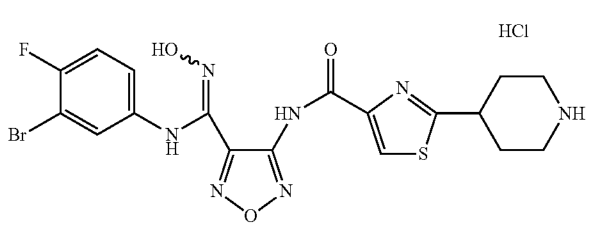 [SMILES: Cl ; O=C(Nc1nonc1C(=NO)Nc1ccc(F)c(Br)c1)c1csc(C2CCNCC2)n1] | N-{4-[(E,Z)-[(3-Bromo-4-fluorophenyl)amino](hydroxyimino)methyl]-1,2,5-oxadiazol-3-yl}-2-piperidin-4-yl-1,3-thiazole-4-carboxamide hydrochloride | Ex. 52 | 510.0, 512.0 |

TABLE 1-continued

| Ex. No. | Structure | Name | Prep. Method | MS (M + 1) |
|---|---|---|---|---|
| 243 | 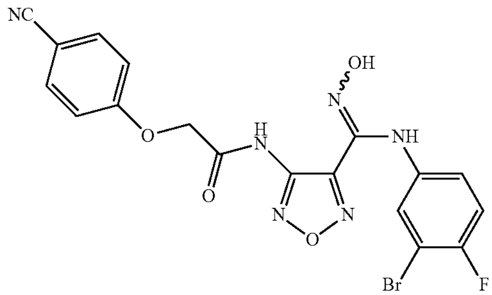 [SMILES: N#Cc1ccc(OCC(=O)Nc2nonc2C(=NO)Nc2ccc(F)c(Br)c2)cc1] | N-{4-[(E,Z)-[(3-Bromo-4-fluorophenyl)amino](hydroxy-imino)methyl]-1,2,5-oxadiazol-3-yl}-2-(4-cyanophenoxy)acetamide | Ex. 57 | 475.0, 476.9 |
| 244 | 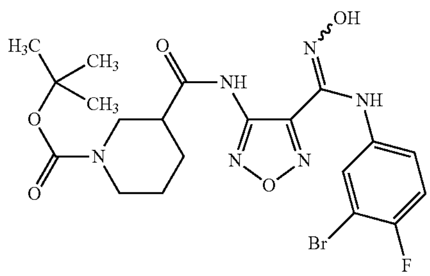 [SMILES: CC(C)(C)OC(=O)N1CCCC(C(=O)Nc2nonc2C(=NO)Nc2ccc(F)c(Br)c2)C1] | tert-Butyl 3-[({4-[(E,Z)-[(3-bromo-4-fluorophenyl)amino](hydroxy-imino)methyl]-1,2,5-oxadiazol-3-yl}amino)carbonyl]piperidine-1-carboxylate | Ex. 51 | 527.0, 529.0 |
| 245 | 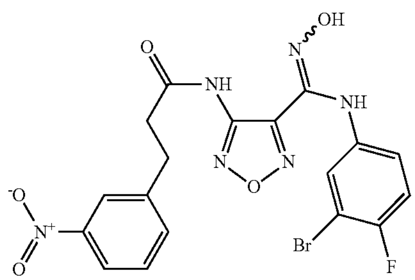 | N-{4-[(E,Z)-[(3-Bromo-4-fluorophenyl)amino](hydroxy-imino)methyl]-1,2,5-oxadiazol-3-yl}-3-(3-nitrophenyl)propanamide | Ex. 51 | 493.0, 494.9 |
| 246 | 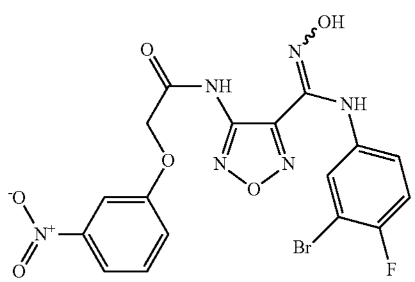 | N-{4-[(E,Z)-[(3-Bromo-4-fluorophenyl)amino](hydroxy-imino)methyl]-1,2,5-oxadiazol-3-yl}-2-(3-nitrophenoxy)acetamide | Ex. 51 | 494.9, 497.0 |
| 247 | 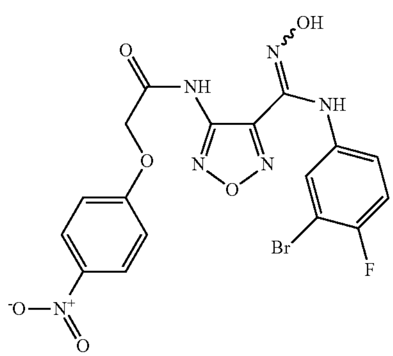 | N-{4-[(E,Z)-[(3-Bromo-4-fluorophenyl)amino](hydroxy-imino)methyl]-1,2,5-oxadiazol-3-yl}-2-(4-nitrophenoxy)acetamide | Ex. 51 | 494.9, 496.9 |

TABLE 1-continued

| Ex. No. | Structure | Name | Prep. Method | MS (M + 1) |
|---|---|---|---|---|
| 248 | 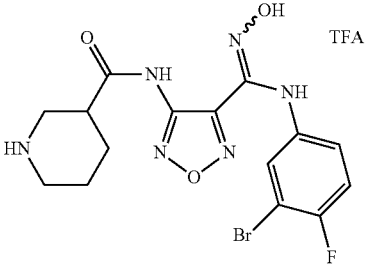 [SMILES: O=C(Nc1nonc1C(=NO)Nc1ccc(F)c(Br)c1)C1CCCNC1] | N-{4-[(E,Z)-[(3-Bromo-4-fluorophenyl)amino](hydroxy-imino)methyl]-1,2,5-oxadiazol-3-yl}piperidine-3-carboxamide trifluoroacetate | Ex. 52 | 426.9, 429.0 |
| 249 | 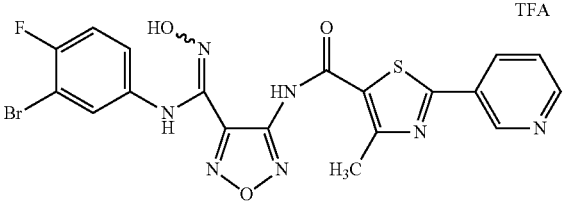 [SMILES: Cc1nc(-c2cccnc2)sc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-4-methyl-2-pyridin-3-yl-1,3-thiazole-5-carboxamide trifluoroacetate | Ex. 57 | 518.0, 520.0 |
| 250 | 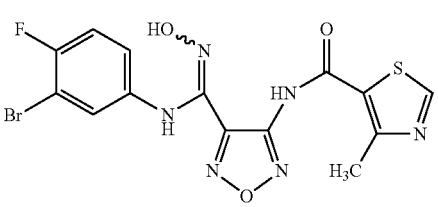 [SMILES: Cc1ncsc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-4-methyl-1,3-thiazole-5-carboxamide | Ex. 57 | 441.0, 443.0 |
| 251 | 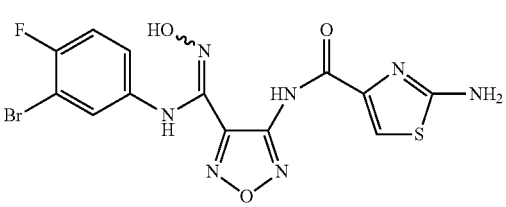 | 2-Amino-N-{4-[(E,Z)-[(3-bromo-4-fluorophenyl)amino](hydroxy-imino)methyl]-1,2,5-oxadiazol-3-yl}-1,3-thiazole-4-carboxamide trifluoroacetate | Ex. 57 | 442.0, 444.0 |
| 252 | 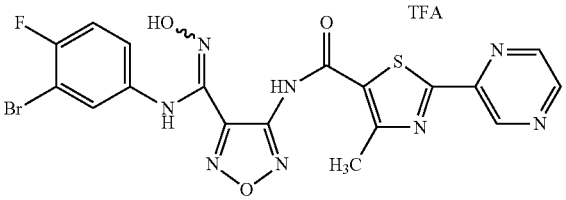 [SMILES: Cc1nc(-c2cnccn2)sc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-4-methyl-2-pyrazin-2-yl-1,3-thiazole-5-carboxamide trifluoroacetate | Ex. 51 | 519.0, 521.0 |
| 253 | 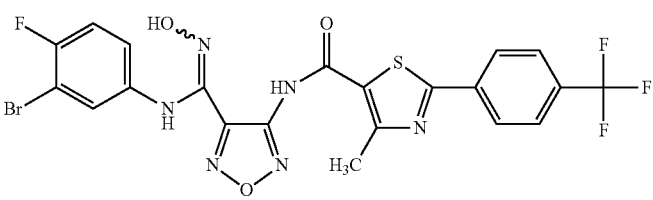 [SMILES: Cc1nc(-c2ccc(C(F)(F)F)cc2)sc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-4-methyl-2-[4-(trifluoromethyl)phenyl]-1,3-thiazole-5-carboxamide | Ex. 51 | 585.0, 587.0 |
| 254 | 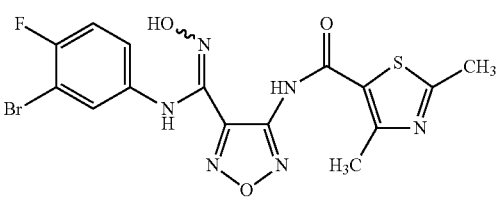 [SMILES: Cc1nc(C)c(C(=O)Nc2nonc2C(=NO)Nc2ccc(F)c(Br)c2)s1] | N-{4-[(E,Z)-[(3-Bromo-4-fluorophenyl)amino](hydroxy-imino)methyl]-1,2,5-oxadiazol-3-yl}-2,4-dimethyl-1,3-thiazole-5-carboxamide | Ex. 57 | 455.0, 457.0 |

TABLE 1-continued

| Ex. No. | Structure | Name | Prep. Method | MS (M + 1) |
|---|---|---|---|---|
| 255 | 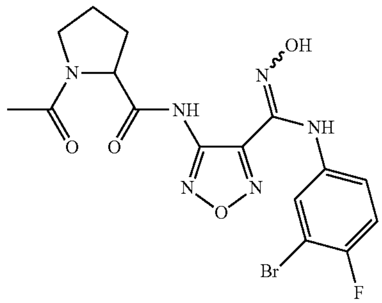 [SMILES: CC(=O)N1CCCC1C(=O)Nc1nonc1C(=NO)Nc1ccc(F)c(Br)c1] | 1-Acetyl-N-{4-[(E,Z)-[(3-bromo-4-fluorophenyl)amino]-(hydroxyimino)methyl]-1,2,5-oxadiazol-3-yl}pyrrolidine-2-carboxamide | Ex. 51 | 454.9, 456.9 |
| 256 | 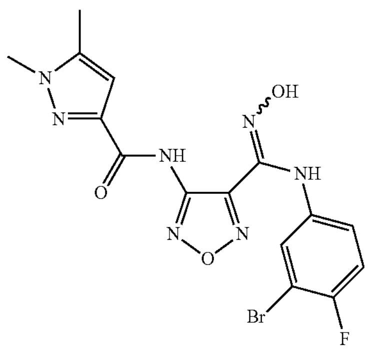 [SMILES: Cc1cc(C(=O)Nc2nonc2C(=NO)Nc2ccc(F)c(Br)c2)nn1C] | N-{4-[(E,Z)-[(3-Bromo-4-fluorophenyl)amino](hydroxyimino)methyl]-1,2,5-oxadiazol-3-yl}-1,5-dimethyl-1H-pyrazole-3-carboxamide | Ex. 35 | 437.9, 439.9 |
| 257 | 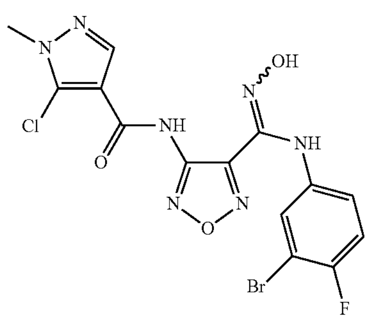 [SMILES: Cn1ncc(C(=O)Nc2nonc2C(=NO)Nc2ccc(F)c(Br)c2)c1Cl] | N-{4-[(E,Z)-[(3-Bromo-4-fluorophenyl)amino](hydroxyimino)methyl]-1,2,5-oxadiazol-3-yl}-5-chloro-1-methyl-1H-pyrazole-4-carboxamide | Ex. 35 | 457.9, 459.9 |
| 258 | 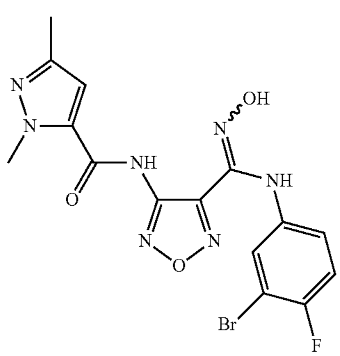 [SMILES: Cc1cc(C(=O)Nc2nonc2C(=NO)Nc2ccc(F)c(Br)c2)n(C)n1] | N-{4-[(E,Z)-[(3-Bromo-4-fluorophenyl)amino](hydroxyimino)methyl]-1,2,5-oxadiazol-3-yl}-1,3-dimethyl-1H-pyrazole-5-carboxamide | Ex. 35 | 438.0, 440.0 |

TABLE 1-continued

| Ex. No. | Structure | Name | Prep. Method | MS (M + 1) |
|---|---|---|---|---|
| 259 | 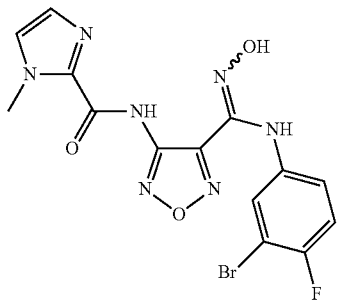 [SMILES: Cn1ccnc1C(=O)Nc1nonc1C(=NO)Nc1ccc(F)c(Br)c1] | N-{4-[(E,Z)-[(3-Bromo-4-fluorophenyl)amino](hydroxy-imino)methyl]-1,2,5-oxadiazol-3-yl}-1-methyl-1H-imidazole-2-carboxamide | Ex. 51 | 424.1, 426.0 |
| 260 | 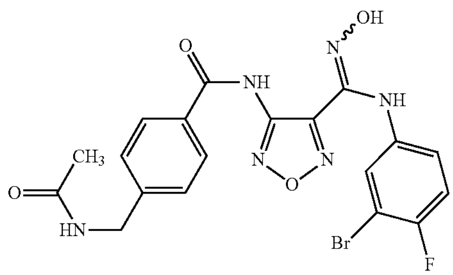 [SMILES: CC(=O)NCc1ccc(C(=O)Nc2nonc2C(=NO)Nc2ccc(F)c(Br)c2)cc1] | 4-[(Acetylamino)methyl]-N-{4-[(E,Z)-[(3-bromo-4-fluorophenyl)amino](hydroxy-imino)methyl]-1,2,5-oxadiazol-3-yl}benzamide | Ex. 56 | 491.0, 493.0 |
| 261 | 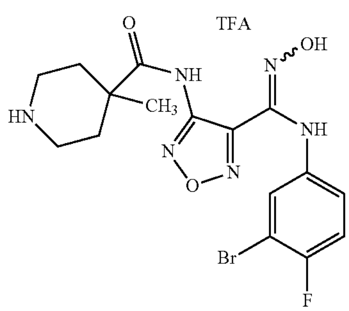 [SMILES: CC1(C(=O)Nc2nonc2C(=NO)Nc2ccc(F)c(Br)c2)CCNCC1] | N-{4-[(E,Z)-[(3-Bromo-4-fluorophenyl)amino](hydroxy-imino)methyl]-1,2,5-oxadiazol-3-yl}-4-methylpiperidine-4-carboxamide trifluoroacetate | Ex. 58 | 441.0, 443.0 |
| 262 | 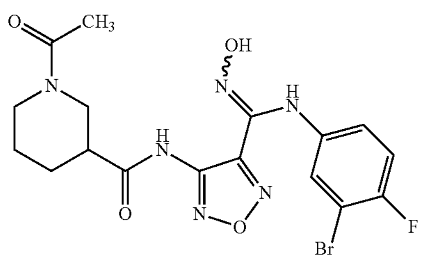 [SMILES: CC(=O)N1CCCC(C(=O)Nc2nonc2C(=NO)Nc2ccc(F)c(Br)c2)C1] | 1-Acetyl-N-{4-[(E,Z)-[(3-bromo-4-fluorophenyl)amino](hydroxy-imino)methyl]-1,2,5-oxadiazol-3-yl}piperidine-3-carboxamide | Ex. 53 | 469.0, 471.0 |
| 263 | 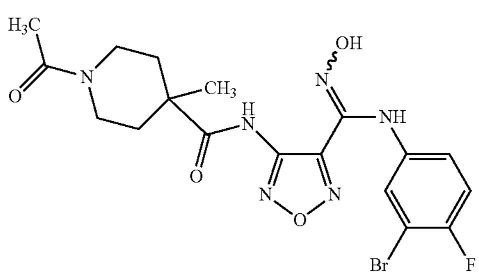 [SMILES: CC(=O)N1CCC(C)(C(=O)Nc2nonc2C(=NO)Nc2ccc(F)c(Br)c2)CC1] | 1-Acetyl-N-{4-[(E,Z)-[(3-bromo-4-fluorophenyl)amino](hydroxy-imino)methyl]-1,2,5-oxadiazol-3-yl}-4-methylpiperidine-4-carboxamide | Ex. 53 | 483.0, 485.0 |

TABLE 1-continued

| Ex. No. | Structure | Name | Prep. Method | MS (M + 1) |
|---|---|---|---|---|
| 264 | 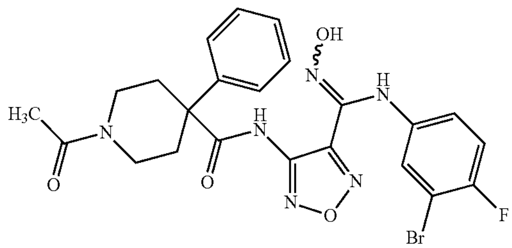 [SMILES: CC(=O)N1CCC(C(=O)Nc2nonc2C(=NO)Nc2ccc(F)c(Br)c2)(c2ccccc2)CC1] | 1-Acetyl-N-{4-[(E,Z)-[(3-bromo-4-fluorophenyl)amino](hydroxyimino)methyl]-1,2,5-oxadiazol-3-yl}-4-phenylpiperidine-4-carboxamide | Ex. 53 | 545.0, 547.0 |
| 265 | 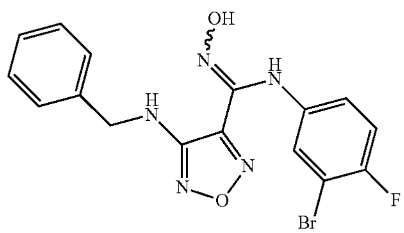 [SMILES: ON=C(Nc1ccc(F)c(Br)c1)c1nonc1NCc1ccccc1] | 4-(Benzylamino)-N-(3-bromo-4-fluorophenyl)-N'-hydroxy-1,2,5-oxadiazole-3-carboximidamide | Ex. 49 | 406.1, 408.0 |
| 266 | 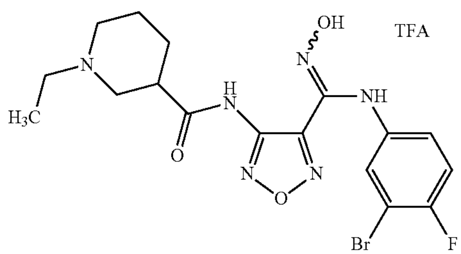 [SMILES: CCN1CCCC(C(=O)Nc2nonc2C(=NO)Nc2ccc(F)c(Br)c2)C1] | N-{4-[(E,Z)-[(3-Bromo-4-fluorophenyl)amino](hydroxyimino)methyl]-1,2,5-oxadiazol-3-yl}-1-ethylpiperidine-3-carboxamide trifluoroacetate | Ex. 55 | 455.0, 457.0 |
| 267 | 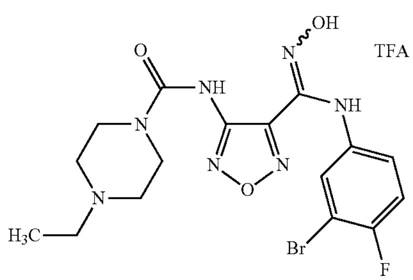 [SMILES: CCN1CCN(C(=O)Nc2nonc2C(=NO)Nc2ccc(F)c(Br)c2)CC1] | N-{4-[(E,Z)-[(3-Bromo-4-fluorophenyl)amino](hydroxyimino)methyl]-1,2,5-oxadiazol-3-yl}-4-ethylpiperazine-1-carboxamide trifluoroacetate | Ex. 48 | 456.0, 458.0 |
| 268 | 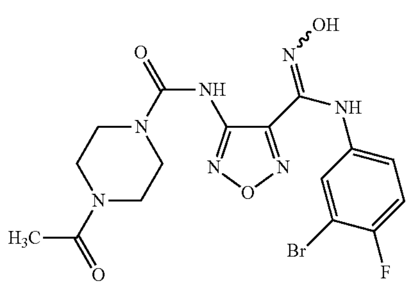 [SMILES: CC(=O)N1CCN(C(=O)Nc2nonc2C(=NO)Nc2ccc(F)c(Br)c2)CC1] | 4-Acetyl-N-{4-[(E,Z)-[(3-bromo-4-fluorophenyl)amino](hydroxyimino)methyl]-1,2,5-oxadiazol-3-yl}piperazine-1-carboxamide | Ex. 48 | 470.0, 472.0 |
| 269 | 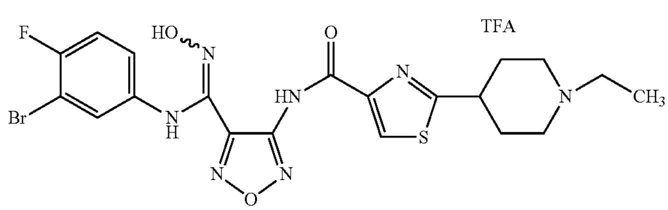 [SMILES: CCN1CCC(c2nc(C(=O)Nc3nonc3C(=NO)Nc3ccc(F)c(Br)c3)cs2)CC1] | N-{4-[(E,Z)-[(3-Bromo-4-fluorophenyl)amino](hydroxyimino)methyl]-1,2,5-oxadiazol-3-yl}-2-(1-ethylpiperidin-4-yl)-1,3-thiazole-4-carboxamide trifluoroacetate | Ex. 55 | 538.0, 540.0 |

| Ex. No. | Structure | Name | Prep. Method | MS (M + 1) |
|---|---|---|---|---|
| 270 | 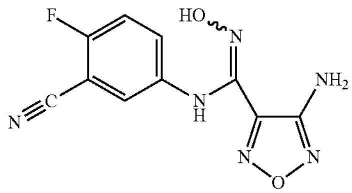 [SMILES: N#Cc1cc(NC(=NO)c2nonc2N)ccc1F] | 4-Amino-N-(3-cyano-4-fluorophenyl)-N'-hydroxy-1,2,5-oxadiazole-3-carboximidamide | Ex. 1 | 263.1 |
| 271 | 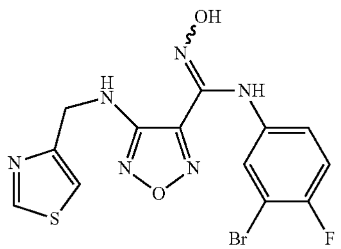 [SMILES: ON=C(Nc1ccc(F)c(Br)c1)c1nonc1NCc1cscn1] | N-(3-Bromo-4-fluorophenyl)-N'-hydroxy-4-[(1,3-thiazol-4-ylmethyl)amino]-1,2,5-oxadiazole-3-carboximidamide | Ex. 60 | 413.0, 415.0 |
| 272 | 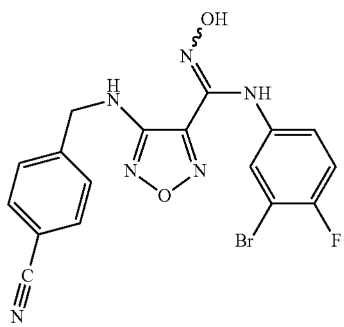 [SMILES: N#Cc1ccc(CNc2nonc2C(=NO)Nc2ccc(F)c(Br)c2)cc1] | N-(3-Bromo-4-fluorophenyl)-4-[(4-cyanobenzyl)amino]-N'-hydroxy-1,2,5-oxadiazole-3-carboximidamide | Ex. 60 | 431.0, 433.0 |
| 273 | 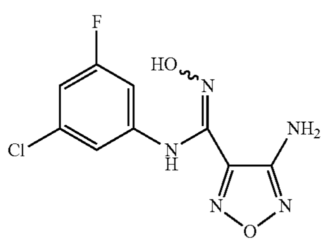 [SMILES: Nc1nonc1C(=NO)Nc1cc(F)cc(Cl)c1] | 4-Amino-N-(3-chloro-5-fluorophenyl)-N'-hydroxy-1,2,5-oxadiazole-3-carboximidamide | Ex. 1 | 272.0 |
| 274 | 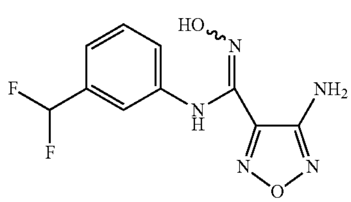 [SMILES: Nc1nonc1C(=NO)Nc1cccc(C(F)F)c1] | 4-Amino-N-[3-(difluoromethyl)phenyl]-N'-hydroxy-1,2,5-oxadiazole-3-carboximidamide | Ex. 1 | 270.1 |
| 275 | 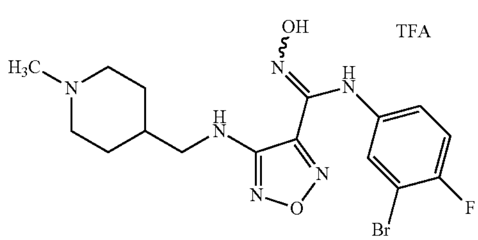 [SMILES: CN1CCC(CNc2nonc2C(=NO)Nc2ccc(F)c(Br)c2)CC1] | N-(3-Bromo-4-fluorophenyl)-N'-hydroxy-4-{[(1-methylpiperidin-4-y)methyl]amino}-1,2,5-oxadiazole-3-carboximidamide trifluoroacetate | Ex. 60 | 427.0, 429.0 |

TABLE 1-continued

| Ex. No. | Structure | Name | Prep. Method | MS (M + 1) |
|---|---|---|---|---|
| 276 | 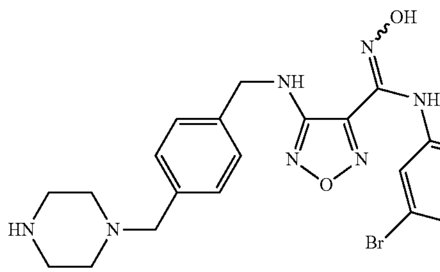 | N-(3-Bromo-4-fluorophenyl)-N'-hydroxy-4-{[4-(piperazin-1-ylmethyl)benzyl]amino}-1,2,5-oxadiazole-3-carboximidamide bis(trifluoroacetate) | Ex. 60 | 504.0, 506.0 |
| 277 | 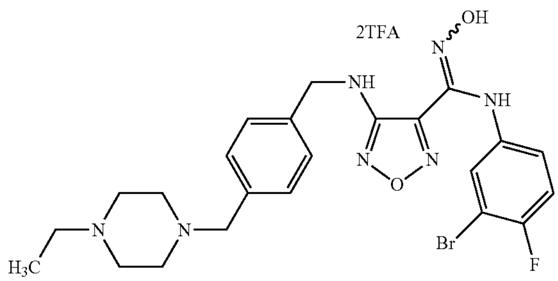 [SMILES: CCN1CCN(Cc2ccc(CNc3nonc3C(=NO)Nc3ccc(F)c(Br)c3)cc2)CC1] | N-(3-Bromo-4-fluorophenyl)-4-({4-[(4-ethylpiperazin-1-yl)methyl]benzyl}amino)-N'-hydroxy-1,2,5-oxadiazole-3-carboximidamide bis(trifluoroacetate) | Ex. 60 | 532.2, 534.2 |
| 278 | 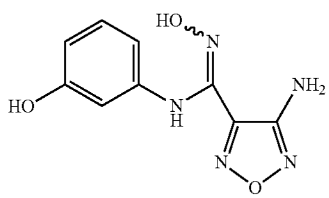 [SMILES: Nc1nonc1C(=NO)Nc1cccc(O)c1] | 4-Amino-N'-hydroxy-N-(3-hydroxyphenyl)-1,2,5-oxadiazole-3-carboximidamide | Ex. 1 | 236.1 |
| 279 | 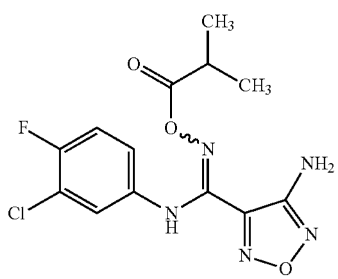 [SMILES: CC(C)C(=O)ON=C(Nc1ccc(F)c(Cl)c1)c1nonc1N] | 4-Amino-N-(3-chloro-4-fluorophenyl)-N'-(isobutyryloxy)-1,2,5-oxadiazole-3-carboximidamide | Ex. 67 | 342.0 |
| 280 | 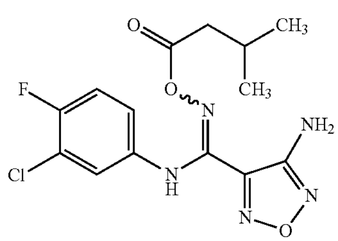 [SMILES: CC(C)CC(=O)ON=C(Nc1ccc(F)c(Cl)c1)c1nonc1N] | 4-Amino-N-(3-chloro-4-fluorophenyl)-N'-[(3-methylbutanoyl)oxy]-1,2,5-oxadiazole-3-carboximidamide | Ex. 67 | 356.0 |
| 281 | 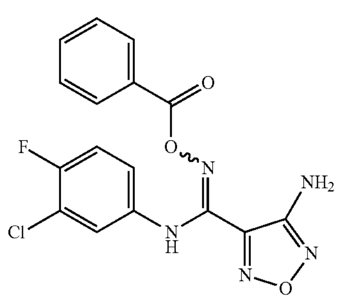 [SMILES: Nc1nonc1C(=NOC(=O)c1ccccc1)Nc1ccc(F)c(Cl)c1] | 4-Amino-N'-(benzoyloxy)-N-(3-chloro-4-fluorophenyl)-1,2,5-oxadiazole-3-carboximidamide | Ex. 67 | 376.0 |

TABLE 1-continued

| Ex. No. | Structure | Name | Prep. Method | MS (M + 1) |
|---|---|---|---|---|
| 282 | 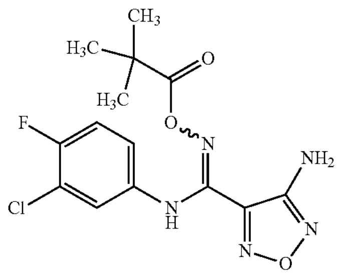 [SMILES: CC(C)(C)C(=O)ON=C(Nc1ccc(F)c(Cl)c1)c1nonc1N] | 4-Amino-N-(3-chloro-4-fluorophenyl)-N'-[(2,2-dimethylpropanoyl)oxy]-1,2,5-oxadiazole-3-carboximidamide | Ex. 67 | 356.0 |
| 283 | 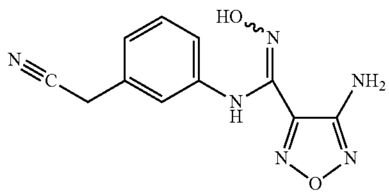 [SMILES: N#CCc1cccc(NC(=NO)c2nonc2N)c1] | 4-Amino-N-[3-(cyanomethyl)phenyl]-N'-hydroxy-1,2,5-oxadiazole-3-carboximidamide | Ex. 1 | 259.1 |
| 284 | 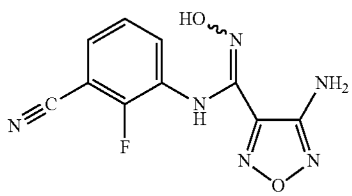 [SMILES: N#Cc1cccc(NC(=NO)c2nonc2N)c1F] | 4-Amino-N-(3-cyano-2-fluorophenyl)-N'-hydroxy-1,2,5-oxadiazole-3-carboximidamide | Ex. 1 | 263.1 |
| 285 | 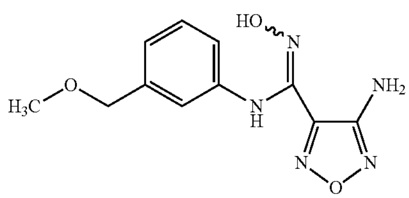 [SMILES: COCc1cccc(NC(=NO)c2nonc2N)c1] | 4-Amino-N'-hydroxy-N-[3-(methoxymethyl)phenyl]-1,2,5-oxadiazole-3-carboximidamide | Ex. 1 | 264.1 |
| 286 | 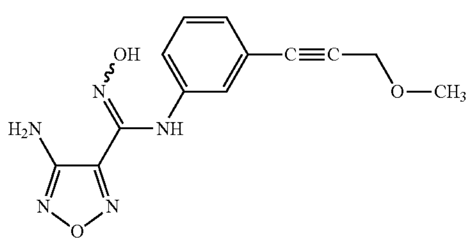 [SMILES: COCC#Cc1cccc(NC(=NO)c2nonc2N)c1] | 4-Amino-N'-hydroxy-N-[3-(3-methoxyprop-1-yn-1-yl)phenyl]-1,2,5-oxadiazole-3-carboximidamide | Ex. 70 | 287.9 |
| 287 | 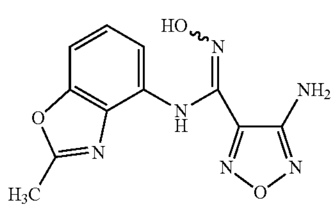 [SMILES: Cc1nc2c(NC(=NO)c3nonc3N)cccc2o1] | 4-Amino-N'-hydroxy-N-(2-methyl-1,3-benzoxazol-4-yl)-1,2,5-oxadiazole-3-carboximidamide | Ex. 1 | 275.0 |
| 288 | 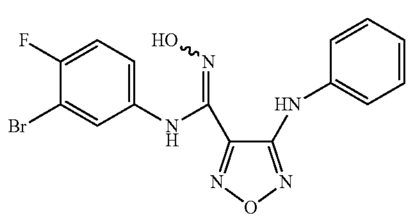 [SMILES: ON=C(Nc1ccc(F)c(Br)c1)c1nonc1Nc1ccccc1] | 4-Anilino-N-(3-bromo-4-fluorophenyl)-N'-hydroxy-1,2,5-oxadiazole-3-carboximidamide | Ex. 69 | 392.0, 394.0 |

TABLE 1-continued

| Ex. No. | Structure | Name | Prep. Method | MS (M + 1) |
|---|---|---|---|---|
| 289 | 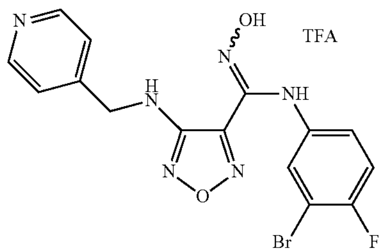 [SMILES: ON=C(Nc1ccc(F)c(Br)c1)c1nonc1NCc1ccncc1] | N-(3-Bromo-4-fluorophenyl)-N'-hydroxy-4-[(pyridin-4-ylmethyl)amino]-1,2,5-oxadiazole-3-carboximidamide trifluoroacetate | Ex. 63 | 406.9, 408.9 |
| 290 | 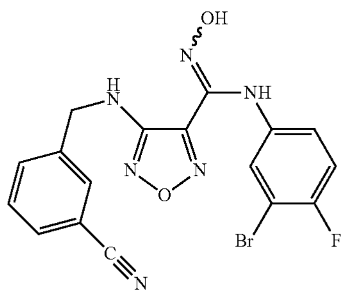 [SMILES: N#Cc1cccc(CNc2nonc2C(=NO)Nc2ccc(F)c(Br)c2)c1] | N-(3-Bromo-4-fluorophenyl)-4-[(3-cyanobenzyl)amino]-N'-hydroxy-1,2,5-oxadiazole-3-carboximidamide | Ex. 64 | 430.9, 432.9 |

*([M − Boc + H] + H)+

Example A

Human idoleamine 2,3-dioxygenasae (IDO) Enzyme Assay

Human idoleamine 2,3-dioxygenasae (IDO) with an N-terminal His tag was expressed in E. coli and purified to homogeneity. IDO catalyzes the oxidative cleavage of the pyrrole ring of the indole nucleus of tryptophan to yield IV'-formylkynurenine. The assays were performed at room temperature as described in the literature using 95 nM IDO and 2 mM D-Trp in the presence of 20 mM ascorbate, 5 µM methylene blue and 0.2 mg/mL catalase in 50 mM potassium phosphate buffer (pH 6.5). The initial reaction rates are recorded by continuously following the absorbance increase at 321 nm due to the formation of N'-formylkynurenine. See: Sono, M., Taniguchi, T., Watanabe, Y., and Hayaishi, O. (1980) J. Biol. Chem. 255, 1339-1345 Compounds of the invention having an $IC_{50}$ less than about 100 µM were considered active.

Example B

Determination of Inhibitor Activity in HeLa Cell-Based Indoleamine 2,3-dioxygenase (IDO)/Kynurenine Assay HeLa cells (#CCL-2) were obtained from the American Type Tissue Culture Collection (ATCC, Manassas, Va.) and routinely maintained in minimum essential medium (eagle) with 2 mM L-glutamine and Earle's BSS adjusted to contain 1.5 g/L sodium bicarbonate, 0.1 mM non-essential amino acids, 1 mM sodium pyruvate and 10% fetal bovine serum (all from Invitrogen). Cells were kept at 37° C. in a humidified incubator supplied with 5% $CO_2$. The assay was performed as follows: HeLa cells were seeded in a 96 well culture plate at a density of $5 \times 10^3$ per well and grown overnight. On the next day, IFN-γ (50 ng/mL final concentration) and serial dilutions of compounds (in total volume of 200 µL culture medium) were added into cells. After 48 hours of incubation, 140 µL of the supernatant per well was transferred to a new 96 well plate. 10 µL of 6.1 N trichloroacetic acid (#T0699, Sigma) was mixed into each well and incubated at 50° C. for 30 min to hydrolyze N-formylkynurenine produced by indoleamine 2,3-dioxygenase to kynurenine. The reaction mixture was then centrifuged for 10 min at 2500 rpm to remove sediments. 100 µL of the supernatant per well was transferred to another 96 well plate and mixed with 100 µl of 2% (w/v) p-dimethylaminobenzaldehyde (#15647-7, Sigma-Aldrich) in acetic acid. The yellow color derived from Kynurenine was measured at 480 nm using a SPECTRAmax 250 microplate reader (Molecular Devices). L-kynurenine (#K8625, Sigma) was used as standard. The standards (240, 120, 60, 30, 15, 7.5, 3.75, 1.87 µM) were prepared in 100 µL culture media and mixed with equal volume of 2% (w/v) p-dimethylaminobenzaldehyde. The percent inhibition at individual concentrations was determined and the average values of duplicates were obtained. The data is analyzed by using nonlinear regression to generate $IC_{50}$ values (Prism Graphpad). See: Takikawa O, et al. (1988). Mechanism of interferon-gamma action. Characterization of indoleamine 2,3-dioxygenase in cultured human cells induced by interferon-gamma and evaluation of the enzyme-mediated tryptophan degradation in its anticellular activity. J. Biol. Chem. 263(4):2041-8. Compounds of the invention having an $IC_{50}$ less than about 100 µM were considered active.

Example C

Determination of Effect of IDO Inhibitors on T Cell Proliferation that is Suppressed by IDO-Expressing Dendritic Cells Monocytes were collected from human peripheral mononuclear cells by leukophoresis. Monocytes were then seeded at a density of $1 \times 10^6$ cells/well in a 96 well plate, using RPMI 1640 medium supplemented with 10% fetal bovine serum and 2 mM L-glutamine (all from Invitrogen). Adherent cells were retained on the plate after overnight culture at 37° C. Adherent monocytes were then stimulated for 5-7 days with 100 ng/ml GM-CSF (#300-03, PeproTech) and 250 ng/ml IL-4 (#200-04, PeproTech), followed by activation with 5 µg/mL LPS from *Salmonella typhimurium* (#437650, Sigma) and 50 ng/mL IFN-γ (#285-IF, R&D Systems) for additional 2 days to induce dendritic cell maturation.

After dendritic cell activation, the medium was replaced with completed RPMI 1640 supplemented with 100-200 U/mL IL-2 (#CYT-209, ProSpec-Tany TechnoGene) and 100 ng/mL anti-CD3 antibody (#555336, PharMingen), T cells ($2-3\times10^5$ cells/well), and serial dilutions of IDO compounds. After incubation for 2 more days, T cell proliferation was measured by BrdU incorporation assay, using a colorimetric Cell Proliferation ELISA kit per manufacturer's instruction (#1647229, Roche Molecular Biochemicals). Cells were continuously cultured for 16-18 hrs in presence of 10 µM BrdU labeling solution. Then, the labeling medium was removed, and 200 µL FixDenat per well was added to the cells and incubated for 30 minutes at room temperature. The FixDenat solution was removed and 100 µL/well anti-BrdU-POD antibody conjugate working solution was added. The reaction was carried out for 90 minutes at room temperature. The antibody conjugate was then removed, and cells were rinsed three times with 200 µL/well washing solution. Finally, 100 µL/well of substrate solution was added and the results were obtained using a microplate reader (Spectra Max PLUS, Molecular Devices) during color development. Multiple readings at various time points were obtained to ensure the data was within the linear range. The data was routinely obtained from replicated experiments, and appropriate controls were included. See: Terness P, et al. (2002). Inhibition of allogeneic T cell proliferation by indoleamine 2,3-dioxygenase-expressing dendritic cells: mediation of suppression by tryptophan metabolites. J. Exp. Med. 196(4):447-57; and Hwu P, et al. (2000). Indoleamine 2,3-dioxygenase production by human dendritic cells results in the inhibition of T cell proliferation. J. Immunol. 164(7):3596-9. Compounds of the invention having an $IC_{50}$ less than about 100 µM were considered active.

Example D

In Vivo Testing of IDO Inhibitors for Antitumor Activity

In vivo anti-tumor efficacy can be tested using modified tumor allograft/xenograft protocols. For instance, it has been described in the literature that IDO inhibition can syngerize with cytotoxic chemotherapy in immune-competent mice (Muller, A. J., et al). This synergy was shown to be dependent on T-cells by comparison of the synergistic effects of an investigational IDO inhibitor in murine tumor xenograft models (e.g. B16 and related variants, CT-26, LLC) grown in immune competent syngenic mice to that observed in syngenic mice treated with neutralizing anti-CD4 antibodies, or the same tumors grown in immune-compromised mice (e.g. nu/nu).

The concept of differential anti-tumor effects in immune-competent versus immune-compromised mice may also permit testing of investigational IDO inhibitors as single agents. For instance, LLC tumors grow well in their syngenic host strain, C57Bl/6. However, if these mice are treated with the IDO inhibitor 1-MT (versus placebo) the formation of tumors is markedly delayed, implying that IDO inhibition was growth inhibitory (Friberg, M., et al). Following this logic, one can examine the efficacy of IDO inhibition in the LLC xenograft tumor model grown in C57Bl/6 immune competent mice and compare that to the effects of IDO inhibitors on LLC tumor growth in nude or SCID mice (or C57Bl/6 mice treated with antibodies that neutralize T-cell activity). As the effects of relieving the tumor-mediated immune suppressive activity of IDO will likely differ depending on the immunogenic potential of different tumor models, genetic modifications can be made to the tumor cells to increase their immunogenic potential. For instance, expression of GM-CSF in B16.F10 cells increases their immunogenic potential (Dranoff, G., et al). As such, in some tumor models (e.g. B16.F10) one can generate [poly]clones that express immune stimulatory proteins such as GM-CSF and test the growth inhibitory effects of IDO inhibitors against tumors established from these tumor cells in both immune-competent and compromised mice.

A third avenue for assessing the efficacy of IDO inhibitors in vivo employs 'pre-immunization' murine tumor allograft/xenograft models. In these models, immune-competent mice are sensitized to a specific tumor antigen or antigens to mimic a therapeutic anti-tumor vaccination. This primes the mice for an anti-tumor response mediated by the immune system when mice are subsequently challenged with murine tumor cell lines (possessing similar tumor antigens to those used for immunization) in xenograft experiments. Expression of IDO has been shown to blunt the anti-tumor response and allow xenografts to grow more rapidly. Importantly, the growth of tumors in this model is inhibited by the IDO inhibitor 1-MT (Uyttenhove, C., et al). This model is particularly attractive as IDO activity is permissive for P815 tumor growth and specific inhibition of IDO should therefore growth inhibitory.

Lastly, therapeutic immunization may be used to evaluate the impact of IDO inhibitors in vivo. For example, it has been demonstrated using B16-BL6 cells that one can challenge Blk/6 mice with an intravenous injection of tumor cells followed by treatment with a well characterized immunogenic peptide (e.g. TRP-2; SVYDFFVWL) expressed by the tumor cells (Ji, et al., J. Immunol, 2005, 175:1456-63). Importantly, immune system modifiers, such as anti-CTL-4 antibody, can improve responses to such therapeutic immunizations. The impact of IDO inhibitors may be evaluated in a similar manner tumor peptide immunization with or without IDO inhibitor. Efficacy is assess by animal survival (time to morbididity) or by the measurement of tumor metastases to the lungs and/or other organs at defined timepoints.

In any/all of the above mentioned models, it may also be possible to directly and/or indirectly measure the number and/or activity of tumor reative immune cells. Methods for measuring the number and/or activity of tumor reactive immune cells are well established and can be performed using techniques familiar to those schooled in the art (Current Protocols in Immunology, vol 4, Coligan, J. E., et al; Immunotherapy of Cancer, Human Press, 2006, Disis, M. L. and references therein). Conceptually, a reduction in the immune suppressive effects of IDO may result in increased numbers or reactivity of tumor specific immune cells. Further, IDO inhibition may further increase the number or reactivity of tumor reactive immune cells when combined with other therapeutics, for example chemotherapeutics and/or immune modulators (e.g. anti-CTLA4 antibody).

All allograft/xenograft experiments can be performed using standard tumor techniques (reviewed by Corbett, et al). The cloning and introduction of genes (e.g. IDO, GM-CSF) into tumor cell lines, can be performed using techniques familiar to those schooled in the art (reviewed in Sambrook, J, et al). See: Corbett, T., Polin, L., et al. In vivo methods for screening and preclinical testing. Cancer Drug Discovery and Development: Anticancer Drug Development Guide: Preclinical Screening, Clinical Trials, and Approval, $2^{nd}$ Ed. Teicher, B. A. and Andrews, P. A., Gumana Press Inc., Totowa, N. J., 2004; Dranoff, G., Jaffee, E., et al. Vaccination with irradiated tumor cells engineered to secrete murine granulocyte-macrophage colony-stimulating factor stimulates potent, specific, and long-lasting anti-tumor immunity. Proc. Natl. Acad. Sci, USA. 90:3539-3543, 1993; Friberg, M., Jennings, R., et al. Indoleamine 2,3-dioxygenase contributes to tumor cell evasion of T cell-mediated rejection. Int. J. Cancer: 101:151-155, 2002; Muller, A. J., DuHadaway, J. B., et al. Inhibition of indoleamine 2,3-dioxygenase, an immunoregulatory target of the cancer suppression gene Bin1, potentiates cancer chemotherapy. Nat. Med. 11:312-319, 2005; Sambrook, J, Russel, D. Molecular Cloning: A laboratory Manual ($3^{rd}$ edition). Cold Spring Harbor Laboratory Press. Cold Spring Harbor, N.Y., USA. 2001; and Uyttenhove, C., Pilotte, L., et al. Evidence for a tumoral immune resistance mechanism based on tryptophan degradation by indoleamine 2,3-dioxygenase. Nat. Med. 9:1269-1274, 2003.

Example E

In Vivo Testing of IDO Inhibitors in Human Immunodeficiency Virus-1 (HIV-1) Encephalitis Model 1. Cell Isolation and Viral Infection Monocytes and PBL can be obtained by countercurrent centrifugal elutriation of leukopheresis packs from HIV-1, 2 and hepatitis B seronegative donors. Monocytes are cultivated in suspension culture using Teflon flasks in Dulbecco's Modififed Eagle's Medium (DMEM, Sigma-Aldrich) supplemented with 10% heat-inactivated pooled human serum, 1% glutamine, 50 µg/mL gentamicin, 10 µg/mL ciprofloxacin (Sigma), and 1000 U/mL highly purified recombinant human macrophage colony stimulating factor. After seven days in culture, MDM are infected with HIV-$1_{ADA}$ at multiplicity of infection of 0.01.

2. Hu-PBL-NOD/SCID HIVE Mice

Four-wk old male NOD/C.B-17 SCID mice can be purchased (Jackson Laboratory). Animals are maintained in sterile microisolator cages under pathogen-free conditions. All animals are injected intraperitoneally with rat anti-CD122 (0.25 mg/mouse) three days before PBL transplantation and twice with rabbit asialo-GM1 antibodies (0.2 mg/mouse) (Wako) one day before and three days after PBL injection ($20 \times 10^6$ cells/mouse). HIV-$1_{ADA}$-infected MDM ($3 \times 10^5$ cells in 10 µL) are injected intracranially (i.c.) eight days following PBL reconstitution generating hu-PBL-NOD/SCID HIVE mice. Immediately following i.c. injection of HIV-1 infected MDM the hu-PBL-NOD/SCID HIVE mice are subcutaneously (s.c) implanted with control (vehicle) or compound pellets (14 or 28 day slow release, Innovative Research). Initial experiments are designed to confirm the induction of virus-specific CTL in the hu PBL-NOD/SCID HIVE animals treated with IDO compounds. This is confirmed by tetramer staining and neuropathologic analyses of MDM elimination from the brain tissue. Then, the experiment is designed to analyze human lymphocyte reconstitution, humoral immune responses, and neuropathological alterations. In these experiments, animals are bled on day 7 and sacrificed at 14 and 21 days after i.c. injection of human MDM. Blood collected in EDTA-containing tubes is used for flow cytometry and plasma is used for detection of HIV-1 p24 using ELISA (Beckman Coulter™). HIV-1-specific antibodies are detected by Western blot tests according to the manufacturer instructions (Cambridge Biotech HIV-1 Western blot kit, Calypte Biomedical). Similar amount of virus-specific antibodies are detected in control and compound-treated animals. A total of three independent experiments can be performed using three different human leukocyte donors.

3. FACScan of Peripheral Blood and Spleen in hu PBL-NOD/SCID HIVE Mice

Two-color FACS analysis can be performed on peripheral blood at wk 1-3 and splenocytes at wk 2 and 3 after i.c. injection of human MDM. Cells are incubated with fluorochrome-conjugated monoclonal Abs (mAbs) to human CD4, CD8, CD56, CD3, IFN-γ (eBioscience) for 30 min at 4° C. To evaluate the cellular immune response, IFN-γ intracellular staining is performed in combination with anti-human CD8 and FITC-conjugated anti-mouse CD45 to exclude murine cells. To determine the Ag-specific CTL, allophycocyanin-conjugated tetramer staining for HIV-$1^{gag}$ (p17 (aa77-85) SLYNTVATL, SL-9) and HIV-$1^{pol}$ [(aa476-485) ILKEPVHGV, IL-9] is performed on phytohemaglutinin/interleukin-2 (PHA/IL-2)-stimulated splenocytes. Cells are stained following the recommendation of the NIH/National Institute of Allergy and Infections Disease, National Tetramer Core Facilities. Data were analyzed with a FACS Calibur™ using CellQuest software (Becton Dickinson Immunocytometry System).

4. Histopathology and Image Analyses

Brain tissue is collected at days 14 and 21 after i.c. injection of MDM, fixed in 4% phosphate-buffered paraformaldehyde and embedded in paraffin or frozen at −80° C. for later use. Coronal sections from the embedded blocks are cut in order to identify the injection site. For each mouse, 30-100 (5-µm-thick) serial sections are cut from the human MDM injection site and 3-7 slides (10 sections apart) are analyzed. Brain sections are deparaffinized with xylene and hydrated in gradient alcohols. Immunohistochemical staining follows a basic indirect protocol, using antigen retrieval by heating to 95° C. in 0.01 mol/L citrate buffer for 30 min for antigen retrieval. To identify human cells in mouse brains, mAb to vimentin (1:50, clone 3B4, Dako Corporation), which identifies all human leukocytes is used. Human MDM and CD8$^+$ lymphocytes are detected with CD68 (1:50 dilution, clone KP 1) and CD8 (1:50 dilution, clone 144B) antibodies, respectively. Virus-infected cells are labeled with mAb to HIV-1 p24 (1:10, clone Kal-1, all from Dako). Reactive murine microglial cells are detected with Iba-1 antibody (1:500, Wako). Expression of human IDO (huIDO) is visualized with Abs obtained from the Department of Cell Pharmacology, Central Research Institute, Graduate School of Medicine, Hokkaido University, Sapporo, Japan. Primary antibodies are detected with the appropriate biotinylated secondary antibodies and visualized with avidin-biotin complexes (Vectastain Elite ABC kit, Vector Laboratories) and horseradish peroxidase (HRP) coupled dextran polymer (EnVision, Dako Corporation). Immunostained sections are counterstained with Mayer's hematoxylin. Sections from which primary antibody is deleted or irrelevant IgG isotype is incorporated served as controls. Two independent observers in a blinded fashion count the numbers of CD8$^+$ lymphocytes, CD68$^+$ MDM and HIV-1 p24$^+$ cells in each section from each mouse. Light microscopic examination is performed with a Nikon Eclipse 800 microscope (Nikon Instruments Inc). Semi-quantitative analysis for Iba1 (percentage of area occupied by immunostaining) is carried out by computer-assisted image analysis (Image-Pro®Plus, Media Cybernetics) as previously described.

5. Statistic Analysis

Data can be analyzed using Prism (Graph Pad) with Student t-test for comparisons and ANOVA. P-values<0.05 were considered significant.

6. Reference

Poluektova L Y, Munn D H, Persidsky Y, and Gendelman H E (2002). Generation of cytotoxic T cells against virus-infected human brain macrophages in a murine model of HIV-1 encephalitis. J. Immunol. 168(8):3941-9.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a cancer selected from cancer of the colon, pancreatic cancer, breast cancer, prostate cancer, lung cancer, brain cancer, ovarian cancer, cervical cancer, testicular cancer, renal cancer, cancer of the head and neck, lymphoma, leukemia, and melanoma in a patient in need thereof, comprising administering to said patient a therapeutically effective amount of a compound of formula:

$$R^{3b}\text{---}(W)_b\text{---}(R^{3a})_a\text{---}\underset{\underset{R^2}{|}}{N}\text{---}\overset{HO\diagdown N}{C}\text{---}\underset{N-O}{\overset{}{\diagup}}\text{---}\overset{H}{N}\text{---}(X^1)_m\text{---}(R^{5a})_n\text{---}(X^2)_p\text{---}R^{5b}$$

or a pharmaceutically acceptable salt thereof, in combination with an antibody selected from an anti-CLTA-4 antibody and an anti-PD-1 antibody, wherein:

W, $X^1$, and $X^2$ are independently selected from $(CR^aR^b)_t$, $(CR^aR^b)_uO(CR^aR^b)_v$, $(CR^aR^b)_uC(O)(CR^aR^b)_v$, $(CR^aR^b)_uC(O)NR^c(CR^aR^b)_v$, $(CR^aR^b)_uC(O)O(CR^aR^b)_v$, $(CR^aR^b)_uC(S)(CR^aR^b)_v$, $(CR^aR^b)_uC(S)NR^c(CR^aR^b)_v$, $(CR^aR^b)_uS(O)(CR^aR^b)_v$, $(CR^aR^b)_uS(O)NR^c(CR^aR^b)_v$, $(CR^aR^b)_uS(O)_2(CR^aR^b)_v$, $(CR^aR^b)_uS(O)_2NR^c(CR^aR^b)_v$, $(CR^aR^b)_uNR^c(CR^aR^b)_v$, and $(CR^aR^b)_uC(=NR^d)NR^c(CR^aR^b)_v$;

$R^2$ is H, $C_{1-6}$ alkyl, or $C_{3-7}$ cycloalkyl;

$R^{3a}$ and $R^{5a}$ are independently selected from $C_{1-8}$ alkyl, $C_{2-8}$ alkenyl, $C_{2-8}$ alkynyl, aryl, cycloalkyl, heteroaryl, and heterocycloalkyl, each optionally substituted by 1, 2, 3, 4 or 5 substituents independently selected from halo, $C_{1-6}$ alkyl, $C_{2-6}$ alkenyl, $C_{2-6}$ alkynyl, haloalkyl, $Cy^1$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{3b}$ is aryl or heteroaryl, each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$R^{5b}$ is selected from H, $C_{1-8}$ alkyl, $C_{2-8}$ alkenyl, $C_{2-8}$ alkynyl, aryl, cycloalkyl, heteroaryl, and heterocycloalkyl, wherein said $C_{1-8}$ alkyl, $C_{2-8}$ alkenyl, $C_{2-8}$ alkynyl, aryl, cycloalkyl, heteroaryl, and heterocycloalkyl are each optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{e3}$, $SR^{e3}$, $C(O)R^{f3}$, $C(O)NR^{g3}R^{h3}$, $C(O)OR^{e3}$, $OC(O)R^{f3}$, $OC(O)NR^{g3}R^{h3}$, $NR^{g3}R^{h3}$, $NR^{g3}C(O)R^{h3}$, $NR^{g3}C(O)OR^{e3}$, $P(R^{f3})_2$, $P(OR^{e3})_2$, $P(O)R^{e3}R^{f3}$, $P(O)OR^{e3}OR^{f3}$, $S(O)R^{f3}$, $S(O)NR^{g3}R^{h3}$, $S(O)_2R^{f3}$, and $S(O)_2NR^{g3}R^{h3}$;

$R^a$ and $R^b$ are independently selected from H, halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{e4}$, $SR^{e4}$, $C(O)R^{f4}$, $C(O)NR^{g4}R^{h4}$, $C(O)OR^{e4}$, $OC(O)R^{f4}$, $OC(O)NR^{g4}R^{h4}$, $NR^{g4}R^{h4}$, $NR^{g4}C(O)R^{h4}$, $NR^{g4}C(O)OR^{e4}$, $P(R^{f4})_2$, $P(OR^{e4})_2$, $P(O)R^{e4}R^{f4}$, $P(O)OR^{e4}OR^{f4}$, $S(O)R^{f4}$, $S(O)NR^{g4}R^{h4}$, $S(O)_2R^{f4}$, and $S(O)_2NR^{g4}R^{h4}$;

$R^c$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^d$ is H, $OR^{d1}$, CN or $NO_2$;

$R^{d1}$ is H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

$R^{e1}$, $R^{e3}$, and $R^{e4}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl and heterocycloalkylalkyl;

$R^{f1}$, $R^{f3}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl and heterocycloalkyl;

$R^{g1}$, $R^{g3}$, and $R^{g4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

$R^{h1}$, $R^{h3}$, and $R^{h4}$ are independently selected from H, $C_{1-6}$ alkyl, $C_{1-6}$ haloalkyl, $C_{2-6}$ alkenyl, $C_{2-6}$ alkynyl, aryl, cycloalkyl, arylalkyl, and cycloalkylalkyl;

or $R^{g1}$ and $R^{h1}$ together with the N atom to which they are attached form a 4-, 5-, 6- or 7-membered heterocycloalkyl group;

or $R^{g3}$ and $R^{h3}$ together with the N atom to which they are attached form a 4-, 5-, 6- or 7-membered heterocycloalkyl group;

or $R^{g4}$ and $R^{h4}$ together with the N atom to which they are attached form a 4-, 5-, 6- or 7-membered heterocycloalkyl group;

a is 0 or 1;

b is 0 or 1;

m is 1;

n is 0 or 1;

p is 0 or 1;

t is, independently, 1, 2, 3, 4, 5 or 6;

u is, independently, 0, 1, 2, 3, 4, 5 or 6; and v is, independently, 0, 1, 2, 3, 4, 5 or 6.

2. The method of claim 1, wherein the antibody is an anti-PD-1 antibody.

3. The method of claim 1, wherein the antibody is an anti-CTLA-4 antibody.

4. The method of claim 1, wherein the antibody is administered simultaneously with said compound or salt.

5. The method of claim 1, wherein the antibody is administered sequentially to said compound or salt.

6. The method of claim 1, wherein the cancer is melanoma.

7. The method of claim 6, wherein the antibody is an anti-PD-1 antibody.

8. The method of claim 6, wherein the antibody is an anti-CTLA-4 antibody.

9. The method of claim 1, wherein said cancer is cancer of the colon.

10. The method of claim 1, wherein said cancer is pancreatic cancer.

11. The method of claim 1, wherein said cancer is breast cancer.

12. The method of claim 1, wherein said cancer is prostate cancer.

13. The method of claim 1, wherein said cancer is lung cancer.

14. The method of claim 1, wherein said cancer is brain cancer.

15. The method of claim 1, wherein said cancer is ovarian cancer.

16. The method of claim 1, wherein said cancer is cervical cancer.

17. The method of claim 1, wherein said cancer is testicular cancer.

18. The method of claim 1, wherein said cancer is renal cancer.

19. The method of claim 1, wherein said cancer is cancer of the head and neck.

20. The method of claim 1, wherein said cancer is lymphoma.

21. The method of claim 1, wherein said cancer is leukemia.

22. The method of claim 1, wherein $R^2$ is H.

23. The method of claim 22 wherein n is 0.

24. The method of claim 23, wherein p is 1.

25. The method of claim 24, wherein $R^{5b}$ is H.

26. The method of claim 25, wherein a is 0.

27. The method of claim 26, wherein b is 0.

28. The method of claim 27, wherein $R^{3b}$ is phenyl optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

29. The method of claim 28, wherein the cancer is melanoma.

30. The method of claim 29, wherein the antibody is an anti-PD-1 antibody.

31. The method of claim 29, wherein the antibody is an anti-CTLA-4 antibody.

32. The method of claim 26, wherein b is 1.

33. The method of claim 32, wherein W is $(CR^aR^b)_r$ or $(CR^aR^b)_u O(CR^aR^b)_v$.

34. The method of claim 33, wherein $R^{3b}$ is heteroaryl, optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, $Cy^2$, CN, $NO_2$, $OR^{e1}$, $SR^{e1}$, $C(O)R^{f1}$, $C(O)NR^{g1}R^{h1}$, $C(O)OR^{e1}$, $OC(O)R^{f1}$, $OC(O)NR^{g1}R^{h1}$, $NR^{g1}C(O)NR^{g1}R^{h1}$, $NR^{g1}R^{h1}$, $NR^{g1}C(O)R^{f1}$, $NR^{g1}C(O)OR^{e1}$, $P(R^{f1})_2$, $P(OR^{e1})_2$, $P(O)R^{e1}R^{f1}$, $P(O)OR^{e1}OR^{f1}$, $S(O)R^{f1}$, $S(O)NR^{g1}R^{h1}$, $S(O)_2R^{f1}$, and $S(O)_2NR^{g1}R^{h1}$.

35. The method of claim 34, wherein the cancer is melanoma.

36. The method of claim 35, wherein the antibody is an anti-PD-1 antibody.

37. The method of claim 35, wherein the antibody is an anti-CTLA-4 antibody.

38. The method of claim 1, wherein said compound is selected from:

N-benzyl-4-(benzylamino)-N'-hydroxy-1,2,5-oxadiazole-3-carboximidamide;

4-[(Anilinocarbonyl)amino]-N-(3-chlorophenyl)-N'-hydroxy-1,2,5-oxadiazole-3-carboximidamide;

tert-Butyl {4-[({4-[(E,Z)-[(3-chlorophenyl)amino](hydroxyimino)methyl]-1,2,5-oxadiazol-3-yl}amino)carbonyl]benzyl}carbamate;

4-(Aminomethyl)-N-{4-[(E,Z)-[(3-chlorophenyl)amino](hydroxyimino)methyl]-1,2,5-oxadiazol-3-yl}benzamide;

4-{[(Benzylamino)carbonyl]amino}-N-(3-bromo-4-fluorophenyl)-N'-hydroxy-1,2,5-oxadiazole-3-carboximidamide;

N-{4-[(E,Z)-[(3-Bromo-4-fluorophenyl)amino](hydroxyimino)methyl]-1,2,5-oxadiazol-3-yl}morpholine-4-carboxamide;

N-(3-Bromo-4-fluorophenyl)-N'-hydroxy-4-(methylamino)-1,2,5-oxadiazole-3-carboximidamide;

N-{4-[(E,Z)-[(3-Bromo-4-fluorophenyl)amino](hydroxyimino)methyl]-1,2,5-oxadiazol-3-yl}piperidine-4-carboxamide;

tert-Butyl 4-{4-[({4-[(E,Z)-[(3-bromo-4-fluorophenyl)amino](hydroxyimino)methyl]-1,2,5-oxadiazol-3-yl}amino)carbonyl]benzyl}piperazine-1-carboxylate;

N-{4-[(E,Z)-[(3-Bromo-4-fluorophenyl)amino](hydroxyimino)methyl]-1,2,5-oxadiazol-3-yl}-4-(piperazin-1-ylmethyl)benzamide;

1-Benzoyl-N-{4-[(E,Z)-[(3-bromo-4-fluorophenyl)amino](hydroxyimino)methyl]-1,2,5-oxadiazol-3-yl}piperidine-4-carboxamide;

N(4)-{4-[(E,Z)-[(3-Bromo-4-fluorophenyl)amino](hydroxyimino)methyl]-1,2,5-oxadiazol-3-yl}-N(1)-phenylpiperidine-1,4-dicarboxamide;

N-{4-[(E,Z)-[(3-Bromo-4-fluorophenyl)amino](hydroxyimino)methyl]-1,2,5-oxadiazol-3-yl}-1-ethylpiperidine-4-carboxamide;

4-[(Benzoylamino)methyl]-N-{4-[(E,Z)-[(3-bromo-4-fluorophenyl)amino]-(hydroxyimino)methyl]-1,2,5-oxadiazol-3-yl}benzamide;

N-{4-[(E,Z)-[(3-Bromo-4-fluorophenyl)amino](hydroxyimino)methyl]-1,2,5-oxadiazol-3-yl}-2-(2-cyanophenoxy)acetamide;

N-{4-[(E,Z)-[(3-Bromo-4-fluorophenyl)amino](hydroxyimino)methyl]-1,2,5-oxadiazol-3-yl}-4-phenylpiperidine-4-carboxamide;

N-(3-Bromo-4-fluorophenyl)-4-({4-[(1,1-dioxidothiomorpholin-4-yl)methyl]benzyl}amino)-N'-hydroxy-1,2,5-oxadiazole-3-carboximidamide;

N-(3-Bromo-4-fluorophenyl)-N'-hydroxy-4-{[4-(morpholin-4-ylmethyl)benzyl]amino}-1,2,5-oxadiazole-3-carboximidamide;

N-(3-Cyano-4-fluorophenyl)-4-({4-[(1,1-dioxidothiomorpholin-4-yl)methyl]benzyl}amino)-N'-hydroxy-1,2,5-oxadiazole-3-carboximidamide;

N-(3-Bromo-4-fluorophenyl)-N'-hydroxy-4-[(pyridin-3-ylmethyl)amino]-1,2,5-oxadiazole-3-carboximidamide;

N-(3-Cyano-4-fluorophenyl)-N'-hydroxy-4-[(pyridin-4-ylmethyl)amino]-1,2,5-oxadiazole-3-carboximidamide;
4-[(3-Cyanobenzyl)amino]-N-(3-cyano-4-fluorophenyl)-N'-hydroxy-1,2,5-oxadiazole-3-carboximidamide;
N-(3-Bromo-4-fluorophenyl)-N'-hydroxy-4-[(1H-tetrazol-5-ylmethyl)amino]-1,2,5-oxadiazole-3-carboximidamide;
N-{4-[(E,Z)-[(3-Chlorophenyl)amino](hydroxyimino)methyl]-1,2,5-oxadiazol-3-yl}cyclopentanecarboxamide;
N-{4-[(E,Z)-[(3-Chlorophenyl)amino](hydroxyimino)methyl]-1,2,5-oxadiazol-3-yl}nicotinamide;
N-{4-[(E,Z)-[(3-Chlorophenyl)amino](hydroxyimino)methyl]-1,2,5-oxadiazol-3-yl}isonicotinamide;
N-{4-[(E,Z)-[(3-Chlorophenyl)amino](hydroxyimino)methyl]-1,2,5-oxadiazol-3-yl}-2-methoxybenzamide;
N-{4-[(E,Z)-[(3-Chlorophenyl)amino](hydroxyimino)methyl]-1,2,5-oxadiazol-3-yl}-3-methoxybenzamide;
N-{4-[(E,Z)-[(3-Chlorophenyl)amino](hydroxyimino)methyl]-1,2,5-oxadiazol-3-yl}-4-methoxybenzamide;
2-Chloro-N-{4-[(E,Z)-[(3-chlorophenyl)amino](hydroxyimino)methyl]-1,2,5-oxadiazol-3-yl}benzamide;
3-Chloro-N-{4-[(E,Z)-[(3-chlorophenyl)amino](hydroxyimino)methyl]-1,2,5-oxadiazol-3-yl}benzamide;
4-Chloro-N-{4-[(E,Z)-[(3-chlorophenyl)amino](hydroxyimino)methyl]-1,2,5-oxadiazol-3-yl}benzamide;
N-{4-[(E,Z)-[(3-Chlorophenyl)amino](hydroxyimino)methyl]-1,2,5-oxadiazol-3-yl}-3,3-dimethylbutanamide;
N-{4-[(E,Z)-[(3-Chlorophenyl)amino](hydroxyimino)methyl]-1,2,5-oxadiazol-3-yl}-4-iodobenzamide;
N-{4-[(E,Z)-[(3-Chlorophenyl)amino](hydroxyimino)methyl]-1,2,5-oxadiazol-3-yl}-4-cyanobenzamide;
N-{4-[(E,Z)-{[4-Fluoro-3-(trifluoromethyl)phenyl]amino}(hydroxyimino)methyl]-1,2,5-oxadiazol-3-yl}nicotinamide;
N-{4-[(E,Z)-{[4-Fluoro-3-(trifluoromethyl)phenyl]amino}(hydroxyimino)methyl]-1,2,5-oxadiazol-3-yl}isonicotinamide;
N-{4-[(E,Z)-[(3-Bromo-4-fluorophenyl)amino](hydroxyimino)methyl]-1,2,5-oxadiazol-3-yl}benzamide;
N-{4-[(E,Z)-[(3-Bromo-4-fluorophenyl)amino](hydroxyimino)methyl]-1,2,5-oxadiazol-3-yl}nicotinamide;
N-{4-[(E,Z)-[(3-Bromo-4-fluorophenyl)amino](hydroxyimino)methyl]-1,2,5-oxadiazol-3-yl}isonicotinamide;
N-{4-[(E,Z)-[(3-Bromo-4-fluorophenyl)amino](hydroxyimino)methyl]-1,2,5-oxadiazol-3-yl}-4-cyanobenzamide;
N-{4-[(E,Z)-[(3-Bromo-4-fluorophenyl)amino](hydroxyimino)methyl]-1,2,5-oxadiazol-3-yl}-3-cyanobenzamide;
N-{4-[(E,Z)-[(3-Bromo-4-fluorophenyl)amino](hydroxyimino)methyl]-1,2,5-oxadiazol-3-yl}-2-naphthamide;
N-{4-[(E,Z)-[(3-Bromo-4-fluorophenyl)amino](hydroxyimino)methyl]-1,2,5-oxadiazol-3-yl}-1-naphthamide;
1-Acetyl-N-{4-[(E,Z)-[(3-bromo-4-fluorophenyl)amino](hydroxyimino)methyl]-1,2,5-oxadiazol-3-yl}piperidine-4-carboxamide;
N-{4-[(E,Z)-[(3-Bromo-4-fluorophenyl)amino](hydroxyimino)methyl]-1,2,5-oxadiazol-3-yl}-2-furamide;
N-{4-[(E,Z)-[(3-Bromo-4-fluorophenyl)amino](hydroxyimino)methyl]-1,2,5-oxadiazol-3-yl}thiophene-2-carboxamide;
N-{4-[(E,Z)-[(3-Bromo-4-fluorophenyl)amino](hydroxyimino)methyl]-1,2,5-oxadiazol-3-yl}-1-phenyl-5-(trifluoromethyl)-1H-pyrazole-4-carboxamide;
4-(Acetylamino)-N-{4-[(E,Z)-[(3-bromo-4-fluorophenyl)amino](hydroxyimino)methyl]-1,2,5-oxadiazol-3-yl}benzamide;
tert-Butyl {4-[({4-[(E,Z)-[(3-bromo-4-fluorophenyl)amino](hydroxyimino)methyl]-1,2,5-oxadiazol-3-yl}amino)carbonyl]benzyl}carbamate;
N-{4-[(E,Z)-[(3-Bromo-4-fluorophenyl)amino](hydroxyimino)methyl]-1,2,5-oxadiazol-3-yl}-1-benzothiophene-2-carboxamide;
N-{4-[(E,Z)-[(3-Bromo-4-fluorophenyl)amino](hydroxyimino)methyl]-1,2,5-oxadiazol-3-yl}-1,3-thiazole-4-carboxamide;
N-{4-[(E,Z)-[(3-Bromo-4-fluorophenyl)amino](hydroxyimino)methyl]-1,2,5-oxadiazol-3-yl}-1-benzothiophene-3-carboxamide;
N-{4-[(E,Z)-[(3-Bromo-4-fluorophenyl)amino](hydroxyimino)methyl]-1,2,5-oxadiazol-3-yl}thiophene-3-carboxamide;
N-{4-[(E,Z)-[(3-Bromo-4-fluorophenyl)amino](hydroxyimino)methyl]-1,2,5-oxadiazol-3-yl}-1H-imidazole-2-carboxamide;
N-{4-[(E,Z)-[(3-Bromo-4-fluorophenyl)amino](hydroxyimino)methyl]-1,2,5-oxadiazol-3-yl}-4-methyl-1,2,3-thiadiazole-5-carboxamide;
N-{4-[(E,Z)-[(3-Bromo-4-fluorophenyl)amino](hydroxyimino)methyl]-1,2,5-oxadiazol-3-yl}-1,2,3-thiadiazole-4-carboxamide;
N-{4-[(E,Z)-[(3-Bromo-4-fluorophenyl)amino](hydroxyimino)methyl]-1,2,5-oxadiazol-3-yl}-2,1-benzisoxazole-3-carboxamide;
4-(Aminomethyl)-N-{4-[(E,Z)-[(3-bromo-4-fluorophenyl)amino](hydroxyimino)methyl]-1,2,5-oxadiazol-3-yl}benzamide;
N-(3-Bromo-4-fluorophenyl)-N'-hydroxy-4-({[(2-phenylethyl)amino]carbonyl}amino)-1,2,5-oxadiazole-3-carboximidamide;
N-(3-Bromo-4-fluorophenyl)-4-{[(cyclopentylamino)carbonyl]amino}-N'-hydroxy-1,2,5-oxadiazole-3-carboximidamide;
N-(3-Bromo-4-fluorophenyl)-4-({[(3-cyanophenyl)amino]carbonyl}amino)-N'-hydroxy-1,2,5-oxadiazole-3-carboximidamide;
N-{4-[(E,Z)-[(3-Bromo-4-fluorophenyl)amino](hydroxyimino)methyl]-1,2,5-oxadiazol-3-yl}-3-tert-butyl-1-methyl-1H-pyrazole-5-carboxamide;
N-{4-[(E,Z)-[(3-Bromo-4-fluorophenyl)amino](hydroxyimino)methyl]-1,2,5-oxadiazol-3-yl}-2-methoxyacetamide;
N-{4-[(E,Z)-[(3-Bromo-4-fluorophenyl)amino](hydroxyimino)methyl]-1,2,5-oxadiazol-3-yl}cyclopentanecarboxamide;
N-{4-[(E,Z)-[(3-Bromo-4-fluorophenyl)amino](hydroxyimino)methyl]-1,2,5-oxadiazol-3-yl}butanamide;
N-{4-[(E,Z)-[(3-Bromo-4-fluorophenyl)amino](hydroxyimino)methyl]-1,2,5-oxadiazol-3-yl}-2-methylpropanamide;
N-{4-[(E,Z)-[(3-Bromo-4-fluorophenyl)amino](hydroxyimino)methyl]-1,2,5-oxadiazol-3-yl}propanamide;
N-{4-[(E,Z)-[(3-Bromo-4-fluorophenyl)amino](hydroxyimino)methyl]-1,2,5-oxadiazol-3-yl}cyclohexanecarboxamide;
N-{4-[(E,Z)-[(3-Bromo-4-fluorophenyl)amino](hydroxyimino)methyl]-1,2,5-oxadiazol-3-yl}-1H-benzimidazole-5-carboxamide;
N-{4-[(E,Z)-[(3-Bromo-4-fluorophenyl)amino](hydroxyimino)methyl]-1,2,5-oxadiazol-3-yl}-2-phenoxyacetamide;

N-{4-[(E,Z)-[(3-Bromo-4-fluorophenyl)amino](hydroxyimino)methyl]-1,2,5-oxadiazol-3-yl}cyclobutanecarboxamide;
N-{4-[(E,Z)-[(3-Bromo-4-fluorophenyl)amino](hydroxyimino)methyl]-1,2,5-oxadiazol-3-yl}-3-methylbutanamide;
N-{4-[(E,Z)-[(3-Bromo-4-fluorophenyl)amino](hydroxyimino)methyl]-1,2,5-oxadiazol-3-yl}-3-pyridin-3-yl-propanamide;
N-{4-[(E,Z)-[(3-Bromo-4-fluorophenyl)amino](hydroxyimino)methyl]-1,2,5-oxadiazol-3-yl}quinoline-6-carboxamide;
N-{4-[(E,Z)-[(3-Bromo-4-fluorophenyl)amino](hydroxyimino)methyl]-1,2,5-oxadiazol-3-yl}-2-(4-chlorophenoxy)acetamide;
N-{4-[(E,Z)-[(3-Bromo-4-fluorophenyl)amino](hydroxyimino)methyl]-1,2,5-oxadiazol-3-yl}-2-(4-bromophenoxy)acetamide;
N-{4-[(E,Z)-[(3-Bromo-4-fluorophenyl)amino](hydroxyimino)methyl]-1,2,5-oxadiazol-3-yl}-2-(4-fluorophenoxy)acetamide;
N-{4-[(E,Z)-[(3-Bromo-4-fluorophenyl)amino](hydroxyimino)methyl]-1,2,5-oxadiazol-3-yl}-2-(4-tert-butylphenoxy)acetamide;
N-{4-[(E,Z)-[(3-Bromo-4-fluorophenyl)amino](hydroxyimino)methyl]-1,2,5-oxadiazol-3-yl}-2-(3-chlorophenoxy)acetamide;
N-{4-[(E,Z)-[(3-Bromo-4-fluorophenyl)amino](hydroxyimino)methyl]-1,2,5-oxadiazol-3-yl}-2-(3,4-dichlorophenoxy)acetamide;
N-{4-[(E,Z)-[(3-Bromo-4-fluorophenyl)amino](hydroxyimino)methyl]-1,2,5-oxadiazol-3-yl}-2-(2-naphthyloxy)acetamide;
N-{4-[(E,Z)-[(3-Bromo-4-fluorophenyl)amino](hydroxyimino)methyl]-1,2,5-oxadiazol-3-yl}-2-(2,3-dichlorophenoxy)acetamide;
N-{4-[(E,Z)-[(3-Bromo-4-fluorophenyl)amino](hydroxyimino)methyl]-1,2,5-oxadiazol-3-yl}-2-(4-chlorophenoxy)-2-methylpropanamide;
N-{4-[(E,Z)-[(3-Bromo-4-fluorophenyl)amino](hydroxyimino)methyl]-1,2,5-oxadiazol-3-yl}-2-(2-chlorophenoxy)acetamide;
N-{4-[(E,Z)-[(3-Bromo-4-fluorophenyl)amino](hydroxyimino)methyl]-1,2,5-oxadiazol-3-yl}-2-(3-methoxyphenoxy)acetamide;
N-{4-[(E,Z)-[(3-Bromo-4-fluorophenyl)amino](hydroxyimino)methyl]-1,2,5-oxadiazol-3-yl}-2-(4-methoxyphenoxy)acetamide;
N-{4-[(E,Z)-[(3-Bromo-4-fluorophenyl)amino](hydroxyimino)methyl]-1,2,5-oxadiazol-3-yl}-2-(2-methoxyphenoxy)acetamide;
Benzyl {4-[(E,Z)-[(3-bromo-4-fluorophenyl)amino](hydroxyimino)methyl]-1,2,5-oxadiazol-3-yl}carbamate;
N-{4-[(E,Z)-[(3-Bromo-4-fluorophenyl)amino](hydroxyimino)methyl]-1,2,5-oxadiazol-3-yl}acetamide;
N-{4-[(E,Z)-[(3-Bromo-4-fluorophenyl)amino](hydroxyimino)methyl]-1,2,5-oxadiazol-3-yl}piperidine-1-carboxamide;
N-(3-Bromo-4-fluorophenyl)-4-({[(3-cyanophenyl)(methyl)amino]carbonyl}amino)-N'-hydroxy-1,2,5-oxadiazole-3-carboximidamide;
4-({[Benzyl(methyl)amino]carbonyl}amino)-N-(3-bromo-4-fluorophenyl)-N'-hydroxy-1,2,5-oxadiazole-3-carboximidamide;
N-{4-[(E,Z)-[(3-Bromo-4-fluorophenyl)amino](hydroxyimino)methyl]-1,2,5-oxadiazol-3-yl}-2-phenylacetamide;
N-{4-[(E,Z)-[(3-Bromo-4-fluorophenyl)amino](hydroxyimino)methyl]-1,2,5-oxadiazol-3-yl}-2-(3-methoxyphenyl)acetamide;
N-{4-[(E,Z)-[(3-Bromo-4-fluorophenyl)amino](hydroxyimino)methyl]-1,2,5-oxadiazol-3-yl}-2-(4-methoxyphenyl)acetamide;
N-{4-[(E,Z)-[(3-Bromo-4-fluorophenyl)amino](hydroxyimino)methyl]-1,2,5-oxadiazol-3-yl}-2-(2-methoxyphenyl)acetamide;
N-{4-[(E,Z)-[(3-Bromo-4-fluorophenyl)amino](hydroxyimino)methyl]-1,2,5-oxadiazol-3-yl}-2-cyanobenzamide;
N-{4-[(E,Z)-[(3-Bromo-4-fluorophenyl)amino](hydroxyimino)methyl]-1,2,5-oxadiazol-3-yl}-3-(3-bromophenyl)propanamide;
N-{4-[(E,Z)-[(3-Bromo-4-fluorophenyl)amino](hydroxyimino)methyl]-1,2,5-oxadiazol-3-yl}-3-(4-bromophenyl)propanamide;
N-{4-[(E,Z)-[(3-Bromo-4-fluorophenyl)amino](hydroxyimino)methyl]-1,2,5-oxadiazol-3-yl}-3-(4-chlorophenyl)propanamide;
N-{4-[(E,Z)-[(3-Bromo-4-fluorophenyl)amino](hydroxyimino)methyl]-1,2,5-oxadiazol-3-yl}-3-(3-chlorophenyl)propanamide;
N-{4-[(E,Z)-[(3-Bromo-4-fluorophenyl)amino](hydroxyimino)methyl]-1,2,5-oxadiazol-3-yl}-3-(2-fluorophenyl)propanamide;
N-{4-[(E,Z)-[(3-Bromo-4-fluorophenyl)amino](hydroxyimino)methyl]-1,2,5-oxadiazol-3-yl}-3-(3-fluorophenyl)propanamide;
N-{4-[(E,Z)-[(3-Bromo-4-fluorophenyl)amino](hydroxyimino)methyl]-1,2,5-oxadiazol-3-yl}-3-(2-chlorophenyl)propanamide;
N-{4-[(E,Z)-[(3-Bromo-4-fluorophenyl)amino](hydroxyimino)methyl]-1,2,5-oxadiazol-3-yl}-3-(3-methylphenyl)propanamide;
N-{4-[(E,Z)-[(3-Bromo-4-fluorophenyl)amino](hydroxyimino)methyl]-1,2,5-oxadiazol-3-yl}-3-(3-(trifluoromethyl)phenyl)propanamide;
N-{4-[(E,Z)-[(3-Bromo-4-fluorophenyl)amino](hydroxyimino)methyl]-1,2,5-oxadiazol-3-yl}-3-(4-fluorophenyl)propanamide;
N-{4-[(E,Z)-[(3-Bromo-4-fluorophenyl)amino](hydroxyimino)methyl]-1,2,5-oxadiazol-3-yl}-3-(2-methoxyphenyl)propanamide;
N-{4-[(E,Z)-[(3-Bromo-4-fluorophenyl)amino](hydroxyimino)methyl]-1,2,5-oxadiazol-3-yl}-3-(3-methoxyphenyl)propanamide;
N-{4-[(E,Z)-[(3-Bromo-4-fluorophenyl)amino](hydroxyimino)methyl]-1,2,5-oxadiazol-3-yl}-3-(4-methoxyphenyl)propanamide;
N-{4-[(E,Z)-[(3-Bromo-4-fluorophenyl)amino](hydroxyimino)methyl]-1,2,5-oxadiazol-3-yl}-3-(4-methylphenyl)propanamide;
N-{4-[(E,Z)-[(3-Bromo-4-fluorophenyl)amino](hydroxyimino)methyl]-1,2,5-oxadiazol-3-yl}-3-[4-(trifluoromethyl)phenyl]propanamide;
3-[2,5-Bis(trifluoromethyl)phenyl]-N-{4-[(E,Z)-[(3-bromo-4-fluorophenyl)amino](hydroxyimino)methyl]-1,2,5-oxadiazol-3-yl}propanamide;
3-[3,5-Bis(trifluoromethyl)phenyl]-N-{4-[(E,Z)-[(3-bromo-4-fluorophenyl)amino](hydroxyimino)methyl]-1,2,5-oxadiazol-3-yl}propanamide;
N-{4-[(E,Z)-[(3-Bromo-4-fluorophenyl)amino](hydroxyimino)methyl]-1,2,5-oxadiazol-3-yl}-2-methyl-3-phenylpropanamide;

2-Benzyl-N-{4-[(E,Z)-[(3-bromo-4-fluorophenyl)amino](hydroxyimino)methyl]-1,2,5-oxadiazol-3-yl}-3,3-dimethylbutanamide;

N-{4-[(E,Z)-[(3-Bromo-4-fluorophenyl)amino](hydroxyimino)methyl]-1,2,5-oxadiazol-3-yl}-1-[4-(trifluoromethyl)pyrimidin-2-yl]piperidine-4-carboxamide;

1-Benzyl-N-{4-[(E,Z)-[(3-bromo-4-fluorophenyl)amino](hydroxyimino)methyl]-1,2,5-oxadiazol-3-yl}-3-tert-butyl-1H-pyrazole-5-carboxamide;

2-(Benzyloxy)-N-{4-[(E,Z)-[(3-bromo-4-fluorophenyl)amino](hydroxyimino)methyl]-1,2,5-oxadiazol-3-yl}acetamide;

N-{4-[(E,Z)-[(3-Bromo-4-fluorophenyl)amino](hydroxyimino)methyl]-1,2,5-oxadiazol-3-yl}-1-(4-chlorophenyl)cyclopentanecarboxamide;

N-{4-[(E,Z)-[(3-Bromo-4-fluorophenyl)amino](hydroxyimino)methyl]-1,2,5-oxadiazol-3-yl}-3-phenoxybenzamide;

N-{4-[(E,Z)-[(3-Bromo-4-fluorophenyl)amino](hydroxyimino)methyl]-1,2,5-oxadiazol-3-yl}-2,4,6-trichlorobenzamide;

N-{4-[(E,Z)-[(3-Bromo-4-fluorophenyl)amino](hydroxyimino)methyl]-1,2,5-oxadiazol-3-yl}-2-methoxybenzamide;

N-{4-[(E,Z)-[(3-Bromo-4-fluorophenyl)amino](hydroxyimino)methyl]-1,2,5-oxadiazol-3-yl}-3-methoxybenzamide;

N-{4-[(E,Z)-[(3-Bromo-4-fluorophenyl)amino](hydroxyimino)methyl]-1,2,5-oxadiazol-3-yl}-2,2-diphenylacetamide;

N-{4-[(E,Z)-[(3-Bromo-4-fluorophenyl)amino](hydroxyimino)methyl]-1,2,5-oxadiazol-3-yl}-4-(trifluoromethoxy)benzamide;

N-{4-[(E,Z)-[(3-Bromo-4-fluorophenyl)amino](hydroxyimino)methyl]-1,2,5-oxadiazol-3-yl}-4-methoxybenzamide;

N-{4-[(E,Z)-[(3-Bromo-4-fluorophenyl)amino](hydroxyimino)methyl]-1,2,5-oxadiazol-3-yl}-3,4-dimethoxybenzamide;

N-{4-[(E,Z)-[(3-Bromo-4-fluorophenyl)amino](hydroxyimino)methyl]-1,2,5-oxadiazol-3-yl}-2-(2-nitrophenoxy)acetamide;

N-{4-[(E,Z)-[(3-Bromo-4-fluorophenyl)amino](hydroxyimino)methyl]-1,2,5-oxadiazol-3-yl}biphenyl-4-carboxamide;

N-{4-[(E,Z)-[(3-Bromo-4-fluorophenyl)amino](hydroxyimino)methyl]-1,2,5-oxadiazol-3-yl}-2-(2,6-dichlorobenzyl)-1,3-thiazole-4-carboxamide;

N-{4-[(E,Z)-[(3-Bromo-4-fluorophenyl)amino](hydroxyimino)methyl]-1,2,5-oxadiazol-3-yl}-2,6-dimethoxybenzamide;

N-{4-[(E,Z)-[(3-Bromo-4-fluorophenyl)amino](hydroxyimino)methyl]-1,2,5-oxadiazol-3-yl}-4-nitrobenzamide;

5-Bromo-N-{4-[(E,Z)-[(3-bromo-4-fluorophenyl)amino](hydroxyimino)methyl]-1,2,5-oxadiazol-3-yl}nicotinamide;

N-{4-[(E,Z)-[(3-Bromo-4-fluorophenyl)amino](hydroxyimino)methyl]-1,2,5-oxadiazol-3-yl}-3,3-dimethylbutanamide;

N-{4-[(E,Z)-[(3-Bromo-4-fluorophenyl)amino](hydroxyimino)methyl]-1,2,5-oxadiazol-3-yl}-2-(2-thienyl)acetamide;

N-{4-[(E,Z)-[(3-Bromo-4-fluorophenyl)amino](hydroxyimino)methyl]-1,2,5-oxadiazol-3-yl}-4-phenylbutanamide;

N-{4-[(E,Z)-[(3-Bromo-4-fluorophenyl)amino](hydroxyimino)methyl]-1,2,5-oxadiazol-3-yl}-2,2-dimethylpropanamide;

N-{4-[(E,Z)-[(3-Bromo-4-fluorophenyl)amino](hydroxyimino)methyl]-1,2,5-oxadiazol-3-yl}-4-(morpholin-4-ylmethyl)benzamide;

N-{4-[(E,Z)-[(3-Bromo-4-fluorophenyl)amino](hydroxyimino)methyl]-1,2,5-oxadiazol-3-yl}-4-[(1,1-dioxidothiomorpholin-4-yl)methyl]benzamide;

N-{4-[(E,Z)-[(3-Bromo-4-fluorophenyl)amino](hydroxyimino)methyl]-1,2,5-oxadiazol-3-yl}-1-(phenylacetyl)piperidine-4-carboxamide;

N-{4-[(E,Z)-[(3-Bromo-4-fluorophenyl)amino](hydroxyimino)methyl]-1,2,5-oxadiazol-3-yl}-1-(methylsulfonyl)piperidine-4-carboxamide;

N-{4-[(E,Z)-[(3-Bromo-4-fluorophenyl)amino](hydroxyimino)methyl]-1,2,5-oxadiazol-3-yl}-2-pyridin-4-yl-1,3-thiazole-4-carboxamide;

N-{4-[(E,Z)-[(3-Bromo-4-fluorophenyl)amino](hydroxyimino)methyl]-1,2,5-oxadiazol-3-yl}-2-nitrobenzamide;

N-{4-[(E,Z)-[(3-Bromo-4-fluorophenyl)amino](hydroxyimino)methyl]-1,2,5-oxadiazol-3-yl}-3-nitrobenzamide;

N-{4-[(E,Z)-[(3-Bromo-4-fluorophenyl)amino](hydroxyimino)methyl]-1,2,5-oxadiazol-3-yl}-1-isopropylpiperidine-4-carboxamide;

tert-Butyl 4-{4-[({4-[(E,Z)-[(3-bromo-4-fluorophenyl)amino](hydroxyimino)methyl]-1,2,5-oxadiazol-3-yl}amino)carbonyl]-1,3-thiazol-2-yl}piperidine-1-carboxylate;

N-{4-[(E,Z)-[(3-Bromo-4-fluorophenyl)amino](hydroxyimino)methyl]-1,2,5-oxadiazol-3-yl}-2-phenyl-1,3-thiazole-4-carboxamide;

N-{4-[(E,Z)-[(3-Bromo-4-fluorophenyl)amino](hydroxyimino)methyl]-1,2,5-oxadiazol-3-yl}-2-methyl-1,3-thiazole-4-carboxamide;

N-{4-[(E,Z)-[(3-Bromo-4-fluorophenyl)amino](hydroxyimino)methyl]-1,2,5-oxadiazol-3-yl}-2-piperidin-4-yl-1,3-thiazole-4-carboxamide;

N-{4-[(E,Z)-[(3-Bromo-4-fluorophenyl)amino](hydroxyimino)methyl]-1,2,5-oxadiazol-3-yl}-2-(4-cyanophenoxy)acetamide;

tert-Butyl 3-[({4-[(E,Z)-[(3-bromo-4-fluorophenyl)amino](hydroxyimino)methyl]-1,2,5-oxadiazol-3-yl}amino)carbonyl]piperidine-1-carboxylate;

N-{4-[(E,Z)-[(3-Bromo-4-fluorophenyl)amino](hydroxyimino)methyl]-1,2,5-oxadiazol-3-yl}-3-(3-nitrophenyl)propanamide;

N-{4-[(E,Z)-[(3-Bromo-4-fluorophenyl)amino](hydroxyimino)methyl]-1,2,5-oxadiazol-3-yl}-2-(3-nitrophenoxy)acetamide;

N-{4-[(E,Z)-[(3-Bromo-4-fluorophenyl)amino](hydroxyimino)methyl]-1,2,5-oxadiazol-3-yl}-2-(4-nitrophenoxy)acetamide;

N-{4-[(E,Z)-[(3-Bromo-4-fluorophenyl)amino](hydroxyimino)methyl]-1,2,5-oxadiazol-3-yl}piperidine-3-carboxamide;

N-{4-[(E,Z)-[(3-Bromo-4-fluorophenyl)amino](hydroxyimino)methyl]-1,2,5-oxadiazol-3-yl}-4-methyl-2-pyridin-3-yl-1,3-thiazole-5-carboxamide;

N-{4-[(E,Z)-[(3-Bromo-4-fluorophenyl)amino](hydroxyimino)methyl]-1,2,5-oxadiazol-3-yl}-4-methyl-1,3-thiazole-5-carboxamide;

2-Amino-N-{4-[(E,Z)-[(3-bromo-4-fluorophenyl)amino](hydroxyimino)methyl]-1,2,5-oxadiazol-3-yl}-1,3-thiazole-4-carboxamide;

N-{4-[(E,Z)-[(3-Bromo-4-fluorophenyl)amino](hydroxyimino)methyl]-1,2,5-oxadiazol-3-yl}-4-methyl-2-pyrazin-2-yl-1,3-thiazole-5-carboxamide;

N-{4-[(E,Z)-[(3-Bromo-4-fluorophenyl)amino](hydroxyimino)methyl]-1,2,5-oxadiazol-3-yl}-4-methyl-2-[4-(trifluoromethyl)phenyl]-1,3-thiazole-5-carboxamide;

N-{4-[(E,Z)-[(3-Bromo-4-fluorophenyl)amino](hydroxyimino)methyl]-1,2,5-oxadiazol-3-yl}-2,4-dimethyl-1,3-thiazole-5-carboxamide;

1-Acetyl-N-{4-[(E,Z)-[(3-bromo-4-fluorophenyl)amino](hydroxyimino)methyl]-1,2,5-oxadiazol-3-yl}pyrrolidine-2-carboxamide;

N-{4-[(E,Z)-[(3-Bromo-4-fluorophenyl)amino](hydroxyimino)methyl]-1,2,5-oxadiazol-3-yl}-1,5-dimethyl-1H-pyrazole-3-carboxamide;

N-{4-[(E,Z)-[(3-Bromo-4-fluorophenyl)amino](hydroxyimino)methyl]-1,2,5-oxadiazol-3-yl}-5-chloro-1-methyl-1H-pyrazole-4-carboxamide;

N-{4-[(E,Z)-[(3-Bromo-4-fluorophenyl)amino](hydroxyimino)methyl]-1,2,5-oxadiazol-3-yl}-1,3-dimethyl-1H-pyrazole-5-carboxamide;

N-{4-[(E,Z)-[(3-Bromo-4-fluorophenyl)amino](hydroxyimino)methyl]-1,2,5-oxadiazol-3-yl}-1-methyl-1H-imidazole-2-carboxamide;

4-[(Acetylamino)methyl]-N-{4-[(E,Z)-[(3-bromo-4-fluorophenyl)amino](hydroxyimino)methyl]-1,2,5-oxadiazol-3-yl}benzamide;

N-{4-[(E,Z)-[(3-Bromo-4-fluorophenyl)amino](hydroxyimino)methyl]-1,2,5-oxadiazol-3-yl}-4-methylpiperidine-4-carboxamide;

1-Acetyl-N-{4-[(E,Z)-[(3-bromo-4-fluorophenyl)amino](hydroxyimino)methyl]-1,2,5-oxadiazol-3-yl}piperidine-3-carboxamide;

1-Acetyl-N-{4-[(E,Z)-[(3-bromo-4-fluorophenyl)amino](hydroxyimino)methyl]-1,2,5-oxadiazol-3-yl}-4-methylpiperidine-4-carboxamide;

1-Acetyl-N-{4-[(E,Z)-[(3-bromo-4-fluorophenyl)amino](hydroxyimino)methyl]-1,2,5-oxadiazol-3-yl}-4-phenylpiperidine-4-carboxamide;

4-(Benzylamino)-N-(3-bromo-4-fluorophenyl)-N'-hydroxy-1,2,5-oxadiazole-3-carboximidamide;

N-{4-[(E,Z)-[(3-Bromo-4-fluorophenyl)amino](hydroxyimino)methyl]-1,2,5-oxadiazol-3-yl}-1-ethylpiperidine-3-carboxamide;

N-{4-[(E,Z)-[(3-Bromo-4-fluorophenyl)amino](hydroxyimino)methyl]-1,2,5-oxadiazol-3-yl}-4-ethylpiperazine-1-carboxamide;

4-Acetyl-N-{4-[(E,Z)-[(3-bromo-4-fluorophenyl)amino](hydroxyimino)methyl]-1,2,5-oxadiazol-3-yl}piperazine-1-carboxamide;

N-{4-[(E,Z)-[(3-Bromo-4-fluorophenyl)amino](hydroxyimino)methyl]-1,2,5-oxadiazol-3-yl}-2-(1-ethylpiperidin-4-yl)-1,3-thiazole-4-carboxamide;

N-(3-Bromo-4-fluorophenyl)-N'-hydroxy-4-[(1,3-thiazol-4-ylmethyl)amino]-1,2,5-oxadiazole-3-carboximidamide;

N-(3-Bromo-4-fluorophenyl)-4-[(4-cyanobenzyl)amino]-N'-hydroxy-1,2,5-oxadiazole-3-carboximidamide;

N-(3-Bromo-4-fluorophenyl)-N'-hydroxy-4-{[(1-methylpiperidin-4-yl)methyl]amino}-1,2,5-oxadiazole-3-carboximidamide;

N-(3-Bromo-4-fluorophenyl)-N'-hydroxy-4-{[4-(piperazin-1-ylmethyl)benzyl]amino}-1,2,5-oxadiazole-3-carboximidamide;

N-(3-Bromo-4-fluorophenyl)-4-({4-[(4-ethylpiperazin-1-yl)methyl]benzyl}amino)-N'-hydroxy-1,2,5-oxadiazole-3-carboximidamide;

N-(3-Bromo-4-fluorophenyl)-N'-hydroxy-4-[(pyridin-4-ylmethyl)amino]-1,2,5-oxadiazole-3-carboximidamide; and N-(3-Bromo-4-fluorophenyl)-4-[(3-cyanobenzyl)amino]-N'-hydroxy-1,2,5-oxadiazole-3-carboximidamide;

N-{4-[[(3-Chlorophenyl)amino](hydroxyimino)methyl]-1,2,5-oxadiazol-3-yl}-2-phenylacetamide;

N-{4-[[(3-Chlorophenyl)amino](hydroxyimino)methyl]-1,2,5-oxadiazol-3-yl}benzamide; and N-{4-[(Benzylamino)(hydroxyimino)methyl]-1,2,5-oxadiazol-3-yl}benzamide;

or a pharmaceutically acceptable salt thereof.

\* \* \* \* \*